US009040626B2

(12) United States Patent
Chien et al.

(10) Patent No.: US 9,040,626 B2
(45) Date of Patent: May 26, 2015

(54) NANOFIBERS AND MORPHOLOGY SHIFTING MICELLES

(75) Inventors: Miao-Ping Chien, San Diego, CA (US); Nathan C. Gianneschi, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/363,645

(22) Filed: Feb. 1, 2012

(65) Prior Publication Data
US 2012/0149843 A1 Jun. 14, 2012

Related U.S. Application Data

(63) Continuation of application No. PCT/US2010/044321, filed on Aug. 3, 2010.

(60) Provisional application No. 61/230,924, filed on Aug. 3, 2009, provisional application No. 61/316,325, filed on Mar. 22, 2010.

(51) Int. Cl.
*A61K 8/02* (2006.01)
*A61K 9/70* (2006.01)
*B82Y 5/00* (2011.01)
*C12N 9/96* (2006.01)
*A61K 9/00* (2006.01)
*A61K 9/107* (2006.01)
*A61K 9/51* (2006.01)
*C12N 9/22* (2006.01)

(52) U.S. Cl.
CPC ............... *C12N 9/96* (2013.01); *A61K 9/0092* (2013.01); *A61K 9/1075* (2013.01); *A61K 9/5115* (2013.01); *C12N 9/22* (2013.01); Y10S 977/89 (2013.01); Y10S 977/906 (2013.01); Y10S 977/915 (2013.01); Y10S 977/916 (2013.01)

(58) Field of Classification Search
CPC . A61K 9/0092; A61K 9/1075; A61K 9/5115; C12N 9/22; C12N 9/96
USPC ............. 424/401, 443, 490; 435/6.1, 91.1; 977/890, 906, 915–916; 525/54.2
See application file for complete search history.

(56) References Cited

U.S. PATENT DOCUMENTS

| 4,647,447 | A | 3/1987 | Gries et al. | |
|---|---|---|---|---|
| 5,539,082 | A | 7/1996 | Nielsen et al. | |
| 5,567,588 | A | 10/1996 | Gold et al. | |
| 2003/0170893 | A1* | 9/2003 | Unger | 435/455 |
| 2004/0001893 | A1 | 1/2004 | Stupp et al. | |
| 2004/0018961 | A1 | 1/2004 | Stupp et al. | |
| 2004/0101564 | A1 | 5/2004 | Rioux et al. | |
| 2006/0182710 | A1* | 8/2006 | Hsiue et al. | 424/78.08 |
| 2011/0158906 | A1* | 6/2011 | Mullen et al. | 424/1.73 |

OTHER PUBLICATIONS

Ding et al. Angew. Chem. Int. Ed. 2007, 46, 1172-1175.*
Alemdaroglu et al., "DNA meets synthetic polymers-highly versatile hybrid materials", Org. Biomol. Chem. 2007, 5:1311-1320.
Boutorin, A.S. et al., "Synthesis of alkylating oligonucleotide derivatives containing cholestrerol or phenzazinium residues at their 3'-terminus and their interaction with DNA within mammalian cells", FEBS Lett. 1989, 254(1,2):129-132.
Chandrawati, Rona et al., "Cholesterol-mediated anchoring of enzyme-loaded liposomes within disulfide-stabilized polymer carrier capsules", Biomaterials 2009, 30:5988-5998.
Chung, Minsub et al., "DNA-tethered membranes formed by giant vesicle rupture", J. Struct. Biol.Oct. 2009, 168(1):190-199.
Cotton, F. Albert et al., "Exceptionally strong electronic coupling between [$Mo_2$] units linked by substituted dianionic quinones", Chem. Commun. 2008, 15:211-213.
Dai, Xinhua et al., "Formation of gold nanoparticles in the presence of o-anisidine and the dependence of the structure of poly(o-anisidine) on synthetic conditions", Langmuire 18:9010-9016, 2002.
Fernyhough, Christine et al., "pH controlled assembly of a polybutadiene-poly(methacrylic acid) copolymer in water: packing considerations and kinetic limitations", Soft Matter 2009, 5:1674-1682.
Gianneschi, Nathan C. et al. "Design of molecular logic devices based on a programmable DNA-regulated semisynthetic enzyme", Angew. Chem. Int. Ed. 2007, 46:3955-3958.
Gissot, Arnaud et al., "Sensitive liposomes encoded with oligonucleotide amphiphiles: a biocompatible switch", Chem. Commun. 2008, 5550-5552.
Godeau, Guilhem et al., "Lipid-conjugated oligonucleotides via "click chemistry" efficiently inhibit hepatitis C virus translation", J. Med. Chem. 2008, 51:4374-4376.
International Preliminary Report on Patentability and Written Opinion dated Feb. 7, 2012 for International Application No. PCT/US2010/044321, 5 pages.
International Search Report dated Mar. 22, 2011 for International Application No. PCT/US2010/044321, 3 pages.
Ishihara, Yoshihiro et al., "Molecule-responsive block copolymer micelles", Chem. Eur. J. 2007, 13:4560-4570.
Israelachvilli, Jacob et al., "Theory of self-assembly of hydrocarbon amphiphiles into micelles and bilayers", J. Chem. Soc., Faraday Trans. 2 1976, 72:1525-1568.
Jakobsen, Ulla et al., "DNA-controlled assembly of soft nanoparticles", J. Am. Chem. Soc. 2008, 130:10462-10463.
Kim, Jong-Ho et al., "Protein-phosphorylation-responsive polymeric nanoparticles for imaging protein kinase activities in single living cells", Angew. Chem., Int. Ed. 46:5779-5782, 2007.
Krieg, Arthur M. et al. "Modification of antisense phosphodiester oligodeoxynucleotides by a 5' cholesteryl moiety increases cellular associations an improves efficacy", Proc. Natl. Acad. Sci. Feb. 1993, 90:1048-1052.

(Continued)

*Primary Examiner* — Janet Epps-Smith
(74) *Attorney, Agent, or Firm* — Mintz, Levin, Cohn, Ferris, Glovsky and Popeo, P.C.

(57) ABSTRACT

The invention discloses novel morphology shifting micelles and amphiphilic coated metal nanofibers. Methods of using and making the same are also disclosed.

17 Claims, 27 Drawing Sheets

(56) References Cited

OTHER PUBLICATIONS

Kurz, Anke et al., "Lipid-anchored oligonucleotides for stable double-helix formation in distinct membrane domains", Angew. Chem. Int. Ed. 2006, 45:4440-4444.

Laromaine, Anna et al. "Protease-Triggered Dispersion of Nanoparticle Assemblies", J. Am. Chem. Soc. 2007, 129:4156-4157.

LaRue, Isaac et al., "Reversible morphological transitions of polystyrene-b-polyisoprene micelles", Macromolecules 2006, 39:309-314.

Li, Yali et al., "pH-responsive shell cross-linked nanoparticles with hydrolytically labile cross-links", Macromolecules 2008, 41:6605-6607.

Li, Zhi et al., "Reversible and chemically programmable micelle assembly with DNA block-copolymer amphiphiles", Nano Letters 2004, 4(6):1055-1058.

Loew, Martin et al., "Contolled assembly of vesicle-based nanocontainers on layer-by-layer particles via DNA hybridization", Small 2009(3), 5:320-323.

MacKellar, Calum et al., "Synthesis and physical properties of anti-HIV antisense oligonucleotides bearing terminal lipophilic groups", Nucleic Acids Res. 1992, 20(13):3411-3417.

Mart, Robert J. "Peptide-based stimuli-responsive biomaterials", Soft Matter 2006, 2:822-835.

Muller, Ulrich F. et al., "Improved polymerase ribozyme efficiency on hydrophobic assemblies", RNA 2008, 14:552-562.

Nagarajan, R. "Molecular packing parameter and surfactant self-assembly: the neglected role of the surfactant tail", Langmuir 2002, 18:31-38.

Nori, Aparna et al., "Intracellular targeting of polymer-bound drugs for cancer chemotherapy", Advanced Drug Delivery Reviews 2005, 57:609-636.

Patolsky, Fernando et al., "Amplified microgravimetric quartz-crystal-microbalance assay of DNA using oligonucleotide-functionalized liposomes or biotinylated liposomes" J. Am. Chem. Soc. 2000, 122:418-419.

Pfeiffer, Indriati et al., "Bivalent cholesterol-based coupling of oligonucleotides to lipid membrane assemblies", J. Am. Chem. Soc. 2004, 126:10224-10225.

Rijcken, C.J.F. et al., "Triggered destabilization of polymeric micelles and vesicles by changing polymers polarity: An attractive tool for drug delivery"; Journal of Controlled Release 2007, 120:131-148.

Rosi, Nathaniel L. et al. "Nanostructures in biodiagnostics", Chem. Rev. 2005, 105:1547-1562.

Roy, Debashish et al., "Triply-responsive boronic acid block copolymers: solution self-assembly induced by changes in temperature, pH, or sugar concentration", Chem. Commun. 2009, 2106-2108.

Shea, Regan et al., "Synthesis, hybridization properties and antiviral activity of lipid-oligodeoxynucleotide conjugates", Nucleic Acids Res. 1990, 18(13):3777-3783.

Stengel, Gudrun et al., "DNA-induced programmable fusion of phospholipid vesicles", J. Am. Chem. Soc. 2007, 129:9584-9585.

Storhoff, James J. et al., "Programmed Materials Synthesis with DNA", Chem. Rev 1999, 99:1849-1862.

Sundararaman, Anand et al., "Reversible restructuring of aqueous block copolymer assemblies through stimulus-induced changes in amphiphilicity", J. Am. Chem. Soc. 2008, 130:12264-12265.

Wang, Yapei et al., "Tuning the amphiphilicity of building blocks: controlled self-assembly and disassembly for functional supromolecular materials", Adv. Mater. 2009, 21:2849-2864.

Wu, Yanrong et al., "DNA aptamer-micelle as an efficient detection/delivery vehicle toward cancer cells", Proc. Natl. Acad. Sci. Jan. 5, 2010, 107(1):5-10.

Xu, Peisheng et al., "Enhanced stability of cores-surface cross-linked micelles fabricated from amphiphilic brush copolymers", Biomacromolecules 2004, 5:1736-1744.

Yoshina-Ishii, Chiaki et al., "General method for modification of liposomes for encoded assembly on supported bilayers", J. Am. Chem. Soc. 2005, 127:1356-1357.

Zhang, Lifeng et al., "Ion-induced morphological changes in "crew-cut" aggregates of amphiphilic block copolymers" Science 1996, 272:1777-1779.

Zou, Jiong et al., "Optical switching of self-assembly and disassembly of noncovalently connected amphiphiles", Langmuir 2007, 23:12791-12794.

\* cited by examiner

PEG = DNA-5'-O-$\overset{\overset{O}{\|}}{\underset{\underset{O^-}{|}}{P}}$-O$\left(\diagdown\diagdown O\right)_5$-$\overset{\overset{O}{\|}}{\underset{\underset{O^-}{|}}{P}}$-O$\left(\diagdown\diagdown O\right)_5$-OH DNA$_1$ = 5'-TCGCACCCA-3'
DNA$_2$ = 5'-PEG-GGAGAGAGACTGGGTGCGA-3'
DNA$_3$ = 5'-TCGCACCCAGTCTCTCTCC-3'

Fig. 3A
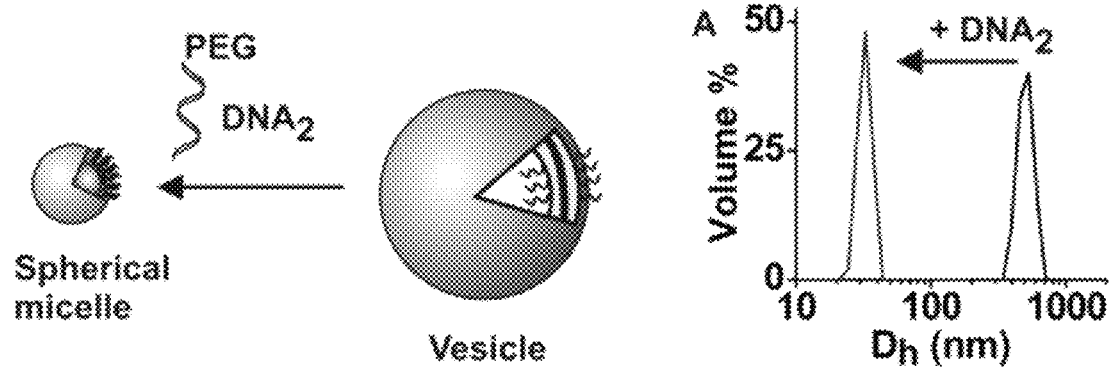
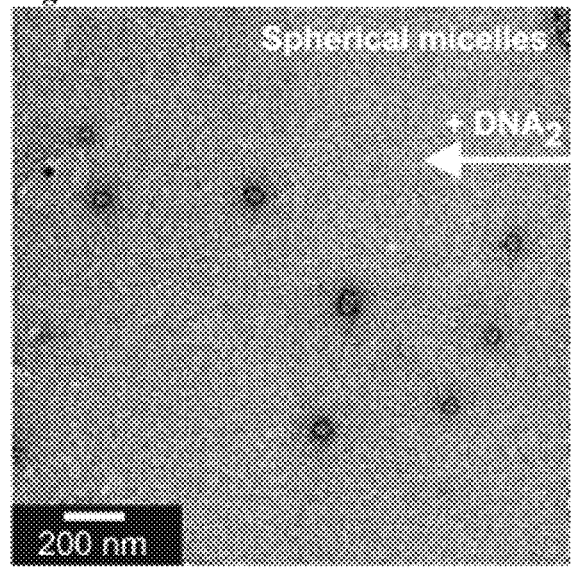
Fig. 3B
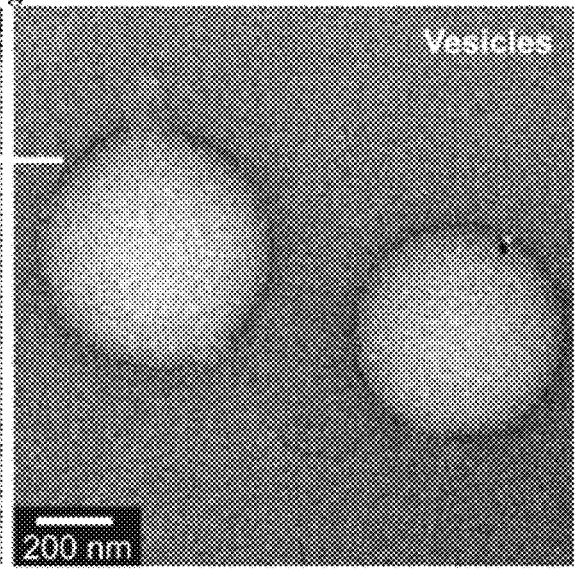
Fig. 3C

↔ 20 nm

↔ 100 nm

↔ 450 nm

↔ 800 nm 1900 nm

Red

Green

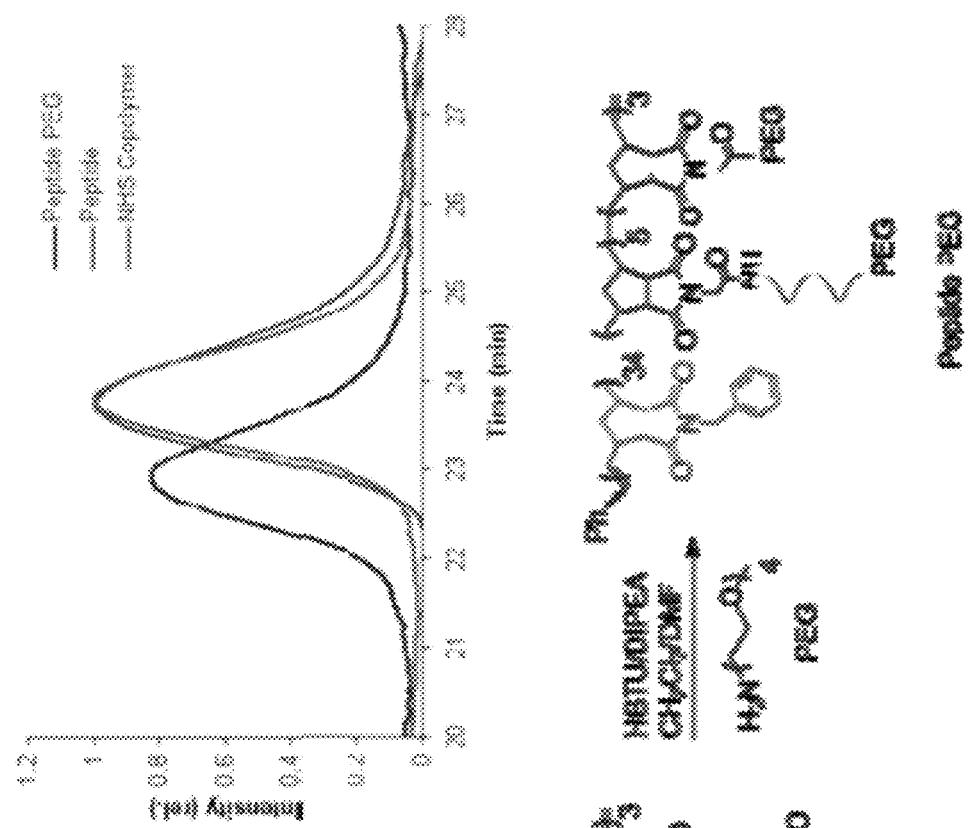
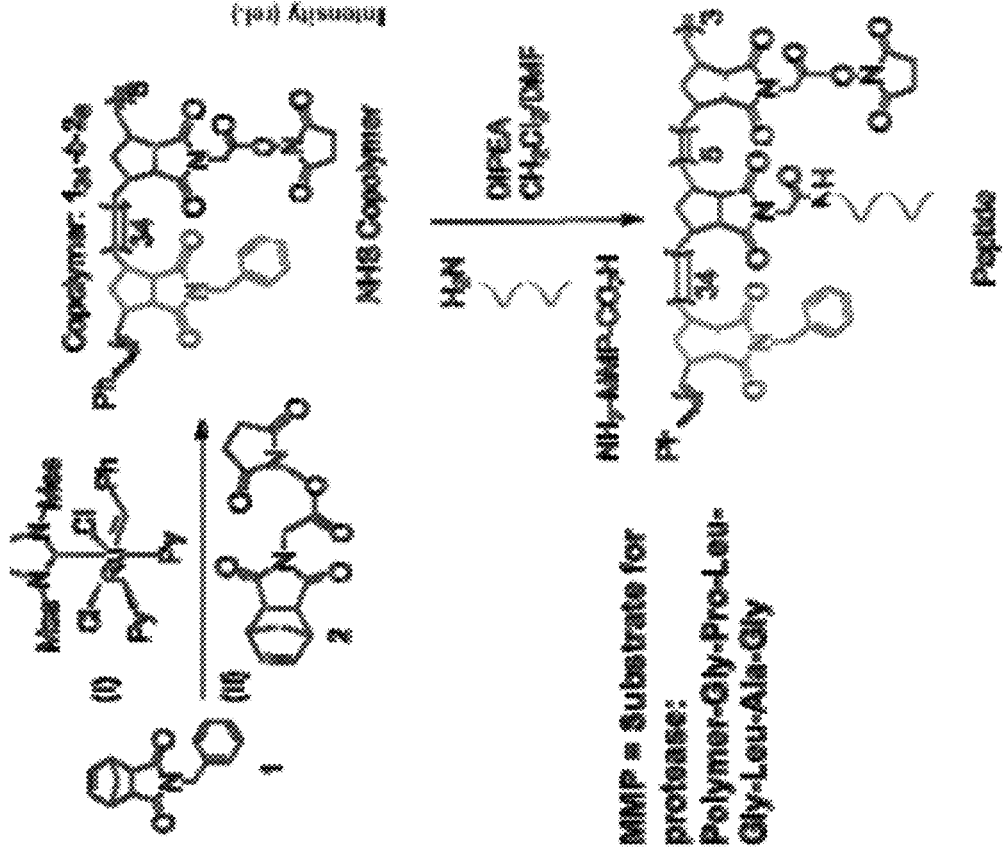
Fig. 12A
Fig. 12B a) ssDNA substrate b) Supramolecular substrate

SEQUENCE LISTING

<160> NUMBER OF SEQ ID NOS: 35

<210> SEQ ID NO 1
<211> LENGTH: 19
<212> TYPE: DNA
<213> ORGANISM: Artificial Sequence
<220> FEATURE:
<223> OTHER INFORMATION: Synthetic DNA sequence of compound DNA(2) having PEG attached at 5'-dG
<220> FEATURE:
<221> NAME/KEY: modified_base
<222> LOCATION: (1)..(1)
<223> OTHER INFORMATION: PEG attached at 5'-dG

<400> SEQUENCE: 1
ggagagagac tgggtgcga                                                19

<210> SEQ ID NO 2
<211> LENGTH: 19
<212> TYPE: DNA
<213> ORGANISM: Artificial Sequence
<220> FEATURE:
<223> OTHER INFORMATION: Synthetic DNA of compound DNA(3).

<400> SEQUENCE: 2
tcgcacccag tctctctcc                                                19

<210> SEQ ID NO 3
<211> LENGTH: 9
<212> TYPE: DNA
<213> ORGANISM: Artificial Sequence
<220> FEATURE:
<223> OTHER INFORMATION: Synthetic DNA of compound DNA(1)-fluorescein having fluorescein attached at 3-'dA.
<220> FEATURE:
<221> NAME/KEY: modified_base
<222> LOCATION: (9)..(9)
<223> OTHER INFORMATION: fluorescein attached at 3'-dA

<400> SEQUENCE: 3 tcgcaccca                                                            9

<210> SEQ ID NO 4
<211> LENGTH: 9
<212> TYPE: DNA
<213> ORGANISM: Artificial Sequence
<220> FEATURE:
<223> OTHER INFORMATION: Synthetic DNA of compound DNA(4)-rhodamine having rhodamine attached at 3-'dA
<220> FEATURE:
<221> NAME/KEY: modified_base
<222> LOCATION: (9)..(9)
<223> OTHER INFORMATION: rhodamine attached at 3'-dA

<400> SEQUENCE: 4 ctcacgaca                                                            9

<210> SEQ ID NO 5
<211> LENGTH: 19
<212> TYPE: DNA
<213> ORGANISM: Artificial Sequence
<220> FEATURE:
<223> OTHER INFORMATION: Synthetic DNA of compound DNA(5) having PEG-PEG attached at 5'-dA
<220> FEATURE:
<221> NAME/KEY: modified_base
<222> LOCATION: (1)..(1)
<223> OTHER INFORMATION: PEG-PEG polyethylene glycol attached at 5'-dA

<400> SEQUENCE: 5
agcgacagac tgtcgtgag                                               19

<210> SEQ ID NO 6
<211> LENGTH: 19
<212> TYPE: DNA
<213> ORGANISM: Artificial Sequence
<220> FEATURE:
<223> OTHER INFORMATION: Synthetic DNA structure of compound DNA(6)

<400> SEQUENCE: 6
ctcacgacag tctgtcgct                                               19

<210> SEQ ID NO 7
<211> LENGTH: 34
<212> TYPE: DNA
<213> ORGANISM: Artificial Sequence
<220> FEATURE:
<223> OTHER INFORMATION: Synthetic DNA of compound DNAzyme

<400> SEQUENCE: 7
ggagagagat ccgagccggt cgaagggtgc gcga                              34

<210> SEQ ID NO 8
<211> LENGTH: 19
<212> TYPE: DNA
<213> ORGANISM: Artificial Sequence
<220> FEATURE:
<223> OTHER INFORMATION: Synthetic DNA of compound In(1) having PEG-PEG
      attached at 5'-dG
<220> FEATURE:
<221> NAME/KEY: modified_base
<222> LOCATION: (1)..(1)
<223> OTHER INFORMATION: PEG-PEG attached at 5'-dG

<400> SEQUENCE: 8
ggagagagac tgggtgcga                                               19

<210> SEQ ID NO 9
<211> LENGTH: 19
<212> TYPE: DNA
<213> ORGANISM: Artificial Sequence
<220> FEATURE:
<223> OTHER INFORMATION: Synthetic DNA of compound In(2)

<400> SEQUENCE: 9
tcgcacccag tctctctcc                                               19

<210> SEQ ID NO 10
<211> LENGTH: 20
<212> TYPE: DNA
<213> ORGANISM: Artificial Sequence
<220> FEATURE:
<223> OTHER INFORMATION: Synthetic DNA compound

<400> SEQUENCE: 10
agagtcatgt ggagagtcca                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic DNA compound

<400> SEQUENCE: 11
caggagtcat gtccaaggtg                                              20

<210> SEQ ID NO 12
<211> LENGTH: 21
<212> TYPE: DNA
<213> ORGANISM: Artificial Sequence
<220> FEATURE:
<223> OTHER INFORMATION: Synthetic RNA/DNA compound having 1,2-dithiane
      attached at 5'-dA and riboadenosine rA at position 10
<220> FEATURE:
<221> NAME/KEY: misc_RNA
<222> LOCATION: (10)..(10)
<223> OTHER INFORMATION: riboadenosine at postion 10

<400> SEQUENCE: 12
agagtcatga tggagagtcc a                                              21

<210> SEQ ID NO 13
<211> LENGTH: 19
<212> TYPE: DNA
<213> ORGANISM: Artificial Sequence
<220> FEATURE:
<223> OTHER INFORMATION: Synthetic DNA of compound DNA(2) having PEG-PEG
      attached at 5'-dG
<220> FEATURE:
<221> NAME/KEY: modified_base
<222> LOCATION: (1)..(1)
<223> OTHER INFORMATION: PEG-PEG attached at 5'-dG

<400> SEQUENCE: 13
ggagagagac tgggtgcga                                                 19

<210> SEQ ID NO 14
<211> LENGTH: 19
<212> TYPE: DNA
<213> ORGANISM: Artificial Sequence
<220> FEATURE:
<223> OTHER INFORMATION: Synthetic DNA of compound DNA(3)

<400> SEQUENCE: 14
tcgcacccag tctctctcc                                                 19

<210> SEQ ID NO 15
<211> LENGTH: 19
<212> TYPE: DNA
<213> ORGANISM: Artificial Sequence
<220> FEATURE:
<223> OTHER INFORMATION: Synthetic DNA of compound DNA(5) having PEG-PEG
      attached at 5'-dA
<220> FEATURE:
<221> NAME/KEY: modified_base
<222> LOCATION: (1)..(1)
<223> OTHER INFORMATION: PEG-PEG attached at 5'-dA

<400> SEQUENCE: 15
agcgacagac tgtcgtgag                                                 19

<210> SEQ ID NO 16
<211> LENGTH: 19
<212> TYPE: DNA
<213> ORGANISM: Artificial Sequence
<220> FEATURE:
<223> OTHER INFORMATION: Synthetic DNA of compound DNA(6)

<400> SEQUENCE: 16
ctcacgacag tctgtcgct                                                 19

<210> SEQ ID NO 17
<211> LENGTH: 19

```
<212> TYPE: DNA
<213> ORGANISM: Artificial Sequence
<220> FEATURE:
<223> OTHER INFORMATION: Synthetic DNA of compound DNA(7)

<400> SEQUENCE: 17
ggagagagac tgggtgcga                                                     19

<210> SEQ ID NO 18
<211> LENGTH: 32
<212> TYPE: DNA
<213> ORGANISM: Artificial Sequence
<220> FEATURE:
<223> OTHER INFORMATION: Synthetic DNA of compound DNAzyme (D-1)

<400> SEQUENCE: 18
ggagagagat ccgagccggt cgaagggtgc ga                                      32

<210> SEQ ID NO 19
<211> LENGTH: 32
<212> TYPE: DNA
<213> ORGANISM: Artificial Sequence
<220> FEATURE:
<223> OTHER INFORMATION: Synthetic DNA of compound DNAzyme (D-2)

<400> SEQUENCE: 19
agcgacagat ccgagccggt cgaagtcgtg ag                                      32

<210> SEQ ID NO 20
<211> LENGTH: 19
<212> TYPE: DNA
<213> ORGANISM: Artificial Sequence
<220> FEATURE:
<223> OTHER INFORMATION: Synthetic DNA/RNA for ssDNA substrate (F-ssDNA)
      having fluorescein attached at 5' end and riboadenosine rA at
      position 9 and Dabcyl atttached at 3'-dC
<220> FEATURE:
<221> NAME/KEY: modified_base
<222> LOCATION: (1)..(1)
<223> OTHER INFORMATION: Fluorescein attached at 5'-dT
<220> FEATURE:
<221> NAME/KEY: misc_RNA
<222> LOCATION: (9)..(9)
<223> OTHER INFORMATION: riboadenosine at position 9
<220> FEATURE:
<221> NAME/KEY: modified_base
<222> LOCATION: (19)..(19)
<223> OTHER INFORMATION: Dabcyl reporter attached at 3'-dC

<400> SEQUENCE: 20
tcgcacccag tctctctcc                                                     19

<210> SEQ ID NO 21
<211> LENGTH: 19
<212> TYPE: DNA
<213> ORGANISM: Artificial Sequence
<220> FEATURE:
<223> OTHER INFORMATION: Synthetic DNA of compound In(1) having PEG-PEG
      at 5'-dG
<220> FEATURE:
<221> NAME/KEY: modified_base
<222> LOCATION: (1)..(1)
<223> OTHER INFORMATION: PEG-PEG attached at 5'-dG

<400> SEQUENCE: 21
ggagagagac tgggtgcga                                                     19

<210> SEQ ID NO 22
<211> LENGTH: 19
```

```
<212> TYPE: DNA
<213> ORGANISM: Artificial Sequence
<220> FEATURE:
<223> OTHER INFORMATION: Synthetic DNA of compound In(2)

<400> SEQUENCE: 22
tcgcacccag tctctctcc                                              19

<210> SEQ ID NO 23
<211> LENGTH: 20
<212> TYPE: DNA
<213> ORGANISM: Artificial Sequence
<220> FEATURE:
<223> OTHER INFORMATION: Synthetic DNA used for preparation of particles
      and having PEG-PEG-fluorescein attached at 3'-dC
<220> FEATURE:
<221> NAME/KEY: modified_base
<222> LOCATION: (20)..(20)
<223> OTHER INFORMATION: PEG-PEG-fluorescein attached at 3'-dC

<400> SEQUENCE: 23
tcgcacccra gtctctctcc                                             20

<210> SEQ ID NO 24
<211> LENGTH: 22
<212> TYPE: DNA
<213> ORGANISM: Artificial Sequence
<220> FEATURE:
<223> OTHER INFORMATION: Synthetic DNA/RNA compound for prepartion of
      DNA for particles having rhodamine-T at position 3 and
      riboadenosine rA at position 12 and PEG-PEG-A attached at 3'-dT
<220> FEATURE:
<221> NAME/KEY: modified_base
<222> LOCATION: (3)..(3)
<223> OTHER INFORMATION: rhodamine incorporated into dT as the dT-TAMRA
      modified phosphoramidite
<220> FEATURE:
<221> NAME/KEY: misc_RNA
<222> LOCATION: (12)..(12)
<223> OTHER INFORMATION: riboadenosine at position 12
<220> FEATURE:
<221> NAME/KEY: modified_base
<222> LOCATION: (22)..(22)
<223> OTHER INFORMATION: PEG-PEG-A attached at 3'-dT

<400> SEQUENCE: 24
cctctcacga cagtctgtcg ct                                          22

<210> SEQ ID NO 25
<211> LENGTH: 22
<212> TYPE: DNA
<213> ORGANISM: Artificial Sequence
<220> FEATURE:
<223> OTHER INFORMATION: Synthetic DNA/RNA compound for preparation of
      DNA for particles having fluorescein incorporated as the
      dT-fluorescein modified from the phosphoramidite at position 3 and
      riboadenosine rA at position 12 and PEG-PEG-A attached at 3'-dC
<220> FEATURE:
<221> NAME/KEY: modified_base
<222> LOCATION: (3)..(3)
<223> OTHER INFORMATION: dT-fluorescein
<220> FEATURE:
<221> NAME/KEY: misc_RNA
<222> LOCATION: (12)..(12)
<223> OTHER INFORMATION: riboadenosine at position 12
<220> FEATURE:
<221> NAME/KEY: modified_base
<222> LOCATION: (22)..(22)
<223> OTHER INFORMATION: PEG-PEG-A attached at 3'-dC

<400> SEQUENCE: 25
ccttcgcacc cagtctctct cc                                          22
```

<210> SEQ ID NO 26
<211> LENGTH: 15
<212> TYPE: PRT
<213> ORGANISM: Artificial Sequence
<220> FEATURE:
<223> OTHER INFORMATION: Synthetic peptide of compound Peptide 1
      (PKA-MMP)

<400> SEQUENCE: 26

Leu Arg Arg Ala Ser Leu Gly Lys Gly Pro Leu Gly Leu Ala Gly
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic peptide of compound Peptide (MMP-PKA)

<400> SEQUENCE: 27

Lys Lys Pro Leu Gly Leu Ala Gly Leu Arg Arg Ala Ser Leu Gly
1               5                   10                  15

<210> SEQ ID NO 28
<211> LENGTH: 7
<212> TYPE: PRT
<213> ORGANISM: Artificial Sequence
<220> FEATURE:
<223> OTHER INFORMATION: Synthetic peptide of compound Peptide 3 (MMP)

<400> SEQUENCE: 28

Gly Pro Leu Gly Leu Ala Gly
1               5

<210> SEQ ID NO 29
<211> LENGTH: 29
<212> TYPE: DNA
<213> ORGANISM: Artificial Sequence
<220> FEATURE:
<223> OTHER INFORMATION: Synthetic DNA of compound DNAzyme-1

<400> SEQUENCE: 29
ggagagagat ccgagccgga agggtgcga                                    29

<210> SEQ ID NO 30
<211> LENGTH: 35
<212> TYPE: DNA
<213> ORGANISM: Artificial Sequence
<220> FEATURE:
<223> OTHER INFORMATION: Synthetic DNA of compound DNAzyme-2

<400> SEQUENCE: 30
aacacacact ccgagccggt cgaaagcttt ctgat                             35

<210> SEQ ID NO 31
<211> LENGTH: 22
<212> TYPE: DNA
<213> ORGANISM: Artificial Sequence
<220> FEATURE:
<223> OTHER INFORMATION: Synthetic DNA/RNA of compound DNA-2 having
      riboadenosine at position 12 and PEG-Fluorescein attached at 3'-dT
<220> FEATURE:
<221> NAME/KEY: misc_RNA
<222> LOCATION: (12)..(12)
<223> OTHER INFORMATION: riboadenosine at position 12
<220> FEATURE:
<221> NAME/KEY: modified_base

```
<222> LOCATION: (22)..(22)
<223> OTHER INFORMATION: PEG-Fluorescein attached at 3'-dT

<400> SEQUENCE: 31
atcagaaagc taggtgtgtg tt                                        22

<210> SEQ ID NO 32
<211> LENGTH: 19
<212> TYPE: DNA
<213> ORGANISM: Artificial Sequence
<220> FEATURE:
<223> OTHER INFORMATION: Synthetic DNA/RNA of compound DNA-1 having
      riboadenodine at position 9 and Fluorescein attached at 3'-dC
<220> FEATURE:
<221> NAME/KEY: misc_RNA
<222> LOCATION: (9)..(9)
<223> OTHER INFORMATION: riboadenosine at position 9
<220> FEATURE:
<221> NAME/KEY: modified_base
<222> LOCATION: (19)..(19)
<223> OTHER INFORMATION: PEG-Fluorescein attached at 3'-dC

<400> SEQUENCE: 32
tcgcacccag tctctctcc                                            19

<210> SEQ ID NO 33
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 33

Leu Arg Arg Ala Ser Leu Gly Lys Gly Pro Leu Gly Leu Ala Gly
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 34

Gly Pro Leu Gly Leu Ala Gly Lys Leu Arg Arg Ala Ser Leu Gly
1               5                   10                  15

<210> SEQ ID NO 35
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 35

Leu Arg Arg Ala Ser Leu Gly
1               5
```

NANOFIBERS AND MORPHOLOGY SHIFTING MICELLES

CROSS-REFERENCES TO RELATED APPLICATIONS

This application is a continuation of PCT/US2010/044321, filed Aug. 3, 2010, which claims the benefit of U.S. Application No. 61/230,924, filed Aug. 3, 2009 and 61/316,325, filed Mar. 22, 2010, each of which is incorporated by reference in its entirety and for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 88654-830139_ST25.TXT, created on Jan. 25, 2012, 10,939 bytes, machine format IBM-PC, MS-Windows operating system, is hereby incorporated by reference.

BACKGROUND OF THE INVENTION

Various non-informational, non-programmable nanoparticles have been known in the art, such as those disclosed in Zhang, et al., *Science* 272:1777-1779, 1996; LaRue et al., *Macromolecules* 39:309-314, 2006; Ishihara et al., *Chem. Eur. J.* 13:4560-4570, 2007; Kim et al., *Angew. Chem., Int. Ed* 46:5779-5782, 2007; Li et al., *Macromolecules* 41:6605-6607, 2008; Roy et al., *Chem. Commun.* 2106-2108, 2009; and Fernyhough et al., *Soft Matter* 5:1674-1682, 2009. There is a need in the art for micelles that are capable of changing morphology in a predictable or programmable way. Provided herein are solutions to these and other problems in the art.

BRIEF SUMMARY OF THE INVENTION

Provided herein, inter alia, are novel micelles capable of changing morphology (e.g. shape) in a controlled manner upon application of the appropriate stimulus as well as amphiphilic coated metal nanofibers. The micelles may be used in a variety of chemical, pharmaceutical and electronic applications as described herein.

In one aspect, a micelle is provided that includes a plurality of aggregated brush copolymers having a hydrophilic portion and a hydrophobic portion:

In another aspect, provided herein are novel methods of altering a morphology of a micelle. The method comprises subjecting the micelle to a stimulus thereby altering the morphology of the micelle. The stimulus is a temperature change, a pH change, a hydrophilic portion binder, or a hydrophilic portion enzyme. In some embodiments, the micelle comprises a plurality of aggregated amphiphilic molecules.

In another aspect, an amphiphilic coated metal nanofiber is provided. The amphiphilic coated nanofiber includes a metal nanofiber bound to a plurality of amphiphilic molecules.

In another aspect, provided herein are methods of making an amphiphilic coated metal nanofiber. The method includes contacting a metal nanoparticle with a micelle, wherein the micelle includes a plurality of aggregated amphiphilic molecules. The metal nanoparticles are allowed to assemble into a metal nanofiber thereby forming the amphiphilic coated metal nanofiber.

BRIEF DESCRIPTION OF THE DRAWINGS

FIGS. 2A-2B: Cryogenic-TEM (cryo-TEM) images showing unilamellar bilayer morphology of the vesicles at different scales of magnification. The scales for FIGS. 2A-2B are provided in the figures. FIGS. 2C-2D: SEM of vesicles at scales depicted in the figures. FIG. 2E: AFM depiction of vesicle structures dry, on a mica surface. FIG. 2F: AFM data showing the flattened height profile of the vesicle structures provided in FIG. 2E.

FIGS. 3A-3C depict DNA-directed vesicle to micelle phase transition. FIG. 3A: FIG. 3A depicts cartoon of phase transition reaction and results monitored by DLS. "$D_h$" refers to Hydrodynamic Diameter). FIG. 3B: Spherical micelles monitored by TEM (negative stain). FIG. 3C: Vesicles monitors by TEM (negative stain). Experimental conditions: Tris (pH 7.4, 50 mM), MgCl$_2$ (50 mM), DNA$_1$-lipid (1 μM), DNA$_2$ (2 μM), room temperature.

FIG. 4H: FIG. 4H depicts a cartoon reaction scheme having reacting species corresponding to each of the images set forth in FIGS. 4A-4F, as indicated by proximity of the reacting species to FIGS. 4A-4F. Legend for FIG. 4H: Green fluorescence: gray; red fluorescence: crosshatched; yellow fluorescence: stippled. FIG. 4A: Representative bright field image of labeled DNA-lipid assemblies. FIG. 4B: DNA$_4$-Rhodamine hybridizes to DNA$_5$ resulting in observed (i.e., green) fluorescence only. FIG. 4C: DNA$_6$ (complementary to DNA$_5$) causes mixing of the two surfactants to give a colocalized signal (i.e., yellow signal) from both dyes. FIG. 4D: DNA$_1$-Fluorescein hybridizes to DNA$_2$ to generate micelles resulting in observed (i.e., red) fluorescence only. FIG. 4E: Addition of DNA$_2$ and DNA$_5$ shifts all structures to micelles leaving little visible fluorescence. FIG. 4F: Upon addition of DNA$_3$ (complementary to DNA$_2$) and DNA$_6$ (complementary to DNA$_5$), surfactants reassemble to give colocalization signal (i.e., yellow) indicative of vesicles containing both dyes. FIG. 4G: DLS data of phase switching cycles with sequential ssDNA input additions. Solution conditions utilized in DLS experiment and prior to slide preparation: Tris (pH 7.4, 50 mM), MgCl$_2$ (50 mM), DNA-surfactant (1 μM), ssDNA input sequences (2 μM), room temperature. Sequences: DNA$_1$-Fluorescein (SEQ ID NO:3); DNA$_4$-Rhodamine (SEQ ID NO:4); DNA$_5$ (SEQ ID NO:5); DNA$_6$ (SEQ ID NO:6).

FIG. 5A: FIG. 5B: FIG. 5B depicts a cartoon reaction scheme showing that DNAzyme addition to spherical micelles causes sequence selective truncation of DNA at the cut-site indicated as a RNA base, rA, in the shell DNA sequence. Addition of In$_1$ to cylindrical micelles increases the volume fraction of DNA by hybridizing to the truncated shell. Subsequent addition of In$_2$ results in formation of In$_1$.In$_2$ duplex and sphere-to-cylinder transition. Amphiphile structures are represented as cones for each respective morphology. FIG. 5C: FIG. 5C depicts transmission electron microscopy (TEM) of 25 nm spherical micelles assembled from initial DNA-brush copolymers. FIG. 5D: FIG. 5D depicts cylindrical morphology formed following DNAzyme addition to spheres. FIG. 5E: FIG. 5E depicts spherical micelles following $In_1$ addition to cylinders. Sequences: DNAzyme: SEQ ID NO:7; $In_1$: SEQ ID NO:8; $In_2$: SEQ ID NO:9.

FIGS. 6A-6B depict reversible phase cycling via isothermal hybridization and invasion (FIG. 6A) and variable temperature DLS (FIG. 6B). FIG. 6A: FIG. 6A depicts Vol. % of species at 396 nm vs. input; measured by DLS 2 hr after each input addition beginning with 25 nm spheres. A $D_h$ of 396 nm is significant as the largest aggregate size class observed by DLS at 2 hr. FIG. 6B: FIG. 6B depicts variable temperature DLS. $D_h$ of largest aggregates in solution at given time points is indicated. Initial spheres (I) were treated with DNAzyme for 18 hrs (II) prior to addition of $In_1$. DLS measurement at t=0 min were taken 1 hr after addition of $In_1$. Ramp rate: 25° C. to 60° C. in 5 min. Instrument cooling time was 60 min; sample was cooled by placing in ice bath for 5 min, then resting at r.t. for 55 min. Second heating cycle conducted 18 hrs later with same ramp rate (25° C. to 60° C. in 5 min) and cooling time (60 min). Conditions: Particles (0.14 g/L), DNAzyme (5 nM), $In_1$ (50 nM), $In_2$ (50 nM), Tris (20 mM, pH 7.4), $MgCl_2$ (50 mM).

FIG. 7A: t=0 min. FIG. 7B: t=2 min. FIG. 7C: t=2 hr. FIG. 7D: t=1 day. FIG. 7E: t=2 days. FIG. 7F: FIG. 7F depicts graph of particle size as a function of time following DNAzyme addition. Curve through upper boxed data depicts average cylinder length ($C_L$) by TEM. Curve through triangle data depicts hydrodynamic diameter ($D_h$) of largest aggregates by DLS. Bottom curve depicts sphere diameter ($S_D$) by TEM. DLS data was taken at the time points shown following DNAzyme addition. Data points for $C_L$ and $S_D$ are averages of multiple measurements made from TEM images, with error bars indicating standard deviations.

FIG. 8A: FIG. 8A depicts TEM image showing bundled cylinder structures analogous to optical images. Optical microscopy images show bright field (FIGS. 8B, 8F and 8J), green fluorescence (FIGS. 8C, 8G and 8K), and red fluorescence images (FIGS. 8E, 8I, 8M) taken after treatment with DNAzyme. FIGS. 8C, 8G and 8K depict cartoon schematic representation of observed reactions. FIGS. 8B-8E: D-1 recognizes only fluorescein labeled particles. FIGS. 8F-8I: D-2 recognizes only rhodamine labeled particles. FIGS. 8J-8M: D-1 and D-2 together cause fiber formation containing both labels. Optical image scale bars=10 μm. Conditions: Micelles (0.14 g/L), DNAzyme (5 nM), Tris (20 mM, pH 7.4), $MgCl_2$ (50 mM). Shell DNA sequences are analogous to that shown in FIGS. 5A-5E, with an extra three bases at the 5'-terminus. The third base from the 5'-amide linkage to the polymer backbone is a dye-labeled thymidine residue.

FIG. 10 depicts the conversion of polymer-peptide amphiphile, with structure e.g. as indicated, to micelles with dialysis. Networks can form from the micelles under the influence of e.g., proteases MMP2- or MMP-2, as known in the art. A truncated peptide shell within a network is depicted in the upper inset to FIG. 10. Micelles can form vesicles under the influence of kinase+ATP/phosphatase reaction as indicated. A phosphorylated peptide shell is depicted in the lower inset to FIG. 10.

FIG. 12A depicts peptide-shell polymeric amphiphile synthesis. Utilizing ring-opening metathesis polymerization polymers may be synthesized via post-polymerization modification with peptides while on solid support or post-cleavage. Peptides may also be directly polymerized as monomers. Sequence: MMP (SEQ ID NO:28). FIG. 12B depicts light scattering intensity data for size-exclusion chromatography of Peptide PEG, peptide conjugated prior to PEG group attachment, and initial NHS copolymer (i.e. ROMP product prior to post-polymerization modification).

FIG. 16A depicts a cartoon reaction scheme leading to the formation of templated gold NP assembly. FIG. 16B (inset to FIG. 16A) depicts a photomicrograph during the sequence set forth in FIG. 16A. FIGS. 16C-16F depict results of electron diffraction, high-resolution TEM (10 nm scale bar), TEM (50 nm scale bar) and TEM (100 nm scale bar), respectively. Sequences: Disulfide modified oligonucleotide for coordination with Au NPs, 1,2-dithiane-AGAGTCATGrATGGAGAGTCCA (SEQ ID NO:12).

FIG. 20A: "No comp-DNA; " FIG. 20B: "comp-DNA-1 hr; " FIG. 20C: "comp-DNA-2 hr; " FIG. 20D: "comp-DNA-4 hr; " FIG. 20E: "Sphere only."

FIG. 22A: Complement to green fibers added at 3 hrs. Black—Green fluorescence. Light grey—Red fluorescence. FIG. 22B: Black—Spheres. Dark Grey—Fibers. Light grey—Fibers+ complementary DNA at 3 hrs. 1 nmole of dT-Flr/dT-Tam fibers mixture were injected into Fiber and FC mice groups and 1 nmole of dT-Flr/dT-Tam spheres mixture were injected into Sphere mice group. Each group has 4 mice. 1 nmole of Complementary DNA were injected into FC (fibers+complement) mice group at 3-hr time point. The serum was collected at each timepoint shown in the graphs, and fluorescent intensity was then measured in 96-well plate reader. Fluorescence wavelength: $\lambda_{ex}$: 485 nm; $\lambda_{em}$: 538 nm. Tamra wavelength: $\lambda_{ex}$: 544 nm; $\lambda_{em}$: 590 nm.

FIG. 26a) DNAzyme-1 triggering by target DNA (DNA-T). FIG. 26b) Selectivity of DNAzyme catalyzed reactions; fluorescence measurements taken 5 minutes following addition of respective DNAzymes. Columns left to right: 1) Signal from P-1 without DNAzyme. 2) P-1 mixed with DNAzyme-t. 3) P-1 mixed with DNAzyme-2. 4) P-2 (from copolymer with sequence, DNA-2) mixed with DNAzyme-2. 5) F-ssDNA mixed with DNAzyme-1. Conditions: Particle DNA (1 μM), DNAzyme (5 nM). DNA-Inh (5 nM). Buffer: Tris (20 mM, pH 7.4), MgCl$_2$ (50 mM), room temp.

Figure 1:
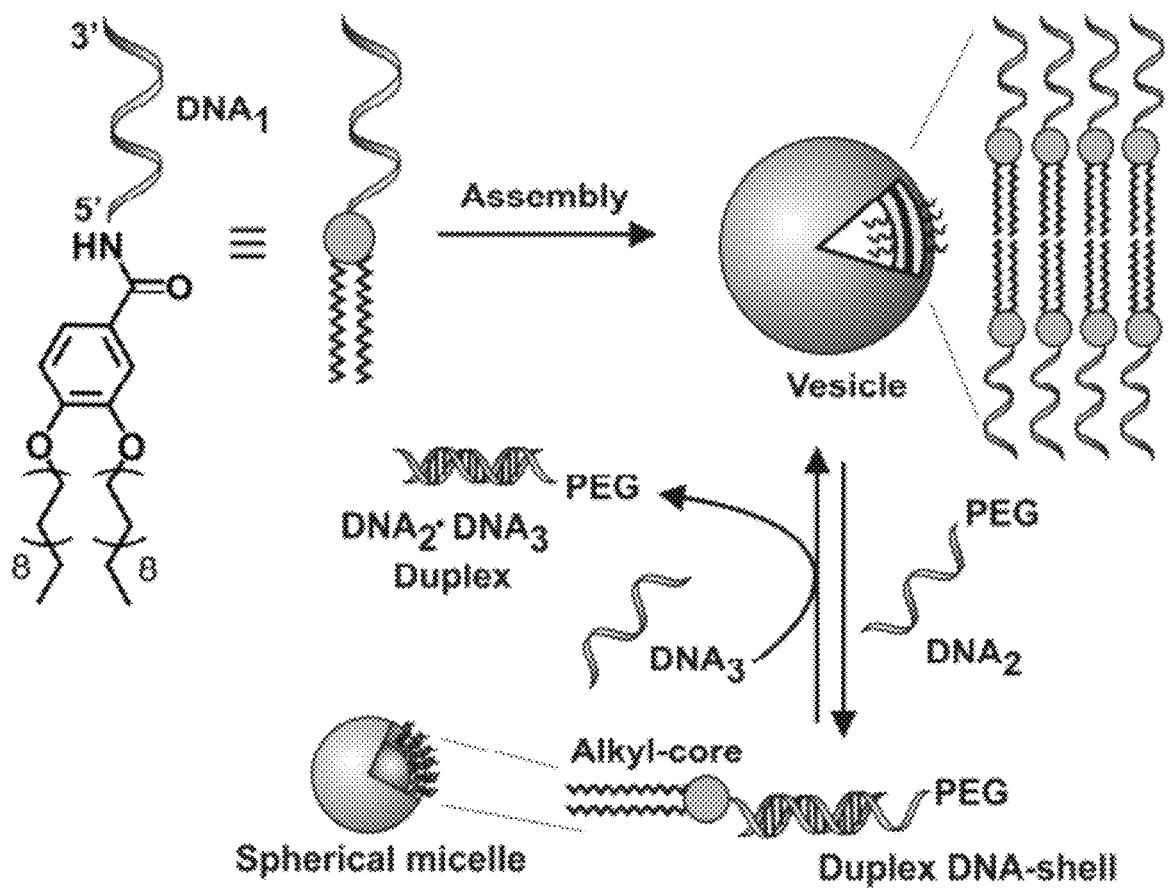
FIG. 1 depicts DNA-programmed lipid phase transitions. DNA-programmed lipid assembles to form spherical lamellar vesicles capable of switching phase to form small spherical micelles in a fully reversible fashion via DNA hybridization (+DNA$_2$) and strand invasion (+DNA$_3$) cycles. Sequences: DNA$_2$ (SEQ ID NO:1); DNA$_3$ (SEQ ID NO:2).
Figure 2A:
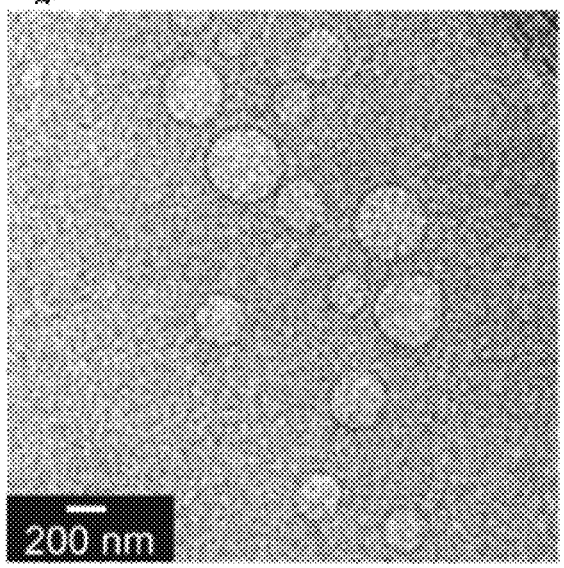
FIGS. 2A-2F depict characterization of unilamellar vesicle structures formed from the self-assembly of DNA$_1$-lipid in aqueous solution.
Figure 2B:
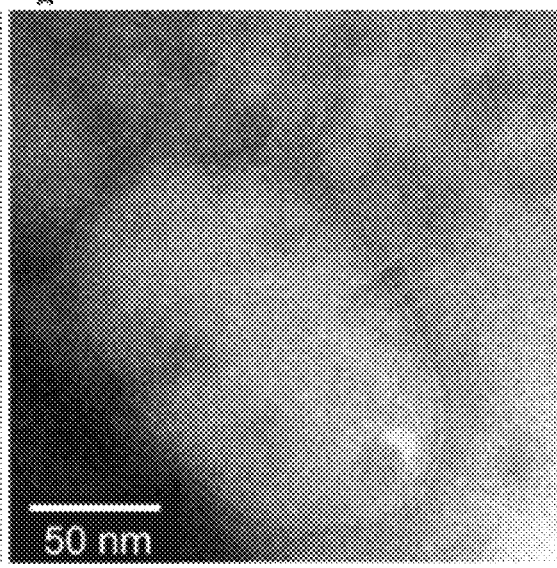
Figure 2C:
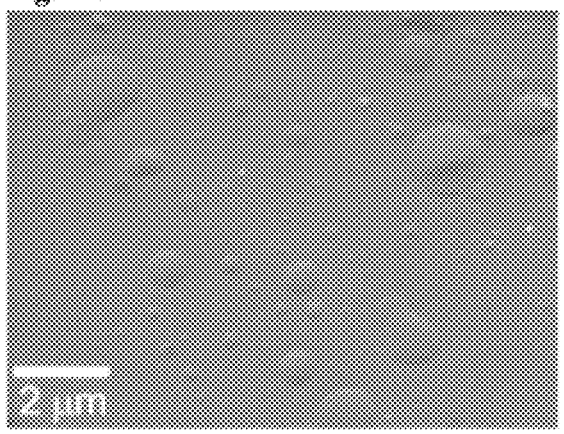
Figure 2D:
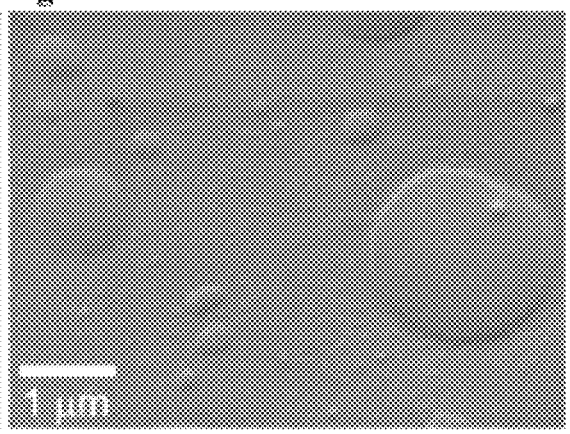
Figure 2E:
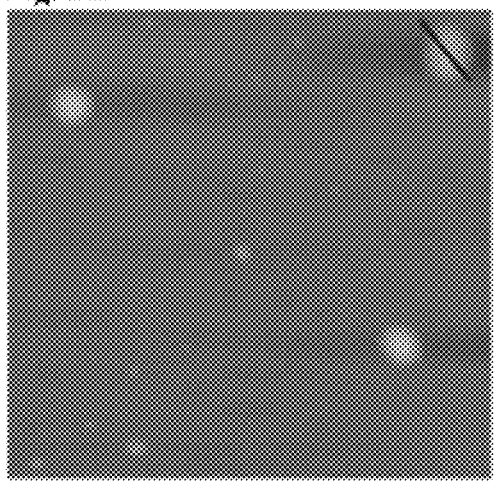
Figure 2F:
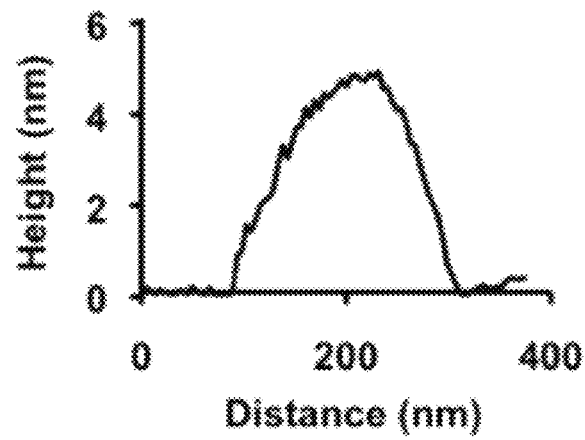

```
DNAzyme-2:
                                         (SEQ ID NO: 30)
5'-AACACACACTCCGAGCCGGTCGAAAGCTTTCTGAT-3';

DNA-2:
                                         (SEQ ID NO: 31)
5'-ATCAGAAAGCTrAGGTGTGTGTT-3'-PEG-Fluorescein.
```

DEFINITIONS

As used herein, the term "micelle," unless specifically stated herein, has its ordinary and accustomed meaning as understood by one of ordinary skill in the art as a noncovalently associated collection (aggregate) of molecules having a hydrophobic portion and a hydrophilic portion (i.e. amphiphilic) wherein the hydrophilic portions of the molecules are aligned to increase contact with a polar solvent (e.g. an aqueous solvent) and the hydrophobic portions are aligned to decrease contact with a polar solvent and/or increase contact amongst the hydrophobic portions.

As used herein, the term "morphology" refers to the form, structure and/or configuration of a micelle provided herein. In some embodiments, morphology refers to the tree dimensional configuration (i.e. shape) of the micelle. The micelles provided herein may assume any shape or conformation known for micelle structures including spheres, lamellars, rods (e.g. cylinder, fiber, etc.) and toroids, and networks. A person having ordinary skill in the art will immediately understand that the term "sphere" in reference to the shape of a micelle refers to a sphere-like shape and not necessarily a perfect geometrical sphere since micelles are typically not completely rigid. Likewise, "lamellar" in reference to a micelle shape means an approximately planar-like structure. The term "rod" in reference to a micelle means a rod-like structure, such as cylinder (or cylinder like structure), fiber (or fiber like structure) or any type of elongated spherical structure. The meaning of these terms are further supported by the examples provided herein and the common knowledge in the art with respect to micelle structure, shape and conformation. The term "network" refers to a specific micelle morphology wherein a group of micelle that interconnect.

As used herein, a "polymer" is a compound that includes a plurality of covalently linked monomers. A polymer can be made from one type of monomer or more than one type of monomer (e.g. a plurality of different monomers). The term "polymer" therefore encompasses copolymers. A polymer can be linear or branched.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

The term "complementary" refers to the natural hydrogen bonding by base pairing between purines and pyrimidines. For example, the sequence A-C-G-T (5'→3') forms hydrogen bonds with its complements A-C-G-T (5'→3') or A-C-G-U (5'→3'). Two single-stranded molecules may be considered partially complementary, if only some of the nucleotides bond, or "completely complementary" if all of the nucleotides bond. The degree of complementarity between nucleic acid strands affects the efficiency and strength of hybridization and amplification reactions. "Fully complementary" refers to the case where bonding occurs between every base pair and its complement in a pair of sequences, and the two sequences have the same number of nucleotides.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 0.41(\% \text{ G+C})$, when a nucleic acid is in aqueous solution at 1 M NaCl (see e.g., Anderson and Young, Quantitative Filter Hybridization, in Nucleic Acid Hybridization (1985). Other references include more sophisticated computations which take structural as well as sequence characteristics into account for the calculation of $T_m$.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., John Wiley & Sons.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$—$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of suitable antibodies of the invention and for use according to the invention, e.g., recombinant, monoclonal, or polyclonal antibodies, many techniques known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121: 210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al.,

*Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

As used herein, a "competitor nucleic acid" refers to a nucleic acid that competitively binds to a reference nucleic acid. A competitor DNA is a competitor nucleic acid wherein the nucleic acid is DNA. In some embodiments, the competitor DNA is a single strand nucleic acid. The single strand competitor nucleic acid, upon contacting a reference double strand nucleic acid, competitively binds to one strand of the reference double strand nucleic acid thereby displacing the other strand of the reference double strand nucleic acid.

As used herein, a "peptide competitor" refers to a peptide that competitively binds to a reference binding partner (such as an antibody, a receptor).

As used herein, the term "enzyme" is a biochemical catalyst and includes nucleic acid (e.g. ribozymes and DNAzymes) and peptide (e.g. protein) enzymes. Enzymes capable of catalyzing the hydrolytic cleavage of particular polymers (e.g. nucleic acid or peptides) or specific chemical bonds are of particular interest for this specific application.

As used herein, a "polysaccharide" is a polymer of sugars. The terms "polysaccharide", "carbohydrate", and "oligosaccharide", may be used interchangeably. The polymer may include natural sugars (e.g., glucose, fructose, galactose, mannose, arabinose, ribose, and xylose) and/or modified sugars (e.g., 2'-fluororibose, 2'-deoxyribose, and hexose). "Saccharide": As used herein, the term "saccharide" refers to monomers of sugars. A saccharide can be a natural sugar (e.g., glucose, fructose, galactose, mannose, arabinose, ribose, and xylose) or a modified sugar (e.g., 2'-fluororibose, 2'-deoxyribose, hexose, etc.).

As used herein, the term "drug" refers to small molecules or biomolecules that alter, inhibit, activate, or otherwise affect biological or chemical events, including drug moieties and prodrugs. For example, drugs may include, but are not limited to, anti-AIDS substances, anti-cancer substances, antibiotics, anti-diabetic substances, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, pyretics, steroidal and non-steroidal anti-inflammatory agents, anti-angiogenic factors, anti-secretory factors, anticoagulants and/or anti-thrombotic agents, local anesthetics, ophthalmics, prostaglandins, anti-depressants, anti-psychotic substances, anti-emetics, and imaging agents. A more complete listing of exemplary drugs suitable for use in the present invention may be found in "Pharmaceutical Substances: Syntheses, Patents, Applications" by Axel Kleemann and Jurgen Engel, Thieme Medical Publishing, 2001; the "Merck Index: An Encyclopedia of Chemicals, Drugs, and Biologicals", edited by Susan Budavari et al., CRC Press, 2006, and the United States Pharmacopeia/National Formulary, published by the United States Pharmcopeial Convention, Inc., Rockville Md., 2009. As used herein, the term "small molecule" refers to molecules, whether naturally-occurring or artificially created (e.g., via chemical synthesis), that have a relatively low molecular weight. Typically, small molecules are monomeric and have a molecular weight of less than about 1500 g/mol. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the FDA under 21 C.F.R. §§500 through 589, incorporated herein by reference, are all considered acceptable for use in accordance with the present invention. In some embodiments, the drug is a prodrug or prodrug moiety. Prodrugs are capable of undergoing chemical changes under physiological conditions to provide the corresponding drug.

The term "high conductivity metal" has its ordinary meaning in the art and refers to metals capable of conducting electricity with low resistivity. Examples of high conductivity metals include, but are not limited to, gold, silver, copper, aluminum and nickel.

As used herein, the term "crystalline," when used to describe a component or product, means that the component or product is crystalline as determined by x-ray diffraction. See, e.g., Remington's Pharmaceutical Sciences, 18.sup.th ed. page 173; The United States Pharmacopeia, 23.sup.rd ed, (1995) pages 1843-1844. As used herein, the term "amorphous" means that the component or product in question is not crystalline as determined by x-ray diffraction.

The terms "hydrophobic" and "hydrophilic" are used herein according to their plain ordinary meaning. Hydrophobic generally refers to materials that are insoluble, sparingly soluble or poorly soluble in water. Hydrophilic generally refers to materials that are soluble or highly soluble in water. For example, a "hydrophobic moiety" or "hydrophobic portion" provided herein is sufficiently insoluble, sparingly soluble or poorly soluble in water and a "hydrophilic moiety" or a "hydrophilic moiety" is sufficiently soluble in water such that a plurality of the amphiphilic molecules or the brush copolymers provided herein are capable of forming a micelle in a polar solvent (e.g. an aqueous solvent such as water or within the cells or tissue of a mammalian). In some embodiments, poorly soluble in water refers to solubility below 1 mg/ml. In some embodiments, sparingly soluble in water refers to solubility below 5 mg/ml. In some embodiments, highly soluble in water refers to solubility greater the 50 mg/ml. In some embodiments, soluble in water refers to solubility above 5 mg/ml.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—O—CH$_3$, —O—CH$_3$, —O—CH$_2$—CH$_3$, and —CN. Up to two heteroatoms may be consecutive, such as, for example, —CH$_2$—NH—OCH$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above; heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl; and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo," as used herein, means an oxygen that is double bonded to a carbon atom.

The term "alkylsulfonyl," as used herein, means a moiety having the formula —S(O$_2$)—R', where R' is an alkyl group as defined above. R' may have a specified number of carbons (e.g., "C$_1$-C$_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily. Found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

DETAILED DESCRIPTION OF THE INVENTION

Micelles

In one aspect, a micelle is provided that includes a plurality of aggregated brush copolymers having a hydrophilic portion and a hydrophobic portion. A "brush copolymer" is a copolymer including a hydrophilic portion and a hydrophobic portion. The hydrophilic portion includes a plurality of nucleic acid moieties or a plurality of peptide moieties covalently linked to a polymer within the brush copolymer. In some embodiments, the polymer forms a central backbone to which nucleic acid moieties or peptide moieties are covalently attached in the hydrophilic portion of the brush copolymer and to which one or more hydrophobic moieties are attached within the hydrophobic portion. Thus, in some embodiments, the brush copolymer includes a central backbone polymer to which a plurality of nucleic acid moieties or a plurality of peptide moieties are covalently attached within the hydrophilic portion and at least one hydrophobic moiety is attached within the hydrophobic portion. In some embodiments, the central backbone polymer is a branched polymer. For example, the central backbone polymer may form an axis that is roughly perpendicular to the nucleic acid or peptides moieties. The nucleic acid or peptide moieties may, therefore, extend out from the central backbone polymer to form a brush-like structure in the hydrophilic portion. The nucleic acids and peptides may be attached to the polymer at different positions along the axis of the polymer (e.g. differential axial spacing). In some embodiments, the central backbone polymer include no more than 1000 monomer units, 500 monomer units, 250 monomer units, 100 monomer units, 50 monomer units, 25 monomer units, or 10 monomer units.

In some embodiments, the brush copolymer has a general structure of W—(HB)$_a$-L-(HL)$_b$-Y. HB is a hydrophobic portion monomer HL is a hydrophilic portion monomer. W and Y are hydrogen or a brush copolymer end moiety wherein W and Y are optionally different. The brush copolymer end moieties may be any appropriate polymer cap (as set forth herein), including a monovalent hydrophobic or hydrophilic portion monomer. The symbol a is an integer from 1 to 1000, 1 to 100, 1 to 50, 1 to 25, 1 to 15, 1 to 10, 1 to 8, 1 to 6, 1 to 4, 1 to 2 or 1. The symbol b (in the context of a brush copolymer) is an integer, from 2 to 1000, 2 to 100, 2 to 50, 2 to 25, 2 to 15, 2 to 10, 2 to 8, 2 to 6, 2 to 4 or 2.

The symbol L represents a bond substituted or unsubstituted alkylene (e.g. $C_1$ to $C_{20}$ alkyelene such as a $C_1$ to $C_{10}$ alkylene), substituted or unsubstituted heteroalkylene (e.g. 2 to 20 membered heteroalkylene such as a 2 to 10 membered heteroalkylene), substituted or unsubstituted cycloalkylene (e.g. $C_3$ to $C_{10}$ cycloalkylene such as a $C_3$ to $C_6$), substituted or unsubstituted heterocycloalkylene (e.g. 3 to 10 membered heterocycloalkylene such as a 3 to 6 membered heterocycloalkylene), substituted or unsubstituted arylene, substituted or unsubstituted heteroarylene. Where the alkylene, heteroalkylene, cycloalkylene, heterocycloalkylene, arylene or heteroarylene is substituted, the substituent may be a substituent group, a size limited substituent group or a lower substituent group. In some embodiments, the alkylene, heteroalkylene, cycloalkylene, heterocycloalkylene, arylene and heteroarylene are unsubstituted.

The hydrophilic portion monomer is a nucleic acid moiety or peptide moiety bound to a monomer unit of the polymer (e.g. the central backbone polymer). Each nucleic acid moiety and peptide moiety include at least one nucleic acid sequence and at least one peptide sequence, respectively (i.e. at least two contiguous nucleotides or two contiguous amino acid, or in some embodiments about 3, 5, 10, 20, 30, 40, 50 or more contiguous nucleotides of amino acids). The nucleic acid moiety and peptide moiety may further include substituents bound to the respective nucleic acid sequence and peptide sequence. The substituents may include detectable moieties (e.g. fluorescent moieties, moieties useful in FRET techniques (FRET moieties), contrast agents) binding moieties, drug moieties (including prodrug moieties) and the like.

The hydrophobic portion of the brush copolymers may include (e.g. the hydrophobic moiety attached to the central backbone polymer may be or include) substituted or unsubstituted phenyl, a lipid moiety, polypropylene oxide, polyethylene, polypropylene, polycarbonate, polystyrene, polysulfone, polyphenylene oxide and polytetramethylene ether. Where a polymer is included in the hydrophobic moiety (e.g. where the hydrophobic moiety is a polymer) the polymer may be referred to herein as a "hydrophobic portion polymer" and may have a molecular weight of between 100-50,000 daltons, e.g., between 200-30,000 daltons or between 500-20,000 daltons. In some embodiment, the hydrophobic portion polymer is a linear polymer. In some embodiment, the hydrophobic portion polymer is a branched polymer (i.e. a branched hydrophobic portion polymer).

In some embodiments, the hydrophobic portion polymer is a lipid moiety. The lipid moiety may be any of the major classes of lipid, including fatty acyls, glycerolipids, glycerophospholipids, sphingolipids, sterol lipids, prenol lipids, saccharolipids and polyketides. Some important examples include a phospholipid, a glycolipid or cholesterol. The lipid moiety may be naturally occurring or synthetic. In some embodiments, the lipid is 3,4-di(octadecycloxy)benzoic acid. In some embodiments, the hydrophobic portion of the micelle includes two molecules of lipid (e.g., 3,4-di(octadecyloxy) benzoic acid) linked to one molecule of a single-strand nucleic acid according to methods provided herein. In some embodiments, lipid-nucleic acid conjugates assemble into a lipid bilayer vesicle.

In some embodiments, hydrophilic moiety is a labeled, single- or multi-stranded, natural or synthetic DNA or RNA, DNA or RNA oligonucleotides, or DNA/RNA hybrids. Conjugates of peptide nucleic acids (PNA) (Nielsen, et al. U.S. Pat. No. 5,539,082) may also be used. In some embodiments, the conjugated oligonucleotide moiety is an aptamer for a particular target molecule, such as a metabolite, dye, hapten, or protein. That is, the oligonucleotides have been selected to bind preferentially to the target molecule. Methods of preparing and screening aptamers for a given target molecule have been previously described and are known in the art (for example, U.S. Pat. No. 5,567,588 to Gold, 1996). In some embodiments, hydrophobic moiety of a nucleic acid brush copolymers (i.e. a brush copolymer having a nucleic acid moiety within the hydrophilic portion) is a lipid moiety. In some embodiments, hydrophobic moiety is not a lipid moiety.

The nucleic acid moiety may include any appropriate number of nucleotides. In some embodiments, the nucleic acid moiety is at least than 50, 40, 30, 20 or 10 nucleotides. In some embodiments, the nucleic acid is less than 10, 20, 30, 40 or 50 nucleotides. In some embodiments, the nucleic acid is about 2, 3, 4, 5, 10, 20, 30, 40 or 50 nucleotides.

In some embodiments, hydrophilic portion includes peptide moiety. The peptide moiety may include labeled or non-labeled, natural or synthetic peptides. In some embodiments, the peptides or polypeptides comprise at least one non-naturally encoded amino acid.

In some embodiments, hydrophobic moiety of peptide-brush copolymer (i.e. a brush copolymer having a peptide moiety within the hydrophilic portion) includes a lipid moiety. In some embodiments, hydrophobic moiety is not a lipid moiety.

The peptide moiety used in the conjugates can contain any number of amino acids. In some embodiments, the peptide moiety includes fewer than 50, 40, 30, 20, 10 or 5 amino acids. In some embodiments, the peptide moiety includes more than 5, 10, 20, 30, 40 or 50 amino acids. In some embodiments, the peptide moiety includes about 5, 10, 20, 30, 40 or 50 amino acids. Certain peptide moieties contain at least five amino acids, e.g. 5 to 40 amino acids. Appropriate peptides include, but are not limited to, neuropeptides, cytokines, toxins, protease substrates, and protein kinase substrates. Additional useful peptide moieties include those that serve as organelle localization peptides, that is, peptides that serve to target the conjugate for localization within a particular cellular substructure by cellular transport mechanisms. In some embodiments, the peptide moiety is a protein conjugate. Useful protein conjugates include enzymes, antibodies, lectins, glycoproteins, histones albumins, lipoproteins, avidin, streptavidin, protein A, protein G, phycobiliproteins and other fluorescent proteins, hormones, toxins and growth factors. Typically, the conjugated protein is an antibody, an antibody fragment, avidin, streptavidin, a toxin, a lectin, or a growth factor.

In some embodiments, the hydrophobic portion monomer (HB), and the hydrophilic portion monomer (HL) have the general structure of (R)—(R')$_n$, wherein R is a monomer of the polymer within the brush copolymer and R' is an attachment moiety. In some embodiments, at least one attachment moiety is a hydrophobic moiety in the hydrophobic portion and at least one attachment moiety is a nucleic acid moiety or peptide moiety in the hydrophilic portion. The symbol n is an integer from 1 to 10, 1 to 5, 1 to 4, 1 to 3, 2, or 1. Each attachment moiety is optionally different. The attachment moiety contains is attached to the monomer using reactive functional group pairs. For example, a nucleic acid may attached to the monomer using complementary reactive functional groups present on the nucleic acid to be attached and the monomer to which the nucleic acid is to be attached (see e.g. description below regarding functional groups for attachment of nucleic acid moieties and peptide moieties). R can be any suitable monomer that, when polymerized, forms a polymer within the brush copolymer. R' may be any suitable hydrophobic moiety where (R)—(R')$_n$ is HB. R' may be any suitable hydrophilic moiety where (R)—(R')$_n$ is HL, wherein at least one of R' is a nucleic acid moiety or a peptide moiety. In some embodiments, R is a substituted or unsubstituted cycloalkyelene, substituted or unsubstituted heterocycloalkylene, substituted or unsubstituted heteroarylene, substituted or unsubstituted arylene. In some embodiments, R is a five- or six-membered ring. In some embodiments, (R)—(R')$_n$ has the formula:

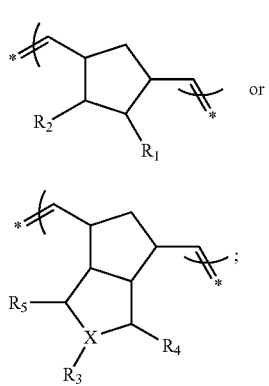

wherein $R_1$, $R_2$, $R_3$, and $R_5$ (corresponding to R') are independently oxo hydrogen, halogen, —CN, —CF$_3$, —NO$_2$, —OH, —SH, a lipid moiety, substituted or unsubstituted alkyl (e.g. substituted or unsubstituted $C_1$ to $C_{20}$ alkyl), substituted or unsubstituted heteroalkyl (e.g. substituted or unsubstituted 2 to 20 membered heteroalkyl), substituted or unsubstituted cycloalkyl (e.g. $C_3$ to $C_{14}$ cycloalkyl including fused ring structures), substituted or unsubstituted heterocycloalkyl (e.g. 3 to 14 membered heterocycloalkyl including fused-ring structures), substituted or unsubstituted aryl (e.g. a $C_6$ to $C_{14}$ aryl including fused ring structures), substituted or unsubstituted heteroaryl (e.g. 5 to 14 membered heteroaryl including fused rings structures), a peptide moiety or nucleic acid moiety. X is —N or —CH. Furthermore, where (R)—(R')$_n$ is a hydrophobic monomer, at least one of $R_1$, $R_2$, $R_3$, and $R_5$ are a hydrophobic moiety and none of $R_1$, $R_2$, $R_3$, and $R_5$ are a hydrophilic moiety (i.e. are not a nucleic acid moiety or a peptide moiety). Likewise, where (R)—(R')$_n$ is a hydrophilic monomer, at least one of $R_1$, $R_2$, $R_3$, and $R_5$ are a nucleic acid moiety or a peptide moiety and none of $R_1$, $R_2$, $R_3$, and $R_5$ is a hydrophobic moiety.

In some embodiments, each substituted group described above in the compounds of Formulae (I) to (II) is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described above in the compounds of Formulae (I) to (IV) are substituted with at least one substituent group. In other embodiments, at least one or all of these groups are substituted with at least one size-limited substituent group. Alternatively, at least one or all of these groups are substituted with at least one lower substituent group.

In other embodiments of the compounds of Formulae (I) to (II), each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and/or each substituted or unsubstituted heterocycloalkyl is a substituted or unsubstituted 3 to 8 membered heterocycloalkyl. In some embodiments of the compounds of Formulae (I) to (II), each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and/or each substituted or unsubstituted heterocycloalkyl is a substituted or unsubstituted 5 to 7 membered heterocycloalkyl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_5$-$C_7$ cycloalkylene, and/or each substituted or unsubstituted heterocycloalkylene is a substituted or unsubstituted 5 to 7 membered heterocycloalkylene. In some embodiments, the brush copolymer of amphiphilic molecules is a chemical species set forth in the Examples section below.

In some embodiments, the nucleic acid moiety or the peptide moiety contains a cleavage site for a hydrophilic portion enzyme. The hydrophilic portion enzyme is an enzyme capable of recognizing a cleavage site within the nucleic acid moiety or the peptide moiety and cleaving the nucleic acid moiety or the peptide moiety. In some embodiments, where the brush copolymer includes a nucleic acid moiety the hydrophilic portion enzyme is a nucleic acid enzyme, such as ribozyme or a DNAzyme. In some embodiments, the nucleic acid enzyme is a DNAzyme. In some embodiments, the hydrophilic portion enzyme is protein enzyme. Where the brush copolymer includes a nucleic acid moiety, the protein enzyme may be an endonuclease or an exonuclease. Where the brush copolymer includes a peptide moiety, the protein enzyme may be a peptidase or protease, such as a matrix metalloproteinases (MMP).

In some embodiments, the micelle changes morphology upon contacting the brush copolymer with a stimulus. In some embodiments, the stimulus is a temperature change (e.g. in the environment in which the micelle is present). For example, where the nucleic acid moiety or the peptide moiety are noncovalently bound to a nucleic acid binder or a peptide binder, respectively, an increase in temperature may disrupt the noncovalent interaction thereby changing the physical characteristics of the hydrophilic portion of the brush copolymer thereby leading to a change in morphology of the micelle. Conversely, a decrease in temperature may lead to the formation of covalent binder between the nucleic acid moiety or the peptide moiety and the nucleic acid binder or the peptide binder. Nucleic acid binders and peptide binders are well known in the art and may be nucleic acids, proteins, aptamers, antibodies and the like (as described more fully below). In another example, where the nucleic acid moiety of the peptide moiety assume a secondary or tertiary structure, an increase in temperature may disrupt the secondary or tertiary structure thereby changing the physical characteristics of the hydrophilic portion of the brush copolymer thereby leading to a change in morphology of the micelle. Conversely, a decrease in temperature may lead to the formation of secondary structure thereby changing the physical characteristics of the hydrophilic portion of the brush copolymer thereby leading to a change in morphology of the micelle.

In other embodiments, the stimulus is a pH change. As with temperature, changes n pH may lead to the disruption or formation of bonding interactions with nucleic acid binders or peptide binders thereby changing the physical characteristics of the hydrophilic portion of the brush copolymer thereby leading to a change in morphology of the micelle. Change in pH may also lead to disruption or formation of secondary or tertiary structures in the nucleic acid moiety or peptide moiety thereby changing the physical characteristics of the hydrophilic portion of the brush copolymer thereby leading to a change in morphology of the micelle.

In other embodiments, the stimulus is a hydrophilic portion binder. A hydrophilic portion binder is a peptide binder or a nucleic acid binder capable of binding to some portion of the peptide moiety or the nucleic acid moiety thereby changing the physical characteristics of the hydrophilic portion of the brush copolymer thereby leading to a change in morphology of the micelle. In some embodiments, the hydrophilic portion binder is a single strand nucleic acid such as a DNA or RNA. The single stranded nucleic acid may be capable of hybridizing to the nucleic acid moiety under stringent hybridization conditions or moderately stringent hybridization conditions. The hydrophilic portion binder may also be a double strand DNA-binding protein, or an antibody (e.g. an antibody fragment).

In some embodiments, the stimulus is a hydrophilic portion enzyme as described herein.

The micelles provided herein may further include one or more drugs (including drug moieties, prodrugs and/or prodrug moiety). In some embodiments, the drug is covalently attached to the brush copolymers. For example, the drug may be covalently attached to the hydrophilic moiety, nucleic acid moiety or peptide moiety such that, upon a morphology change in the micelle, the drug is exposed to solvent thereby allowing the drug to performs its biological function. The drug may be attached to the hydrophilic moiety, nucleic acid moiety or peptide moiety using a linker that is cleavable upon exposure to the solvent or components within the solvent such as enzymes (e.g. esterases, peptidases, etc.). In some embodiments, the drug is non-covalently bound to the brush copolymers, e.g. by electrostatic interaction, van der waals interaction, or hydrophobic forces thereby retaining the drug within the micelle. Upon a conformational change of the micelle (e.g. due to application or contact with a stimulus as described below), the drug may be released into the surrounding solvent. Thus, where a drug is contained within a micelle, the drug may be releasable upon contacting the micelle (e.g. brush copolymers) with a stimulus (as discussed herein). Typically, the covalently attached drug molecules is releasable in the presence of a drug-releasing enzyme. Thus, in some embodiments, the micelle is a drug delivery vehicle or a pharmaceutical composition. As detailed in the examples, in some embodiments, a drug is releasable upon a morphology change of the micelle, e.g., from rods to spheres. As demonstrated in the Examples using a small molecule dye, morphology transition of the micelle can be utilized for the uptake and release of drug molecules. For example, the brush copolymers can be designed to have drug molecules bound within the hydrophobic portion or hydrophilic portion. In some embodiments, the drug molecules non-covalently attach to hydrophobic portion polymers when the micelle has a rod-shaped structure. When the micelle undergoes morphology change to a sphere-shaped structure, the drug molecules are released from hydrophobic portion polymers. In some embodiments, a drug is releasable upon morphology change of the micelle in response to a temperature change or a pH change. The morphology of a micelle can be altered by a temperature change or a pH change in the micelle and/or in the micelle environment such as the solvent or tissue in which the micelle is in. Accordingly, the drug molecules can be designed to be target certain diseased cells or tissues having an abnormal pH or temperature range. Therefore, in some embodiments, the drug-containing micelles do not release the drug molecule in normal tissues or cells. The same drug-containing micelles, however, undergo morphology changes in response to particular pH or temperature ranges in diseased tissues or cells. Accompanying the morphology change, the drug molecules contained in the micelles are released. The micelle can be designed so that the attached drugs are releasable upon morphology change of the micelle in response to a disease activity associated with a disease state, e.g., high protease abundance. In some embodiments, the disease is a cancer. The micelle can be used for targeted cancer treatment. In some embodiments, the stimulus is a drug-releasing enzyme. For example, the drug is covalently bound to the brush copolymer via a covalent bond. The drug molecule can be attached to hydrophobic or hydrophilic portion polymers. In some embodiments, the drug is covalently attached to the brush copolymer via a ester bond. Accordingly, the drug-releasing enzyme is an esterase. Other releasable linker and other drug-releasing enzymes are well known in the art, and can be used in combination with the present invention.

As discussed above, in some embodiments the micelle further comprises a detectable moiety such as a fluorogenic tag or a contrast agent In some embodiments, relaxivity of the contrast agent (e.g. for use in medical imaging) is altered upon contacting the brush copolymer with a stimulus as described above.

The contrast agents may be any type of contrast agent known to one of skill in the art. The most common contrast agents basically fall into one of four groups; X-ray reagents, radiography reagents, magnetic resonance imaging agents, quantum dots, contrast agent nanoparticles, and ultrasound agents. The X-ray reagents include ionic, iodine-containing reagents as well as non-ionic agents such as Omnipaque® (Nycomed) and Ultravist® (Schering). Radiographic agents include radioisotopes as disclosed below. Magnetic Resonance Imaging reagents include magnetic agents such a Gadolinium and iron-oxide chelates. Ultrasound agents include microbubbles of gas and a number of bubble-releasing formulations. The radionuclides may be diagnostic or therapeutic. Examples of radionuclides that are generally medically useful include: Y, Ln, Cu, Lu, Tc, Re, Co, Fe and the like such as $^{90}$Y, $^{111}$Ln, $^{67}$Cu, $^{77}$Lu, $^{99}$Tc and the like. Radionuclides that are suitable for imaging organs and tissues in vivo via diagnostic gamma scintillation photometry include the following: .gamma.-emitting radionuclides: $^{111}$Ln, $^{113m}$Ln, $^{67}$Ga, $^{68}$Ga, $^{99m}$Tc, $^{51}$Cr, $^{197}$Hg, $^{203}$Hg, $^{169}$Yb, $^{85}$Sr, and $^{87}$Sr. The preparation of chelated radionuclides that are suitable for binding by Fab' fragments is taught in U.S. Pat. No. 4,658,839 (Nicoletti et al.). Paramagnetic metal ions, suitable for use as imaging agents in MRI include the lanthanide elements of atomic number 57-70, or the transition metals of atomic numbers 21-29, 42 or 44. U.S. Pat. No.

4,647,447 (Gies et al.) including MRI imaging via chelated paramagnetic metal ions and is incorporated herein by reference.

In some embodiments, examples of contrast agents suitable for use in combination with the brush copolymer provided herein include contrast agents for enhanced visualization in vivo using magnetic resonance imaging (MRI), or derivative technologies thereof. Such contrast agents may include, but are not limited to, agents that include tantalum, gadolinium, samarium, and other agents that are known to the art. Examples of MRI contrast agents include, but are not limited to, ferric chloride, ferric ammonium citrate, gadolinium-DTPA (Gd-DTPA) with and without mannitol, Gd-DOTA, Gd-EDTA, $GdCl_3$, Gadodiamide, Gadoteridol, gadopentetate dimeglumine, Cr(III) agents, Mn(III)TPPS4 (manganese(III) tetra-[4-sulfanatophenyl]porphyrin), Fe(III) TPPS4, manganese dichloride, Fe-EHPG (iron(III) ethylenebis-(2-hydroxyphenylglycine)), $^{99}$mTc-iminodiacetate (Tc-IDA), chromium diethyl HIDA meglumine (Cr-HIDA), Gd-BOPTA (gadobenate dimeglumine), manganese(II)-dipyridoxal diphosphate (Mn-DPDP), gadolinium oxide, superparamagnetic iron oxides (SPIO, also "small particle iron oxides"), ultrasmall supermagnetic particle iron oxides (USPIO, also "ultrasmall particle iron oxides"), and the like. One aspect of the present invention affords a method of reducing the toxicity of various agents such as contrast agents like Fe(III) TPPS4, by containing the agent within the hydrogel core of the microspheres disclosed herein. Additional examples of radiopaque materials, MRI-visible materials, ferromagnetic materials, and contrast agents are described, for example, in Rioux et al., U.S. Patent Application Publication No. US 2004/0101564 A1, published on May 27, 2004, and entitled "Embolization", which is incorporated herein by reference.

In some embodiments, examples of contrast agents suitable for use in combination with the brush copolymer provided herein further include contrast agents for conventional radiographic imaging with radio-opaque agents such as cesium, iodine, or ionic or nonionic iodine-containing compounds may be used in combination with the brush copolymers provided herein. Examples of iodine contrast agents include both ionic and non-ionic agents, including, but not limited to, Diatrizoate, Metrizoate, Ioxaglate, Iopamidol, Iohexyl, Ioxilan, Iopromide, Iodixanol, Ioxitalamin, and the like. Generally, the term "radio-opaque" agent refers to any substance or agent which blocks, absorbs, scatters, or reflects any radiation outside the visible light spectrum, including, but not limited to, X-rays (in the wavelength range of 0.01 to 10 nm), beta rays (having, for example, velocities of about 35,000 to 180,000 miles per second), gamma rays (having an energy in the range of $10^4$ to $10^7$ eV), radiation used in radiation therapy (for example, therapy to treat cancer), and other harmful radiation (such as that resulting from nuclear disasters and nuclear weapons). Suitable radio-opaque agents include, but are not limited to, those comprising platinum, gold, silver, bismuth, mercury, lead, barium, calcium, zinc, aluminum, iron, gallium, iodine, tungsten, and any combination thereof. Other suitable radio-opaque agents include, but are not limited to, those commercially available as radio-opaque agents for medical uses, such as ionic and nonionic intravenous radiocontrast agents, diagnostic barium and gastrographin preparations, and gallium preparations. In one embodiment, the radio-opaque agent blocks, absorbs, scatters, or reflects any radiation outside the visible light spectrum, including, but not limited to, X-rays, beta rays, and gamma rays, which are emitted from radioisotopes, such as those used in the medical industry (for example, in radiation therapy and medical diagnostic testing). Examples of radio-isotopes in clinical use include, but are not limited to, radio-isotopes of gallium (for example, $^{67}$Ga or $^{68}$Ga), iodine (for example, $^{123}$I, $^{126}$I, $^{131}$I, $^{132}$I, or $^{133}$I), indium (for example, $^{111}$In or $^{113}$In), thallium (for example, $^{201}$Tl or $^{203}$Tl), as well as $^{3}$H, $^{11}$C, $^{14}$C, $^{13}$N, $^{18}$F, $^{22}$Na, $^{24}$Na, $^{31}$Si, $^{32}$P, $^{35}$S, $^{36}$Cl, $^{38}$Cl, $^{42}$K, $^{45}$Ca, $^{51}$Cr, $^{52}$Mn, $^{54}$Mn, $^{55}$Fe, $^{59}$Fe, $^{a}$Co, $^{63}$Zn, $^{65}$Zn, 68Zn, $^{82}$Br, $^{85}$K, $^{85}$Kr, $^{89}$Sr, $^{99}$Tc, $^{99}$mTc, $^{99}$mRe, $^{101}$Re, $^{105}$Re, $^{121}$mTe, $^{122}$mTe, $^{125}$mRe, $^{137}$Cs, $^{165}$Tm, $^{167}$Tm, $^{168}$Tm, $^{81}$mKr, $^{33}$Xe, $^{90}$Y, $^{213}$Bi, $^{77}$Br, $^{18}$F, $^{95}$Ru, $^{97}$Ru, $^{103}$Ru, $^{105}$Ru, $^{107}$Hg, $^{203}$Hg, $^{182}$Ta, $^{192}$Ir, $^{198}$Au, and the like.

Examples of fluorogenic tags include, without limitation, 2,4-dinitrofluorobenzene, "pipsyl" derivatives, 4-methylumbelliferone, orthonitrophenyl, para-nitrophenyl, para-nitroanilide, 4-methoxy-J-naphthylamide, 7-amido-4-chloro-3-indoxyl, and formazan, ATTO-TAG CBQCA (3-(4-carboxybenzoyl)quinoline-2-carboxaldehyde or CBQCA) and ATTO-TAG FQ (3-(2-furoyl)quinoline-2-carboxaldehyde) (Molecular Probes, Eugene, Oreg.), and the like. See, for example, website probes.invitrogen.com/media/pis/mp02333.pdf (retrieved on Nov. 11, 2005) for additional information on these dyes.

Thus, the micelle further comprises a contrast agent and/or a fluorogenic tag. The contrast agent and/or the fluorogenic tag can be covalently or non-covalently attached to the brush copolymers, e.g. by electrostatic interaction, van der waals interaction, or hydrophobic forces. Various micelle containing a contrast agent and/or a fluorogenic tag can be made as described in herein. Various methods of altering morphology of the micelle can be used as described herein. For example, the morphology of the micelle can be altered by subjecting said micelle to a stimulus (as described herein such as a temperature change, a pH change, a hydrophilic portion binder, or a hydrophilic portion enzyme) thereby altering the morphology of the micelle, as described herein.

In some embodiments, relaxivity of the contrast agent is altered upon a morphology change in the micelle in response to a stimulus. For example, in some embodiments, the contrast agent is attached to the hydrophobic portion polymer. Therefore, the contrast agent is buried inside a sphere-shaped structure. In this case, relaxivity of the contrast agent increases upon a morphology change from spheres to fibers, e.g., with increased access to water in the environment and increased water exchange rates. Consequently, signal intensity of the contrast agent increases.

In some embodiments, the contrast agent is attached to the hydrophilic portion polymer. Therefore, the contrast agent is placed in the shell of a sphere-shaped structure. In this case, the relaxivity increases concomitant with a slowing in the tumbling rate of the material to which the chelate is attached. Similarly, relaxivity of the contrast agent changes upon a morphology change.

In some embodiments, relaxivity of the contrast agent is altered upon morphology change of the micelle in response to a temperature change or a pH change. The morphology of a micelle can be altered by a temperature change or a pH change in the micelle and/or in the micelle environment such as the solvent or tissue in which the micelle is in. Accordingly, the micelle can be designed to be detect certain diseased cells or tissues or otherwise linked to the activity associated with certain diseases, e.g., an abnormal pH or temperature range.

The micelle can be designed to detect other activities associated with a disease state, e.g., high protease abundance. In this case, the micelle undergoes morphology changes in response to the disease states/activities, thereby detecting the disease state by detecting a change in relaxivity of the contrast agent.

In some embodiments, when employing a DNAzyme to cleave the nucleic acid moiety, the hydrophilic portion of the micelle comprises a sufficient number and/or density of nucleic acid moieties such that the turnover of the DNAzyme is increased relative to the turnover of the DNAzyme when cleaving a solution phase nucleic acid. This property may be exploited by using the micelle in detection assays wherein the nucleic acid moiety includes a DNAzyme cleavage site and a detectable label, wherein the cleavage of the nucleic acid moiety by the DNAzyme results in release of a nucleic acid fragment having a detectable label. Detection of the release detectable label indicates the presence of the micelles and/or the DNAzyme. In some embodiments, the micelle is attached to a target to be detected. This embodiment is further set forth in the examples below.

Methods of Altering Morphology

In another aspect, provided herein are methods of altering a morphology of a micelle. The micelle includes a plurality of aggregated amphiphilic molecules. The method includes subjecting the micelle to a stimulus (e.g. contacting the micelle with a hydrophilic portion binder or a hydrophilic portion enzyme or subjecting the micelle to a change in temperature or pH), wherein the stimulus is a temperature change, a pH change, a hydrophilic portion binder, or a hydrophilic portion enzyme (as discussed above) thereby altering the morphology of the micelle. An "amphiphilic molecule" is a molecule including a hydrophilic portion and a hydrophobic portion, wherein the hydrophilic portion includes at least one nucleic acid moiety or peptide moieties covalently linked to a polymer within the amphiphilic molecules. In some embodiments, the amphiphilic molecule is a brush copolymer. In other embodiments, the amphiphilic molecule is a modified brush copolymer referred to herein as an "amphiphilic copolymer." An amphiphilic copolymer has all of the elements of the brush copolymer described above except the hydrophilic potion may include only one nucleic acid moiety or only one peptide moiety (e.g. the symbol b is 1). In other embodiments, the amphiphilic molecule is a primary amphiphilic molecule. A primary amphiphilic molecule is a hydrophobic moiety covalently bound (directly of through a linker) to a hydrophobic moiety. Thus, the primary amphiphilic molecule may have the formula HPM-L-HLM, wherein L is a linker (as described above), HPM is a hydrophobic moiety (as discussed above) and HLM is a hydrophilic moiety (as discussed above). Therefore, in some embodiments, the amphiphilic molecule is a primary amphiphilic molecule, a brush copolymer or an amphiphilic copolymer.

In some embodiments, the morphology of the micelle is altered (or changes) from a sphere to a rod upon subjecting the micelle to a nucleic acid cleaving enzyme (e.g. a DNAzyme, exonuclease or endonuclease), wherein the hydrophilic portion includes a nucleic acid moiety. For example, where the nucleic acid cleaving enzyme is a DNAzyme, the nucleic acid is a single-stranded DNA. The nucleic acid cleaving enzyme (e.g. the DNAzyme, endonuclease or exonuclease) cleaves the nucleic acid upon contacting the micelle with the nucleic acid cleaving enzyme.

In some embodiments, the morphology of the micelle is altered from a rod to a sphere upon subjecting the micelle to a single-strand nucleic acid binder, wherein the hydrophilic portion is a single-strand nucleic acid moiety. The single-strand nucleic acid binder is capable of hybridizing to the single-strand nucleic acid moiety (e.g. under stringent hybridization conditions or moderately stringent hybridization conditions).

In some embodiments, the morphology of the micelle is altered from a sphere to a rod upon subjecting the micelle to a single-stranded nucleic acid competitor, wherein the hydrophilic portion is a double-strand nucleic acid moiety. The single-stranded nucleic acid competitor is capable of hybridizing to one strand of the double-stranded nucleic acid moiety (e.g. under stringent hybridization conditions or moderately stringent hybridization conditions). A person having ordinary skill will immediately understand that only one strand of the double-stranded nucleic acid moiety is covalently bound to the remainder of the amphiphilic molecule.

In some embodiments, the morphology of the micelle is altered from a sphere to a vesicle upon contacting the micelle with a kinase, wherein the hydrophilic portion includes a peptide moiety. The peptide moiety includes a substrate (e.g. cognizant amino acid sequence or amino acid) for the kinase. The kinase is capable of phosphorylating the substrate within the peptide moiety upon subjecting the micelle to the kinase.

In some embodiments, the morphology of the micelle is altered from a vesicle to a sphere upon contacting the micelle with a phosphatase, wherein the hydrophilic portion includes a peptide moiety. The peptide moiety includes a substrate (e.g. a cognizant phosphorylated amino acid or sequence including a phosphorylated amino acid). The phosphatase is capable of dephosphorylating the peptide moiety upon contacting the micelle with the phosphatase.

In some embodiments, the morphology of the micelle is altered from a sphere to a network upon contacting the micelle with a protease. The hydrophilic portion includes a peptide moiety including a substrate for the protease. The protease is capable of cleaving the substrate within the peptide moiety upon subjecting the micelle to the protease.

In some embodiments, the morphology of the micelle is altered from a vesicle to a sphere upon contacting the micelle with a single-strand nucleic acid binder. The hydrophilic portion includes a single-strand nucleic acid moiety. The single-strand nucleic acid binder is capable of hybridizing to the single-strand nucleic acid moiety. In some embodiments, the hydrophobic portion includes a lipid moiety.

In some embodiments, the morphology of the micelle is altered from a sphere to a vesicle upon contacting the micelle with a single-strand nucleic acid competitor. The hydrophilic portion is a double-strand nucleic acid moiety. The single-strand nucleic acid competitor is capable of hybridizing to one strand of the double-strand nucleic acid moiety. In some embodiments, the hydrophobic portion include a lipid moiety.

As described above, the micelles provided herein can be changed by a stimulus. For example, the compositions or structures of the hydrophilic portion can be altered by a hydrophilic portion binder capable of binding to some portion of a nucleic acid moiety (i.e. a nucleic acid binder) or a peptide moiety (i.e. a peptide binder). Various molecules that bind to the nucleic acid moieties of the hydrophilic portion can be used as hydrophilic portion binders. One example of hydrophilic portion binders is a single strand nucleic acid (e.g., DNA, RNA or PNA) that is complementary or partially complementary to the nucleic acid moieties contained in the hydrophilic portion. Upon the binding of the complementary or partially complementary single strand nucleic acid, and due to the base pairing between the single strand nucleic acid and the nucleic acid moieties contained in the hydrophilic portion, the volume of the hydrophilic portion of the micelle increases. The micelle is unable maintain the morphology and therefore a change in morphology occurs (e.g., a sphere to rod transition). As a result, the micelle adopts a different morphology, e.g., a sphere-shaped structure. Other morphologies can be adopted, e.g., by varying the length of the single strand nucleic acid. In some embodiments, the hydrophilic portion binder, e.g., the single strand nucleic acid is conjugated to a hydrophilic, non-nucleotide linker, e.g., a polyethylene glycol linker.

Other hydrophilic portion binders can be peptide-based or protein-based. For example, in some embodiments, the hydrophilic portion binder is a nucleic acid-binding protein, e.g., a single-strand nucleic acid binding protein, a double-strand nucleic acid binding protein. The nucleic acid binding proteins can be DNA-binding proteins, or RNA-binding proteins, depending on the nucleic acid moieties used in the hydrophilic portion. In addition, the nucleic acid binding proteins also include antibodies to nucleic acids, e.g., anti-DNA antibodies or anti-RNA antibodies.

As detailed herein, the morphology of the micelle may be altered from a rod to a sphere upon subjecting the micelle to a single-strand nucleic acid binder which binds to a single-strand nucleic acid hydrophilic portion. For example, the single-strand nucleic acid binder is capable of hybridizing to the single-strand nucleic acid hydrophilic portion. The single-strand nucleic acid binder and the single-strand nucleic acid hydrophilic portion can be DNA, RNA, PNA, or DNA/RNA hybrid. The process and degree of this hybridization can be controlled in a dose-dependent fashion, e.g., by controlling the amount of the single-strand nucleic acid binder. In some embodiments, the micelle is altered from a rod to a sphere when more than 25%, 50%, 75% of the nucleic acid moieties of the single-strand nucleic acid hydrophilic portion is hybridized by a single-strand nucleic acid binder.

As also detailed herein, the morphology of the micelle having a double-strand nucleic acid hydrophilic portion may be altered from a sphere to a rod upon subjecting the micelle to a single-strand nucleic acid competitor. The single-strand nucleic acid competitor is capable of hybridizing to one strand of the double-strand nucleic acid hydrophilic portion. When the single-strand nucleic acid competitor binds to the complementary or partially complementary strand of the double-strand nucleic acid hydrophilic portion, it dissociates this strand from the hydrophilic portion. The double-strand nucleic acid hydrophilic portion is left with a single-strand nucleic acid. As discussed herein, with this structure/composition change, the morphology of the micelle may correspondingly changes e.g., from a sphere to a rod. The process and degree of this dissociation can be controlled in a dose-dependent fashion, e.g., by controlling the amount of the single-strand nucleic acid competitor. In some embodiments, the micelle is altered from a rod to a sphere when more than 25%, 50%, 75% of the double-strand nucleic acid hydrophilic portion is converted into a single-strand nucleic acid hydrophilic portion.

The morphology of the micelle may therefore conveniently switch back and forth between two micelle structures upon application of the appropriate stimulus, e.g., between spheres and rods. In some embodiments, the morphology of the micelle can switch back and forth among several micelle structures, e.g., rods, spheres, vesicles, cylinders, toroids, and networks. For example, in some embodiments, the morphology of the micelle can switch back and forth between spheres and rods by the action of a single-strand nucleic acid binder and a single-strand nucleic acid competitor. As detailed in the examples, the morphology of a micelle having a single-strand nucleic acid hydrophilic portion is altered from a rod to a sphere upon subjecting the micelle to a single-strand nucleic acid binder. The morphology of the resulting micelle now having a double-strand nucleic acid hydrophilic portion can then be altered from a sphere to a rod upon subjecting the micelle to a single-strand nucleic acid competitor.

In some embodiments, the nucleic acid moieties of the hydrophilic portion can be attenuated by a hydrophilic portion enzyme, and thereby change the composition and the structure of the micelle. For example, in some embodiments, the hydrophilic portion enzyme is an enzyme that cleaves the nucleic acid moieties of the hydrophilic portion.

In some embodiments, the hydrophilic portion enzyme is a DNAzyme, which is an enzymatic nucleic acid molecule that does not require the presence of a 2'-OH group within it for its activity. In some embodiments, DNAzymes can have an attached linker(s) or other attached or associated groups, moieties, or chains containing one or more nucleotides with 2'-OH groups. DNAzymes can be synthesized chemically or expressed endogenously in vivo, by means of a single stranded DNA vector or equivalent thereof. Examples of DNAzymes are generally reviewed in Usman et al., International PCT Publication No. WO 95/11304; Chartrand et al., 1995, *NAR* 23:4092; Breaker et al., 1995, *Chem. Bio.* 2:655; Santoro et al., 1997, *PNAS* 94:4262; Breaker, 1999, *Nature Biotechnology*, 17:422-423; and Santoro et. al., 2000, *J. Am. Chem. Soc.*, 122:2433-39; Perrin et al., 2001, *JACS*, 123: 1556. Additional DNAzyme motifs can be selected for using techniques similar to those described in these references, and hence, are within the scope of the present invention.

In some embodiments, the hydrophilic portion enzyme is a nuclease, e.g., an endonuclease or an exonuclease. Examples of nucleases include: exonuclease I, exonuclease II, exonuclease III, DNA polymerase II, DNA polymerase III (E subunit), exonucleases IVA and IVB, RecBCD (exonuclease V), exonuclease VII, exonuclease VIII, Red, dRpase, endonuclease I, endonuclease III, endonuclease IV, endonuclease V, endonuclease VII, endonuclease VIII, fpg, uvrABC, mutH, vsr endonuclease, ruvC, ecoK, ecoB, mcrBC, mcrA, mrr, and topoisomerases (such as topoisomerase I, topoisomerase II, topoisomerase III and topoisomerase IV). Examples of RNA nucleases include, *E. coli* ribonucleases, such as endoribonuclease I, M, R, III, P, E, K, H, HII, IV, F, N, P2, 0, PC and PIV, and exonucleases such as polynucleotide phosphorylase, oligoribonuclease, and exoribonucleases II, D, BN, T, PH and R. In some embodiments, the nuclease is exonuclease III. In some embodiments, the nuclease is a nicking endonuclease, e.g., Nt.BstNBI or Nt.CviPII.

In some embodiments, the hydrophilic portion enzyme is a ribozyme, e.g., a ribonucleic acid molecule that can cleave other RNA molecules in specific-regions. A wide variety of ribozymes may be utilized within the context of the present invention, including for example, Group I intron ribozymes (Cech et al., U.S. Pat. No. 4,987,071); Group II Introns (Michel, et al., *EMBO J.* 2:33 38 1983), hairpin ribozymes (Hampel et al., *Nucl. Acids Res.* 18:299 304, 1990, U.S. Pat. No. 5,254,678 and European Patent Publication No. 0 360 257), hammerhead ribozymes (Rossi, J. J. et al., *Pharmac. Ther.* 50:245 254, 1991; Forster and Symons, *Cell* 48:211 220, 1987; Haseloff and Gerlach, *Nature* 328:596 600, 1988; Walbot and Bruening, *Nature* 334:196, 1988; Haseloff and Gerlach, *Nature* 334:585, 1988), hepatitis delta virus ribozymes (Perrotta and Been, *Biochem.* 31:16, 1992); *Neurospora* Vakrud satellite (VS) ribozymes (Anderson and Collins, *Mol. Cell.* 5: 4690478, 2000, RNase P ribozymes (Takada et al., *Cell* 35:849, 1983); as well as other types of ribozymes (see e.g., WO 95/29241, and WO 95/31551). Further examples of ribozymes include those described in U.S. Pat. Nos. 5,116,742, 5,225,337 and 5,246,921.

As detailed in the examples, the morphology of the micelle can be altered from a sphere to a rod upon subjecting the micelle to a hydrophilic portion enzyme (e.g., a DNAzyme, an exonuclease, or an endonuclease). For example, the nucleic acid moieties of the hydrophilic portion are single-strand DNA molecules, which are substrates for a DNAzyme. Upon binding to the DNAzyme, the single strand DNA substrates are cleaved by the action of the DNAzyme. Similarly, as detailed in the examples, the morphology of the micelle can also be altered from a sphere to a rod upon subjecting the micelle to an exonuclease or an endonuclease. In these cases, the nucleic acid moieties of the hydrophilic portion are substrates (e.g., double-strand DNAs or RNAs) for an exonuclease or an endonuclease.

In some embodiments, the nucleic acid moieties of the hydrophilic portion can be attenuated by nucleic acid cleaving reagent, e.g., any agent, compound, or substance that can be used to break a nucleotide bond or otherwise restrict a nucleic acid into smaller units. Examples of nucleic acid cleaving reagents include, without limitation, include Bleomycin (Burger, *Chem. Rev.* 1998, 98 (3):1153-1169).

Various molecules that bind to the peptide moieties of the hydrophilic portion can be used as hydrophilic portion binders. One example of hydrophilic portion binders is antibody to the peptide moieties of the hydrophilic portion. Upon the binding of the antibody, the micelle can not longer maintain, e.g., a rod-shaped structure. As a result, the micelle adopts a different morphology, e.g., a sphere-shaped structure. Other morphologies can be adopted, e.g., by varying the sizes or subtypes of the antibody. Other hydrophilic portion binders can be used. For example, in some embodiments, the hydrophilic portion binder is receptor protein or a fragment of receptor protein wherein the receptor binds to the peptide moieties of the hydrophilic portion. For example, in some embodiments, the peptide moieties of the hydrophilic portion are receptor-binding fragments of cytokines. In this case, the corresponding cytokine receptor or its binding domain can be used as the hydrophilic portion binder. Other peptide-binding substances well-known in the art can also be used, e.g., nanobodies, synbodies.

The morphology of the micelle can be altered from a rod to a sphere upon subjecting the micelle to a hydrophilic portion binder which binds to a peptide moiety. The process and degree of this binding an be controlled in a dose-dependent fashion, e.g., by controlling the amount of the hydrophilic portion binder. In some embodiments, the micelle is altered from a rod to a sphere when more than 25%, 50%, 75% of the peptide moieties of the hydrophilic portion is bound by a hydrophilic portion binder.

The morphology of the micelle having a peptide moiety bound with a binding partner (e.g., an antibody, a synbody, or a receptor) can be altered from a sphere to a rod upon subjecting the micelle to a peptide competitor. The peptide competitor is capable of competitively binding to the binding partner of the peptide moieties of the peptide hydrophilic portion. When the peptide competitor binds to the binding partner of the peptide moieties of the peptide hydrophilic portion, it dissociates this binding partner from the hydrophilic portion. The peptide hydrophilic portion is left with an unbound peptide. As discussed above, with this structure/composition change, the morphology of the micelle correspondingly changes, e.g., from a sphere to a rod. The process and degree of this dissociation can be controlled in a dose-dependent fashion, e.g., by controlling the amount of the peptide competitor. In some embodiments, the micelle is altered from a rod to a sphere when more than 25%, 50%, 75% of the binding partners of the peptide moieties of the hydrophilic portion are dissociated from the hydrophilic portion.

In some embodiments, the peptide moieties of the hydrophilic portion can be attenuated by a hydrophilic portion enzyme, and thereby change the composition and the structure of the micelle. For example, in some embodiments, the hydrophilic portion enzyme is an enzyme that cleaves the peptide moieties of the hydrophilic portion. In some embodiments, the hydrophilic portion enzyme is an enzyme that modifies the peptide moieties of the hydrophilic portion.

In some embodiments, the hydrophilic portion enzyme is a protease, e.g., an enzyme which can hydrolyze a polypeptide. Exemplary proteases include, but not limited to, serine, cysteine, metallo- and aspartic proteases. In some embodiments, the protease is an alkaline microbial protease or a trypsin-like protease. Specific non-limiting examples of proteases include thermolysin, trypsin, chymotrypsin, plasmin, kallikrein, thrombin, papain, plasmin, cathepsin B, renin, chymosin, Endoproteinase Glu-C, Endoproteinase Asp-N, Endoproteinase Lys-C, Endoproteinase Arg-C, Endoproteinase Arg-N, Factor Xa protease, enterokinase, V5 protease, and the tobacco etch virus protease, pepsin, cathepsin, elastase, carboxypeptidases, aminopeptidases, subtilisin, $V_8$ protease, prolinase and other endo- or exopeptidases In some embodiments, the protease is a serine protease or a metalloprotease. Further non-limiting examples of proteases include aminopeptidases, including prolyl aminopeptidase (3.4.11.5), X-pro aminopeptidase (3.4.11.9), bacterial leucyl aminopeptidase (3.4.11.10), thermophilic aminopeptidase (3.4.11.12), lysyl aminopeptidase (3.4.11.15), tryptophanyl aminopeptidase (3.4.11.17), and methionyl aminopeptidase (3.4.11.18); serine endopeptidases, including chymotrypsin (3.4.21.1), trypsin (3.4.21.4), cucumisin (3.4.21.25), brachyurin (3.4.21.32), cerevisin (3.4.21.48) and subtilisin (3.4.21.62); cysteine endopeptidases, including papain (3.4.22.2), ficain (3.4.22.3), chymopapain (3.4.22.6), asclepain (3.4.22.7), actimidain (3.4.22.14), caricain (3.4.22.30) and ananain (3.4.22.31); aspartic endopeptidases, including pepsin A (3.4.23.1), Aspergillopepsin I (3.4.23.18), Penicillopepsin (3.4.23.20) and Saccharopepsin (3.4.23.25); and metalloendopeptidases, including Bacillolysin (3.4.24.28). Commercially available proteases include Alcalase, Savinase, Primase, Duralase, Esperase, Kannase, and Durazym (available from Novozymes A/S), Maxatase, Maxacal, Maxapem, Properase, Purafect, Purafect OxP, FN2, FN3 and FN4 (available from Genencor International Inc.). Also useful in the present invention are protease variants, such as those disclosed in EP 130,756 (Genentech), EP 214,435 (Henkel), WO 87/04461 (Amgen), WO 87/05050 (Genex), EP 251.446 (Genencor), EP 260.105 (Genencor), Thomas et al., (1985), Nature. 318, p. 375-376, Thomas et al., (1987), J. Mol. Biol., 193, pp. 803-813, Russel et al., (1987), Nature, 328, p. 496-500, WO 88/08028 (Genex), WO 88/08033 (Amgen), WO 89/06279 (Novozymes A/S), WO 91/00345 (Novozymes A/S), EP 525 610 (Solvay) and WO 94/02618 (Gist-Brocades N.V.). The activity of proteases can be determined as described in METHODS OF ENZYMATIC ANALYSIS, third edition, 1984, Verlag Chemie, Weinheim, vol. 5.

In some embodiments, the hydrophilic portion enzyme is a matrix metalloproteinase (MMP), e.g., zinc-binding endopeptidases that when active can degrade one or more components of the extracellular matrix. Examples of MMPs include all members of the MMP family including collagenases (MMP-1, MMP-8 and MMP-13), gelatinases (MMP-2 and MMP-9), stromelysins (MMP-3 and MMP-10), metalloelastase, Membrane-type MMPs (MT-MMP; MMP-14, MMP 15, MMP-16, MMP-17, MMP-24, and MMP-25), and others (MMP-7, MMP-11, MMP-12, MMP-19, MMP-20 and MMP-23).

In some embodiments, the hydrophilic portion enzyme is a kinase, e.g., a member of transferase class enzymes that are able to transfer a phosphate group from a donor molecule to an amino acid residue of a protein. See Kostich, M., et al., Human Members of the Eukaryotic Protein Kinase Family, *Genome Biology* 3 (9):research 0043.1-0043.12, 2002 herein incorporated by reference in its entirety, for a detailed discussion of protein kinases and family/group nomenclature. Representative, non-limiting examples of kinases include Abl, Abl(T3151), ALK, ALK4, AMPK, Arg, Arg, ARKS, ASK1, Aurora-A, Axl, Blk, Bmx, BRK, BrSK1, BrSK2, BTK, CaMKI, CaMKII, CaMKIV, CDK1/cyclinB, CDK2/cyclinA, CDK2/cyclinE, CDK3/cyclinE, CDK5/p25, CDK5/p35, CDK6/cyclinD3, CDK7/cyclinH/MAT1, CDK9/cyclin T1, CHK1, CHK2, CK1(y), CK1δ, CK2, CK2α2, cKit(D816V), cKit, c-RAF, CSK, cSRC, DAPK1, DAPK2, DDR2, DMPK, DRAK1, DYRK2, EGFR, EGFR(L858R), EGFR(L861Q), EphA1, EphA2, EphA3, EphA4, EphA5, EphA7, EphA8, EphB1, EphB2, EphB3, EphB4, ErbB4, Fer, Fes, FGFR1, FGFR2, FGFR3, FGFR4, Fgr, Flt1, Flt3(D835Y), Flt3, Flt4, Fms, Fyn, GSK3β, GSK3α, Hck, HIPK1, HIPK2, HIPK3, IGF-1R, IKKβ, IKKα, IR, IRAK1, IRAK4, IRR, ITK, JAK2, JAK3, JNK1α1, JNK2α2, JNK3, KDR, Lck, LIMK1, LKB1, LOK, Lyn, Lyn, MAPK1, MAPK2, MAPK2, MAPKAP-K2, MAPKAP-K3, MARK1, MEK1, MELK, Met, MINK, MKK4, MKK6, MKK7β, MLCK, MLK1, Mnk2, MRCKβ, MRCKα, MSK1, MSK2, MSSK1, MST1, MST2, MST3, MuSK, NEK2, NEK3, NEK6, NEK7, NLK, p70S6K, PAK2, PAK3, PAK4, PAK6, PAR-1Bα, PDGFRβ, PDGFRα, PDK1, PI3K beta, PI3K delta, PI3K gamma, Pim-1, Pim-2, PKA(b), PKA, PKBβ, PKBα, PKBγ, PKCμ, PKCβI, PKCβII, PKCα, PKCγ, PKCδ, PKCε, PKCζ, PKCη, PKCθ, PKCι, PKD2, PKG1β, PKG1α, Plk3, PRAK, PRK2, PrKX, PTK5, Pyk2, Ret, RIPK2, ROCK-I, ROCK-II, ROCK-II, Ron, Ros, Rse, Rsk1, Rsk1, Rsk2, Rsk3, SAPK2a, SAPK2a(T106M), SAPK2b, SAPK3, SAPK4, SGK, SGK2, SGK3, SIK, Snk, SRPK1, SRPK2, STK33, Syk, TAK1, TBK1, Tie2, TrkA, TrkB, TSSK1, TSSK2, WNK2, WNK3, Yes, ZAP-70, ZIPK. In some embodiments, the kinases may be ALK, Aurora-A, Axl, CDK9/cyclin T1, DAPK1, DAPK2, Fer, FGFR4, GSK3β, GSK3α, Hck, JNK2α2, MSK2, p70S6K, PAK3, PI3K delta, PI3K gamma, PKA, PKBβ, PKBα, Rse, Rsk2, Syk, TrkA, and TSSK1. In yet other embodiments the kinase is selected from the group consisting of ABL, AKT, AURORA, CDK, DBF2/20, EGFR, EPH/ELK/ECK, ERK/MAPKFGFR, GSK3, IKKB, INSR, JAK DOM 1/2, MARK/PRKAA, MEK/STE7, MEKK/STE11, MLK, mTOR, PAK/STE20, PDGFR, PI3K, PKC, POLO, SRC, TEC/ATK, and ZAP/SYK.

In some embodiments, the hydrophilic portion enzyme is a phosphatase, e.g., an enzyme that dephosphorylates its substrate; i.e., it hydrolyses phosphoric acid monoesters into a phosphate ion and a molecule with a free hydroxyl group. Phosphatases can be subdivided based upon their substrate specificity. Tyrosine-specific phosphatases include protein tyrosine phosphatasel B (PTP1B), phosphacan, SHP/SHPTP, and striatum enriched phosphatase (STEP). Serine/threonine specific phosphatases include PP1 (a, β, γ1, γ2), PP2A, PP2B (AKA calcineurin), PP2C, PPP, and PP5. Dual specificity phosphatases have the ability to dephosphorylate both tyrosine and serine/threonine residues. Examples of dual specificity phosphatases include vaccinia H1 related (VHR) phosphatase.

As detailed in the examples, the morphology of the micelle can be altered from a sphere to a network upon subjecting the micelle to a hydrophilic portion enzyme (e.g., a protease, or a matrix metalloproteinase). For example, the peptide moieties of the hydrophilic portion comprise substrates for a matrix metalloproteinase. Upon contacting the micelle to a matrix metalloproteinase, e.g., a MMP-2 or MMP-9, the MMP substrates are cleaved by the action of the MMPs. Similarly, the morphology of the micelle can also be altered from a sphere to a network upon subjecting the micelle to a protease. In these cases, the peptide moieties of the hydrophilic portion are substrates for a protease, e.g., thrombin.

As detailed in the examples, the morphology of the micelle can be altered from a sphere to a vesicle upon subjecting the micelle to a hydrophilic portion enzyme (e.g., a peptide/protein modifying enzyme such as a protein kinase in the presence of ATP). Various peptide/protein modifying enzymes known in the art can be used to modify the peptide moieties of the hydrophilic portion. In some embodiments, the peptide moieties of the hydrophilic portion comprise substrates for a protein kinase. The structure changes caused by this modification on the peptide moieties of the hydrophilic portion can disturb the structure of the micelle. As a result, the micelle can not longer maintain a sphere-shaped structure, and adopts a different morphology to accommodate this internal structure change. In some embodiments, the peptide moieties of the hydrophilic portion comprise substrates for protein kinase A.

As detailed in the examples, the morphology of the micelle can be altered from a vesicle to a sphere upon subjecting the micelle to a second hydrophilic portion enzyme (e.g., a peptide/protein modifying enzyme such as a protein phosphatase). Various peptide/protein modifying enzymes known in the art can be used to modify the peptide moieties of the hydrophilic portion. In some embodiments, the peptide moieties of the hydrophilic portion comprise substrates for a protein phosphatase.

The morphology of the micelle can therefore conveniently switch back and forth between two micelle structures, e.g., between spheres and vesicles. In some embodiments, the morphology of the micelle can switch back and forth among several micelle structures, e.g., rods, spheres, vesicles, cylinders, toroids, and networks. For example, in some embodiments, the morphology of the micelle can switch back and forth between spheres and vesicles by the action of first peptide/protein modifying enzyme and a second peptide/protein modifying enzyme. As detailed in the examples, the morphology of a micelle having a hydrophilic portion comprising a substrate for a protein kinase is altered from a sphere to a vesicle upon subjecting the micelle to a protein kinase. The morphology of the resulting micelle can then be altered from a vesicle back to a sphere upon dephosphorylation by a protein phosphotase.

In some embodiments, the peptide moieties of hydrophilic portion can be attenuated by polypeptide cleaving reagent, e.g., any agent, compound, or substance that can be used to break a peptide bond or otherwise restrict a peptide into smaller units, e.g., smaller peptides or amino acids. Examples of polypeptide cleaving reagents include, without limitation, include cyanogen bromide and hydroxylamine.

Amphiphilic Coated Nanofibers

In another aspect, provided herein are amphiphilic coated metal nanofibers including a metal nanofiber bound to a plurality of amphiphilic molecules (as described above). In some embodiments, the metal nanofiber is a crystalline metal nanofiber. In other embodiments, the metal nanofiber is an amorphous nanofiber. The metal nanofiber may be bound to the amphiphilic molecules via any appropriate metal binding mode, include coordination bonds, covalent bond and/or ionic bonds. In some embodiments, the metal is a high conductivity metal, such as gold, silver, copper, aluminum or nickel. In some embodiment, the metal is gold.

In some embodiments, as described above; the amphiphilic molecules comprise a hydrophilic portion and a hydrophobic portion. The hydrophilic portion may include a plurality of nucleic acid moieties or peptide moieties. The properties and characteristics of amphiphilic molecules are discussed above an equally applicable to the amphiphilic coated metal nanofibers disclosed herein.

A metal nanofiber, as used herein, refers to fiber (e.g. wire) including metal having a small diameter, typically less than 100 microns. In some embodiments, the diameter is less than 10 microns. In other embodiments, the diameter is less than 1 micron. In other embodiments, the diameter is less than 500 nm. In other embodiments, the diameter is less than 250 nm. In other embodiments, the diameter is less than 100 nm. In other embodiments, the diameter is less than 50 nm. In other embodiments, the diameter is less than 10 nm. In other embodiments, the diameter is less than 5 nm. In other embodiments, the diameter is less than 1 nm. The metal nanofibers provided herein are typically capable of efficiently conducting electricity. In some embodiments, the metal nanofiber is composed entirely of metal. In some embodiments, the metal nanofiber is a crystalline metal nanofiber. In some embodiments, the metal is a high conductivity metal. In some embodiments, the metal is gold.

In another aspect, provided herein are methods of making an amphiphilic coated metal nanofiber. The method includes contacting a metal nanoparticle with a micelle, wherein the micelle includes a plurality of aggregated amphiphilic molecules. The metal nanoparticles are allowed to assemble into a metal nanofiber thereby forming the amphiphilic coated metal nanofiber. The method is typically performed in a polar solvent, such as an aqueous solution.

In some embodiments, the nanoparticle is an activated surface metal nanoparticle. In some embodiments, the nanoparticle has a diameter of 1 nm to 15 nm. In some embodiments, the nanoparticle has a diameter of 2 nm to 10 nm. In some embodiments, the nanoparticle has a diameter of about 2 nm or about 1 nm. In some embodiments, the metal is a high conductivity metal. In some embodiments, the metal is gold, silver, copper, aluminum and nickel (e.g. gold). The properties and characteristics of the micelle, metal nanofiber and amphiphilic molecules are discussed above an equally applicable to methods of making the nanofibers described herein.

In some embodiments, the metal is a high conductivity metal. In some embodiments, the metal is a high conductivity alloy. In some embodiments, the metal is a high conductivity compound. Examples of the metal, alloy, compound or the like with high conductivity include gold, silver, copper, nickel, palladium, aluminum, iron, titanium, platinum, tungsten, chromium, molybdenum, cobalt, or combinations thereof, and a nitride thereof and the like (for example, titanium nitride (TiN), tungsten nitride (WN), and molybdenum nitride (MoN)); an alkali metal such as lithium (Li) or cesium (Cs), an alkali earth metal such as magnesium (Mg), calcium (Ca) or strontium (Sr), and an alloy including any thereof (MgAg, AlLi); and a rare-earth metal such as europium (Er) or ytterbium (Yb) and an alloy thereof, and the like are given. Examples of alloys having high conductivity also include aluminum-copper alloy, titanium alloy, stainless steel, and Inconel.

Functional Groups for Attachment of Nucleic Acid Moieties, Peptide Moieties and Hydrophobic Moieties.

Various procedures for functionalization of the 5'- or 3'-termini of nucleic acids may be found in Chu and Orgel *DNA* (1985) 4:327-331; Connolly and Rider *Nucl. Acids Res.* (1985) 13:4485-4502. Depending upon the functionalities, various reactions may be employed to produce amides, esters, both inorganic and organic, oxygen and sulfur ethers, amines, or the like. In working with carboxyl groups, various activating groups may be employed, such as carbonyldiimidazole, carbodiimides, succinimidyl ester, para-nitrophenyl ester, etc. Various active functionalities can be employed, such as isocyanates, diazo groups, imino chlorides, imino esters, anhydrides, acyl halides, sulfinyl halides, isothiocyanates, sulfonyl chlorides, etc. Conditions for carrying out the various reactions in joining non-nucleotide moieties to nucleotide moieties may be found in Chu and Orgel *DNA* (1985) 4:327-331; Smith, et al. *Nucl. Acids. Res.* (1985) 13:2399-2412.

A peptide can be covalently bonded via one or more of the amino acid residues of the peptide to a functional group (e.g., a terminal reactive group) on the attachment moiety of the hydrophobic portion polymer. The functional group on the attachment moiety of the hydrophobic portion polymer selectively reacts with free amino or other reactive groups on the peptide. Potential reactive sites include: N-terminal amino group, epsilon amino groups on lysine residues, as well as other amino, imino, carboxyl, sulfhydryl, hydroxyl, and other hydrophilic groups. Peptide-lipid conjugates can also be prepared by any of a number of means for forming, e.g., an amide bond between the amino group of a lipid molecule and the carboxy terminus of an amino acid sequence.

In addition, click chemistry can be used for conjugating the hydrophobic portion and the hydrophilic portion to one another, polymerizing the polymer backbone monomers, the hydrophobic moiety to the remainder of the amphiphilic molecule, the peptide moiety to the remainder of the molecule, or the nucleic acid moiety to the remainder of the molecule. The click reaction is known to proceed quickly and selectively under physiological conditions. In contrast, most conjugation reactions are carried out using the primary amine functionality on proteins (e.g. lysine or protein end-group). Because most proteins contain a multitude of lysines and arginines, such conjugation occurs uncontrollably at multiple sites on the protein. This is particularly problematic when lysines or arginines are located around the active site of an enzyme or other biomolecule. Thus, provided herein are methods of conjugating the hydrophobic portion and the hydrophilic portion of the block copolymer via Click chemistry.

In some embodiments, the hydrophobic moiety or monomer that forms the central polymer backbone has a functional group that is an acetylene or an acetylene derivative which is capable of undergoing [3+2] cycloaddition reactions with complementary azide-bearing functional group. In some embodiments, the hydrophobic moiety or monomer that forms the central polymer backbone has a functional group that is an azide or an azide derivative which is capable of undergoing [3+2] cycloaddition reactions with complementary alkyne-bearing functional group (i.e. click chemistry).

Click chemistry has become a popular method of bioconjugation due to its high reactivity and selectivity, even in biological media. See Kolb, H. C.; Finn, M. G.; Sharpless, K. B. *Angew. Chem. Int. Ed.* 2001, 40:2004-2021; and Wang, Q.; Chan, T. R.; Hilgraf, R.; Fokin, V. V.; Sharpless, K. B.; Finn, M. G. *J. Am. Chem. Soc.* 2003, 125:3192-3193. In addition, currently available recombinant techniques permit the introduction of azides and alkyne-bearing non-canonical amino acids into proteins, cells, viruses, bacteria, and other biological entities that consist of or display proteins. See Link, A. J.; Vink, M. K. S.; Tirrell, D. A. *J. Am. Chem. Soc.* 2004, 126, 10598-10602; Deiters, A.; Cropp, T. A.; Mukherji, M.; Chin, J. W.; Anderson, C.; Schultz, P. G. *J. Am. Chem. Soc.* 2003, 125:11782-11783.

In some embodiments, the [3+2] cycloaddition reaction are transition metal catalyzed. Copper-containing molecules which catalyze the "click" reaction include, but are not limited to, copper bromide (CuBr), copper chloride (CuCl), copper sulfate ($CuSO_4$), copper iodide (CuI), $[Cu(MeCN)_4]$(OTf), and $[Cu(MeCN)_4](PF_6)$. Organic and inorganic metal-binding ligands can be used in conjunction with metal catalysts and include, but are not limited to, sodium ascorbate, tris(triazolyl)amine ligands, tris(carboxyethyl)phosphine (TCEP), and sulfonated bathophenanthroline ligands.

In some embodiments, the hydrophobic moiety or monomer that forms the central polymer backbone has a functional group that is an hydrazine or hydrazide derivative which is capable of undergoing reaction with functional group containing aldehydes or ketones to form hydrazone linkages. In some embodiments, the hydrophobic portion polymer (or the attachment moiety of the hydrophobic portion polymer as described herein) has a functional group that is an aldehyde or ketone derivative which is capable of undergoing reaction with s containing a hydrazine or hydrazide derivative to form hydrazone linkages.

In some embodiments, the hydrophobic moiety or monomer that forms the central polymer backbone has a functional group that is a hydroxylamine derivative which is capable of undergoing reaction with functional groups containing aldehydes or ketones. In some embodiments, the hydrophobic moiety or monomer that forms the central polymer backbone has a functional group that is an aldehyde or ketone which is capable of undergoing reaction with functional groups containing a hydroxylamine, or a hydroxylamine derivative.

In some embodiments, the hydrophobic moiety or monomer that forms the central polymer backbone has a functional group that is an aldehyde or ketone derivative which is capable of undergoing reaction with primary or secondary amines to form imine linkages. In another embodiment, the hydrophobic moiety or monomer that forms the central polymer backbone has a functional group that is a primary or secondary amine which is capable of undergoing reaction with aldehyde or ketone functionality to form imine linkages. It will be appreciated that imine linkages can be further converted to stable amine linkages by treatment with a suitable reducing agent (e.g. lithium aluminum hydride, sodium borohydride, sodium cyanoborohydride, etc.)

In some embodiments, the hydrophobic moiety or monomer that forms the central polymer backbone has a functional group that is an amine (primary or secondary) or alcohol which is capable of undergoing reaction with functional groups containing activated esters (e.g. 4-nitrophenol ester, N-hydroxysuccinimide, pentafluorophenyl ester, ortho-pyridylthioester), to form amide or ester linkages. In some embodiments, the hydrophobicmoiety has a functional group that is an activated ester which is capable of undergoing reaction with functional groups possessing amine (primary or secondary) or alcohols to form amide or ester linkages.

In some embodiments, the hydrophobic moiety or monomer that forms the central polymer backbone has a functional group that is an amine or alcohol which is bound to functional groups with carboxylic acid functionality using a suitable coupling agent. In some embodiments, the hydrophobic moiety or monomer that forms the central polymer backbone has a functional group that is a carboxylic acid functionality which is bound to functional groups containing amine or alcohol functionality using a suitable coupling agent. Such coupling agents include, but are not limited to, carbodiimides (e.g. 1-ethyl-3-(3-dimethylaminopropyl)-carbodiimide (EDC), diisopropyl carbodiimide (DIC), dicyclohexyl carbodiimide (DCC)), aminium or phosphonium derivatives (e.g. PyBOP, PyAOP, TBTU, HATU, HBTU), or a combination of 1-hydroxybenzotriazole (HOBt) and a aminium or phosphonium derivative.

In some embodiments, the hydrophobic moiety or monomer that forms the central polymer backbone has a functional group that is an electrophile such as maleimide, a maleimide derivative, or a bromoacetamide derivative, which is capable of reaction with functional groups containing thiols or amines. In some embodiments, the hydrophobic moiety or monomer that forms the central polymer backbone has a functional group that is a nucleophile such as an amine or thiol which is capable or reaction with an electrophilic functionality such as maleimide, a maleimide derivative, or a bromoacetamide derivative.

In some embodiments, the hydrophobic moiety or monomer that forms the central polymer backbone has a functional group that is a ortho-pyridyl disulfide moiety which undergoes disulfide exchange with functional groups containing thiol functionality. In some embodiments, the hydrophobic moiety or monomer that forms the central polymer backbone has a functional group that is a thiol or thiol derivative which undergoes disulfide exchange with functional groups containing ortho-pyridyl disulfide functionality. It will be appreciated that such exchange reactions result in a disulfide linkage which is reversible in the presence of a suitable reducing agent (e.g. glutathione, dithiothreitol (DTT), etc.).

Pharmacokinetics

Controlled and programmable manipulation of micelle morphology provided herein surprisingly enables a dramatic improvement of pharmacokinetics of novel micelles. As discussed in the previous sections, the process and degree of morphology change of the micelle can controlled in a dose-dependent fashion, e.g., by controlling the amount of the single-strand nucleic acid binder. In addition, morphology change of the micelle are moderately programmable, e.g., a morphology of the micelle can be altered in a sequence-specific manner.

As detailed in the examples, blood circulation time of the micelle nanoparticles can be regulated by altering the morphologies of the micelle, e.g., for rods (fibers) to spheres, or vice versa. In some embodiments, blood circulation time of the micelle nanoparticles is increased by 10, 20, 30, 40, 50, 60, 70, or more than 70 times by switching from one morphology (e.g., spheres) to a different morphology (e.g., fibers) . For example, in some embodiments, blood circulation time of the micelle nanoparticles is increased from several hours to several days. In some embodiments, blood circulation time of the micelle nanoparticles is decreased by 10, 20, 30, 40, 50, 60, 70, or more than 70 times by switching from one morphology (e.g., fibers) to a different morphology (e.g., spheres). Blood circulation time of the micelle nanoparticles can be similarly regulated by switching the micelles among several different morphologies described herein, e.g., vesicles, rods, spheres, networks, fibers, etc.

As detailed in the examples, cell entry rates of the micelle nanoparticles can also be regulated by altering the morphologies of the micelle, e.g., for rods (fibers) to spheres, or vice versa. It was observed in the present invention that micelles having certain morphologies (e.g., spheres) can be taken up by the cells much faster as compared to micelles having other morphologies (e.g., fibers or rods). In some embodiments, cell entry rate of the micelle nanoparticles is increased by 2, 3, 4, 5, or more than 5 times by switching from one morphology (e.g., fibers) to a different morphology (e.g., spheres). For example, in some embodiments, more than 50% sphere nanoparticles enters the cells or tissues in less than 24 hours. When converted into fibers, less than 20% fiber nanoparticles enters the cells or tissues within 24 hours. In some embodiments, cell entry rate of the micelle nanoparticles is decreased by 2, 3, 4, 5, or more than 5 times by switching from one morphology (e.g., spheres) to a different morphology (e.g., fibers). Cell entry rates of the micelle nanoparticles can be similarly regulated by switching the micelles among several different morphologies described herein, e.g., vesicles, rods, spheres, networks, fibers, etc.

It is sometimes desired, when using nanoparticles as drug delivery vehicles or contrast agents, to have the nanoparticles accumulated in certain tissues. In some embodiments, tissue accumulation of the micelle nanoparticles can by controlled by altering micelle morphology of the micelle.

EXAMPLES

Example 1

Smart Lipids for Programmable Nanomaterials

Introduction. Biological compartments rely on their ability to change morphology in response to patterns of specific stimuli to facilitate many of the processes necessary for life.[1] Mimicking and understanding this type of behavior is of interest in the development of synthetic nanostructures for a diverse range of materials applications.[2] To this end, a significant body of research exists describing efforts to trigger and manipulate the morphology of discrete assemblies of amphiphiles[3] utilizing stimuli such as pH,[4] temperature,[5] small molecules[6] or ions,[7] enzymes[8] and light.[9,10] These triggering mechanisms work primarily by changing and tuning the amphiphilic properties of the building blocks in situ.[11] However, methods enabling truly programmable soft, discrete nanoscale morphology are rare, requiring a method for encoding materials with information.[12] Herein, we present an approach to such materials inspired by the success of lipid-anchored oligonucleotides as programmable tools for studying and mimicking natural lipid assemblies and their interactions including vesicle fusion processes.[2f,13]

Nucleic acids are increasingly finding a role as construction and informational elements in chemical systems and in materials because they are unique in their ability to store and transfer encoded information with high fidelity.[14] Here, DNA is utilized to instruct the assembly of three-dimensional aggregates of amphiphiles. See FIG. 1. The selective DNA-encoded, stimuli-induced shifting of size and morphology of the aggregates is demonstrated via fluorescence microscopy, transmission electron microscopy (TEM) and dynamic light scattering (DLS). Together these studies show that short oligonucleotide conjugated lipids[13] (i.e., "DNA-programmed lipids") spontaneously assemble into unilamellar vesicular liposomes, and undergo reversible, in situ vesicle-to-micelle phase transitions in response to specific DNA signals. This represents a simple approach to phase switchable soft materials and a tool for building well-defined, programmable supramolecular assemblies.

Results and Discussion. The DNA-programmed lipids consist of two alkyl (e.g., 18-carbon alkyl)hydrophobic tails, linked covalently to the 5'-termini of 9-mer single stranded DNA (ssDNA) oligonucleotides that perform as hydrophilic head groups. It is believed that the short DNA sequence is necessary to allow vesicle formation while providing the required binding energy to allow duplex formation at room temperature with complementary DNA sequences. The design strategy is based on well-established rules that govern the assembly of amphiphiles in solution,[11] and it was reasoned that by manipulating the size, shape and charge of the polar head group of each surfactant molecule via DNA hybridization and displacement cycles, one would be able to guide a material through a series of reversible, programmed phase transitions. These systems are designed such that phase transitions are controlled by selective changes in surfactant structure that shift the equilibrium free energy minimum. Therefore, DNA hybridization generates "new" surfactants that are in equilibrium between monomer and vesicle (ssDNA polar head groups), or monomer and micelle (duplex DNA polar head groups). The isothermal phase transitions are enabled by mixing the DNA-lipid assemblies sequentially with several short ssDNA strands, as illustrated in FIG. 1.

DNA-programmed lipids are conveniently synthesized via conjugation (e.g., by reaction with 3,4-di(octadecyloxy)benzoic acid) to 5'-amino modified oligonucleotides bound to solid support immediately following DNA synthesis. After conjugation, the sequences were washed, cleaved and deprotected from the support. The resulting ammonium hydroxide solutions were diluted in buffer (Tris, 50 mM, pH 7.4) giving clear solutions and were dialyzed against the buffer for several days. This preparation yielded uniformly shaped, spherical vesicles approx. 500 nm in diameter as characterized by cryo-TEM, SEM and AFM (FIG. 2), DLS (FIG. 3), and fluorescence microscopy (FIG. 4). The unilamellar bilayer architecture of these vesicle assemblies was confirmed by cryo-TEM (FIG. 2) with bilayer thicknesses of 8-9 nm, consistent with an end-on arrangement of surfactant tails as illustrated in the cartoon scheme in FIG. 1. SEM and AFM images show flattened structures for the vesicles on surfaces consistent with their hollow morphology (confirmed by cryo-TEM) leading to collapse in the dried state.[15] In solution, zeta-potential measurements show vesicles have increased stability with increasing ionic strength consistent with a charge shielding effect in the polyanionic shell (−13 mV at 5 mM $MgCl_2$, −19 mV at 10 mM $MgCl_2$).

To facilitate phase transition to spherical micelles (FIG. 3), the vesicles were mixed for several hours with partially complementary single stranded 19-base DNA sequences modified at their 5'-termini with two 18-member ethylene glycol phosphoramidites ($DNA_2$ in FIG. 1). The system was designed such that $DNA_2$ addition to $DNA_1$-lipid assemblies would cause an increase in steric and electronic repulsion in the polar head group. DNA hybridization was confirmed by melting temperature studies, consistent with the expected stability of the duplex in the micelle shell. Therefore, the newly formed double stranded DNA-lipid is better accommodated within the micelle phase and accordingly, there is a shift in structure of the observed aggregates from vesicles to 20-25 nm micelles (critical micelle concentration=300 nM). On these grounds we reasoned the process should be reversible as directed by predictable DNA duplex formation. Therefore, $DNA_3$, a 19-base ssDNA strand perfectly complementary to $DNA_2$, was designed to reverse the phase transition by invasion into the 9-base pair duplex $DNA_1$-$DNA_2$, releasing the more thermodynamically stable 19-base pair duplex, $DNA_2$-$DNA_3$. In this manner the vesicles could be first "destroyed" yielding spherical micelles and could be subsequently "repaired" in a cyclical fashion, either isothermally, or thermally.

Figures 4A, 4B, 4C, 4D, 4E, 4F, 4G, 4H:
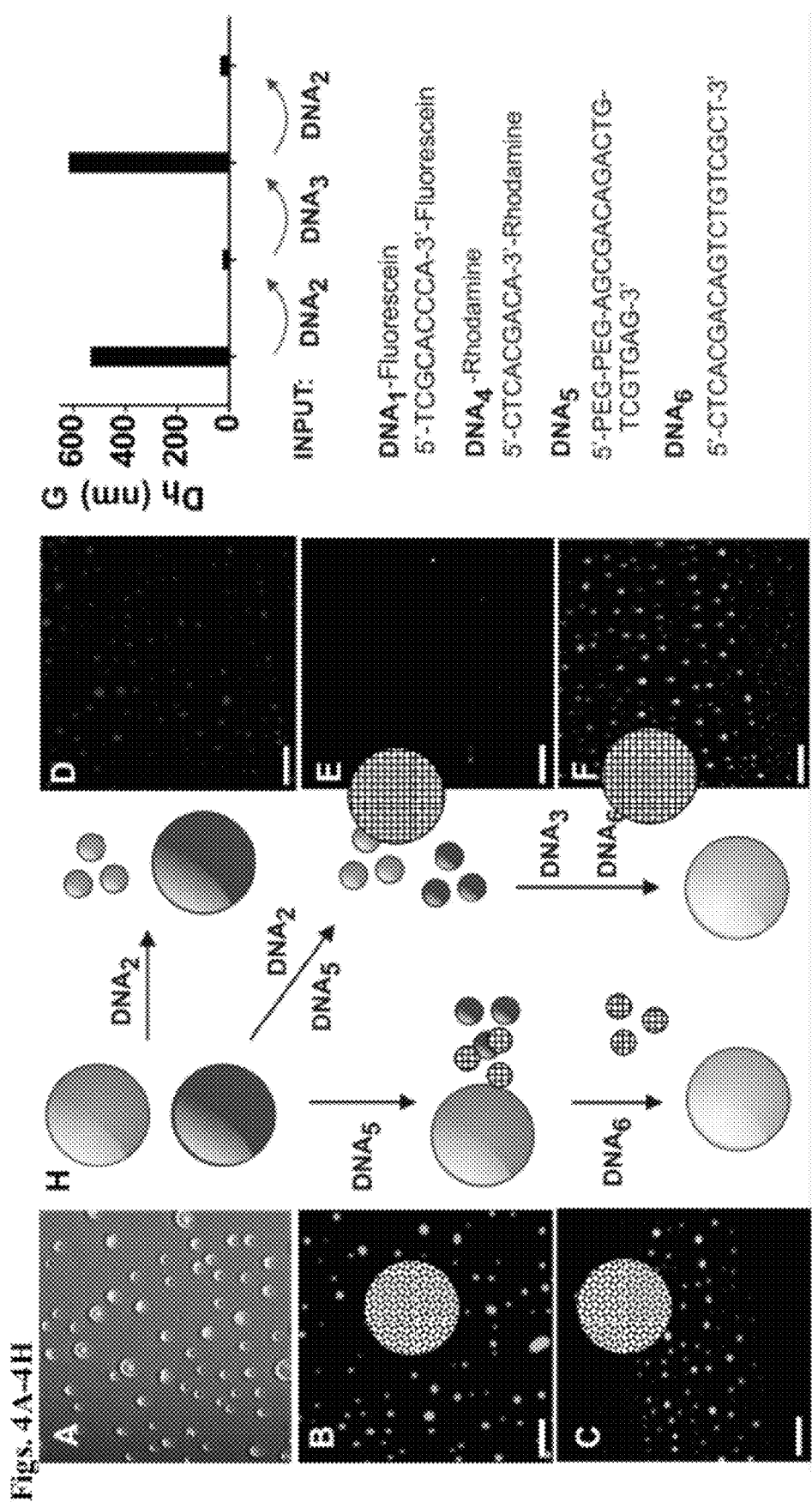
FIGS. 4A-4H depict specificity and reversibility of DNA-programmed phase shifting. Scale bar=1 μm. Two different DNA-lipids were 3'-labeled with two different dyes: DNA$_1$-Fluorescein and DNA$_4$-Rhodamine. All fluorescence images are red/green channel merges.

The DNA-sequence selective, reversible assembly process could be visualized using a two-color dye experiment by fluorescence microscopy and by DLS (FIGS. 4A-4G). DNA-lipids covalently labeled at the 3'-terminus with fluorescein ($DNA_1$-Fluorescein) or with rhodamine ($DNA_4$-Rhodamine) were allowed to assemble separately into "green" or "red" vesicles respectively, and were then mixed together. These solutions were then treated with two different ssDNA strands designed to specifically hybridize with one or the other dye-labeled vesicles. Upon addition of $DNA_5$, a polyethylene glycol (PEG) modified ssDNA strand partially complementary to the rhodamine-labeled $DNA_4$-lipid, only green fluorescence was observed, with the new 20 nm "red" spheres sized below the optical resolution limit and giving low intensity, diffuse background fluorescence (FIG. 4B). The opposite process was observed when only the fluorescein-labeled vesicles were shifted to small spherical micelles via addition of $DNA_2$ (FIG. 4D). When both labeled vesicles are shifted to micelles, little fluorescence at either wavelength is observed (FIG. 4E). The reversibility is illustrated via the addition of strands ($DNA_3$ and $DNA_6$) capable of invading into the duplex present in the shell of the small spherical micelles to regenerate the initial surfactant molecule and shift the equilibrium back to the vesicular phase (as shown in FIG. 1 for $DNA_3$ addition to spheres containing the $DNA_1$-$DNA_2$ duplex). Following this reversion to vesicles, the formation of mixed dye assemblies is observed as orange/yellow structures in merged fluorescence microscopy images (FIG. 4C and FIG. 4F). Essentially, this is a DNA-directed phase separation process giving mixed dye assemblies for matched surfactants and single color systems for unmatched surfactants.

DLS data of the switching cycles confirm the reversibility of this process (FIG. 4G) with successive additions of DNA input sequences accessing large and small aggregates of spherical or vesicular morphology (see Supporting Information for correlated TEM data). Similarly, raising the temperature of the micelle solution above 30° C. (observed by variable temperature DLS) gave an increase in aggregate size (hydrodynamic diameter, $D_h$) consistent with melting of the duplex and recovery of ssDNA-lipid.

Conclusion. DNA-programmed lipids are a synthetic tool for building soft, nanoscale materials. Moreover, this approach to surfactant assembly and manipulation of phase represents an example of a programmable, reversible trigger for nanostructure morphology. With this tool in hand, informational, encoded membranes are made possible where DNA-programmed lipids are selectively responsive, in a logical manner to multiple input signals. Without wishing to be bound by any theory, it is believed that such materials are valuable in a range of settings including the development of programmable liposomes for smart, triggerable biodiagnostic and drug delivery vehicles.

REFERENCES CITED IN EXAMPLE 1

(1) Gennis, R. B. BIOMEMBRANES. Springer-Verlag: New York, 1989.
(2) (a) Hartgerink, et al., *Science* 2001, 294:1684-1688. (b) Discher Dennis, E.; Eisenberg, A. *Science* 2002, 297:967-73. (c) Zhang, Q.; et al., *J. Am. Chem. Soc.* 2004, 126:988-989. (d) Gong, Y.; et al., *Am. Chem. Soc.* 2006, 128:14430-14431. (e) Vriezema, D. M.; et al., *Angew. Chem., Int. Ed.* 2007, 46:7378-7382. (f) Peer, D.; et al., *Nat. Nanotechnol.* 2007, 2:751-760. (g) Lee, S.-M.; et al., *J. Am. Chem. Soc.* 2007, 129:15096-15097. (h) Smart, T.; et al., *Nano Today* 2008, 3:38-46. (i) Chen, C.-L.; et al., *Am. Chem. Soc.* 2008, 130:13555-13557. (j) Chandrawati, R.; et al., *Biomaterials* 2009, 30:5988-5998. (k) Chan, Y.-H. M.; et al., *Proc. Natl. Acad. Sci.* 2009, 106:979-984.
(3) Wang, Y.; Xu, H.; Zhang, X. *Adv. Mat.* 2009, 21:1-16.
(4) (a) Butun, V.; Billingham, N. C.; Armes, S. P. *J. Am. Chem. Soc.* 1998, 120:11818-11819. (b) Li, Y.; Du, W.; Sun, G.; Wooley, K. L. *Macromolecules* 2008, 41:6605-6607. (c) Versluis, F.; Tomatsu, I.; Kehr, S.; Fregonese, C.; Tepper, A. W. J. W.; Stuart, M. C. A.; Ravoo, B. J.; Koning, R. I.; Kros, A. *J. Am. Chem. Soc.* 2009, 131:13186-13187.
(5) Sundararaman, A.; Stephan, T.; Grubbs, R. B. *J. Am. Chem. Soc.* 2008, 130:12264-12265.
(6) Ishihara, Y.; Bazzi, H. S.; Toader, V.; Godin, F.; Sleiman, H. F. *Chem. Eur. J.* 2007, 13:4560-4570.
(7) Zhang, L.; Yu, K.; Eisenberg, A. *Science* 1996, 272:1777-1779.
(8) (a) Kim, J.-H.; Lee, S.; Park, K.; Nam, H. Y.; Jang, S. Y.; Youn, I.; Kim, K.; Jeon, H.; Park, R.-W.; Kim, I.-S.; Choi, K.; Kwon, I. C. *Angew. Chem., Int. Ed.* 2007, 46:5779-5782. (b) Amir, R. J.; Zhong, S.; Pochan, D. J.; Hawker, C. J. *J. Am. Chem. Soc.* 2009, 131:13949-13951. (c) Azagarsamy, M. A.; Sokkalingam, P.; Thayumanavan, S. *J. Am. Chem. Soc.* 2009, 131:14184-14185.
(9) Zou, J.; Tao, F.; Jiang, M. *Langmuir* 2007, 23:12791-12794.
(10) Roy, D.; Cambre, J. N.; Sumerlin, B. S. *Chem. Commun.* 2009, 2106-2108.
(11) (a) Tanford, C. THE HYDROPHOBIC EFFECT: FORMATION OF MICELLES AND BIOLOGICAL MEMBRANES; 2nd ed.; John Wiley & Sons, Inc: New York, 1980. (b) Israelachvilli, J. N.; Mitchell, D. J.; Ninham, B. W. *J. Chem. Soc., Faraday Trans.* 2 1976, 72, 1525-68. (c) Jain, S.; Bates, F. S. *Science* 2003, 300:460-464. (d) Nagarajan, R. *Langmuir* 2002, 18:31-38.
(12) (a) F. E. Alemdaroglu, A. Herrmann, *Org. Biomol. Chem.* 2007, 5:1311. (b) Alemdaroglu, F. E.; Alemdaroglu, N. C.; Langguth, P.; Herrmann, A. *Macromol. Rapid Commun.* 2008, 29:326-329. (c) Chien, M.-P.; Rush, A. P.; Thompson, M. P.; Gianneschi, N. C. *Angew. Chem. Int. Ed.* 2010, In Press.
(13) (a) Boutorin, A. S.; Gus'kova, L. V.; Ivanova, E. M.; Kobetz, N. D.; Zarytova, V. F.; Ryte, A. S.; Yurchenko, L. V.; Vlassov, V. V. *FEBS Lett.* 1989, 254:129-132. (b) Shea, R. G.; Marsters, J. C.; Bischofberger, N. *Nucleic Acids Res.* 1990, 18:3777-3783. (c) MacKellar, C.; Graham, D.; Will, D. W.; Burgess, S.; Brown, T. *Nucleic Acids Res.* 1992, 20:3411-3417. (d) Krieg, A. M.; Tonkinson, J.; Matson, S.; Zhao, Q.; Saxon, M.; Zhang, L. M.; Bhanja, U.; Yakubov, L.; Stein, C. A. Proc. Natl. Acad. Sci. 1993, 90:1048-1052. (e) Patolsky, F.; Lichtenstein, A.; Willner, I. *J. Am. Chem. Soc.* 2000, 122:418-419. (f) Pfeiffer, I.; Hook, F. *J. Am. Chem. Soc.* 2004, 126:10224-10225. (g) Yoshina-Ishii, C.; Miller, G. P.; Kraft, M. L.; Kool, E. T.; Boxer, S. G. *J. Am. Chem. Soc.* 2005, 127:1356-1357. (h) Kurz, A.; Bunge, A.; Windek, A.-K.; Rost, M.; Flasche, W.; Arbuzova, A.; Strohbach, D.; Muller, S.; Liebscher, J.; Huster, D.; Herrmann, A. *Angew. Chem. Int. Ed.* 2006, 45:4440-4444. (i) Stengel, G.; Zahn, R.; Hook, F. *J. Am. Chem. Soc.* 2007, 129:9584-9585. (j) Gissot, A.; Di Primo, C.; Bestel, I.; Giannone, G.; Chapuis, H.; Barthelemy, P. *Chem. Commun.* 2008, 5550-5552. (k) Jakobsen, U.; Simonsen, A. D.; Vogel, S. *J. Am. Chem. Soc.* 2008, 130:10462-10463. (l) Godeau, G.; Staedel, C.; Barthelemy, P. *J. Med. Chem.* 2008, 51:4374-4376. (i) Muller, U. F.; Bartel, D. P. *RNA*, 2008, 14:552-562. (m) Loew, M.; Kang, J.; Dahne, L.; Hendus-Altenburger, R.; Kaczmarek, O.; Liebscher, J.; Huster, D.; Ludwig, K.; Bottcher, C.; Herrmann, A.; Arbuzova, A. *Small* 2009, 5:320-323. (n) Chung, M.; Lowe, R. D.; Chan, Y.-H. M.; Ganesan, P. V.; Boxer, S. G. *J. Struct. Biol.* 2009, 168:190-199. (o) Chan, Wu, Y.; Sefah, K.; Liu, H.; Wang, R.; Tan, W. *Proc. Natl. Acad. Sci.* 2010, 107:5-10.
(14) (a) Seeman, N. C. *J. Theor. Biol.* 1982, 99:237-247. (b) Adleman, L. M. *Science* 1994, 266:1021-4. (c) Winfree, E.; Liu, F. R.; Wenzier, L. A.; Seeman, N. C. *Nature*, 1998, 394:539-544. (d) Storhoff, J. J.; Mirkin, C. A. *Chem. Rev.* 1999, 99:1849-1862. (e) Yurke, B.; Turberfield, A. J.;

Mills, A. P., Jr.; Simmel, F. C.; Neumann, J. L. *Nature* 2000, 406:605-608. (f) Stojanovic, M. N.; Stefanovic, D. *Nat. Biotechnol.* 2003, 21:1069-1074. (g) Frezza, B. M.; Cockroft, S. L.; Ghadiri, M. R. *J. Am. Chem. Soc.* 2007, 129: 14875-14879. (h) Seeman, N. C. *Mol. Biotechnol.* 2007, 37:246-257. (i) Venkataraman, S.; Dirks Robert, M.; Rothemund Paul, W. K.; Winfree, E.; Pierce Niles, A. *Nat Nanotechnol* 2007, 2:490-494. (j) F. A. Aldaye, A. L. Palmer, H. F. Sleiman, *Science* 2008, 321:1795. (k) He, Y.; Ye, T.; Su, M.; Zhang, C.; Ribbe, A. E.; Jiang, W.; Mao, C. *Nature* 2008, 452:198-201. (l) Dietz, H.; Douglas, S. M.; Shih, W. M. *Science* 2009, 325:725-730.

(15) Moughton, A. O.; O'Reilly, R. K. *Chem. Commun.* 2010, 46:1091-1093.

Experimental Section

General Methods. All reagents were bought from TCI or Sigma-Aldrich and used without further purification. DNA synthesis reagents and modifiers were bought from Glen Research or AZCO scientific. 3,4-di(octadecyloxy)benzoic acid was synthesized via a standard literature procedure (Tuffin, R. P.; Toyne, K. J.; Goodby, J. W. *J. Mater. Chem.* 1996, 6, 1271-1282). All DNA was synthesized on an ABI-391 via standard solid phase synthesis on controlled pore glass supports. Fluorescence measurements were performed on a Zeiss LSM confocal fluorescence microscope. Reaction volumes of 50 µL were used in all fluorescence experiments of this type. HPLC purifications of DNA strands were performed on a Clarity 5u Oligo-RP phenomonex column (150×4.60 mm) with a binary gradient using a Hitachi-Elite LaChrom L-2130 pump equipped with UV-Vis detector (Hitachi-Elite LaChrom L-2420). Gradient: (Solvent A: 50 mM triethylammonium acetate, pH 7.5; Solvent B: 100% methanol; gradient: 10-45% B from 0-28 minutes, 45-60% B from 28-34 minutes, and 60-70% B from 34-40 minutes, Flow rate: 1 mL/min). To confirm DNA and DNA-surfactant molecular weights, MALDI-TOF mass spectrometry was performed on a ABI MALDI Voyager (equipped with ThermoLaser Science, VSL-337ND) using THAP matrix (2,4,6-trihydroxyacetophenone monohydrate) (18 mg), ammonium citrate (7 mg), acetonitrile:water (1 mL, 1:1). DNA-surfactant and DNA concentrations were determined via UV-Vis on a Hitachi U-2810 spectrophotometer. $D_h$ was determined by DLS on a Nano-ZS90 Malvern Instrument. Zeta potential was also measured on the Nano-ZS90 Malvern instrument. TEM images were acquired on carbon grids (Ted Pella, INC.) with 1% uranyl acetate stain on a FEI Tecnai G2 Sphera at 200 KV. The identities of organic molecules were confirmed by $^1H$ (400 MHz) and $^{13}C$ (100 MHz) NMR spectra recorded on a Varian Mercury Plus spectrometer. Mass spectra of organic molecules were obtained at the UCSD Chemistry and Biochemistry Molecular Mass Spectrometry Facility.

Preparation of $DNA_1$ (5'-$NH_2$-TCGCACCCA-3'). A 1 µmol 3'-dA-CPG was utilized as the support. The oligonucleotide was synthesized in the standard manner. A small portion of the synthesized oligonucleotide attached to the CPG was separated and subjected to cleavage and deprotection by ammonium hydroxide overnight. This oligonucleotide was characterized by MALDI-MS. Mass calcd: 2818.8; Mass obs: 2840.6.

Preparation of $DNA_2$ (5'-PEG-PEG-GGAGAGAGACTGGGTGCGA-3', SEQ ID NO:13). A 1 µmol 3'-dA-CPG was utilized as the support, with two PEG phosphoramidites (C18-spacer, Glen Research) as the terminus. The oligonucleotide was synthesized in the standard manner leaving the final base protected with a DMT group. Following cleavage and deprotection by ammonium hydroxide overnight, the oligonucleotide was purified by HPLC (retention time=35 min), treated with acetic acid followed by solvent removal and characterized by MALDI-MS. Mass calcd: 6955.2; Mass obs: 6964.1.

Preparation of Fluorescein modified ssDNA ($DNA_1$-Fluorescein) (5'-$NH_2$-TCGCACCCA-3'-Fluorescein). A 1 µmol 3'-Fluorescein-CPG (Glen Research) was utilized as the support, with a 5'-amino modifier (5-member modifier, Glen Research) as the terminus. The oligonucleotide was synthesized in the standard manner. A small portion of the synthesized oligonucleotide attached to the CPG was separated and subjected to cleavage and deprotection by ammonium hydroxide overnight. This oligonucleotide was characterized by MALDI-MS. Mass calcd: 3417.4; Mass obs: 3440.7.

Preparation of Rhodamine modified ssDNA ($DNA_4$-Rhodamine) (5'-$NH_2$-CTCACGACA-3'-Rhodamine). A 1 µmol 3'-Rhodamine-CPG (Glen Research) was utilized as the support. The oligonucleotide was synthesized in the standard manner. A small portion of the synthesized oligonucleotide attached to the CPG was separated and subjected to cleavage and deprotection by 0.05 M potassium carbonate in methanol overnight. This oligonucleotide was characterized by MALDI-MS. Mass calcd: 3466.4; Mass obs: 3477.9.

Preparation of $DNA_3$ (5'-TCGCACCCAGTCTCTCTCC-3', SEQ ID NO:14). A 1 µmol 3'-dC-CPG was utilized as the support. The oligonucleotide was synthesized in the standard manner leaving the final base protected with a DMT group. Following cleavage and deprotection by ammonium hydroxide overnight, the oligonucleotide was purified by HPLC (retention time=32 min), treated with acetic acid followed by solvent removal and characterization by MALDI-MS. Mass calcd: 5635.7; Mass obs: 5693.1.

Preparation of $DNA_5$ (5'-PEG-PEG-AGCGACAGACTGTCGTGAG-3', SEQ ID NO:15). A 1 µmol 3'-dG-CPG was utilized as the support, with two PEG phosphoramidites (C18-spacer, Glen Research) as the terminus. The oligonucleotide was synthesized in the standard manner leaving the final base protected with a DMT group. Following cleavage and deprotection by ammonium hydroxide overnight, the oligonucleotide was purified by HPLC (retention time=36 min), treated with acetic acid followed by solvent removal and characterized by MALDI-MS. Mass calcd: 6566.5; Mass obs: 6533.9.

Preparation of $DNA_6$ (5'-CTCACGACAGTCTGTCGCT-3', SEQ ID NO:16). A 1 µmol 3'-T-CPG was utilized as the support. The oligonucleotide was synthesized in the standard manner leaving the final base protected with a DMT group. Following cleavage and deprotection by ammonium hydroxide overnight, the oligonucleotide was purified by HPLC (retention time=30 min), treated with acetic acid followed by solvent removal and characterization by MALDI-MS. Mass calcd: 5739.8; Mass obs: 5712.6.

Preparation of $DNA_7$ (5'-GGAGAGAGACTGGGTGCGA-3', SEQ ID NO:17). A 1 µmol 3'-dA-CPG was utilized as the support. The oligonucleotide was synthesized in the standard manner leaving the final base protected with a DMT group. Following cleavage and deprotection by ammonium hydroxide overnight, the oligonucleotide was purified by HPLC (retention time=30 min), treated with acetic acid followed by solvent removal and characterized by MALDI-MS. Mass calcd: 5982.9; Mass obs: 5941.6.

DNA conjugation to 3,4-di(octadecyloxy)benzoic acid, particle formation and DNA-lipid characterization. 3,4-di(octadecyloxy)benzoic acid (100 µmol, 66 mg) was partially dissolved in 0.5 mL of DMSO, followed by addition of 0.2 mL of N,N-diisopropylethylamine and HBTU (100 µmol, 40 mg). The resulting solution was a light yellow, partially dissolved, soapy suspension. This solution was added via two 1 mL syringes inserted either side of the capsule containing the CPG-bound-DNA. The solution was pushed back and forth across the beads between the syringes several times, wrapped in parafilm to seal, and then left at room temperature for 24 hours. The beads were then washed twice with 2 mL DMSO and twice with 2 mL of acetonitrile. The resulting CPG beads were dried with a stream of nitrogen, removed from the capsule and then treated with 1 mL of ammonium hydroxide for 18 hours. At this time, the CPG was filtered away from the ammonium hydroxide solution. The solution was diluted with 1 mL Tris buffer (50 mM, pH 7.4) and placed in 3500 g/mol molecular weight cut off dialysis tubing and dialyzed against 2 L of buffer for 24 hours. The buffer was changed, and the solution transferred to 20,000 g/mol molecular weight cut off tubing and dialyzed again for 48 hours. The DNA-surfactants were then characterized by directly analyzing the vesicle samples by MALDI-MS. No free DNA was observed by MALDI following dialysis. The following MALDI data was performed using a 1:1 THAP:DHB (2,5-dihydroxybenzoic acid) matrix. Matrix formulations: THAP matrix -(2,4,6-tri-hydroxyacetophenone monohydrate) (18 mg), ammonium citrate (7 mg), acetonitrile:water (1 mL, 1:1). DHB matrix (15.4 mg/mL, methanol/water 1:1). $DNA_1$-lipid: Mass calcd: 3461.1; Mass obs: 3477.1. Rhodamine-$DNA_4$-lipid: Mass calcd: 4109.5; Mass obs: 4175.9. Fluorescein-$DNA_1$-lipid: Mass calcd: 4060.4; Mass obs: 4050.6.

Addition of DNA input strands—General conditions. Experiments were carried out in final volumes of 50 μL, Tris/$MgCl_2$ (50 mM/50 mM, pH 7.4) at room temperature. DNA-surfactant concentrations in the final particle solutions were determined by UV-Vis from absorbance of DNA in the DNA-lipid at $\lambda_{260}$ and each solution was adjusted to 1 μM. Each addition of DNA as described in the main text was performed via the addition of 2 μM of each DNA strand.

Fluorescence Experiments. General Procedure for conducting fluorescence microscopy experiments. 15-20 μL of sample was used. DNA-lipid assemblies with structures confirmed by TEM and DLS along with appropriate input ssDNA strands were deposited on glass slides and sealed under a cover slip. The edge of the cover slip was then sealed with nail polish after the sample was air dried.

Critical Micelle Concentration (CMC) determination. A stock solution of pyrene was prepared by adding 1 mg pyrene in 10 mL of 20 mM Tris buffer (pH 7.4) and sonicating for 12 hrs, followed by centrifugation at 12,000×g for 5 min. The supernatant containing pyrene as the fluorescent probe was utilized for this assay and measured on a plate reader fluorometer, SPECTRAMAX GEMINI EM (Molecular Devices). DNA-lipid concentration was measured via UV absorbance and micelles were accordingly diluted serially in 96-well microplates (black well, black bottom, FIA, Greiner Bio-One). Excitation was done over a 300-360 nm wavelength range and the emission was recorded at 390 nm. The slit width for excitation was fixed at 1 nm. The concentration was plotted on a logarithmic scale and the critical micelle concentration was determined at the intercept of the two tangents drawn where the decreasing surface tension becomes constant.

Zeta potential measurement with variable MgCl2 concentration. DNA-lipid at 1 μM concentration was added to 20 mM Tris buffer (pH 7.4) with variable $MgCl_2$ concentration (0, 5, 7.5, and 10 mM). The zeta potential of these samples with variable $MgCl_2$ concentrations was then measured by a Nano-ZS90 Malvern instrument. Zeta potential was not performed in the $MgCl_2$ concentration above 10 mM.

Hydrodynamic diameter measurement for variable MgCl2 concentration. DNA-lipid at 1 μM concentration was added to 20 mM Tris buffer (pH 7.4) with variable $MgCl_2$ concentration (0, 25, 50, 100, and 250 mM). The hydrodynamic diameter ($D_h$) of these samples with variable $MgCl_2$ concentrations was then measured with a Nano-ZS90 Malvern instrument.

Melting curve of DNA-lipid/DNA2 duplex. An aliquot of 6 μM $DNA_2$ was added with 6 μM DNA-lipid and allowed to hybridize for 30 min before performing the melting curve experiment. This assay was performed in Tris/$MgCl_2$ buffer (20 mM/200 mM, pH 7.4). The sample was heated to 60° C. and cooled gradually, over which the UV-Vis absorbance at $\lambda_{260}$ was measured at different temperature points as shown in the plot shown below.

Cryo-TEM imaging. Cryo-TEM images of vesicular structures formed from DNA-programmed lipids at different magnifications are obtained using standard methods.

Time course of aggregation. The time course of aggregation was determined as a plot of hydrodynamic diameter ($D_h$) versus time (min) of aggregates formed after addition of $DNA_3$ to a micelle with $DNA_1$-lipid/$DNA_2$ duplex.

Effect of temperature on $D_h$. The dependence of $D_h$ on temperature as assessed. Size change is induced by temperature as a result of DNA duplex formation and melting.

DLS analysis of Dh. The phase shifts induced by DNA sequences with a PEG linker ($DNA_2$) and without a PEG linker (DNA) are monitored by DLS, as described herein.

Characterization of vesicular structure by AFM and SEM. Vesicles were imaged by AFM, and height profiles were determined as known in the art.

Switching cycles. Representative TEM data of the switching between vesicle-sphere-vesicle were obtained as a supplement to the data provided in FIG. 4G.

Fluorescently labeled surfactant particles. TEM data were obtained for the green and red particles used in the fluorescence microscopy study described for FIGS. 4A-4H above, by methods known in the art. In addition, the DLS data for vesicles were obtained. These DLS data shows the same approx. 500 nm sized aggregates observed by TEM and optical microscopy.

Supplemental experimental results for FIGS. 4A-4H. The table following provides a key for the following Experiments 1-10, which are supplemental to the data shown in FIGS. 4A-4H above. Plus signs in the columns indicate what was added to the mixture. In the experimental description which follows for Experiments 1-10, where multiple input DNA strands are added to particles, the incubation times are 12 hrs for the initial addition, and 5 hrs for the second prior to measurements. This process allowed the formation of each duplex in turn. For example, $DNA_2$ was added to vesicles and allowed to mix for 12 hours, followed by addition of $DNA_3$ which was allowed 5 hours of mixing prior to fluorescence measurements.

| Exp. | Green Vesicles | Red Vesicles | $DNA_2$ | $DNA_5$ | $DNA_3$ | $DNA_6$ |
|---|---|---|---|---|---|---|
| 1 | + | | | | | |
| 2 | | + | | | | |
| 3 | + | | + | | | |
| 4 | | + | | + | | |
| 5 | + | + | + | | | |
| 6 | + | + | | + | | |
| 7 | + | + | + | + | | |
| 8 | + | + | | | + | |
| 9 | | + | | + | | + |
| 10 | + | + | + | + | + | + |

Experiment 1. Green vesicles are observed under the conditions of Experiment 1. See table above.

Experiment 2. Red vesicles are observed under the conditions of Experiment 2. See table above.

Experiment 3. Green vesicles are barely observed under the conditions of Experiment 3. See table above.

Experiment 4. Red vesicles are barely observed under the conditions of Experiment 4. See table above.

Experiment 5. Green vesicles are not observed in the green channel under the conditions of Experiment 5. See table above. Red vesicles are observed in the red channel under the conditions of Experiment 5.

Experiment 6. Green vesicles are observed in the green channel under the conditions of Experiment 6. See table above. Red vesicles are not observed in the red channel under the conditions of Experiment 6.

Experiment 7. Green vesicles are barely observed in the green channel under the conditions of Experiment 7. See table above. Red vesicles are barely observed in the red channel under the conditions of Experiment 7.

Experiment 8. Green vesicles are observed in the green channel under the conditions of Experiment 8. See table above.

Experiment 9. Green vesicles are observed in the green channel under the conditions of Experiment 9. See table above.

Experiment 10. Green vesicles are observed in the green channel under the conditions of Experiment 10. See table above. Red vesicles are observed in the red channel under the conditions of Experiment 10.

Example 2

Programmed Shape Shifting Micelles

Introduction. Nanoscale particles capable of reversible and defined changes in morphology in response to stimuli are expected to have broad utility in a range of settings including targeted drug delivery, detection strategies, soft templates and self-healing materials. Programmable materials with these properties are unknown despite the many elegant examples of stimuli-responsive soft nanoparticles and micelles.[1-11] Inspired by the utility of DNA as an informational molecule in nanotechnology,[12-20] we report DNA-encoded polymeric materials capable of in situ controlled, selective, reversible and user-defined shifts in morphology. The design is based on polymeric micelles formed from a novel set of amphiphilic DNA-brush copolymers. See FIGS. 5A-5E).[16,21] Utilizing the sequence selective recognition properties of DNA,[22] and its performance as a substrate for selective enzymatic cleavage,[23,24] information stored in the micelle shell was read and manipulated in several modes causing dramatic changes in morphology and particle size.

Figure 5A:
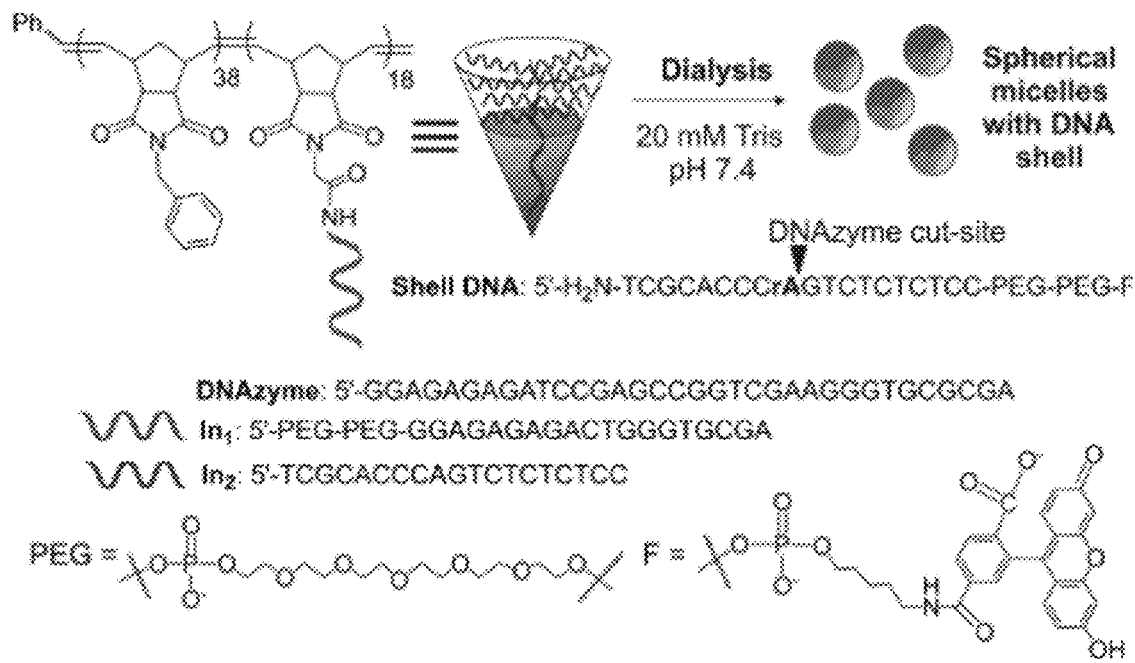
FIGS. 5A-5E depict aspects of DNA-brush copolymers assembling into micelles with spherical or cylindrical morphologies depending on amphiphile structure manipulated in situ by DNA selective interactions.
Figure 5B:
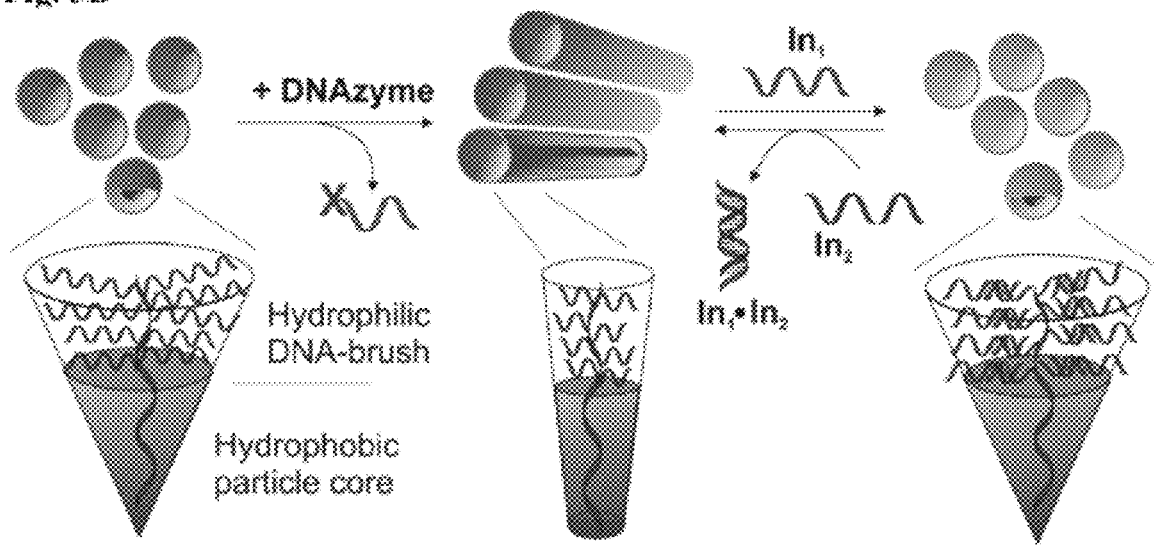
Figure 5C:
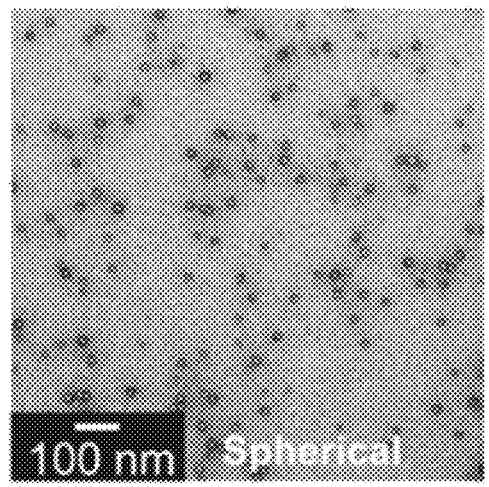
Figure 5D:
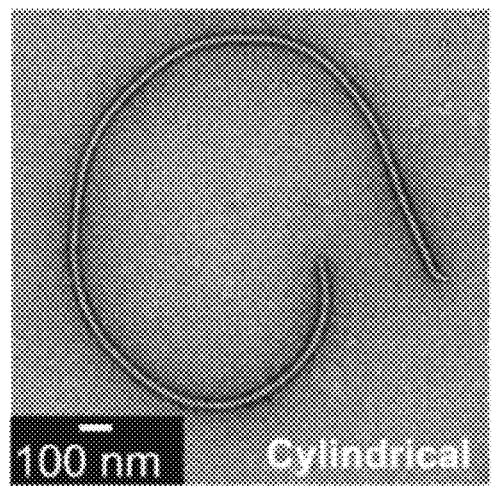
Figure 5E:
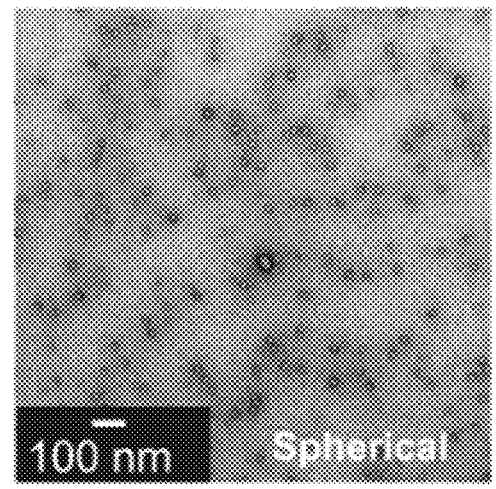

The design rationale for DNA-programmed micelle morphology is based on rules governing the aggregation of amphiphilic block copolymers.[25,26] Briefly, the phase (shape, size, overall morphology) of assembled amphiphiles is controlled by their geometric structure and electrostatics.[27] Therefore, it was hypothesized that DNA-brush copolymer amphiphiles would assemble into micelles with morphologies governed by sequence selective interactions allowing manipulation of the magnitude of steric and electrostatic repulsions in the micelle shells. Changes in geometric structure of the amphiphile are represented in FIG. 5A with larger cone angles giving higher surface curvature aggregates (i.e. spheres). To demonstrate the concept of DNA-programmed micelle phase transition, three types of sequence selective interactions were chosen: 1) enzymatic cleavage, 2) isothermal hybridization of complementary single stranded DNA (ssDNA), 3) thermal melting and annealing of DNA duplexes.

Results and Discussion. The DNA-brush copolymer amphiphiles assemble into spherical micelles (spheres, FIGS. 5A-5B) approximately 25 nm in diameter as characterized by transmission electron microscopy (TEM), dynamic light scattering (DLS) and atomic force microscopy (AFM). The DNA-brush copolymer amphiphiles contain a RNA base (rA) as a enzymatic cleavage site, two 18-member ethylene glycol moieties to increase steric bulk of the hydrophilic block, and a fluorescein tag to allow monitoring of reactions occurring at the particle shell. To facilitate a sphere-to-cylinder phase transition the spherical micelles were mixed with a DNA-based phosphodiesterase (DNAzyme[24]) conveniently synthesized to recognize a given DNA sequence and cut at a RNA base. This resulted in complete, rapid catalytic turnover of the DNA substrate that formed the bulk of the hydrophilic block, leaving a truncated ssDNA sequence. Subsequent phase transition occurs from sphere-to-cylinder as the "new" surfactants reorganize and pack accordingly. To facilitate a cylinder-to-sphere phase transition, a 19-base input DNA sequence ($In_1$) was added. This sequence was designed to form a 9-base duplex with the truncated DNA in the cylinder shell. Subsequent cylinder-to-sphere transition occurs as the bulky, extended duplex is better accommodated in the spherical micelle phase. Therefore, the new structures (rightmost spheres, FIG. 5B) contain a non-covalent DNA-duplex amenable to sphere-to-cylinder phase transition utilizing DNA strand invasion.[28,29] This was achieved via addition of a perfectly complementary 19-base ssDNA ($In_2$) designed to invade into the shorter 9-base duplex in the micelle shell. The more thermodynamically stable 19-base long duplex ($In_1 \bullet In_2$) departs, leaving the truncated ssDNA amphiphile to reassemble into the cylindrical phase.

Figure 6A:
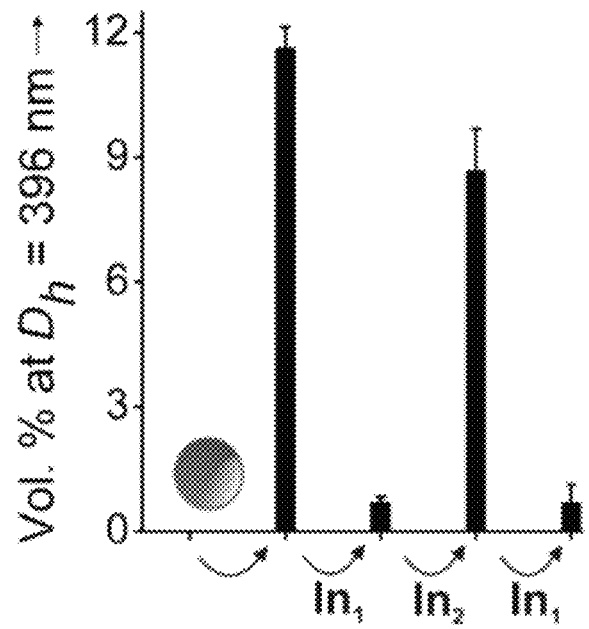
FIG. 6A depicts a cartoon reaction scheme with polymer structure, DNA sequences and DNA-modifier structures as indicated. The initial DNA-brush copolymers assemble into spherical micelles.

Reversibility was examined in solution by DLS and by TEM to confirm morphology. DLS data for isothermal DNA-directed phase transitions are shown as the volume % of particles at the 396 nm size class, resulting from various input additions after two-hour incubations. See FIGS. 6A-6B. Initially, solutions of the spherical particles show no observable scattering intensity for aggregates above 30 nm. Indeed, particle diameter ($D_h$=hydrodynamic diameter) is constant in the absence of DNAzyme over a time scale of many weeks. However, mixing spherical particles with DNAzyme for two hours causes the expected expansion in $D_h$ (FIG. 6A). Next, this solution was mixed with $In_1$ showing the expected contraction in $D_h$. Subsequent addition of $In_2$ results in duplex $In_1 \bullet In_2$, regenerating the truncated shell structure and causing another expansion of particle size. To complete the isothermal cycle, the particles were again treated with $In_1$ resulting in regeneration of small aggregates. In addition, this isothermal phase cycling process was monitored by the uptake and release of a small molecule dye.

Figure 6B:
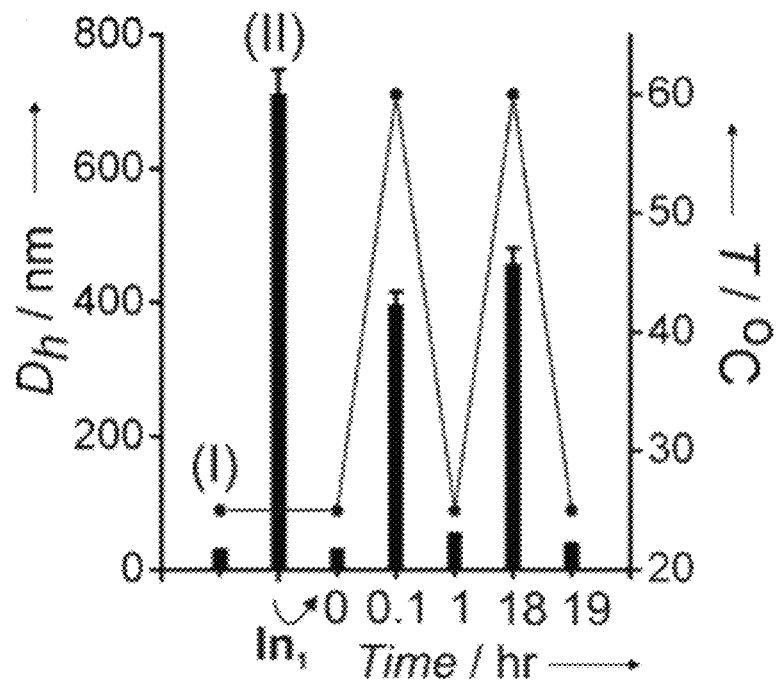
Figure 7A:
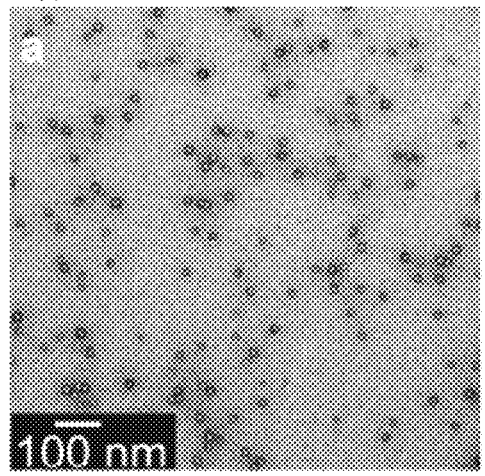
FIGS. 7A-7F depict DNA-directed size and phase change with time. Conditions: Initial particle (0.14 g/L), Tris (20 mM, pH 7.4), $MgCl_2$ (50 mM). DNAzyme (5 nM) mixed with particles at t=0 min. Each of FIGS. 7A-7E include a cartoon below indicating observed species and approximate size.
Figure 7A:
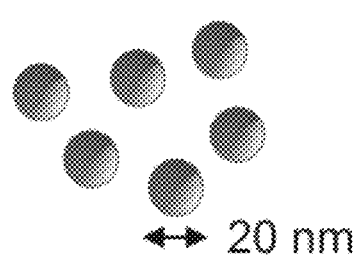
Figure 7B:
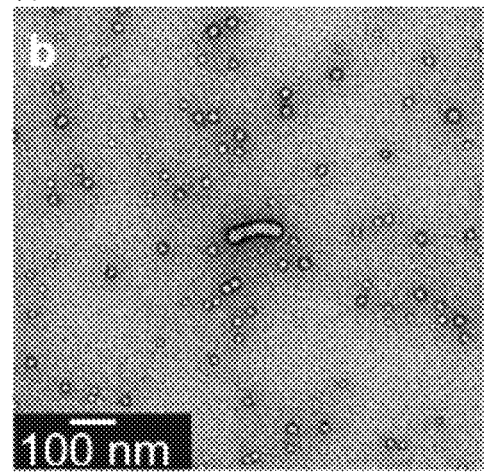
Figure 7B:
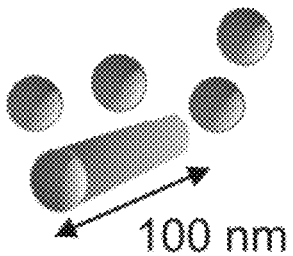
Figure 7C:
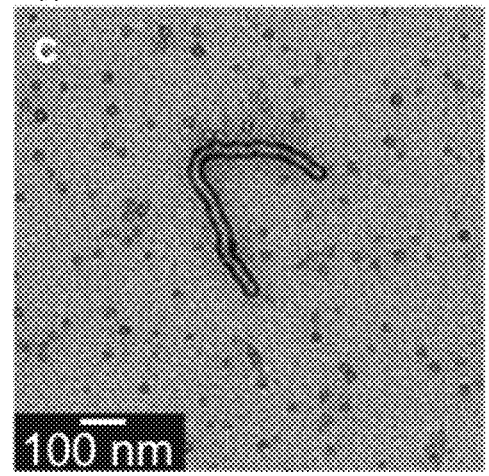
Figure 7C:
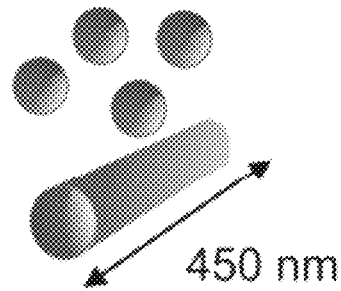
Figure 7D:
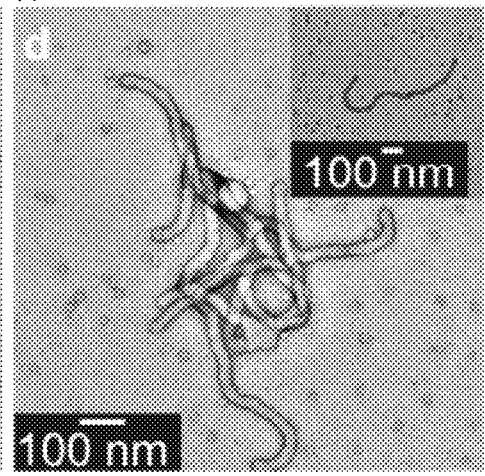
Figure 7D:
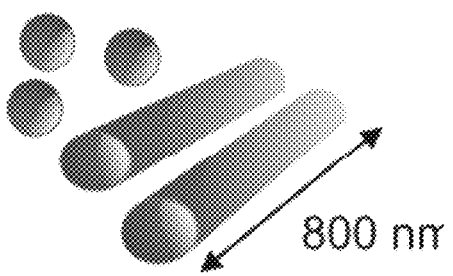
Figure 7E:
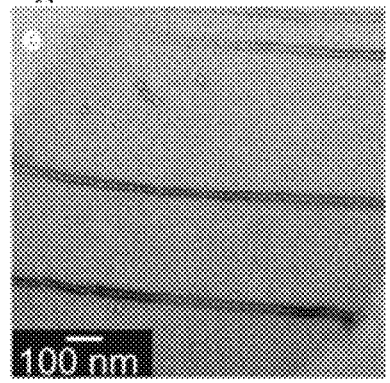
Figure 7F:
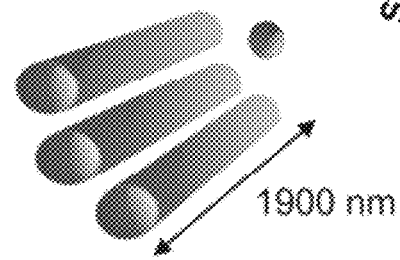
Figure 7F:
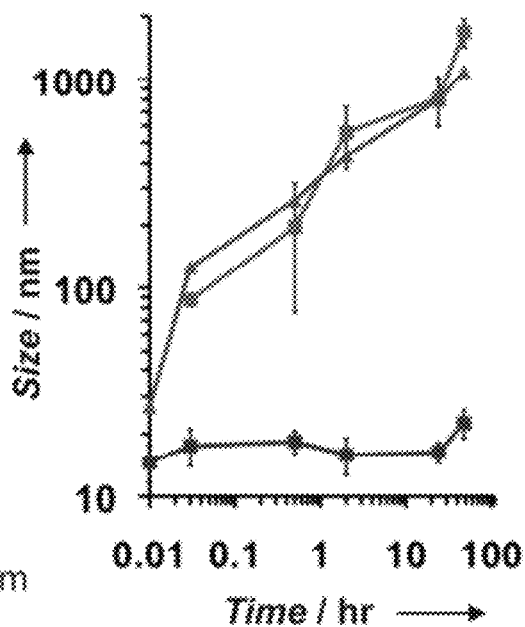
Figure 8A:
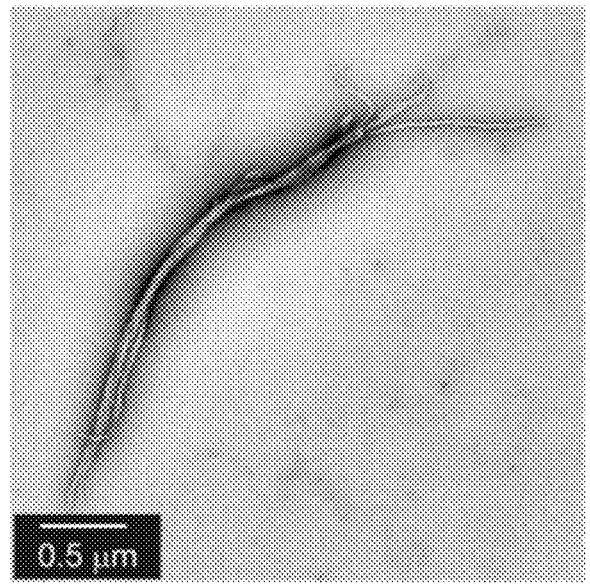
FIGS. 8A-8M depict sequence selective phase shifting observed by fluorescence microscopy. Mixtures of rhodamine and fluorescein labeled particles were treated with DNAzymes (D-1 and/or D-2) each capable of selectively cleaving either red or green labeled shell DNA strands.
Figure 8B:
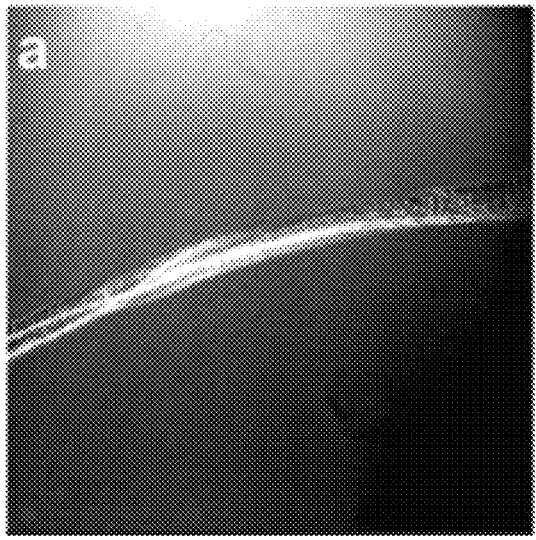
Figure 8C:
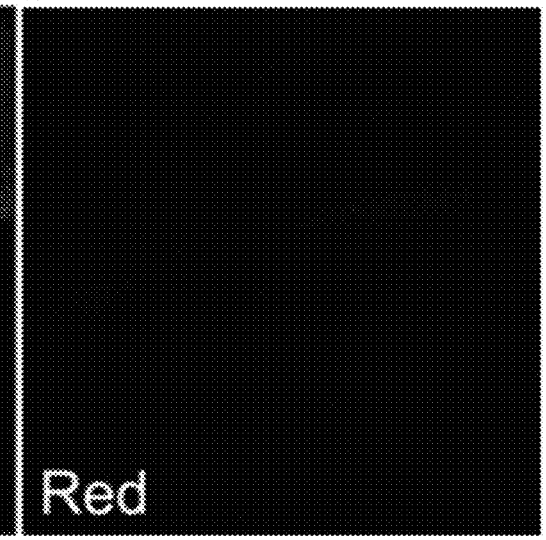
Figure 8D:
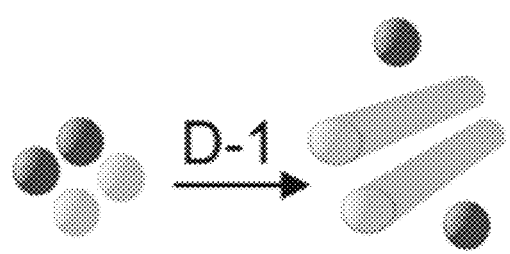
Figure 8E:
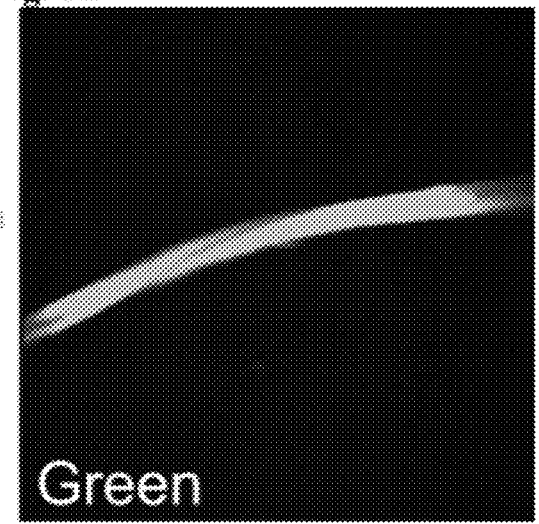
Figure 8F:
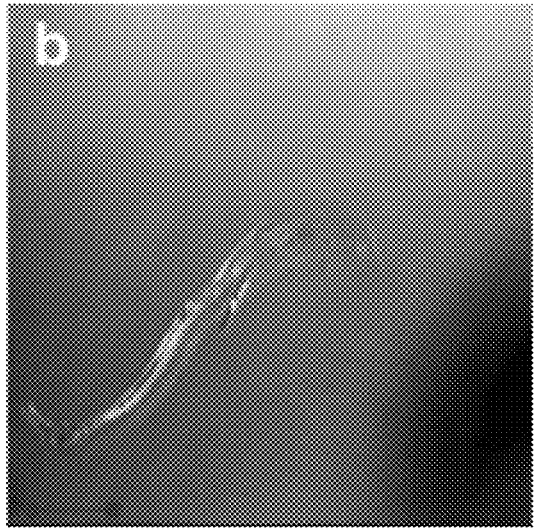
Figure 8G:
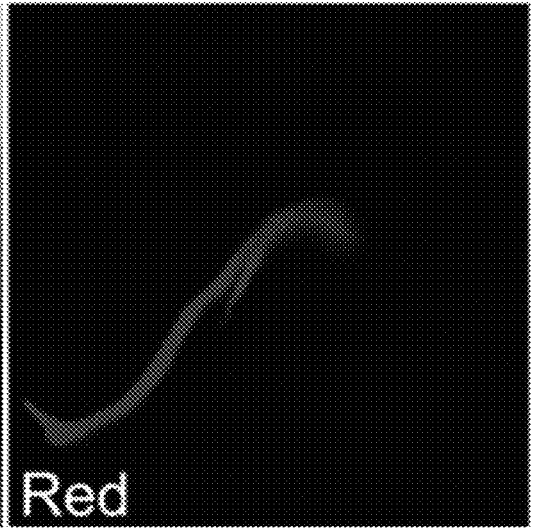
Figure 8H:
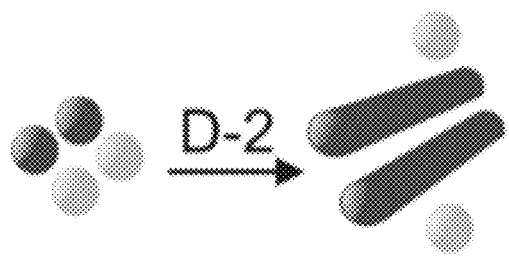
Figure 8I:
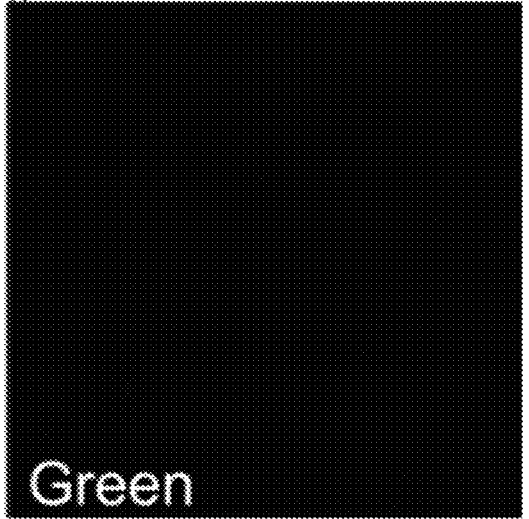
Figure 8J:
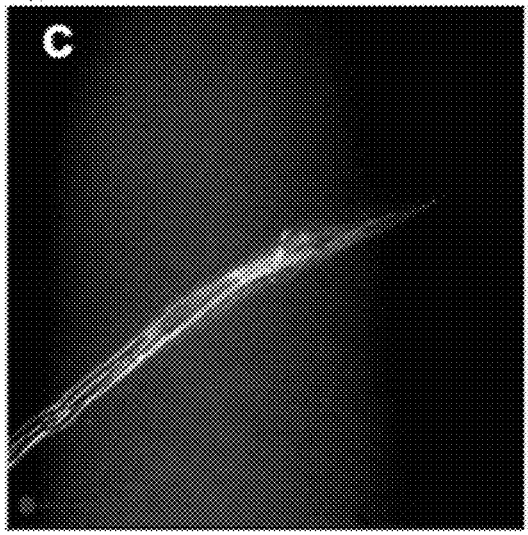
Figure 8K:
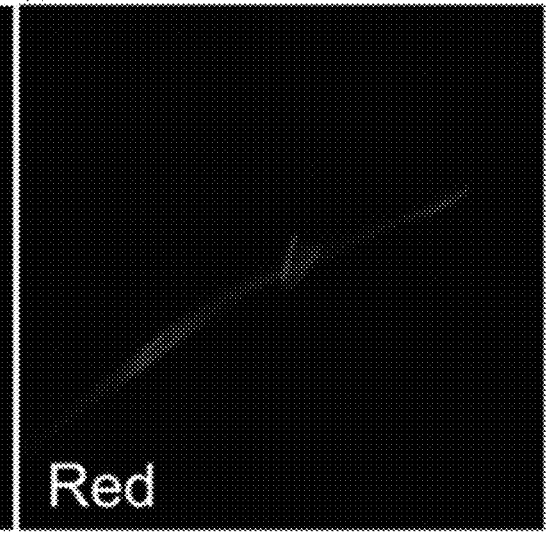
Figure 8L:
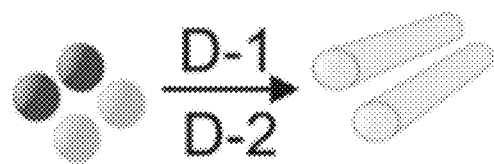
Figure 8M:
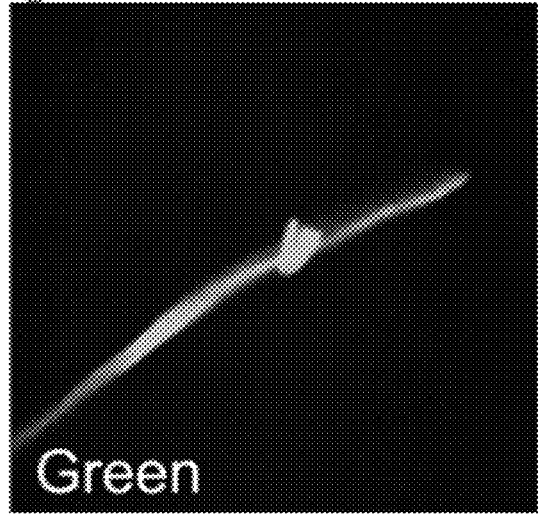

The hybridization state of complementary oligonucleotides is disrupted at elevated temperatures. The isothermal cycling experiments (FIG. 6A) show a dependence of the morphology on the hybridization state of the DNA. Similarly, cycling the temperature of the solution resulted in aggregate size changes depending on whether or not the DNA in the amphiphile was in duplex or single stranded form (FIG. 6B). These data show a correlation between the temperature of the solution and the aggregate size in solution. That is, size increases above the melting temperature of the DNA duplex and decreases below the melting temperature. These data complement the isothermal cycling experiment showing the same correlation with respect to hybridization state of the amphiphile.

To further elucidate the mechanism and assess the selectivity of the DNAzyme-directed phase transition, the process was examined via TEM and DLS (FIGS. 7A-7D), and studied by fluorescence microscopy (FIG. 8A-8M). TEM and DLS data show a solution populated with a decreasing concentration of intact 25 nm spheres and growing cylindrical aggregates with time. TEM data correlates with the increase in hydrodynamic diameter ($D_h$) observed by DLS (FIG. 7A-7F). At the 1-day time point (FIG. 7D) cylinders can be observed in high density with the inset representative of TEM data showing the presence of individual, well-defined cylinders. After two days in the presence of DNAzyme, TEM data confirms low concentrations of intact spherical structures (FIG. 7E), and the presence of cylinders in excess of 1 µm in length. This constitutes an approximate 100-fold increase in size and a dramatic change in morphology giving clear solutions and no precipitation. Insight into the mechanism of this process is provided by the observation that complete turnover of the shell DNA of the initial spheres is achieved rapidly prior to complete phase transition. Therefore, competing equilibria for monomeric amphiphile assembly are rapidly established following DNAzyme addition resulting in cylinder growth (amphiphile cylinder versus amphiphile sphere).

A series of fluorescence microscopy experiments were conducted to test if a mixed population of particles encoded with different DNA sequences could respond independently and selectively in the presence of competing DNAzymes. Two fluorescent particles containing two different DNA sequences were synthesized; one labelled with a fluorescein dye (via a fluorescein-thymidine [FlrT] phosphoramidite) and the other labelled with a rhodamine dye (via a rhodamine-thymidine [RhT] phosphoramidite). Conveniently, micron sized fibers (bundles of cylinders) could be imaged via light microscopy with 25 nm spheres below the resolution limit contributing to diffuse background fluorescence of much lower intensity than the fibers. The red and green fluorescent particles were mixed together and treated with two different DNAzymes (D-1 and D-2) each complementary to one of the dye labelled particles. Introduction of the DNAzyme selective for the sequence within the green particle shell (D-1) resulted in green fluorescent cylinder formation with no observable red fluorescence (FIGS. 8B-8E). Conversely, only red particles react with the DNAzyme selective for the sequence within their shell (D-2). This is confirmed by the absence of green fluorescence in the images of these cylinder structures and the appearance of red fluorescent cylinders. See FIGS. 8F-8I. Finally, when mixed with D-1 and D-2, both spheres in the mixture reacted, causing the formation of structures containing both red and green fluorophores. See FIGS. 8J-8M. These studies provide evidence supporting the conclusion that truncation of the DNA is a necessary requirement for phase transition and is indeed sequence selective. This experiment is possible because the two amphiphiles are chemically similar except for the information encoded in their respective DNA sequences. This makes each particle type in the mixed population independently addressable, a feature not easily accessible to systems designed to respond to non-informational stimuli such as temperature, light, or pH.

Figure 9A:
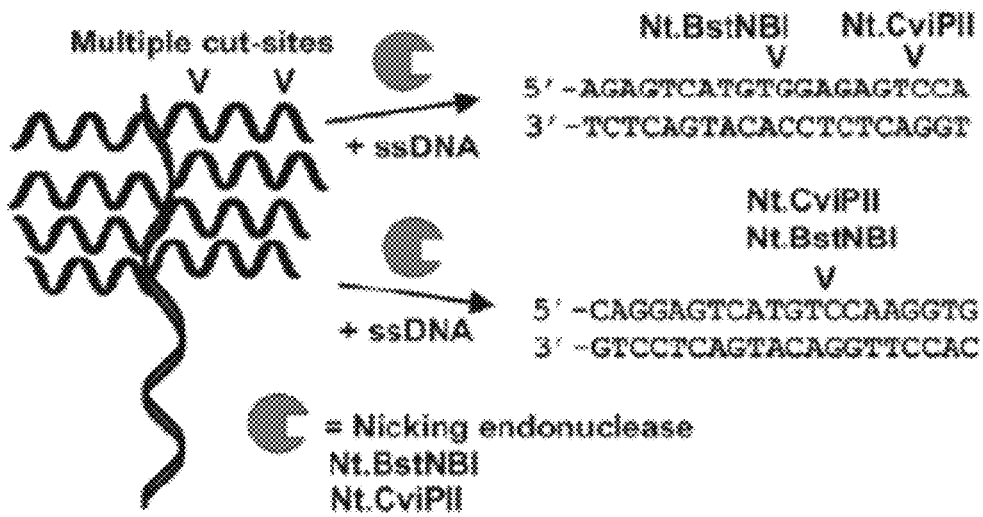
FIG. 9A depicts DNA sequences as substrates for nicking endonucleases. Enzymes recognize duplex DNA and cleave at the designated locations in the figure, cutting the shell DNA and releasing the bottom strand.
Figure 9B:
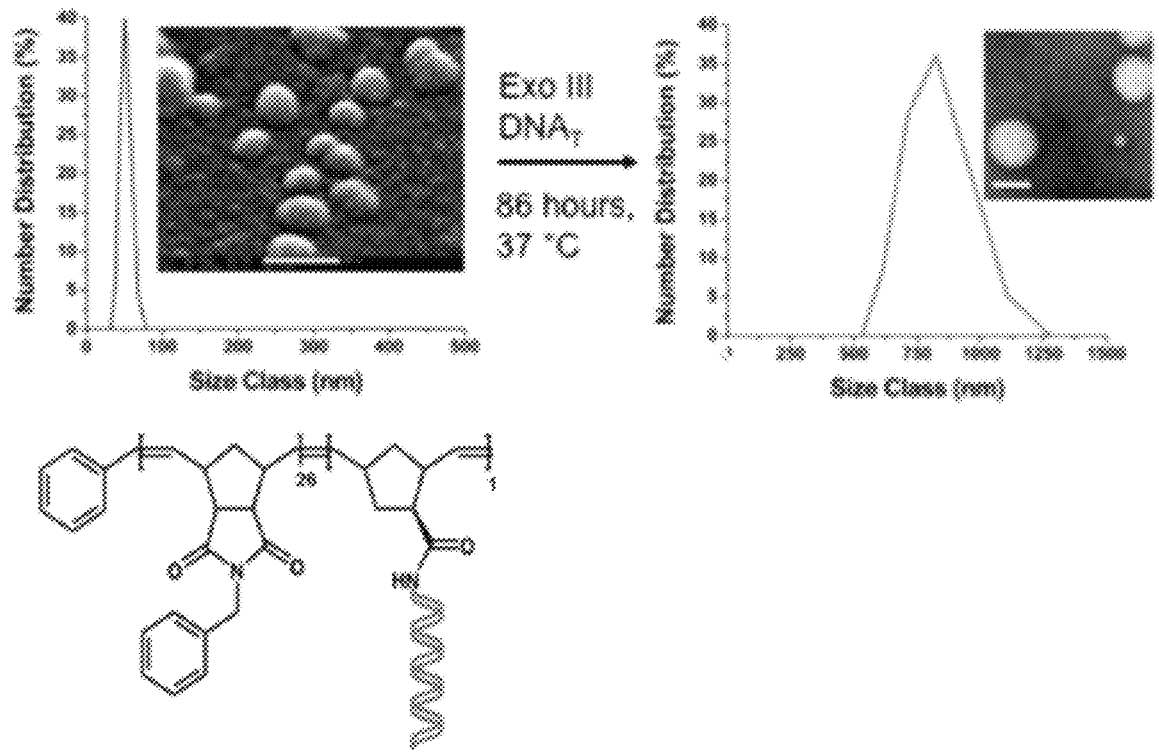
FIG. 9B depicts a copolymer, singly modified with one ssDNA shown in chemical structure below graph (mass of copolymer confirmed by light scattering) which forms spherical micelles (DLS and SEM shown). Upon treatment with Exo III and $DNA_T$ complementary to the shell DNA, degradation occurs in the shell, with a concomitant increase in aggregate size (DLS data). TEM data (inset, to right) shows vesicle-like structures. Scale bars: SEM—200 nm, TEM—500 nm. Sequences: AGAGTCATGTG-GAGAGTCCA (SEQ ID NO:10); CAGGAGTCATGTC-CAAGGTG (SEQ ID NO:11).

DNAzymes are single stranded DNA sequences and easily penetrate the single stranded DNA shells of the particles, but there was a concern that this would not be true for larger, globular enzymes. Our initial studies show that enzymes can be used in this way, and we have been able to process particle shells using Exonuclease III observing evidence of a subsequent phase transition. Accordingly, nicking endonucleases are useful to cleave particle shells at a variety of positions and to study these systems as part of our exploration of various phases and the morphology changes. One outcome is the ability to avoid using RNA bases, with significantly reduced sensitivity of these systems to unwanted cleavage reactions during purification, and a simplification of the system in general. Without wishing to be bound by any theory, it is believed that the success with Exo III (FIGS. 9A-9B) indicates that other nucleases operate on the particle shell. However, in cases where the enzymatic approach proves inefficient within polymer brushes, then the DNAzymes continue to work sufficiently for catalytic turnover of the particle shells. With a range of enzymatic strategies in hand for cleaving shells of formed micellar architectures we can explore reversible phase cycling utilizing DNA-hybridization and/or enzymatic ligation strategies.

Conclusion. There is demonstrated herein the utility of DNA as an informational tool for morphology control in discrete, stimuli-responsive, nanoscale polymeric materials[13] This approach is ammenable for extension to a variety of stimuli given the versatility of nucleic acids as molecules capable of multiple modes of selective recognition. In a broader context, the development of generally applicable methods for predictably controlling size, shape and functionality of soft materials at the nanometer length scale is critical for realizing their tremendous potential.[30-39]

REFERENCES FOR EXAMPLE 2

[1] Y. Wang, et al., *Adv. Mat.* 2009, 21:1.
[2] L. Zhang, et al., *Science* 1996, 272:1777.
[3] V. Butun, N. C. et al., *J. Am. Chem. Soc.* 1998, 120:11818.
[4] I. LaRue, M et al., *Macromolecules* 2006, 39:309.
[5] X. Liu, M. Jiang, Angew. Chem. 2006, 118, 3930; *Angew. Chem., Int. Ed.* 2006, 45:3846.
[6] Y. Ishihara, et al., *Chem. Eur. J.* 2007, 13:4560.
[7] J.-H. Kim, et al., *Angew. Chem.* 2007, 119:5881-5884. *Angew. Chem., Int. Ed.* 2007, 46:5779.
[8] Y. Li, et al. Wooley, *Macromolecules* 2008, 41:6605.
[9] D. Roy, et al., *Chem. Commun.* 2009, 2106.
[10] C. Fernyhough, et al., *Soft Matter* 2009, 5:1674.
[11] R. J. Amir, et al., *J. Am. Chem. Soc.* 2009, 131:13949.
[12] N. C. Seeman, *Mol. Biotechnol.* 2007, 37:246.
[13] F. A. Aldaye, et al., *Science* 2008, 321:1795.
[14] K. V. Gothelf, T. H. LaBean, *Org. Biomol. Chem.* 2005, 3:4023.
[15] J. J. Storhoff, C. A. Mirkin, *Chem. Rev.* 1999, 99:1849.
[16] F. E. Alemdaroglu, A. Herrmann, *Org. Biomol. Chem.* 2007, 5:1311.
[17] Y. He, et al., *Nature* 2008, 452:198.
[18] Y. Ofir, et al., *Chem. Soc. Rev.* 2008, 37:1814.
[19] S. Venkataraman, et al., *Nat. Nanotechnol.* 2007, 2:490.
[20] L. M. Adleman, *Science* 1994, 266:1021.
[21] Z. Li, et al., *Nano Letters* 2004, 4:1055.
[22] J. D. Watson, F. H. Crick, *Nature* 1953, 171:737.
[23] T. J. Kelly, Jr., H. O, Smith, *J Mol Biol* 1970, 51:393.
[24] S. W. Santoro, G. F. Joyce, *Proc. Natl. Acad. Sci. U.S.A.* 1997, 94:4262.
[25] J. N. Israelachvilli, et al., *J. Chem. Soc., Faraday Trans.* 2 1976, 72:1525.
[26] S. Jain, F. S. Bates, *Science* 2003, 300:460.
[27] R. Nagarajan, *Langmuir* 2002, 18:31.
[28] P. Hazarika, et al., *Angew. Chem.* 2004, 116:6631; *Angew. Che. Int. Ed.* 2004, 43:6469.

[29] D. Y. Zhang, E. Winfree, *J. Am. Chem. Soc.* 2009, 131: 17303.
[30] D. Smith, et al., *Polym. Rev.* 2007, 47:419.
[31] Y. Geng, P. et al., *Nat. Nanotechnol.* 2007, 249.
[32] A. Kishimura, et al., *Angew. Chem.* 2007, 119:6197; *Angew. Chem. Int. Ed.* 2007, 46:6085.
[33] K. T. Kim, et al., J. C. M. van Hest, *Adv. Mat.* 2009, 21:1.
[34] Y. Xia, et al., *J. Am. Chem. Soc.* 2009, 131:18525.
[35] J. A. MacKay, et al., *Nature Mater.* 2009, 8:993.
[36] R. N. Shah, et al., *Proc. Natl. Acad. Sci.* 2010, 107:3293.
[37] D. Peer, et al., *Nat. Nanotechnol.* 2007, 2:751.
[38] R. Haag, *Angew. Chem., Int. Ed.* 2004, 43:278.
[39] S. Nayak, L. A. Lyon, *Angew. Chem., Int. Ed.* 2005, 44:7686.

Experimental Section

General Methods. All reagents were bought from Sigma-Aldrich and used without further purification except DNA synthesis reagents and modifiers bought from Glen Research and AZCO. Anhydrous toluene and dichloromethane were purified using a Dow-Grubbs two-column purification system (Glasscontour System, Irvine, Calif.)—Pangborn, A. B. et al., *Organometallics* 1996, 15, 1518-1520. (N-glycine)-5-norborene-exo-2,3-dicarboximide was prepared as described by Biagini et al. (*Tetrahedron*, 1995, 51, 7247). (IMesH$_2$)(C$_5$H$_5$N)$_2$(Cl)$_2$Ru=CHPh was prepared as described by Sanford et al. (*Organometallics*, 2001, 20, 5314). Polymerizations were performed under dry dinitrogen atmospheres with anhydrous solvents. All DNA was synthesized on an ABI-391 via standard solid phases synthesis on controlled pore glass supports. Fluorescence measurements were performed with a microplate reader (Perkin Elmer, HTS7000 Plus, $\lambda_{ex}$=485 nm, $\lambda_{em}$=535 nm) using black 96 well plates. Reaction volumes of 100 µL were used in all fluorescence experiments of this type. HPLC purifications of DNA strands were performed on a Clarity 5u Oligo-RP phenomonex column (150× 4.60 mm) with a binary gradient using a Hitachi-Elite LaChrom L-2130 pump equipped with UV-Vis detector (Hitachi-Elite LaChrom L-2420). Gradient: (Solvent A: 50 mM triethylammonium acetate, pH 7.5; Solvent B: 100% methanol; gradient: 10-45% B from 0-28 minutes, 45-60% B from 28-34 minutes, and 60-70% B from 34-40 minutes, Flow rate: 1 mL/min). To confirm DNA molecular weight, MALDI-TOF mass spectrometry was performed on a ABI MALDI Voyager (equipped with ThermoLaser Science, VSL-337ND) using THAP matrix (2,4,6-trihydroxyacetophenone monohydrate) (18 mg), ammonium citrate (7 mg), acetonitrile:water (1 mL, 1:1). Polymer polydispersity and molecular weight were determined by size-exclusion chromatography (PhenomonexPhenogel 5u 10, 1K-75K, 300×7.80 mm in series with a PhenomexPhenogel 5u 10, 10K-1000K, 300× 7.80 mm (DMF)) or (Jordi Gel DVB 1000A, 500×10 mm, (CHCl$_3$)) using a Hitachi-Elite LaChrom L-2130 pump equipped with a multi-angle light scattering detector (DAWN-HELIOS: Wyatt Technology) and a refractive index detector (Hitachi L-2490) normalized to a 30,000 MW polystyrene standard. Particle and DNA concentrations were determined via UV-Vis on a Hitachi U-2810 spectrophotometer. $D_h$ was determined by DLS on a Nano-ZS90 Malvern Instruments. TEM images were acquired on a carbon grid (Ted Pella, INC.) with 1% uranyl acetate stain on a FEI Tecnai G2 Sphera at 200 KV. $^1$H (400 MHz) and $^{13}$C (100 MHz) NMR spectra were recorded on a Varian Mercury Plus spectrometer. Chemical shifts ($^1$H) are reported in δ (ppm) relative to the CDCl$_3$ residual proton peak (7.27 ppm). Chemical shifts ($^{13}$C) are reported in δ (ppm) relative to the CDCl$_3$ carbon peak (77.00 ppm). Mass spectra were obtained at the UCSD Chemistry and Biochemistry Molecular Mass Spectrometry Facility.

Preparation of DNAzyme (D-1) (5'-GGAGAGAGATC-CGAGCCGGTCGAAGGGTGCGA-3', SEQ ID NO:18). A 1 µmol dA-CPG was utilized as the support. The oligonucleotide was synthesized in the standard manner leaving the final base protected with a DMT group. Following cleavage and deprotection by ammonium hydroxide overnight, the oligonucleotide was purified by HPLC (retention time=26 min), treated with acetic acid, followed by solvent removal and characterization by MALDI-MS. Mass calcd: 10029.6; Mass obs: 10040.7.

Preparation of DNAzyme (D-2) (5'-AGCGACAGATC-CGAGCCGGTCGAAGTCGTGAG-3', SEQ ID NO:19). A 1 µmol dG-CPG was utilized as the support. The oligonucleotide was synthesized in the standard manner leaving the final base protected with a DMT group. Following cleavage and deprotection by ammonium hydroxide overnight, the oligonucleotide was purified by HPLC (retention time=26 min), treated with acetic acid, followed by solvent removal and characterization by MALDI-MS. Mass calcd: 9924.5; Mass obs: 9919.3.

Preparation of fluorogenic ssDNA substrate (F-ssDNA) (Fluorescein-5'-TCGCACCCrAGTCTCTCTCC-3'-Dabcyl, SEQ ID NO:20). A 1 µmol 3'-Dabcyl-CPG from Glen Research was utilized as the support, with a 5'-Fluorescein phosphoramidite as the terminus. rA (RNA base) was incorporated as a TOM-protected base. The oligonucleotide was synthesized in the standard manner. Following cleavage and deprotection by ammonium hydroxide/ethanol in 3:1 ratio for 4 hrs, the oligonucleotide was purified by HPLC (retention time=33 min), and characterized by MALDI-MS. Mass calcd: 6670.7; Mass obs: 6674.5.

Preparation of In$_1$ (5'-PEG-PEG-GGAGAGAGACTGGGTGCGA-3', SEQ ID NO:21). A 1 µmol dA-CPG was utilized as the support, with PEGphosphoramidite (C18-spacer, Glen Research) as the 5'-terminus. The oligonucleotide was synthesized in the standard manner. Following cleavage and deprotection by ammonium hydroxide overnight, the oligonucleotide was purified by HPLC (retention time=35 min), and characterized by MALDI-MS. Mass calcd: 6955.2; Mass obs: 6964.1.

Preparation of In$_1$ (5'-TCGCACCCAGTCTCTCTCC-3', SEQ ID NO:22). A 1 µmol dC-CPG was utilized as the support. The oligonucleotide was synthesized in the standard manner leaving the final base protected with a DMT group. Following cleavage and deprotection by ammonium hydroxide overnight, the oligonucleotide was purified by HPLC (retention time=32 min), treated with acetic acid followed by solvent removal and characterization by MALDI-MS. Mass calcd: 5635.7; Mass obs: 5693.1.

Preparation of DNA for particles shown in FIG. 5 (NH$_2$-5'-TCGCACCCrAGTCTCTCTCC-3'-PEG-PEG-Fluorescein, SEQ ID NO:23). A 1 µmol Fluorescein-CPG was utilized as the support. rA was incorporated as a TOM-protected base. The oligonucleotide was synthesized in the standard manner with a 5' amino group (5'-amino modifier 5, Glen Research) at the terminus. Following cleavage and deprotection by ammonium hydroxide/ethanol in a 3:1 ratio for 4 hrs, the oligonucleotide was purified by HPLC (retention time=30 min), and characterized by MALDI-MS. Mass calcd: 7083.7, Mass obs: 7102.4.

Preparation of DNA for particles shown in FIG. 8 as Rhodamine labeled material. (NH$_2$-5'-CC-RhT-CTCAC-GACrAGTCTGTCGCT-3'-PEG-PEG-A, SEQ ID NO:24). A 1 µmol dA-CPG was utilized as the support. rA was incorporated as a TOM-protected base. Rhodamine was incorporated as the dT-TAMRA modified phosphoramidite available from Glen Research: 5'-Dimethoxytrityloxy-5-[N-((tetramethyl-rhodaminyl)-aminohexyl)-3-acrylimido]-2'-deoxy-uridine-3'-[(2-cyanoethyl)-(N,N-diisopropyl)]-phosphoramidite. The oligonucleotide was synthesized in the standard manner, with a 5' amino group at the terminus. Following cleavage and deprotection by 0.05 M potassium carbonate treatment in methanol for 4 hrs, the oligonucleotide was purified by HPLC (retention time=27 min), and characterized by MALDI-MS. Mass calcd: 8385.9, Mass obs: 8425.9.

Preparation of DNA for particles shown in FIG. 8 as Fluorescein labeled material (NH$_2$-5'-CC-FlrT-TCGCAC-CCrAGTCTCTCTCC-3'-PEG-PEG-A, SEQ ID NO:25). A 1 µmol dA-CPG was utilized as the support. rA was incorporated as a TOM-protected base. Fluorescein was incorporated as the dT-Fluorescein modified phosphoramidite available from Glen Research: 5'-Dimethoxytrityloxy-5-[N-((3',6'-dipivaloylfluoresceinyl)-aminohexyl)-3-acrylimido]-2'-deoxy-uridine-3'-[(2-cyanoethyl)-(N,N-diisopropyl)]-phosphoramidite. The oligonucleotide was synthesized in the standard manner, with a 5' amino group at the terminus. Following cleavage and deprotection by 0.05 M potassium carbonate treatment in methanol for 4 hrs, the oligonucleotide was purified by HPLC (retention time=26 min), and characterized by MALDI-MS. Mass calcd: 8237.9, Mass obs: 8229.4.

Preparation of DNA for loading experiment and for calibration curves related to catalysis analysis (DNA-F) (5'-GGAGAGAGACTGGGTGCGA-Fluorescein-3'). A 1 µmol fluorescein-CPG was utilized as the support. The oligonucleotide was synthesized in the standard manner. Following cleavage and deprotection by ammonium hydroxide overnight, the oligonucleotide was purified by HPLC (retention time=26 min), and characterized by MALDI-MS. Mass calcd: 6551.9, Mass obs: 6573.5.

Preparation of (N-Benzyl)-5-norborene-exo-2,3-dicarboximide. 1. To a stirred solution of N-benzylamine (2.85 g, 26.6 mmol) in dry toluene (125 mL) was added 5-norbornene-exo-2,3-dicarboxylic anhydride (4.10 g, 25.0 mmol) and triethylamine (3.83 mL, 27.5 mmol). The reaction was heated to reflux overnight under a nitrogen atmosphere. The reaction was cooled to room temperature and washed with 10% HCl (3×50 mL) and brine (2×50 mL). The aqueous layers were combined and extracted with EtOAc (60 mL). The combined organic layers were dried with MgSO$_4$, filtered and concentrated to dryness giving a pale yellow solid that was recrystallized from ethyl acetate/hexanes to give 1 (4.98 g, 79%) as off white crystals. $^1$H NMR (CDCl$_3$): δ (ppm) 1.07 (d, 1H, CH$_2$, J=9.6 Hz,), 1.42 (d, 1H, CH$_2$, J=9.6 Hz), 2.69 (s, 2H, 2×CH), 3.26 (s, 2H, 2×CH), 4.61 (s, 2H, CH$_2$), 6.28 (s, 2H, CH=CH), 7.25-7.40 (m, 5H, Ar). $^{13}$C NMR (CDCl$_3$): δ (ppm) 42.18, 42.28, 45.13, 47.62, 127.74, 128.48, 135.76, 137.76, 177.48. LRMS (CI), 253.99 [M+H]$^+$. HRMS, expected [M+H]$^+$: 254.1176. Found: 254.1175.

Preparation of (N-acetyloxy-2,5-pyrrolidinedione)-5-norborene-exo-2,3-dicarboximide, 2. To a 25 mL round bottom flask containing (N-glycine)-5-norborene-exo-2,3-dicarboximide, (0.250 g, 1.13 mmol), N-hydroxysuccinimide, (0.220 g, 1.90 mmol), DCC, (0.390 g, 1.90 mmol) and DMAP (0.230 g, 1.90 mmol) was added dry CH$_2$Cl$_2$ (10 mL). The reaction was stirred at room temperature under a nitrogen atmosphere overnight. The reaction mixture was filtered to remove the urea then concentrated to dryness. The residue was dissolved in EtOAc, washed with 10% HCl (3×10 mL), and the organic layer dried with MgSO$_4$. The resulting solution was filtered and concentrated to drynessin vacuo. Recrystallization from ethyl acetate/hexanes gave 2 (0.18 g, 50% yield) as fine white crystals. $^1$H NMR (CDCl$_3$): δ (ppm) 1.51, (d, 1H, CH$_2$, J=9.9 Hz), 1.56, (d, 1H, CH$_2$ J=9.9 Hz), 2.78, (s, 2H, 2×CH), 2.84, (s, 4H, 2×CH$_2$), 3.32, (s, 2H, 2×CH), 4.57, (s, 2H, CH$_2$), 6.30, (s, 2H, CH=CH). $^{13}$C NMR (CDCl$_3$): δ (ppm) 25.49, 37.07, 42.81, 45.51, 47.96, 137.93, 163.12, 168.19, 176.32. LRMS (CI), 318.85 [M+H]$^+$. HRMS, expected [M+Na]$^+$: 341.0744. Found: 341.0743.

Polymer synthesis. A general method utilized in polymerization reactions (see below for preparation) in described in Scheme 2-1 following. For analysis purposes a sample of the first block in the copolymer is quenched prior to addition of the second monomer. This is used to confirm block size and is compared with weight fraction analysis of the copolymer by SEC-MALS.

Scheme 2-1

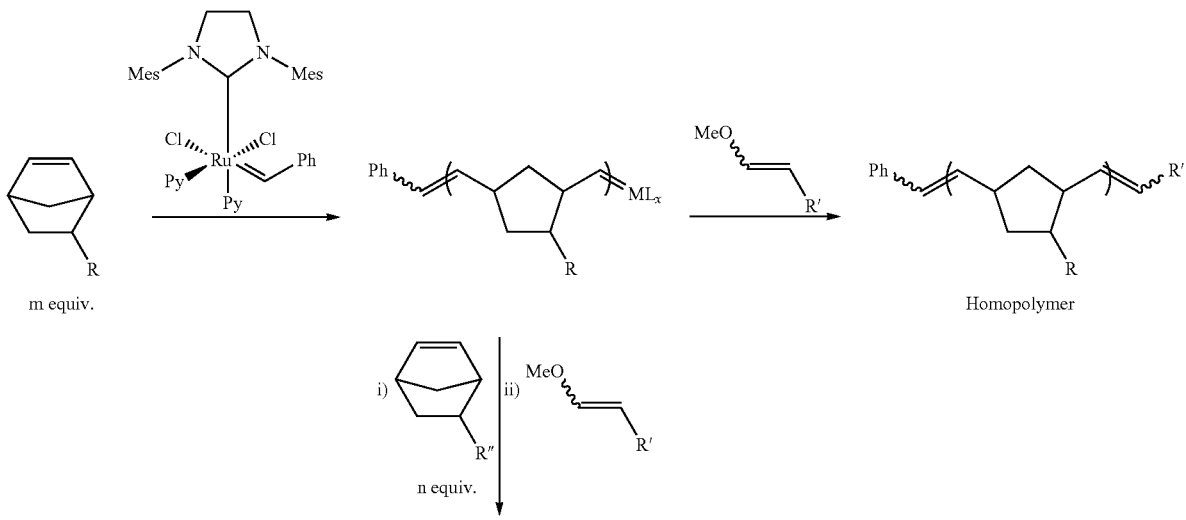

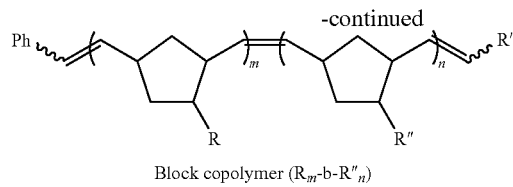

Block copolymer ($R'_m$-b-$R''_n$)

Backbone Copolymer ($1_{38}$-b-$2_{18}$). To a stirred solution of 1 (0.400 g, 1.58 mmol) in dry $CH_2Cl_2$ (2 mL) cooled to −78° C. was added a solution of the catalyst $((IMesH_2)(C_5H_5N)_2(Cl)_2Ru=CHPh)$ (41.0 mg, 0.00564 mmol) in dry $CH_2Cl_2$ (1 mL) also cooled to −78° C. After 5 min the cold bath was removed and the reaction was left to stir under nitrogen while warming to room temperature. After 40 min a 0.25 mL aliquot was removed and quenched with ethyl vinyl ether. After 25 min the polymer was precipitated by addition to cold MeOH to give the homopolymer (Block A) as an off white solid. To the remaining reaction mixture a solution of 2 (0.164 g, 0.517 mmol), in dry $CH_2Cl_2$ (1 mL) was added. The mixture was left to stir under $N_2$ for 40 min followed by quenching with ethyl vinyl ether (0.100 ml). After 25 min the solution was concentrated to approx. ⅓ the original volume then precipitated by addition to cold MeOH to give the copolymer as an off white solid. $^1$H NMR of the polymer confirms the absence of monomer (no olefin peak at 6.30 ppm) and the presence of broad trans and cis olefin peaks of the polymer backbone at 5.73 and 5.50 ppm respectively. SEC-MALS: homopolymer of 1: Mw=9814, Mw/Mn=1.019, 1=38. Copolymer of 1-b-2: Mw=15380, Mw/Mn=1.023, 2=18.

DNA conjugation. 0.05 µmol of copolymer was dissolved in 0.25 mL of chloroform, followed by addition of 1 equiv. of N,N-Diisopropylethylamine (DIPEA) and 0.2 µmol of HBTU to which 0.1 mL of acetonitrile was added. Freshly synthesized CPG-support-bound-DNA was removed from the capsule and placed in a 1.5 mL Eppendorf tube to which was added copolymer mixture described above. This reaction was shaken at room temperature overnight, deprotected in ammonium hydroxide/ethanol (3:1 ratio) for 4 hrs, and reduced in vacuo to approx. 50 µL.

Spherical micelle formation. To the DNA-brush copolymer in 50 µL of water was added 1 mL of Tris buffered water (20 mM, pH 7.4). This solution was then transferred to a 10,000 MWCO dialysis tubing. Buffer was changed three times, one time per day.

DNAzyme catalysis experiments. Fluorescence was directly measured at time points of 2 min, 5 min, 10 min, and 15 min after adding DNAzyme to F-ssDNA solutions in a 96-well plate. Maximum fluorescence for the DNAzyme (5 nM) added to micellar particles (0.14 g/L) at 15 minutes was set to a value of 1 for normalization of data. Complete consumption of particle bound substrate was confirmed by a calibration curve plotted for fluorescence vs concentration of a fluorescein-modified oligonucleotide (DNA-F—see above for synthesis and sequence). i.e. plateau in resulting curve is due to consumption of substrate not product inhibition. Each assay was repeated three times with error bars representing standard deviation for each time point. Fluorescent product from shell DNA cleavage was measured from supernatant that passed through a 10,000 MWCO spin tube filter. i.e. particles are left behind, and fluorescent product comes through for analysis at each time point.

Phase transition studies. Spherical micelles at 1 µM with DNAzyme (5 nM) were used in studies of phase transitions. The experiments were run in Tris/$MgCl_2$ (20 mM, pH 7.4, $MgCl_2$, 50 mM) solutions at room temperature. TEM grids were prepared at time points as indicated in FIGS. 7A-7F. 4 µL of sample was spotted on the grid for 1 min, and washed with water (8 drops), then stained with 1% uranyl acetate solution in water (3 drops) then wicked away with filter paper. DLS samples were also taken at the same time points, from the same solutions. Phase transition TEM data arising from reversible switching experiments were obtained. Cylinder lengths ($C_L$) reported in FIGS. 7A-7F were determined as the average of multiple TEM images at given time points.

Particle concentration/amount and DNA loading. Particle concentrations were determined by UV-Vis and DNA loading confirmed by a fluorescence experiment as described here. Spherical micelles (3 nmol of DNA—determined by absorbance) was incubated with DNA labeled with fluorescein tag (see above for synthesis of DNA-F) (6 nmol) for 30 min (Tris, 20 mM, $MgCl_2$, 50 mM, pH 7.4) and centrifuged at 14,000×g for 5 min over a 10,000 MWCO spin tube to remove the unbound DNA-F, then washed 5 times with 500 µL buffer and spun after every wash; the flow-through was discarded. This was followed by addition of 1 mL water for 5 min, which was spun at 14000×g for 5 min twice. Flow-through of labeled DNA was collected and concentration calculated by UV-Vis. The amount collected was 2.85 nmol, approximating the original value calculated (3 nmoles) of DNA in solution on micelle.

Characterization of cleaved DNA from micellar particles (FIGS. 5A-5E). The flow-through from 10,000 MWCO centrifugation of cleaved DNA fragments post treatment with DNAzyme was collected and concentrated in vacuo to 50 µL. The product was desalted and characterized by MALDI-MS. Mass calcd: 4187.9, Mass obs: 4194.4.

Uptake and release of coumarin dye: monitoring reversible phase transition via phase dependent encapsulation behaviour. 7-hydroxycoumarin was dissolved in 50 µL of DMSO and diluted in 1 mL water to make a 1 mM solution. This solution was diluted further to 1 µM when added to test solutions. Micelles (0.14 g/L) in buffer (Tris, 20 mM, $MgCl_2$ 50 mM, pH 7.4) were treated with 5 nM DNAzyme for 30 min on a 10,000 MWCO spin tube followed by separation of free dye by centrifugation. $In_1$ (50 nM) was then added to hybridize to the DNA fragment on the particle, and the flow through was analyzed at time points of 2 min, 30 min and 2 hr. $In_2$ (200 nM) was then added for 30 min to hybridize to $In_1$. All reactions were performed on 10,000 MWCO spin tubes and spun at 14,000×g for 5 min and the flow-through analyzed.

This procedure involved experiments consisting of mixing the particles with 7-hydroxycoumarin in solution over a 10,000 g/mol molecular weight cut-off (MWCO) centrifuge tube filter. Following incubation with various inputs, the solutions were spun at 14,000×g and the flow-through collected for spectrophotometric analysis. Uptake of coumarin dye is observed as a decrease in fluorescence, while release or exclusion of dye results in an increase in fluorescence according to the amount in solution free to pass through the filter. A decrease in fluorescence is observed 3 hr following DNAzyme addition, and remarkably, the particles expel dye upon contraction seen as a steady recovery of fluorescence between 2 min and 1 hr following In$_1$ addition. Addition of In$_2$ causes an expansion of particle size as described in FIGS. 6A-6B, together with uptake of dye as evidenced by a decrease in observed fluorescence intensity.

Fluorescence microscopy experiments conducted as shown in FIGS. 8A-8M: General procedure for conducting fluorescence microscopy experiments. 15-20 µL of sample was used for the fluorescence microscope. Micelle/DNAzyme solutions with structures confirmed by TEM and DLS were deposited on glass slides and sealed under a cover slip. The edge of the cover slip was then sealed with nail polish after the sample was dried.

Reagents. DNAzyme (D-1), used in FIGS. 8A-8M: complementary to fluoroscein labeled micelles has the structure 5'-GGAGAGAGATCCGAGCCGGTCGAAGGGT-GCGA-3' (SEQ ID NO:18). DNAzyme (D-2), used in FIGS. 8A-8M: complementary to rhodamine labeled micelles has structure 5'-AGCGACAGATCCGAGCCGGTC-GAAGTCGTGAG-3' (SEQ ID NO:19). DNA in particles shown in FIGS. 8A-8M, as Rhodamine labeled NH$_2$-5'-CC-RhT-CTCACGACrAGTCTGTCGCT-3'-PEG PEG-A (SEQ ID NO:24). DNA in particles shown in FIGS. 8A-8M, as Fluorescein labeled NH$_2$-5'-CC-FlrT-TCGCAC-CCrAGTCTCTCTCC-3'-PEG-PEG-A (SEQ ID NO:25).

Example 3

Multienzyme Responsive Micellar Nanoparticles

Introduction. The development of techniques for programming nanoparticles to respond to specific stimuli is essential if they are to be used in biomedical applications such as targeted drug delivery or diagnostics. Of these stimuli, enzymes are especially attractive as they propagate an amplified response catalytically and can be highly substrate specific. Depending on the design and intended function of the nanoparticles, they could respond in a number of ways such as degrading and releasing their payload, changing their morphology, or undergoing modifications that affect their aggregation state, thereby causing a change in the magnetic, fluorescence or other properties of the material. Block copolymer amphiphiles are well-suited for the development of functional stimuli-responsive systems as changes in the chemical or physical nature of the hydrophilic portion of an amphiphile can lead to formation, destruction, or morphology transition of the supramolecular assemblies they form. However, while tunable amphiphilicity for controlling nanoscale assemblies is tremendously useful and has now been demonstrated for a range of stimuli, examples of enzymatically-triggered systems are exceptionally rare. With this in mind, we hypothesized that enzyme substrates could be utilized as hydrophilic head groups in polymeric amphiphiles for formation of enzymatically regulated micellar nanoparticles.

Figure 10:
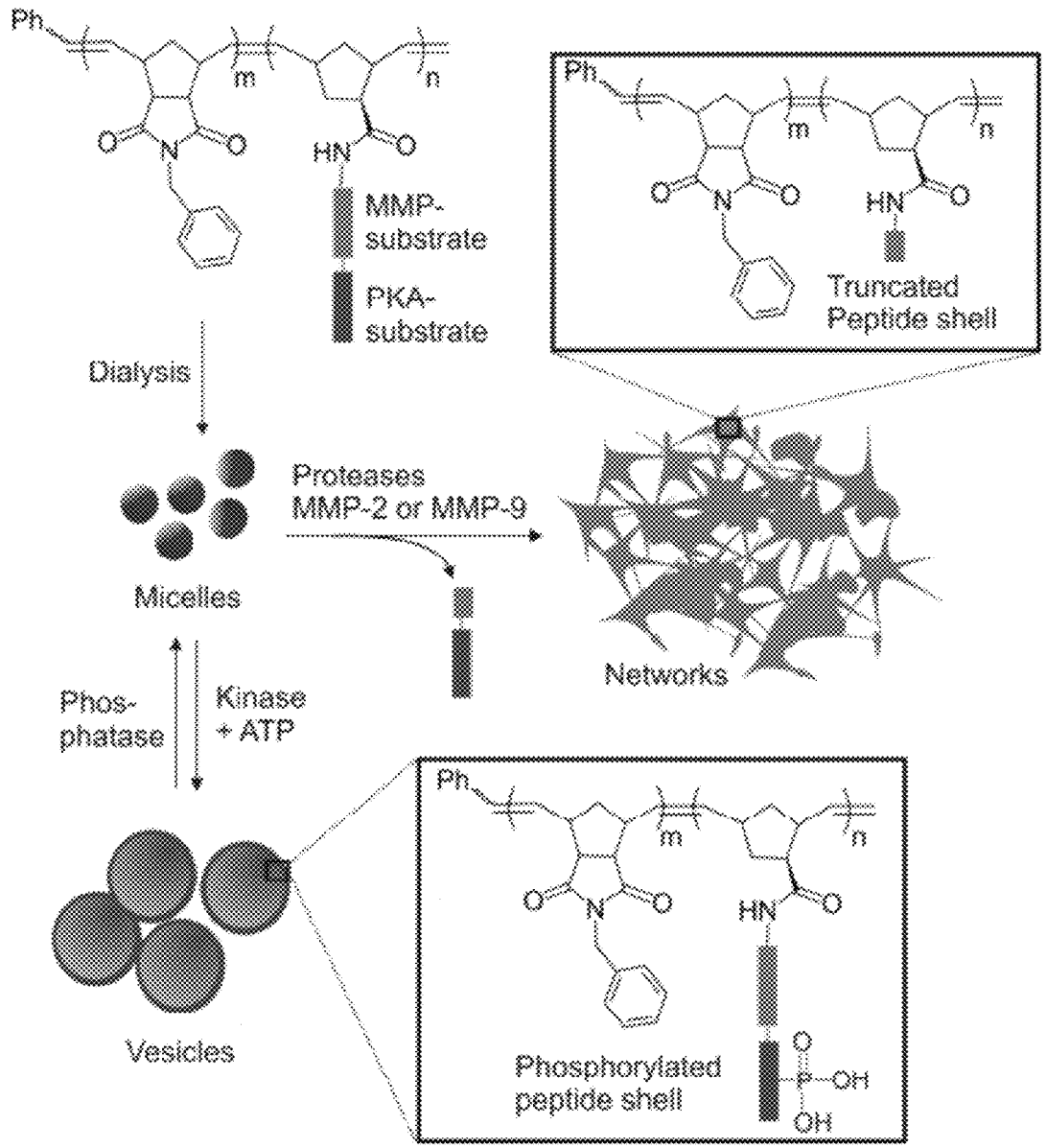
FIG. 10 depicts the observation that peptide-shell polymeric amphiphiles assemble into spherical micelles approximately 20 nm in diameter, with low polydispersity. The arrangement of peptide substrates within the micelle corona combined with certain enzymes generates a variety of morphologies of polymeric amphiphile aggregates.

The design consists of amphiphilic copolymers with hydrophilic peptide substrate brushes. The peptides were designed as substrates for four different cancer-associated enzymes; protein kinase A (PKA), protein phosphatase-1 (PP1), and matrix-metalloproteinases MMP-2 and MMP-9. By incorporating peptides of selected sequences as polar head groups within brush copolymer amphiphiles, enzymatic reactions selective for those substrates could be used to modulate particle morphology and the aggregation behaviour of the copolymer amphiphiles (FIG. 10). This type of modulation is analogous to post translational modification processes utilized to manipulate biomolecules in natural systems. It was reasoned that enzymatic reactions occurring within the shell of the particles would facilitate subtle and/or drastic changes in the steric, bulk, and electrostatic properties of the amphiphiles, and would therefore result in changes to the overall architecture via the establishment of new equilibria for surfactant aggregation. That is, the manner in which surfactants pack together determines the overall morphology of the aggregates formed by them.

Results and Discussion. We employed ring-opening metathesis polymerization (ROMP) in order to demonstrate the feasibility of peptide-programmable polymer aggregation. See FIG. 12A. This method is functional-group tolerant and is capable of generating block copolymers with low polydispersity. Most importantly, this allowed the synthesis of polymers with a well-defined block structure amenable to post-polymerization modification. See FIG. 10. The initial block copolymer, which was characterized by size exclusion chromatography and multiangle light scattering (SEC-MALS), consisted of a benzyl-norbornene type monomer and an N-hydroxysuccinimide monomer for conjugation with peptides. Conjugation reactions were performed by stirring a solid support-bound, freshly synthesized peptide in a solution of the polymer, followed by filtration of unreacted polymer and rinsing of the support. Cleavage from the solid support and deprotection gave the peptide-brush copolymer conjugates following solvent removal (see Supporting Information). The peptide copolymer was dissolved in ethanol (50 µL), diluted with buffered water (1 mL, Tris, 50 mM, pH 7.4), transferred to 10,000 molecular weight cut-off dialysis tubing, and dialyzed against 1 L of buffered water (Tris, 50 mM). The formation of spherical particles 20 nm in diameter was confirmed by transmission electron microscopy (TEM), atomic force microscopy (AFM), scanning electron microscopy (SEM) and dynamic light scattering (DLS: hydrodynamic diameter, D$_h$) (FIG. 12B).

Particles formed with only a MMP shell show limited solubility (most likely due to the small number of peptide monomers incorporated), therefore, one may increase the solubility of the peptide block by incorporation of polyethylene glycol (PEG). We have synthesized both combinations of peptide-PEG polymer blocks. i.e. polymer-peptide-PEG and polymer-PEG-peptide. The syntheses of the necessary PEG monomer is given in Scheme 1 following.

Scheme 1. Synthesis of PEG monomer 7.

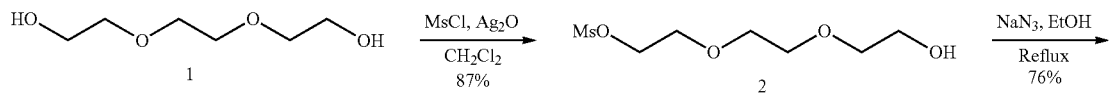

-continued

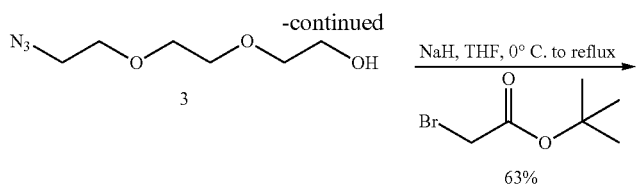

3

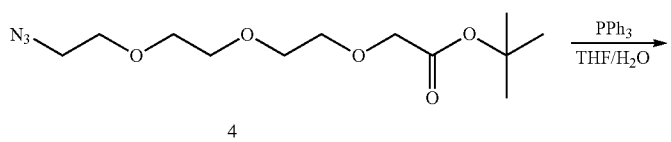

4

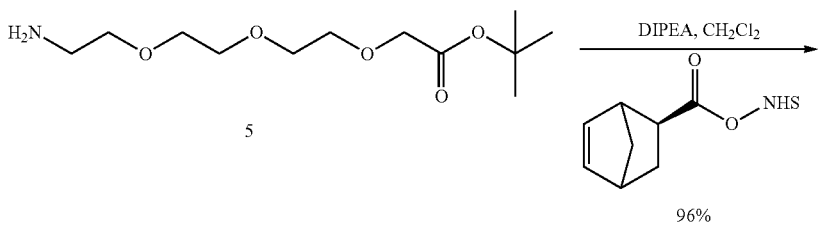

5

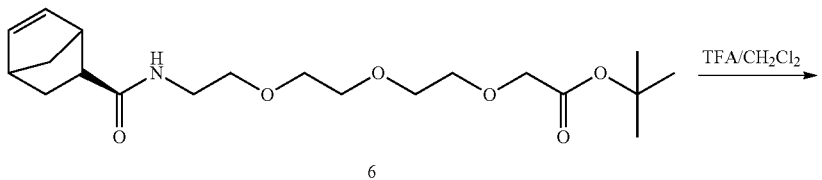

6

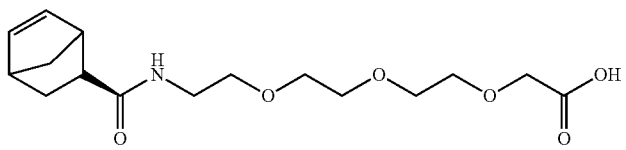

7

Triethylene glycol is treated with mesyl chloride in the presence of silver oxide to give the mono substituted derivative in 87% yield. Treatment with sodium azide gives 3 which is converted to the protected t-butyl ester in 63% yield. Conversion of the azide to the amine is followed by coupling to norbornene NHS ester in 96% yield. Deprotection of the ester with TFA gives the desired monomer 7 which can be further functionalized after polymerization. We chose to use a post-polymerization modification (PPM) strategy rather than polymerizing monomers containing the peptide sequence for two reasons. First, conjugating the peptide to the polymer worked quite well and second, we could make a larger quantity of material using a PPM strategy than a direct polymerization strategy. The syntheses of the two peptide-polymer systems and their particle syntheses are given in Scheme 2 following.

Scheme 2. Synthesis of peptide-PEG polymers 10 and 13 and particles P1 and P2.
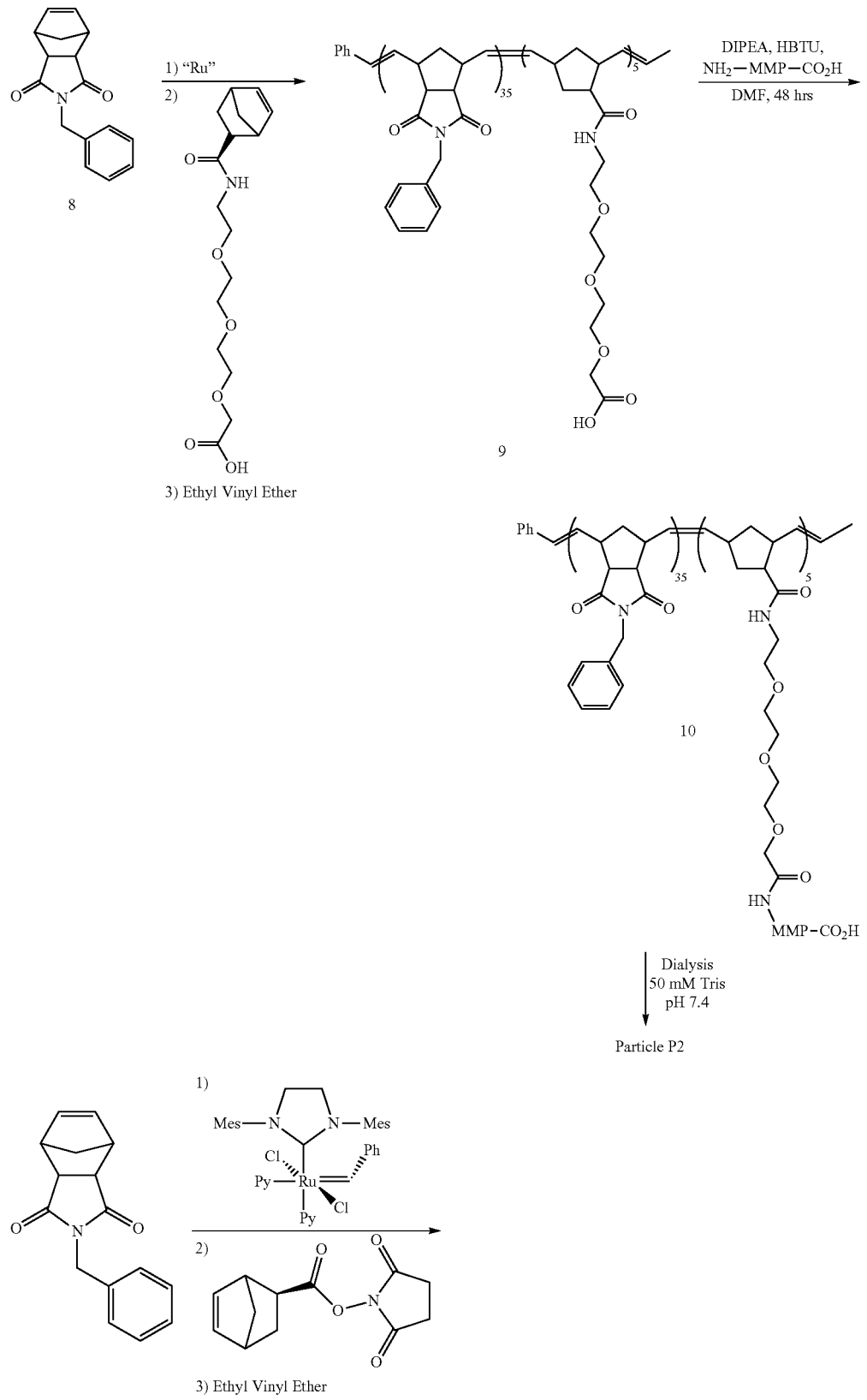

-continued

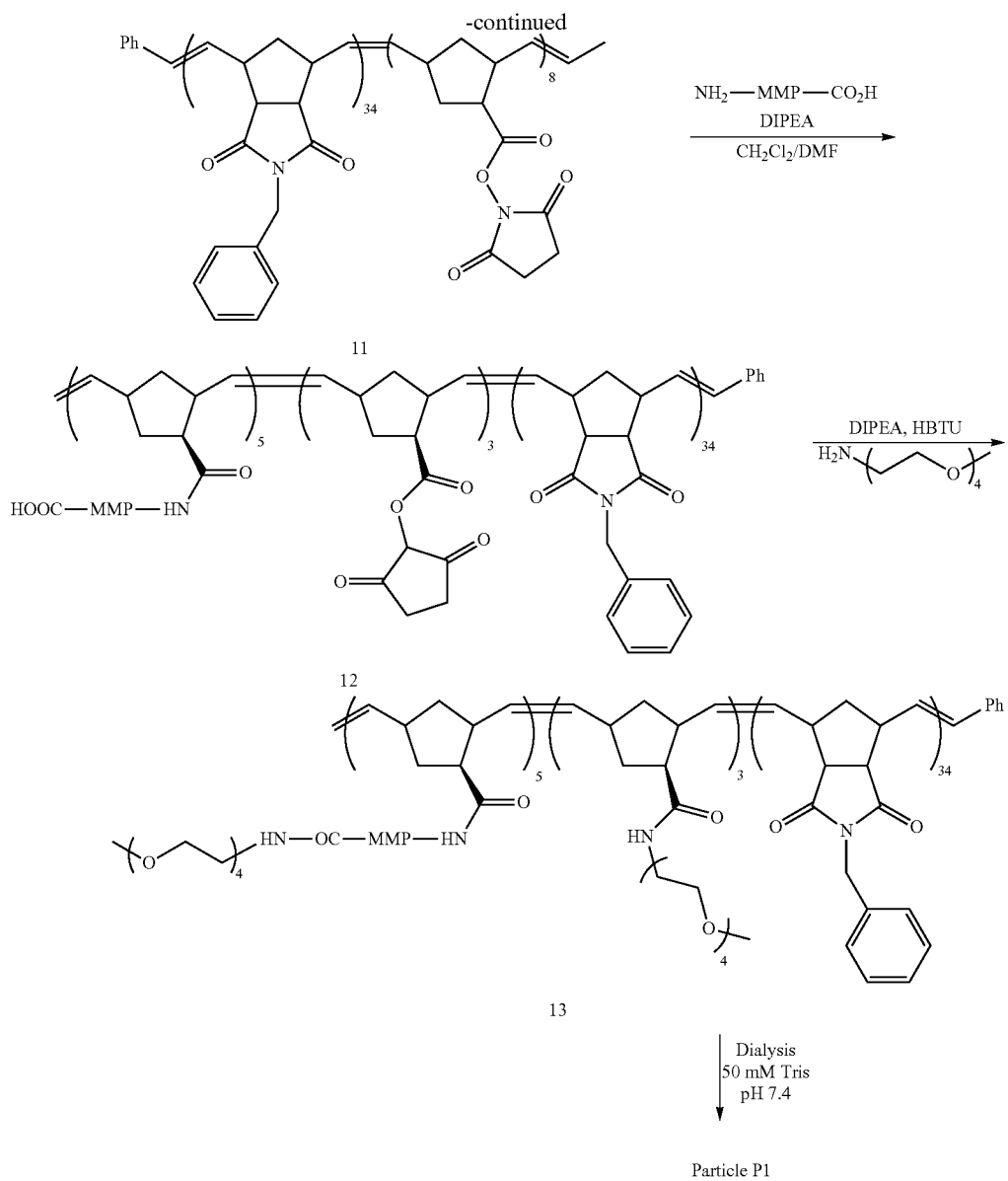

Particle P1

The polymers were characterized by SEC-MALS, and it was determined that they both contain 5 peptide units.

Particles P1 and P2 were characterized by DLS and TEM and observed to form relatively mondisperse solutions with a size of approximately 20 or 30 nm for P1 and P2 respectively.

Figure 11:
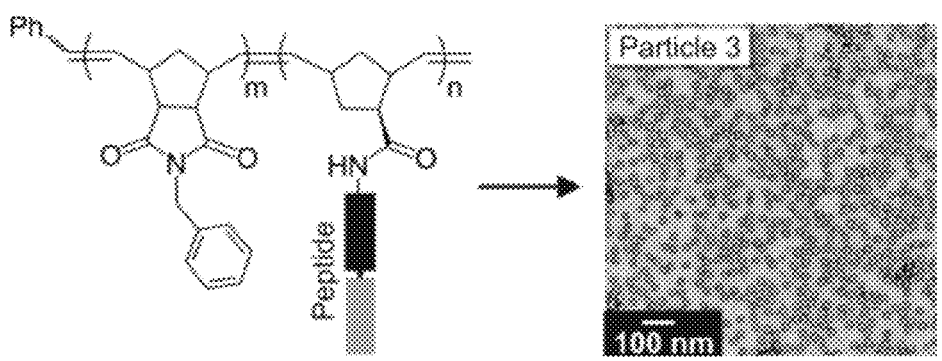
FIG. 11 depicts the chemical structure of a peptide-shell polymeric amphiphile and a photomicrograph of Particle P3. See Table 1.
Figure 13A:
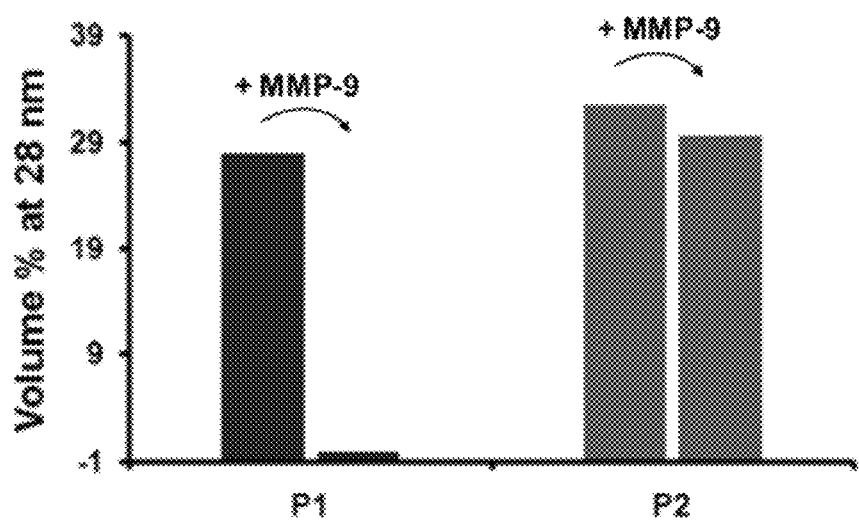
FIG. 13A depicts DLS results of treatment of particles P1 and P2 with MMP-9 at 37° C. for 21 hrs.
Figure 13B:
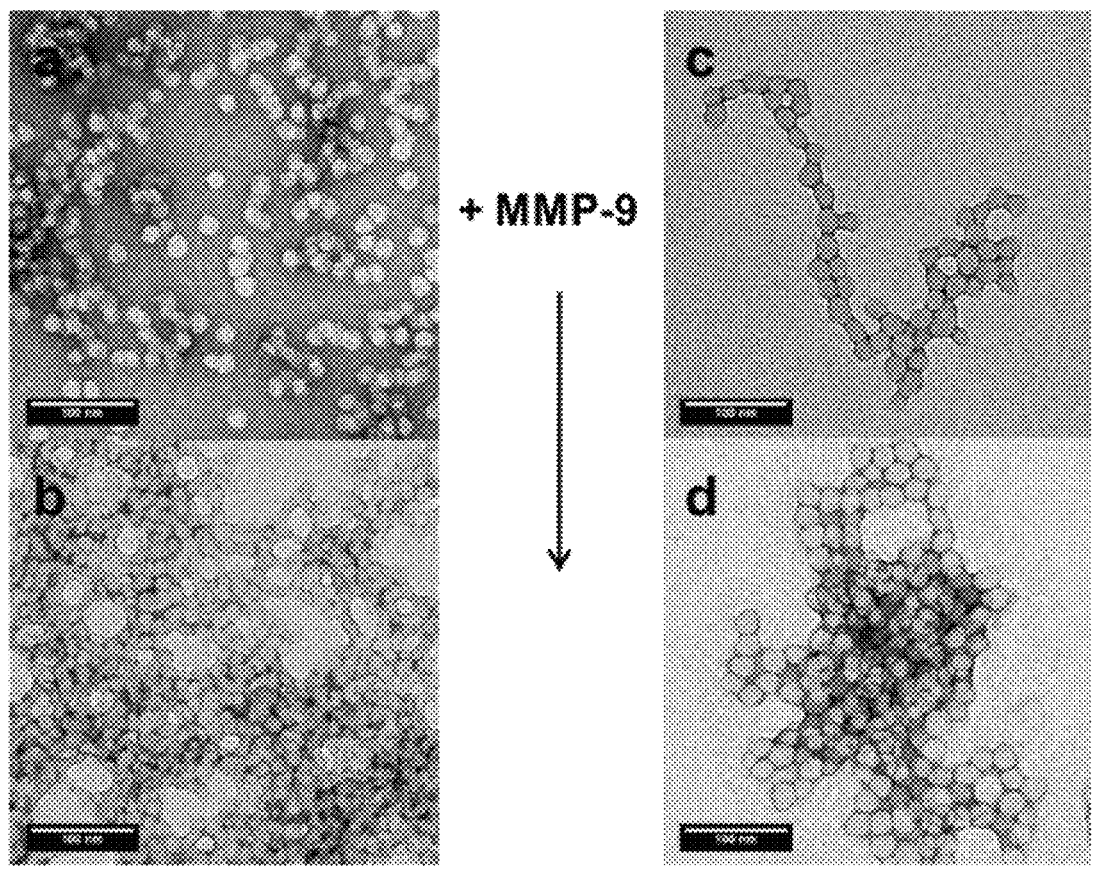
FIG. 13B depicts TEM results for particles P1 and P2 under these conditions. Particle P2 does not undergo a morphology change upon treatment with enzyme (TEM images panel c and panel d) whereas treatment of particle P1 with MMP-9 results in an increase in the hydrodynamic radius (20 nm to ~150 nm) with a broad distribution, while TEM images show an aggregated "network" type structure (panel a and panel b).

Particles P1 and P2 were treated with enzyme MMP-9 at 37° C. for 21 hrs and then characterized by DLS and TEM (FIGS. 13A-13B). Particle P2 does not undergo a morphology change upon treatment with enzyme (TEM images c and d) whereas treatment of particle P1 with MMP-9 results in an increase in the hydrodynamic radius (20 nm to ~150 nm) with a broad distribution, while TEM images show an aggregated "network" type structure (a and b). These results are consistent with those obtained for P3, and P4 described in Table 1 following. FIG. 11 depicts the chemical structure of a peptide-shell polymeric amphiphile and a photomicrograph of Particle P3 as set forth in Table 1. Most notably, that to induce a change in morphology the length of the fragment cut by the enzyme must be longer than the three amino acid segment of MMP. Addition of the PEG unit at the carboxylic terminus of the peptide results in the loss of a much longer fragment causing a larger change in the volume fraction of the hydrophilic block which is now significant enough to result in a morphology change.

TABLE 1

Peptide-shell polymeric amphiphiles assemble into spherical micelles.

| Particle | Peptide sequence[a] | m[b] | n |
|---|---|---|---|
| P3 | H$_2$N-RRASLGKGPLGLAG (SEQ ID NO: 33) | 34 | 6 |

TABLE 1-continued

Peptide-shell polymeric amphiphiles assemble into spherical micelles.

| Particle | Peptide sequence[a] | m[b] | n |
|---|---|---|---|
| P4 | ⟡-NH-GPLGLAGKLRRASLG (SEQ ID NO: 34) | 34 | 6 |
| P1 | ⟡-NH-GPLGLAG-(OCH₂CH₂)₃-OMe | 27 | 8 |
| P2 | ⟡-NH-(CH₂CH₂O)₂-CH₂-C(O)-NH-GPLGLAG | 35 | 5 |

[a]PKA substrate: LRRASLG (SEQ ID NO: 35). MMP substrate: GPLGLAG (SEQ ID NO: 28). Peptides are conjugated to the polymer through the amino termini.
[b]Block sizes estimated from molecular weight determined via SEC-MALS.

Figure 14:
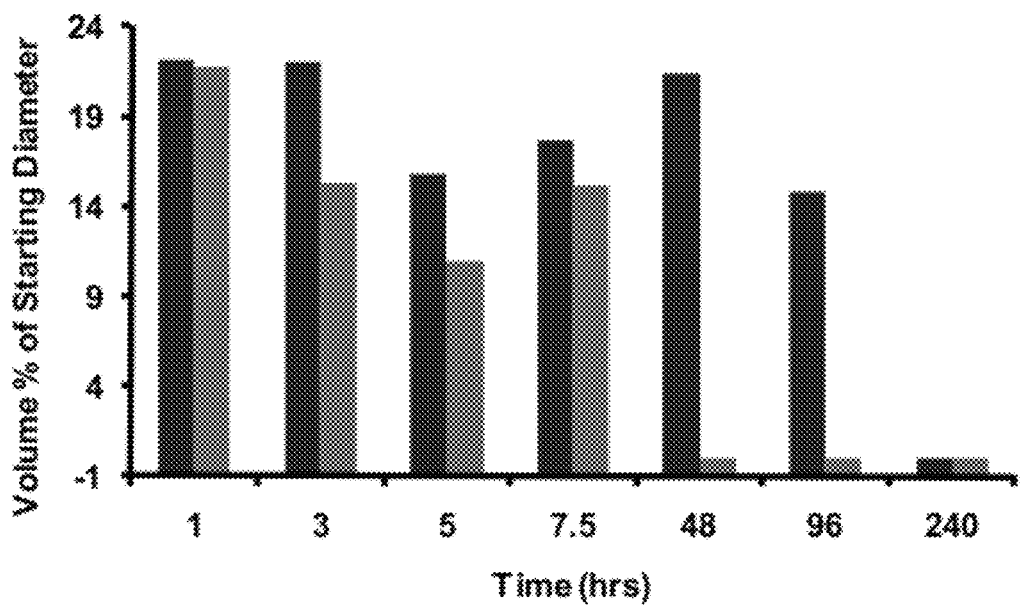
FIG. 14 depicts volume-% of starting diameter as a function of time after treatment of particles P1 and P3 with MMP-9. For each pair of data in the histogram, P1 is to the left (black), and P3 and to the right (gray).

An additional experiment was conducted to probe the effect of the PEG unit on the rate of enzyme cleavage. Particles P1 and P4 were treated with MMP-9 and DLS measurements were conducted at different time points throughout the reaction. FIG. 14 shows the volume percent of the original particles (i.e. loss of starting material). Particle P3 (FIG. 14) has structure

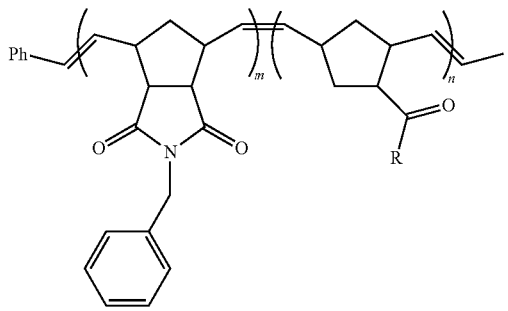

where m=34, n=14, and R=NH-MMP-PKA-COOH. From the plot it is seen that particles P1 which contain a PEG unit take at least twice as long to undergo a change in morphology after treatment with enzyme. This information is useful toward increasing the lifetime of particle systems in the presence of enzymes before they are ultimately degraded. This has implications in drug delivery as particles that can remain intact longer have a greater chance of reaching the desired destination before releasing their drug payloads.

Figure 15:
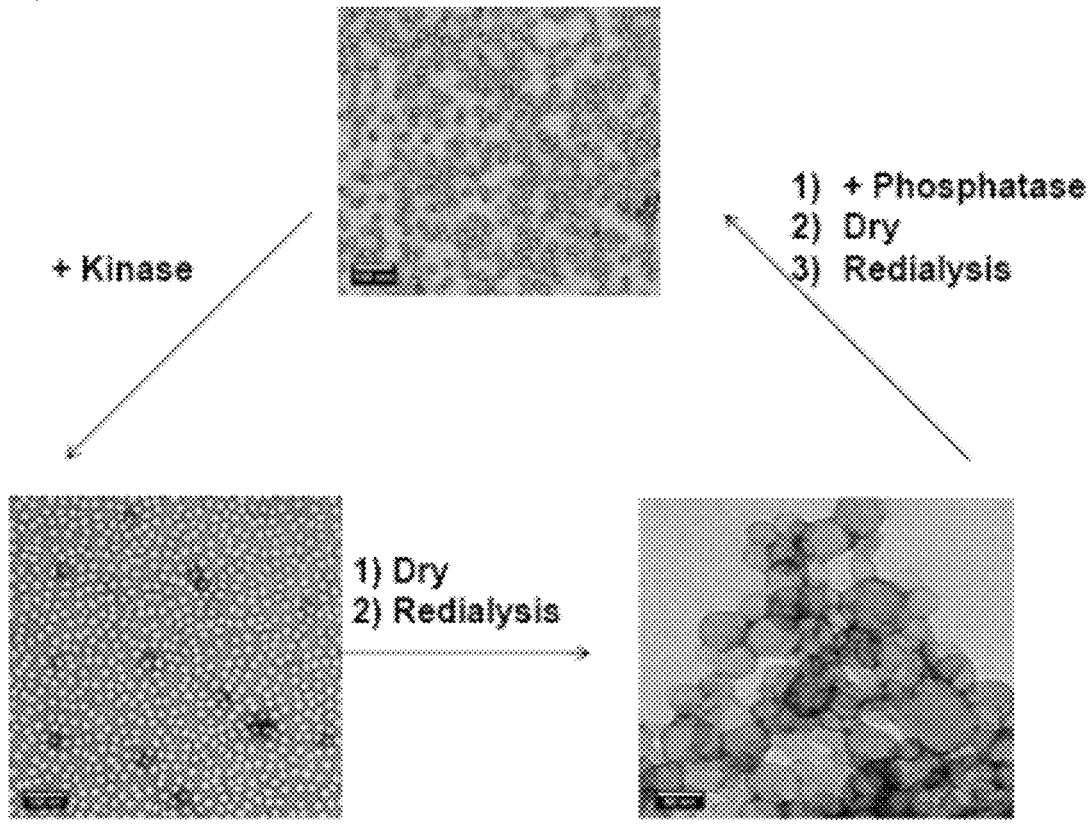
FIG. 15 depicts the response of particle P3 to treatment with kinases (phosphorylation) and phosphatases (dephosphorylation). This is a reversible process as judged by TEM data. Experimental conditions are described below.

In addition to reactions and morphology transitions facilitated by proteases, these materials will also respond to kinases and phosphatases (FIG. 15). These phosphorylations and dephosphorylations are reversible, as are the resulting phase/morphology transitions. To our knowledge these data represent the only example of such enzymatically controlled, reversible phase transition of a polymeric micelle.

Conclusion. Proteins, peptides, and nucleic acids are attractive synthons for the development of functional biomedical materials because they are selective as substrates for enzymes, have inherently specific recognition properties and consist of uniform structural elements. Herein, the concept of enzymatically controlled micellar nanoparticle morphology is introduced utilizing a biomolecule-programmed amphiphilic copolymer approach.

Experimental 2-(2-(2-hydroxyethoxy)ethoxy)ethyl methanesulfonate, 2. To a stirred solution of triethylene glycol 1 (15.0 g, 99.0 mmol) and Ag₂O (25.5 g, 111 mmol) in CH₂Cl₂ 175 mL was added dropwise a solution of mesylchloride (11.44 g, 99.0 mmol) in CH₂Cl₂ 30 mL. The reaction was stirred at room temperature for 48 hrs, then filtered through celite and the filtrate concentrated to dryness to give a clear oil that was purified by column chromatography (10% IPA in ethyl acetate) to give the desired monosubstituted product.[13]

2-2-(2-azidoethoxy)ethoxy)ethanol, 3. To a stirred solution of 2 (5.0 g, 22 mmol) in EtOH 110 mL was added NaN₃ (2.13 g, 33 mmol). The resulting mixture was heated to reflux overnight, then cooled to room temperature and concentrated to dryness. The residue was taken up in CH₂Cl₂ and washed with brine (×2), the organic layer was dried MgSO₄, filtered and concentrated to dryness to give 3 as a clear oil.[13]

Tert-butyl 2-(2-(2-(2-azidoethoxy)ethoxy)ethoxy)acetate, 4. Alcohol 3 (1.0 g, 5.23 mmol) was placed under vacuum overnight and then dissolved in dry CH₂Cl₂ 20 mL, add molecular sieves and cooled to 0° C. NaH (82 mg, 3.42 mmol) was added carefully to the solution and left to stir for 15 min then add the tertbutyl bromoacetate dropwise and let the reaction stir for 4 hrs. TLC shows starting material so add NaH (100 mg) and let stir for 2 hrs. TLC shows starting material so add tert-butyl bromoacetate (0.2 mL) and let stir overnight. The reaction mixture was quenched with H₂O then concentrated to dryness. The residue was purified by flash chromatography 1:1 (hexanes:EtOAc) to give 830 mg, 50% of 4 as a yellow oil.

Tert-butyl-2-(2-(2-(2-aminoethoxy)ethoxy)ethoxy)-acetate, 5. To a 0° C. solution of azide 4 (30 mg, 2.72 mmol) in dry THF 25 mL was added PPh₃ (85.6 g, 3.26 mmol), the resulting solution was warmed to room temperature with stirring under a N₂ atmosphere overnight. Water 1.5 mL was added to the reaction, which was stirred for 6 hrs longer. Dilute the reaction mixture with water and wash with toluene (×4). The aqueous layer was concentrated to dryness to give 5 as a yellow oil.

Tert-butyl-2-(2-(2-(2-((6R)-bicyclo[2.2.1]hept-2-enecarboxamido)-ethoxy)-ethoxy)-ethoxy)acetate, 6. To a stirred solution of 5 (143 mg, 0.514 mmol) in dry CH₂Cl₂ 5 mL was added norbornene NHS ester (121 mg, 0.514 mmol) and DIPEA (132 mg, 1.02 mmol). The mixture was stirred at room temperature under a nitrogen atmosphere overnight. The reaction was concentrated to dryness to give 189 mg (96%) of 6 as a pale yellow oil. A solution of 6 (180 mg) in a 1:1 mixture of TFA/CH₂Cl₂ was stirred to 6 hrs, and concentrated to dryness to give a yellow oil.

General Polymerization Method. The general polymerization method is depicted in Scheme 3-1 following.

Scheme 3-1. General polymerization method.

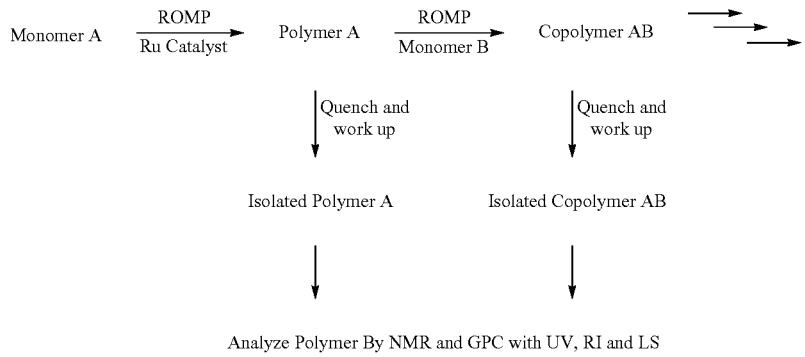

Analyze Polymer By NMR and GPC with UV, RI and LS

To a dried schlenk flask containing monomer A (3.15 mmol) was added dry $CH_2Cl_2$ (2 mL) and the solution cooled to −78° C. To this was added a solution of the catalyst (0.0105 mmol) in dry $CH_2Cl_2$ (0.5 mL) also cooled to −78° C. After 5 min the cold bath was removed and the reaction was left to stir under nitrogen while warming to room temperature. After 40 min a 0.30 mL aliquot was removed and quenched with ethyl vinyl ether. After 25 min the polymer was precipitated by addition to cold MeOH to give the homopolymer (Block A) as an off white solid. To the remaining reaction mixture a solution of B (0.277 mmol), in dry $CH_2Cl_2$ (1 mL) was added. The mixture was left to stir under $N_2$ for 40 min followed by quenching with ethyl vinyl ether (0.100 ml). After 25 min the solution was concentrated to ⅓ it's volume then precipitated by addition to cold MeOH to give the copolymer as an off white solid.

Conjugation of MMP peptide to Polymer 12. To a stirred solution of polymer 11 and peptide in a 2:1 mixture of dry $CH_2Cl_2$ and DMF was added Dipea. The mixture was stirred overnight under $N_2$, and then concentrated to dryness to give a grey powder. Analysis by SEC-MALS give a polymer with a MW of 11240 (5 peptide units added) and PDI of 1.006.

Conjugation of PEG amine to MMP Polymer conjugate 13. In a round bottom flask containing the polymer-peptide conjugate 12, HBTU (41 mg, 0.108 mmol), PEG amine (11 mg, 0.054 mmol) in DMF (2 mL) was added Dipea (19 uL, 0.108 mmol). The mixture was stirred under $N_2$ for 48 hrs then concentrated to dryness to give a grey solid. SEC-MALS: MW (14510 g/mol), PDI 1.014.

Conjugation of MMP peptide to PEG carboxylic acid polymer 10. To a stirred solution of PEG polymer 9 (42 mg, 4 umol) in DMF (2 mL) was added Dipea (7 uL, 5.17 mmol) followed by HBTU (15 mg, 40 umol). After stirring for 5 min the peptide (23 mg, 40 umol) was added and the solution stirred for 48 hrs under $N_2$. Concentrate to dryness to give a brown residue that was dissolved in $CH_2Cl_2$ and precipitated by addition to 10 mL of a cold solution of 1:1 Ether/Hexanes. The precipitate was collected by centrifugation (4000 rpm, 20 min) and dried to give a rubbery solid. SEC-MALS: MW (14000 g/mol, 5 units).

General methods. All reagents were bought from Sigma-Aldrich and used without further purification. Anhydrous toluene and dichloromethane were purified using a Dow-Grubbs two-column purification system (Glasscontour System, Irvine, Calif.).[1] 1-{[(2S)-bicyclo[2.2.1]hept-5-en-2-yl-carbonyl]oxy}-2,5-pyrrolidinedione (2) was prepared as described by Pontrello et al.[2] $(IMesH_2)(C_5H_5N)_2(Cl)_2$Ru=CHPh was prepared as described by Sanford et al.[3]

Polymerizations were performed under dry dinitrogen atmospheres with anhydrous solvents. MMP-2 and MMP-9 were acquired from Calbiochem, as solutions in 200 mM NaCl, 50 mM Tris-HCl, 5 mM $CaCl_2$, 1 μM $ZnCl_2$, 0.05% BRIJ® 35 Detergent, 0.05% $NaN_3$, pH7.0. PKA and PP1 were acquired from NEW ENGLAND BioLabs Inc. as solution in 50 mM NaCl, 20 mM Tris-HCl (pH 7.0), 1 mM $Na_2EDTA$, 2 mM DTT and 50% glycerol and 200 mM NaCl, 50 mM HEPES (pH7.0), 1 mM $MnCl_2$, 0.1 mM EGTA, 2.5 mM dithiothreitol, 0.025% Tween-20, 50% glycerol, respectively. HPLC analysis of peptides were performed on a Jupiter 4u Proteo 90A phenomenex column (150×4.60 mm) with a binary gradient using a Hitachi-Elite LaChrom L-2130 pump equipped with UV-Vis detector (Hitachi-Elite LaChrom L-2420). Gradient: (Solvent A: 0.1% TFA in water; Solvent B: 99.0% acetonitrile, 0.9% water, 0.1% TFA; gradient: 10-80% B from 5-30 minutes, 80-90% B from 30-32 minutes, and 90% B from 32-40 minutes, Flow rate: 1 mL/min). To confirm peptide molecular weight, MALDI-TOF mass spectrometry was performed on a ABI MALDI Voyager (equipped with ThermoLaser Science, VSL-337ND) using alpha-CHC matrix (alpha-cyano-4-hydroxycinnamic acid) (Agilent technologies). Polymer polydispersity and molecular weight were determined by size-exclusion chromatography (Phenomenex Phenogel 5u 10, 1 K-75K, 300×7.80 mm in series with a Phenomex Phenogel 5u 10, 10K-1000K, 300×7.80 mm (0.05 M LiBr in DMF)) using a Hitachi-Elite LaChrom L-2130 pump equipped with a multi-angle light scattering detector (DAWN-HELIOS: Wyatt Technology) and a refractive index detector (Hitachi L-2490) normalized to a 30,000 MW polystyrene standard. Particle concentrations were determined via standard Bradford protein assay method on a Perkin Elmer HTS 7000 Bio Assay Reader. $D_h$ was determined by DLS on a Nano-ZS90-. TEM images were acquired on a carbon grid (Ted Pella, INC.) with 1% uranyl acetate stain on a FEI Tecnai G2 Sphera at 200 KV. AFM images were acquired on a Veeco Multimode Scanning Probe Microscope (Veeco) with silicon probe (TED PELLA, Inc.) on mica substrate. SEM images were acquired on a FEI XL ESEM-FEG (FEI Company) with mica substrate. Fluorescence measurements for CMC determination (see below) were taken on SPECTRAMAX GEMINI EM (Molecular Devices). $^1H$ (400 MHz) and $^{13}C$ (100 MHz) NMR spectra were recorded on a Varian Mercury Plus spectrometer. Chemical shifts ($^1H$) are reported in δ (ppm) relative to the $CDCl_3$ residual proton peak (7.27 ppm). Chemical shifts ($^{13}C$) are reported in δ (ppm) relative to the $CDCl_3$ carbon peak (77.00 ppm). Mass spectra were obtained at the UCSD Chemistry and Biochemistry Molecular Mass Spectrometry Facility.

Preparation of Peptide-1 (PKA-MMP substrate), Peptide-2 (MMP-PKA substrate) and Peptide-3 (MMP substrate). Peptides were synthesized by Fmoc-based solid phase peptide synthesis using preloaded Wang resins. Fmoc deprotection was performed with 20% piperidine in DMF (2×5 min) and coupling of the consecutive amino acid was carried out with HBTU and DIPEA (resin/amino acid/HBTU/DIPEA 1:3:3:4). The final peptide was cleaved from the resin by treatment with trifluoracetic acid (TFA)/Dichloromethane (DCM) (1:1) for 2 h. The resin was washed with DCM and ether and the combined organics were evaporated in vacuo to give an off white solid.

Peptide 1 sequence (PKA-MMP): Leu-Arg-Arg-Ala-Ser-Leu-Gly-Lys-Gly-Pro-Leu-Gly-Leu-Ala-Gly (SEQ ID NO:26): HPLC (retention time=15.00 min). MALDI-MS: Mass calcd: 1466; Mass obs: 1468.

Peptide 2 sequence (MMP-PKA): Lys-Lys-Pro-Leu-Gly-Leu-Ala-Gly-Leu-Arg-Arg-Ala-Ser-Leu-Gly (SEQ ID NO:27): HPLC (retention time=14.66 min). MALDI-MS: Mass calcd: 1537; Mass obs: 1539.

Peptide 3 sequence (MMP): Gly-Pro-Leu-Gly-Leu-Ala-Gly (SEQ ID NO:28): HPLC (retention time=14.8 min). MALDI-MS: Mass calcd: 584; Mass obs: 582.

(N-Benzyl)-5-norborene-exo-2,3-dicarboximide, 1. To a stirred solution of N-benzylamine (2.85 g, 26.6 mmol) in dry toluene (125 mL) was added 5-norbornene-exo-2,3-dicarboxylic anhydride (4.10 g, 25.0 mmol) and triethylamine (3.83 mL, 27.5 mmol). The reaction was heated to reflux overnight under a nitrogen atmosphere. The reaction was cooled to room temperature and washed with 10% HCl (3×50 mL) and brine (2×50 mL). The aqueous layers were combined and extracted with EtOAc (60 mL). The combined organic layers were dried with $MgSO_4$, filtered and concentrated to dryness giving a pale yellow solid that was recrystallized from ethyl acetate/hexanes to give 1 (4.98 g, 79%) as off white crystals. $^1$H NMR ($CDCl_3$): δ (ppm) 1.07 (d, 1H, $CH_2$, J=9.6 Hz,), 1.42 (d, 1H, $CH_2$, J=9.6 Hz), 2.69 (s, 2H, 2×CH), 3.26 (s, 2H, 2×CH), 4.61 (s, 2H, $CH_2$), 6.28 (s, 2H, CH=CH), 7.25-7.40 (m, 5H, Ar). $^{13}$C NMR ($CDCl_3$): δ (ppm) 42.18, 42.28, 45.13, 47.62, 127.74, 128.48, 135.76, 137.76, 177.48. LRMS (CI), 253.99 [M+H]$^+$. HRMS, expected [M+H]$^+$: 254.1176. Found: 254.1175.

2-(2-(2-hydroxyethoxy)ethoxy)ethyl methanesulfonate, 3. To a stirred solution of triethylene glycol (15.0 g, 99.0 mmol) and $Ag_2O$ (25.5 g, 111 mmol) in $CH_2Cl_2$ 175 mL was added dropwise a solution of mesylchloride (11.44 g, 99.0 mmol) in $CH_2Cl_2$ 30 mL. The reaction was stirred at room temperature for 48 hrs, then filtered through celite and the filtrate concentrated to dryness to give a clear oil that was purified by column chromatography (10% IPA in ethyl acetate) to give the desired monosubstituted product.[4]

2-2-(2-azidoethoxy)ethoxy)ethanol, 4. To a stirred solution of 3 (5.0 g, 22 mmol) in EtOH 110 mL was added $NaN_3$ (2.13 g, 33 mmol). The resulting mixture was heated to reflux overnight, then cooled to room temperature and concentrated to dryness. The residue was taken up in $CH_2Cl_2$ and washed with brine (×2), the organic layer was dried $MgSO_4$, filtered and concentrated to dryness to give 4 as a clear oil.[4]

Tert-butyl 2-(2-(2-(2-azidoethoxy)ethoxy)ethoxy)-acetate, 5. Alcohol 4 (1.0 g, 5.23 mmol) was placed under vacuum overnight and then dissolved in dry $CH_2Cl_2$ 20 mL, add molecular sieves and cooled to 0° C. NaH (82 mg, 3.42 mmol) was added carefully to the solution and left to stir for 15 min then add the tertbutyl bromoacetate dropwise and let the reaction stir for 4 hrs. TLC shows starting material so add NaH (100 mg) and let stir for 2 hrs. TLC shows starting material so add tert-butyl bromoacetate (0.2 mL) and let stir overnight. The reaction mixture was quenched with H2O then concentrated to dryness. The residue was purified by flash chromatography 1:1 (hexanes:EtOAc) to give 830 mg, 50% of 5 as a yellow oil.[5]

Tert-butyl-2-(2-(2-(2-aminoethoxy)ethoxy)ethoxy)-acetate, 6. To a 0° C. solution of azide 5 (30 mg, 2.72 mmol) in dry THF 25 mL was added $PPh_3$ (85.6 g, 3.26 mmol), the resulting solution was warmed to room temperature with stirring under a $N_2$ atmosphere overnight. Water 1.5 mL was added to the reaction, which was stirred for 6 hrs longer. Dilute the reaction mixture with water and wash with toluene (×4). The aqueous layer was concentrated to dryness to give 6 as a yellow oil. $^1$H NMR ($CDCl_3$): δ (ppm) 1.48 (s, 9H, $CH_3$), 2.08 (bs, 2H, $NH_2$) 2.88 (t, 2H, $CH_2$, J=4 Hz) 3.40 (t, 2H, $CH_2$, J=4 Hz), 3.65-3.75 (m, 8H, $CH_2$), 4.03 (s, 2H, $CH_2$). $^{13}$C NMR ($CDCl_3$): δ (ppm) 28.20, 41.84, 69.12, 70.36, 70.58, 70.67, 70.70, 70.79, 81.65, 169.77. LRMS (ESI), 264.08 [M+H]$^+$. HRMS, expected [M+H]$^+$: 264.1085. Found: 264.1807.

Tert-butyl-2-(2-(2-(2-((6R)-bicyclo[2.2.1]hept-2-enecarboxamido)-ethoxy)-ethoxy)-ethoxy)acetate,7. To a stirred solution of 6 (143 mg, 0.514 mmol) in dry $CH_2Cl_2$ 5 mL was added norbornene NHS ester (121 mg, 0.514 mmol) and DIPEA (132 mg, 1.02 mmol). The mixture was stirred at room temperature under a nitrogen atmosphere overnight. The reaction was concentrated to dryness to give 189 mg (96%) of 7 as a pale yellow oil. $^1$H NMR ($CDCl_3$): δ (ppm) 1.29 (m, 2H, 1×$CH_2$, CH), 1.70 (d, 1H, $CH_2$, J=8.2 Hz), 1.88 (m, 1H, CH), 2.03 (m, 1H, CH), 2.88 (bs, 1H, CH), 2.91 (bs, 1H, CH), 3.42 (m, 2H, $CH_2$), 3.54 (m, 2H, $CH_2$), 3.6-3.7 (m, 8H, $CH_2$), 3.99 (s, 2H, $CH_2$), 6.05-6.15 (m, 2H, CH=CH), 6.31 (bs, 1H, NH). $^{13}$C NMR ($CDCl_3$): δ (ppm) 28.25, 31.08, 39.42, 41.72, 44.65, 46.45, 47.38, 69.11, 70.18, 70.32, 70.68, 70.80, 81.85, 136.27, 138.27, 169.76, 175.92. LRMS (ESI), 384.21 [M+H]$^+$. HRMS, expected [M+H]$^+$: 384.2381. Found: 384.2379.

1-((2R)-bicyclo[2.2.1]hept-5-en-2-yl)-1-oXo-5,8,11-trioxa-2-azamidecan-13-oic acid, 8. A solution of 7 (180 mg) in a 1:1 mixture of TFA/$CH_2Cl_2$ was stirred to 6 hrs. Concentrate to dryness to give 8 as a yellow oil. $^1$H NMR ($CD_3OD$): δ (ppm) 1.31 (m, 2H, 1×$CH_2$, CH), 1.70 (d, 1H, $CH_2$, J=8.2 Hz), 1.84 (m, 1H, CH), 2.13 (m, 1H, CH), 2.66 (bs, 2H, CH), 3.36 (t, 2H, $CH_2$, J=5.4 Hz), 3.53 (t, 2H, $CH_2$, J=5.4 Hz), 3.6-3.7 (m, 8H, $CH_2$), 4.13 (s, 2H, $CH_2$), 6.14 (m, 2H, CH=CH). $^{13}$C NMR ($CD_3OD$): δ (ppm) 31.34, 40.06, 42.90, 45.26, 47.19, 48.76, 69.20, 70.79, 71.37, 71.67, 71.72, 71.84, 137.48, 139.13, 17, 4.12, 178.64. LRMS (ESI), 328.35 [M+H]$^+$. HRMS, expected [M+Na]$^+$: 350.1574. Found: 350.1575.

Backbone Copolymer ($1_{34}$-b-$2_{14}$). To a stirred solution of 1 (80 mg, 0.315 mmol) in dry $CH_2Cl_2$ (2 mL) cooled to −78° C. was added a solution of the catalyst ((IMesH$_2$)($C_5H_5N$)$_2$(Cl)$_2$Ru=CHPh) (6.03 mg, 0.00829 mmol) in dry $CH_2Cl_2$ (0.5 mL) also cooled to −78° C. After 5 min the cold bath was removed and the reaction was left to stir under nitrogen while warming to room temperature. After 40 min a 0.30 mL aliquot was removed and quenched with ethyl vinyl ether. After 25 min the polymer was precipitated by addition to cold MeOH to give the homopolymer (Block A) as an off white solid. To the remaining reaction mixture a solution of 2 (31 mg, 0.131 mmol), in dry $CH_2Cl_2$ (0.5 mL) was added. The mixture was left to stir under $N_2$ for 40 min followed by quenching with ethyl vinyl ether (0.100 ml). After 25 min the solution was concentrated to approx. 1/3 the original volume then precipitated by addition to cold MeOH to give the copolymer as an off white solid. $^1$H NMR of the polymer confirms the absence of monomer (no olefin peak at 6.30 ppm) and the presence of broad trans and cis olefin peaks of the polymer backbone at 5.73 and 5.50 ppm respectively.

SEC-MALS: (a) Homopolymer of 1: Mw=8553, Mw/Mn=1.019, 1=34; Copolymer of 1-b-2 (I): Mw=11940, Mw/Mn=1.010, 2=14. (b) Homopolymer of 1: Mw=6898, Mw/Mn=1.052, 1=27. Copolymer of 1-b-2 (II): Mw=8891, Mw/Mn=1.024, 2=8. (c) Homopolymer of 1: Mw=8886, Mw/Mn=1.004, 1=35. Copolymer of 1-b-8 (III): Mw=10500, Mw/Mn=1.024, 8=5.

Representative Peptide-Polymer Conjugation Reactions. 1 µmol of copolymer I was dissolved in 1 mL of Dimethylformamide (DMF), followed by addition of 3 equiv. of N,N-Diisopropylethylamine (DIPEA) and 1.5 equiv. of peptide. The reaction was stirred at room temperature for 20 hrs, and precipitated by addition to 10 mL cold methanol followed by centrifugation at 4000×g.

SEC-MALS: PKA-MMP conjugate; MW=19470 g/mol (6 peptide units added), PDI=1.014. MMP-PKA conjugate; MW=77720 g/mol (aggregate of 4 polymeric units containing 5 peptide units), PDI=1.173.

Conjugation of MMP peptide to Polymer II. To a stirred solution of polymer II (30 mg) and peptide (33 mg 2 equivalents) in a 2:1 mixture of dry $CH_2Cl_2$ and DMF was added DIPEA. The mixture was stirred overnight under $N_2$, and then concentrated to dryness to give a grey powder. SEC-MALS: MW=11240 g/mol (5 peptide units added), PDI=1.006.

Conjugation of PEG amine to MMP Polymer conjugate. In a round bottom flask containing the polymer-peptide conjugate, HBTU (41 mg, 0.108 mmol), 2,5,8,11-tetraoxamidecan-13-amine[6] (11 mg, 0.054 mmol) in DMF (2 mL) was added DIPEA (19 uL, 0.108 mmol). The mixture was stirred under $N_2$ for 48 hrs then concentrated to dryness to give a grey solid. SEC-MALS: MW=14510 g/mol, PDI=1.014.

Conjugation of MMP peptide to PEG carboxylic acid polymer III. To a stirred solution of PEG polymer (III) (42 mg, 4 µmol) in DMF (2 mL) was added DIPEA (7 µL, 5.17 mmol) followed by HBTU (15 mg, 40 µmol). After stirring for 5 min the peptide (23 mg, 40 µmol) was added and the solution stirred for 48 hrs under $N_2$. Concentrate to dryness to give a brown residue that was dissolved in $CH_2Cl_2$ and precipitated by addition to 10 mL of a cold solution of 1:1 Ether/Hexanes. The precipitate was collected by centrifugation (4000 rpm, 20 min) and dried to give a rubbery solid. SEC-MALS: MW=14000 g/mol (5 units added), PDI=1.013.

Spherical Micelle Formation. The peptide-brush copolymer was dissolved in 250 µL of DMSO/DMF in 1:1 ratio followed by addition of 750 µL of Tris buffered water (50 mM, pH 7.4). This solution was then transferred to a 3,500 MWCO dialysis tubing and left for 3 days. The buffer was changed three times, once time per day.

Critical Micelle Concentration Determination. A stock solution of pyrene was prepared by adding 1 mg pyrene to 10 mL water followed by sonication for 4 hrs. The solution was then subject to centrifugation at 12,000×g. The pyrene contained in the supernatant was used as the fluorescent probe for this assay and measured by fluorometer SPECTRAMAX GEMINIT™ EM (Molecular Devices). Peptide micelles were diluted serially in 96-well FIA microplates (Greiner Bio-One). Excitation was carried out from in the 300-360 nm wavelength range and the emission was recorded at 390 nm. The slit widths for excitation were fixed at 1 nm. The concentration was plotted on a logarithmic scale and the critical micelle concentrations were determined at the intercept of the two crossing lines where the decreasing surface tension becomes constant.

Enzyme activation. To 0.4 µL of enzyme was added 0.4 µL of a 24 mM p-aminophenyl mercuric acetate solution in freshly prepared 0.1 M NaOH. The enzyme solution was heated at 37° C. for 2 hrs.

Phase Transition Studies via MMP-2, or MMP-9 Addition. MMP-2 (100 µU) and MMP-9 (100 µU) with 20 µM nanoparticles were incubated in Tris-HCl solution (50 mM, pH 7.4), respectively. Reactions were performed at 37° C. for 24 hrs. DLS, TEM, AFM, and SEM samples were taken at the same time points, from the same solutions.

Phase Transition Studies via Protein Kinase A (PKA) Addition. 20 µM nanoparticles with PKA (2500 U), ATP (2 mM) were incubated in PKA reaction buffer (100 µL, 50 mM Tris-HCl, 10 mM $MgCl_2$, pH 7.5) at 30° C. for 24 hrs. DLS, TEM, AFM, and SEM samples were taken at the same time points, from the same solution.

Phase Transition Studies via DMSO Addition. 20 µM nanoparticles with PKA (2500 U), ATP (2 mM) were incubated in PKA reaction buffer (100 µL, 50 mM Tris-HCl, 10 mM $MgCl_2$, pH 7.5) at 30° C. for 24 hrs. The phosphorylated nanoparticles solution was mixed with DMSO solution (final DMSO concentration 40%) at room temperature for 6 hrs. DLS, TEM, AFM, and SEM samples were taken at the same time points, from the same solution.

Phase Transition Studies via Protein Phosphatase (PP1) Addition. 20 µM nanoparticles with PKA (2500 U), ATP (2 mM) were incubated in PKA reaction buffer (100 µL, 50 mM Tris-HCl, 10 mM $MgCl_2$, pH 7.5) at 30° C. for 24 hrs. PKA activity was inactivated at 65° C. for 20 mins. The phosphorylated nanoparticle with PP1 (2.5 U) and $MnCl_2$ (1 mM) were incubated in PP1 reaction buffer (50 mM HEPES, 10 mM NaCl, 2 mM DTT, 0.01% Brij 35, pH 7.5) at 30° C. for 24 hrs. DLS, TEM, AFM, and SEM samples were taken at the same time points, from the same solution.

Protein Kinase A (PKA) activity assay. Radioactive [$\gamma$-$^{32}$P] ATP (4500 Ci/mmole) was obtained from MP Biomedicals LLC. 20 µM nanoparticles with PKA (2500 U), and $\gamma$-$^{32}$P-ATP ($2.22\times10^{-6}$ µmole) were incubated in PKA reaction buffer (100 µL, 50 mM Tris-HCl, 10 mM $MgCl_2$, pH 7.5) at 30° C. for 6 hrs. PKA was inactivated by heating at 65° C. for 20 mins. The phosphorylated nanoparticle with PP1 (2.5 U) and $MnCl_2$ (1 mM) were incubated in PP1 reaction buffer (50 mM HEPES, 10 mM NaCl, 2 mM DTT, 0.01% Brij 35, pH 7.5) at 30° C. for 24 hrs. This solution was then dialyzed for 3 days in 3,500 MWCO dialysis tubing (Thermo scientific). The buffer was changed six times, twice per day. The radiolabeled polymer-peptide products were transferred into scintillation vials, mixed with 4 ml of scintillation cocktail (Fisher SX23-5) and counted using Beckman Coulter LS6500 Multi-Purpose Scintillation-Counter.

Particle Degradation Rate Study. 20 uL of nanoparticles diluted with 60 uL of water were treated incubated with MMP-9 at 37° C. At given time points the solutions were analyzed by DLS, followed by further incubation at 37° C.

CryoTEM. Small (3 µl) aliquots of micelles (Tris buffered water, 50 mM, pH 7.4) were vitrified for cryoTEM via standard, rapid freeze-plunging procedures[7]. Samples were applied to Quantifoil holey grid s (Ted Pella Inc.) that had been glow discharged using an Emitech K350 glow discharge unit and plasma-cleaned for 90 s in an E.A. Fischione 1020 unit. Sample was loaded onto the grids at 4° C. for 30 s then plunged into liquid ethane and transferred into a precooled Gatan 626 cryo-transfer holder, which maintained the specimen at liquid-nitrogen temperature in the FEI Sphera microscope. Micrographs were recorded on a 2K×2K Gatan CCD camera 200 keV under low-dose conditions (~10 e/Å$^2$) and at a nominal magnification of 50,000×.

3D Image Reconstruction. 27 micrographs, exhibiting minimal specimen drift and image astigmatism were recorded at underfocus settings of between 1.69 and 3.13 µm. The pixel size at the specimen was 2.033 Å. The EMAN boxer program (website: blake.bcm.tmc.edu/eman/) was used to extract 1750 individual particle images, each 137×137 pixels in size and to preprocess them as described elsewhere[7]. We next used the RMC procedure[8] to generate an initial reconstructed model at ~30 Å resolution from 150 particle images. This map then served as a starting model to initiate full orientation and origin determinations of the entire set of images by using AUTO3DEM[9]. Corrections to compensate in part for the effects of the microscope contrast-transfer function were performed as described elsewhere.[10,11]

The final 3D map, reconstructed from 1749 particles, was computed out to a resolution of 26 Å with a Gaussian function applied to attenuate the Fourier data smoothly to zero from 19.2 to 16.1 Å. The resolution was estimated to be 26 Å by Fourier-shell correlation analysis [0.5 threshold criterion,[12] but we doubt the reliability of this value owing to the sample inhomogeneity.

REFERENCES FOR EXAMPLE 3

(1) Pangborn, A. B. G., M. A.; Grubbs, R. H.; Rosen, R. K.; Timmers, F. J. *Organometallics* 1996, 15:1518-1520.
(2) Pontrello, J. K.; Allen, M. J.; Underbakke, E. S.; Kiessling, L. L. *Journal of the American Chemical Society* 2005, 127:14536-14537.
(3) Sanford, M. S.; Love, J. A.; Grubbs, R. H. *Organometallics* 2001, 20:5314-5318.
(4) Jeong, S. W.; O'Brien, D. F. *The Journal of Organic Chemistry* 2001, 66:4799-4802.
(5) Romanova, I. P.; Yusupova, G. G.; Balandina, A. A.; Latypov, S. K.; Yakhvarov, D. G.; Nifant'ev, N. E.; Yashunskii, D. V.; Sinyashina, O. G. *Russ. Chem. Bull.* 2007, 56:1495-1500.
(6) Voicu, R.; Boukherroub, R.; Bartzoka, V.; Ward, T.; Wojtyk, J. T. C.; Wayner, D. D. M. *Langmuir* 2004, 20:11713-11720.
(7) Baker, T. S., N. H. Olson, S. D. Fuller *Microbiology Microbiology and Molecular Biology Reviews* 1999, 63:862-922.
(8) Yan X., K. A. D., J. Tang, T. S. Baker *Journal of Structural Biology* 2007, 157:211-225.
(9) Yan X., R. S. S., T. S. Baker *Journal of Structural Biology* 2007, 157:73-82.
(10) Zhang, X., S. B. Walker, P. R. Chipman, M. L. Nibert, and T. S. Baker *Nature Structural & Molecular Biology* 2003, 10:1011-1018.
(11) Bowman, V., E. Chase, A. Franz, P. R. Chipman, K. Perry, T. S. Baker, and T. J. Smith *Journal of Virology* 2002, 76:12250-12258.
(12) Harauz, G., M. van Heel *Optik* 1986, 73:46-156.

Example 4

A Bioorganic Template for Inorganic Nanowire Synthesis

Introduction. Biomolecular assemblies are attractive as nanoscale templates in the hierarchical synthesis of unidimensional inorganic materials. Inherent to these templates are desirable properties including order at the nanometerlength scale and well-defined patterns of selective recognition elements. This is the fundamental source of current interest in assemblies such as viruses and microtubules as the structural base for templating higher order synthetic structure. However, despite the potential for chemically and genetically modifying these structures, a major inherent limitation is that one is largely restricted to the natural amino acids. By contrast, purely synthetic unidimensional organic materials while chemically diverse, lack the programmability and structural order of natural systems. A synthetic strategy is presented, inspired by the versatility of DNA as an informational element in the directed assembly of nanoscale materials. This approach to the hierarchical assembly of inorganic materials is utilized in the synthesis of crystalline gold nanowires.

Figure 16A:
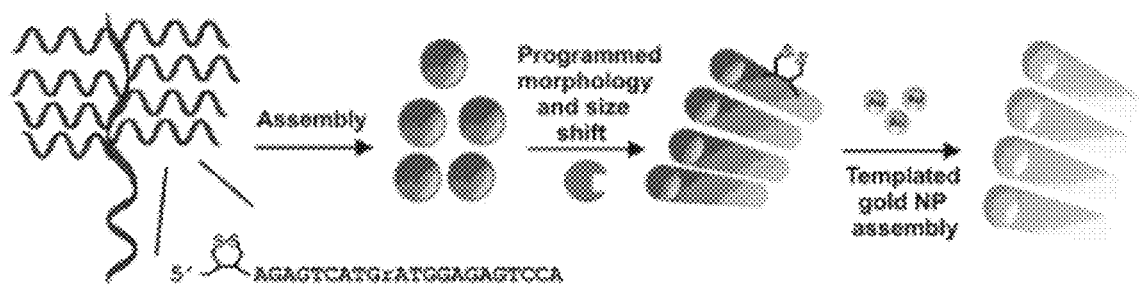
FIGS. 16A-16F depict the finding that flexible cylindrical phase micelles can function as a template for the formation of rigid, crystalline, gold nanowires in several hours at room temperature. Conditions: $2.25 \times 10^{11}$ particles in 15 ml added to cylindrical micelles (1 mM with respect to DNA) for 24 hrs at room temperature. Gold particles are 2 nm in diameter in the data shown here.
Figure 16B:
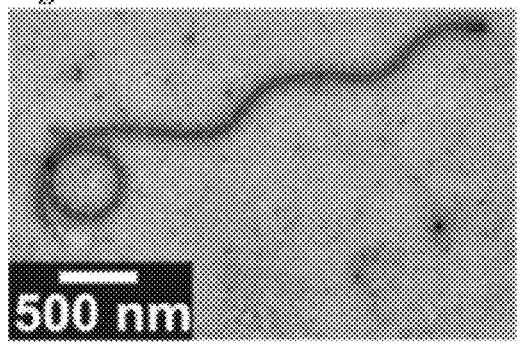
Figure 16C:
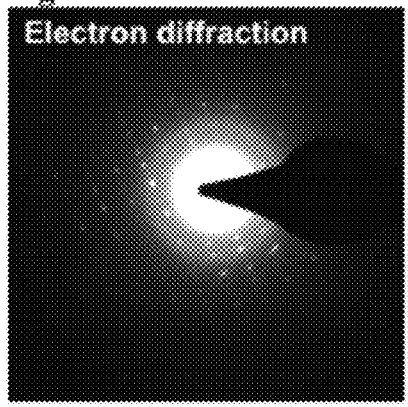
Figure 16D:
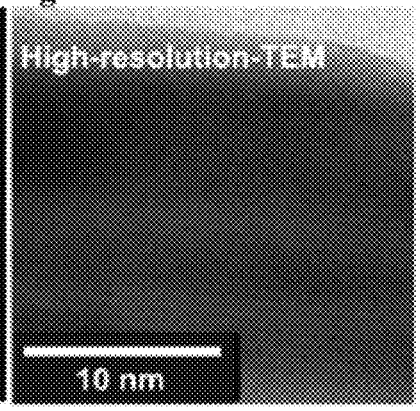
Figure 16E:
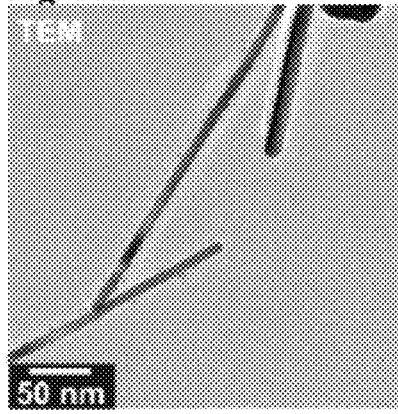
Figure 16F:
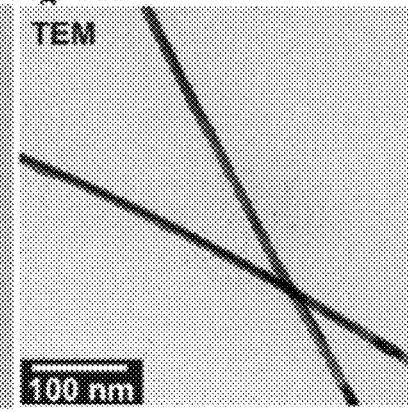

Results and Discussion. We reasoned that with a method for selectively accessing the various phases available to a micellar soft material in hand, one could facilitate the morphology dependent, hierarchical assembly of higher order materials. This stems from the knowledge that ordered biological materials serve as templates in a similar manner. The synthetic strategy used here for soft template construction takes advantage of well-established properties of amphiphilic block copolymers to control aggregate morphology. Therefore, the polar head group of the polymeric amphiphile is a brush of DNA that can be manipulated in a sequence selective fashion to guide the polymeric material between phases (FIG. 16A). Block copolymers were synthesized via ring-opening metathesis polymerization followed by post-synthetic modification with 5'-amino modified DNA oligonucleotides while on solid support. The DNA sequence contains several critical features: 1) Disulphide modification for gold coordination, 2) RNA base, to facilitate sequence selective strand cleavage, 3) 18-member polyethylene glycol modifications to provide steric bulk in sphere generation. Spherical micelles (25 nm in diameter via dynamic light scattering and TEM) are generated via the spontaneous assembly of the DNA-brush copolymers upon dialysis transferring the materials from DMF to buffered aqueous conditions. The ordered cylindrical phase results when these spherical micelles are treated with a DNAzyme evolved to cut the DNA substrate in the shell of the micelle at the single RNA base (rA). This process takes several days at room temperature, or several hours at 40° C. to go to completion. At room temperature the material can be observed as it progresses through to the ordered cylindrical phase giving rise to tangled, or bundled fiber structures via growth of intermediate materials of various dimensions.

Treatment of the defined cylindrical fiber structures with 2 nm citrate stabilized gold nanoparticles and gives rise to crystalline gold nanowires. This phenomenon is extraordinarily selective for the cylindrical phase material as demonstrated by the failure of spherical materials, or intermediate materials to facilitate nanowire formation. Furthermore, brush copolymers were synthesized with a truncated DNA sequence. These amphiphiles give a mixture of poorly defined particles when allowed to assemble at room temperature that do not facilitate templation. Interestingly these materials include toroidal particles that appear to be intermediates toward cylindrical architectures during phase transition. Upon heating this solution to 40 degrees for 4 hours, the cylindrical fiber structures are generated as observed via the enzymatic cleavage of spherical structures. These fibers facilitate the templation reaction. Therefore, whether or not the material is in the ordered cylindrical phase determines if a template exists or not. This implies that this is a process directed by the soft material aggregate morphology and not simply surfactant effects. This is an intriguing and novel phenomenon.

The material was characterized by HR-TEM illustrating atomic resolution, and evidence of twinned lamellae architectures is also observed for similar nanowire structures.

Optimization of this process via dilution of the 2 nm gold particles was performed yielding rough surfaces at very low concentrations. 20 nm gold particles do not undergo this transformation to crystalline wires.

Conclusion. Given the range of options available utilizing DNA sequence recognition, and without wishing to be bound by any theory, it is believed that these materials present an intriguing platform for the templated synthesis of a range of nanoscale materials. For example, the bottom-up approach to one-dimensional nanostructures is of increasing interest for the development of a variety of useful structures including biomolecule functionalized structures for ordered patterning.

Example 5

Drug Delivery Systems

Background and Significance. The dose-limiting side effects associated with many clinically effective chemotherapeutics present a major hurdle in the treatment of cancer and as such there is a need for advanced methods enabling targeted drug delivery.[1,2] The challenge is to develop a material for the targeted delivery of cocktails of drugs and signaling molecules to specific diseased tissue and cell types in a highly targeted manner for treatment and analysis of particular disease states before and during delivery. To date, the vast majority of drug delivery vehicles utilize non-informational stimuli to initiate drug release including, pH changes,[4] temperature changes[5] and the action of poorly selective proteases.[6] We propose a general strategy for synthesizing nanoscale drug delivery vehicles from informational DNA-polymer and/or Peptide-polymer conjugates enabling us to encode and program their formation and their deformation via highly sequence selective response to other nucleic acids and/or enzymes. Materials programmed in this fashion are expected to function as versatile drug and signaling molecule delivery devices capable of responding to patterns of stimuli in a predetermined fashion, a feature not possible in current systems.

Discrete nanoscale materials as programmable devices for theranostics. It is now widely accepted that well-defined, discrete, nanoscale objects have great promise in providing a means for packaging and targeting therapeutics and diagnostics in a single device.[7] Simply, this is because cooperative assemblies of molecules are capable of coupling together complex functionalities such as targeting, signaling, and drugging, not accessible to the individual components alone. Certainly, this size regime and the multifunctional design strategy has been exploited to great effect by viruses. Therefore, there are two common properties exploited by all discrete nanoscale particles for drug delivery and/or imaging: 1) Materials may be packaged on the surface or the core of the particle, along with active targeting groups such as antibodies, peptides, or vitamins. 2) All particles within this size regime seek to take advantage of the relatively leaky vasculature of tumors to deliver drug containing vehicles via the enhanced permeability and retention (EPR)[1] effect. Despite the enormous benefit we stand to gain from incorporating this kind of dual functionality into such materials, there remains a tremendous gap between our exquisite knowledge of small molecule synthesis and synthesis at the nanoscale.[8] Moreover the majority of delivery vehicles are either static structures capable of releasing their contents or degradable systems that release their contents via particle disassembly. There is one key question posed by the proposed research: How do we create a class of materials that report on their environments by changing morphology in predictable ways such that they signal detection events while simultaneously releasing a drug molecule. Detection and delivery are coupled in a new way by this approach to in the following manner:

1) Detection: The stimuli response results in a new intact structure containing reporter molecules (MRI agents, fluorophores) in detectable, high densities but now in a different environment (different relaxation times, quenching effects etc.). Therefore, we have a turn-on response and a stimulated state, without complete particle destruction meaning we maintain high concentrations of localized reporter molecules.

2) Drug delivery: Drugs may be covalently or non-covalently incorporated into the structures and therefore we can generate systems with variable drug release profiles. As the particles undergo aggregation with each other and phase changes they will release drugs either passively or by allowing enzymes to interact with biodegradable groups as they are exposed.

Furthermore, we aim to address a key, fundamental and general issue inherent to non-viral delivery vehicles. Currently we lack the ability to sufficiently control non-covalent assembly and disassembly in aqueous solution conditions where competing interactions make specificity very difficult to achieve and programmable structure control impossible. These assemblies need to be able to operate in aqueous, physiological solutions, making this one of the key hurdles to the development of effective targeted therapeutics and diagnostics via this approach. We will address this issue by utilizing nucleic acids as nanoscale building blocks guiding the assembly of polymers into core-shell micelles. In this manner, materials are encoded with information specifying size, shape and reactivity because nucleic acids are unique molecules in their ability to predictably form complex structures in aqueous solution and interact specifically with enzymes in a sequence selective fashion. Another key deficiency is a lack of effective biomarkers to enable targeting.[9] Our approach will be to couple multiple targeting techniques including incorporation of antibodies specific for overexpressed receptors on cancer cells and groups that may react with enzymes specific to disease states such as proteases. The self-assembly approach to these materials means we can incorporate multiple functional groups of these types into a single entity and therefore couple the fate of the material to multiple stimuli in a facile manner. Indeed, materials capable of responding to patterns of simuli may be the way of the future for disease responsive materials in general. The proposed approach will allow access to this kind of differentially responsive, nuanced material.

Breakthroughs in nanoscale synthesis of functional drug delivery vehicles will have a broad, long-term impact on human health especially related to chemotherapeutics where specificity is desperately needed. The past 100 years of chemical research have provided many tools for the design and synthesis of small organic molecules capable of functioning as therapeutics. We now stand on a new frontier in chemical synthesis and we expect control over nanoscale chemistry will provide opportunities for this cutting edge field of research to expand beyond promise and into the clinic. It should be noted that this proposal is limited to the use of DNA oligonucleotides that are not resistant to nucleases present in vivo. However, many strategies now exist for rendering oligonucleotides resistant to nucleases, including modification of backbones, non-degradable termini, or changes certain bases within sequences. Much of this work has been done to aid in the efficacy of DNA delivery especially in the case of antisense technology. It is therefore anticipated that any adaptation of this approach to in vivo studies in the future will be facile in at least this respect.

Characteristics of Self-Assembly Mechanisms of Block Copolymers and a New Approach to the Design of Stimuli Responsive materials. The proposed research seeks to develop a new kind of stimuli responsive material. The design rationale will take advantage of what is currently known about the types of materials formed from the assembly of amphilphilic block copolymers in aqueous solution. By synthesizing block copolymers of a given molecular weight and weight fraction of each kind of polymer block, hydrophilic or hydrophobic, one can expect to access a given morphology. Simply, we seek to install addressable domains into the shell of self-assembled particles that can allow us to reversibly move between phases by changing the ratio of hydrophilic to hydrophobic blocks in situ. These changes will be encoded into the material, and "decoded" by the action of sequence specific enzymes of various types. Ultimately the enzymes, or combinations of enzymes, associated with given disease states may be used to mold and craft these materials in a programmed manner. Phase transitions between discrete spherical particles and the vesicular phase are mediated in this case by sequence selective DNA interactions.

Studies relevant to Aim #1: To synthesize and characterize nanoscale (20 nm to 1000 nm) polymeric nanoparticles with biomolecule shells and demonstrate predictable size and shape changes initiated by sequence specific interactions. Initial studies have focused on establishing that amphiphilic DNA-brush copolymers can form well-defined nanoparticles via self-assembly, and then undergo sequence selective reactions resulting in changes in the morphology of the material. Work towards achieving Specific Aim #1 has been broken down into two parts: 1) Synthesis and full characterization of a pool of hydrophobic monomers and block copolymers containing conjugation groups for reaction with amino-modified oligonucleotides to form brush copolymers; and 2) exploration of synthetic methodologies for particle formation and structural analysis. As described in the previous section, the rationale for these investigations relies on the observation that block copolymers with varying hydrophilic to hydrophobic ratios phase separate and assemble to generate various structures in solution. These data show that specific interactions at the shell of micellar particles formed from DNA-brush copolymers can be used to change this hydrophilic:hydrophilic ratio and change the aggregation properties resulting in morphology changes.

A set of polymers has been made via ring-opening metathesis polymerization (ROMP[12-14]) and characterized by size-exclusion chromatography (SEC) with multi-angle laser light scattering (MALS) to demonstrate control over the polymer backbone structure. Conjugation of various DNA sequences has been performed followed by dialysis in aqueous media, and the resulting structures characterized by transmission electron microscopy (TEM) and dynamic light scattering (DLS). The synthesis and successful polymerization of hydrophobic monomers (1-5, 9 and 10) were performed to probe properties important in micelle formation with respect to the type of monomers and molecular weight of resulting polymer blocks incorporated into the core of polymeric micelles.[15-19] These monomers have been polymerized to molecular weights ranging from 4000 g/mol to over 100,000 g/mol in several hours with very low polydispersity as determined by SEC-MALS. Importantly, the living nature of ROMP allows sequential addition of monomers to generate block copolymers. Block copolymerizations of hydrophobic monomers such as 1 with 8 and 9 proceed with low polydispersity as confirmed by SEC-MALS. Monomers such as 6 have been synthesized to allow further tuning of polymer solubility and particle formation by adjusting water solubility. These monomers will be of use in future studies with increasing monomer complexity (i.e. drugs, fluorophores, MRI agents). Monomers 7-8 were synthesized to allow conjugation of the polymers to 5'-amino terminated DNA sequences. These conjugation reactions are performed by treating the solid support bound, freshly synthesized oligonucleotide (synthesized on an ABI 394 DNA synthesizer by standard techniques in our laboratories) with a fully characterized block copolymer. Conjugation of single stranded DNA (ssDNA) to copolymers of 1 and 7, results in an amphiphilic brush copolymer soluble in DMF. These DNA-polymer brushes are then characterized by SEC-MALS (data not shown). For example, two PEG-based phosphoramidites and a fluorophore were incorporated by standard phosphoramidite chemistry on controlled pore glass (CPG) solid supports at the 3'-terminus of the DNA oligonucleotide. Therefore, the shell of the particle contains a brush of multiple, hydrophilic, fluorescent DNA strands. Particles are formed via dialysis over several days[19] and are analyzed showing monodisperse 25 nm particles in solution (DLS) and via TEM. These particles may be analyzed, e.g., by atomic-force microscopy (AFM), to further characterize their three-dimensional structure and provide an assessment of their monodispersity and overall morphology given various preparative conditions; e.g. effect of longer dialysis times (>4 days), different buffers (ionic strength, PBS), or annealing (heating and cooling cycles).

While it is not possible to discern their internal structure directly from the microscopy data obtained to date, the size of these particles implies they are core-shell as illustrated. In addition, static light scattering data fit to core-shell models and correlate with dynamic light scattering data. Certainly, DNA is exposed on the surface as evidenced by various hybridization and reactivity studies as will be shown below. However, at this time we are unable to completely rule out the possibility that these structures may be onion-like with internal layers of DNA. Regardless, we now have several systems with various DNA sequences and copolymer compositions each of which generate particles between 20-300 nm depending on relative block length (DNA brush to hydrophobic monomer ratios), overall molecular weight of the copolymers, and length of the oligonucleotide (data not shown). For the systems examined to date, particle formation is independent of oligonucleotide sequence and tolerant of a variety of hydrophobic monomers. Despite the exceptional success we have had in making spherical, monodisperse particles via this method we aim to expand our search of the parameter space to achieve this specific aim. That is, we propose a systematic study of polymer molecular weight and weight fraction of different blocks to examine particle formation. This will be particularly important in optimizing the approach (see Research Design and Methods). The data suggest this will be a fruitful exploration and a necessary one as we explore the viability of this platform and synthetic methodology to nanoscale materials.

Results from our laboratories have demonstrated the principle of DNA sequence selective control over the size and aggregation properties of these materials. A central aim of the proposed study is gaining an understanding of the mechanism of these processes, because despite demonstrating sequence selective control in our studies we need to master predictable aggregation and fully characterize the phase transitions observed. Methods for achieving this are disclosed herein.

There are many different methods for selectively cleaving nucleic acids.[20-22] The work described herein includes studies on catalytic cleavage reactions in order to manipulate the particles via changes in the DNA shell. Many enzymes use DNA as a template and/or a substrate, are readily available and are currently utilized in biochemical settings for manipulating DNA for a range of purposes including detection (e.g. PCR[23,24]) and genetic engineering. Some of these enzymes work on specific sequences within double stranded helices (e.g. restriction enzymes[22]) and some utilize specific secondary structures and/or termini as substrates (e.g. Exonuclease III)[25]. In our studies we chose to use a DNAzyme[26] to cut the DNA brush at a specific RNA base in the DNA sequence. The DNAzyme utilized here[26] is a simple, unmodified oligonucleotide and can incorporate any sequence of interest in regions flanking the active domain. Therefore, modifying it to cut at a given site, and bind to particular sequences within the particles is easily accomplished via solid phase synthesis on a commercial DNA-synthesizer. Given the initial success of this approach, extension to traditional enzymes should be straightforward. The DNAzyme was designed as a complement to the ssDNA in the polymer brush of the shell of the particle which consists of a 19 base long sequence synthesized with an RNA base at the $9^{th}$ position from the 5'-terminus (rA). The conserved catalytic domain of the DNAzyme is positioned across from the RNA base with the cut site. Importantly, in the absence of DNAzyme the particles are stable for many weeks.

Initial experiments to examine the responsiveness of the particles to the DNAzyme involved mixing the particles with DNAzyme in buffer on top of a molecular weight cut off spin filter tube. At given times these reactions were subjected to centrifugation to separate any fluorescently tagged ssDNA product from the particles. This basic protocol was turned into a proof-of-concept DNA detection assay to determine the lowest detectable concentration of DNA via this amplification method.[3,27-34] This assay consists of mixing the particles with an inhibited DNAzyme (DNAzyme hybridized to a blocking, or inhibitor sequence) and adding ssDNA target strands at various concentrations. Centrifugation of these reactions over a molecular weight cut off filter at various times allowed for analysis of the flow-through by fluorescence spectroscopy. In this manner, catalytically amplified detection of pM concentrations of ssDNA was achieved. These experiments, designed to determine the lower limit of detection of the DNA target sequence, confirm that the particles respond to a range of activated DNAzyme concentrations and suggest this process occurs in a selective fashion. This effect is of great importance to the success of the overall proposed strategy as it implies that low concentrations of catalyst are capable of transforming these particles.

ssDNA substrate. To further characterize these materials the kinetics of the DNAzyme with the particle substrate were compared to those with a ssDNA substrate. These experiments confirmed a 40-fold increase in the apparent $k_{cat}$ over that observed for ssDNA substrate with the same DNAzyme. Furthermore, the ssDNA substrate suffers from product inhibition and therefore the DNAzyme is capable of only 1.5 turnovers in our hands[26] as opposed to the observed 400 turnovers in the case of the nanoparticle substrate (2 µM substrate, 5 nM catalyst). These results confirm the catalytic nature of the amplification observed in the detection assay and confirm the efficiency of the DNAzyme in effecting changes at the particle shell. That is, the particles assemble via cooperative interactions and disassemble cooperatively by virtue of high effective DNA concentrations within the particle shell.

Solution phase studies. Initial solution phase studies of the particles were performed to confirm their sizes following formation via dialysis. Morphology changes upon DNAzyme addition were also monitored by dynamic light scattering and by transmission electron microscopy. Upon mixing DNAzyme with the particles a bimodal distribution is observed as they go through the enlargement process via aggregation of the smaller particles into cylindrical structures. These images present an exciting and instructive snapshot of the phase shift process, to be explored in more detail to elucidate the mechanism.

It is interesting to note the uniform 1 µm rod structures observed after two days in the presence of catalytic quantities of DNAzyme. The aligned patterning observed in this panel is presumably a drying effect, however, it is interesting to note they are arranged end to end in this image forming extended lines on the surface of the TEM grid. This complete phase transition from sphere to cylinder is evidence for the viability of this approach, with respect to programmed phase change. A key part of achieving this specific aim will be to learn how to drive these materials further across the phase diagram; to accomplish this a systematic search of parameter space will be conducted. To confirm the sequence selectivity of this process a DNAzyme was synthesized using another DNA sequence chosen to be non-complementary to the original particle and no size change was observed with time (data not shown).

To further test the programmability of these systems a reversible expansion and contraction cycle was designed for the sequential addition of DNA sequences that cut (DNAzyme) and hybridize to (input ssDNA sequences, $In_1$ and $In_2$) the shell of the particle. These processes were monitored by DLS and TEM to observe size changes concurrent with specific DNA interactions. Note, this was performed with larger particles synthesized using a higher molecular weight polymer as part of our investigations into these materials. This reversible control over particle size demonstrates the potential utility of this approach to particle design and the extraordinary control offered by this design. Moreover, it offers the ability to contract larger aggregates to form smaller spherical particles. A major question remaining relates to the actual internal structure of the larger aggregates. Elucidating this will be a key part of the proposed research program as we explore their ability to foster unique imaging capabilities that depend on changes in internal architectures.

Figure 17:
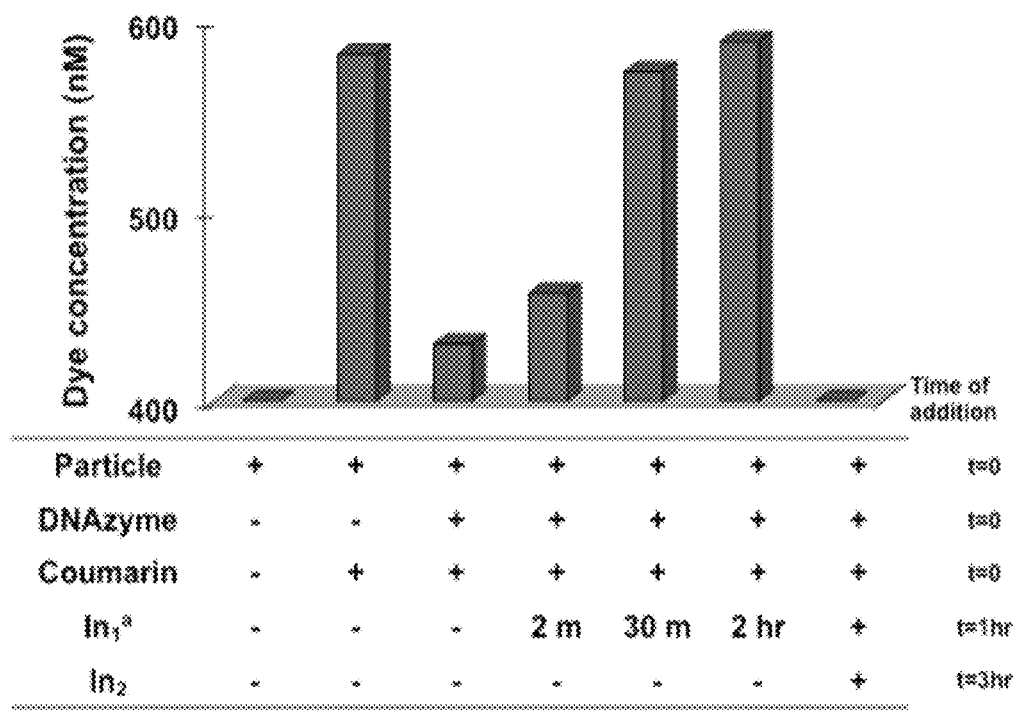
FIG. 17 depicts a histogram and associated table showing uptake and release of coumarin dye via DNA-programmed expansion and contraction of micellar aggregates. Baseline level set at 400 nM coumarin for this experiment determined from calibration curve (data not shown). Nanoparticle (2 μM, from copolymer: $1_{38}$-b-DNA$_{18}$). 5 nM DNAzyme (5 nM). In$_1$ (50 nM) and In$_2$ (200 nM). Coumarin (700 nM) Tris (20 mM), pH 7.4, 200 μL. MgCl$_2$ (50 mM).

Preliminary studies relevant to Aim #3: To demonstrate the controlled release and/or activation of reporter and/or drug molecules from the core of the particles concomitant with the programmed shape change. Preliminary results to determine the uptake and release properties of these materials confirm the plausibility of this approach. 80 nm spheres have been successfully formed using copolymers of $5_{36}$-b-$DNA_8$ (5=coumarin dye modified norbornene monomer). A key preliminary result is summarized in FIG. 17. Particles were placed on a 50,000 molecular weight cut-off spin tube with reagents and inputs as shown in FIG. 17. At the time points indicated, the columns were placed in a centrifuge and spun at 14,000 rpm for 5 min to separate any encapsulated dye from free dye. All measurements were made 3 hr after mixing of components (t=3 hr), except for the $In_1$ and $In_2$ experiments indicated in the table: Measurements were taken at 1 hr 2 min; 1 hr 30 min; and 3 hr for these experiments. Several critical observations can be made from this data: 1) Small particles (particles+coumarin expt.) take up very little dye under these conditions as evidenced by the high dye concentration observed passing through the filter. 2) Expansion of the particles (DNAzyme addition) in the presence of coumarin dye results in a significant decrease in coumarin dye coming through the filter implying encapsulation in the enlarged particles. 3) Upon addition of $In_1$ the particles begin to release coumarin dye as they contract back to small particle sizes.

This data complements the observations of expansion and contraction observed by light scattering measurements. The process of programmed shrinkage is evident when measuring fluorescence increase over time as the particles contract over time from 2 min, to 30 min to 2 hr following addition of $In_1$. $In_2$ has been shown by DLS (previous section) to cause a size increase of these particles by displacing $In_1$ causing a lowering of the amount and bulk of the hydrophilic DNA brush vs the hydrophobic core. Here we observe a concomitant uptake of coumarin dye, giving relative fluorescence indistinguishable from background signal observed in the absence of dye (far left bar). Interestingly, this system has a more efficient uptake profile compared to a single expansion. That is, this system has gone through an expansion-contraction-expansion cycle in the presence of the dye via sequential addition of DNAzyme-$In_1$-$In_2$.

Conclusions. Key Conclusions from Preliminary Studies that Correlate to the Specific Aims include the following.

1) Sequence selective interactions at the shell of these micellar materials effects dramatic changes in aggregation properties leading to overall changes in morphology. In particular, these materials respond to very low concentrations of molecular stimuli as evidenced by DNA-detection studies. Furthermore, these changes are reversible and selective making this a potentially versatile approach.

2) Connecting the change in phase of these materials with differences in their ability to take up materials from their environment is a key part of the proposed research. Certainly, the ability of these systems to take up and release dye is an important demonstration of the proposed concept of drug delivery and signaling capability.

Research Design and Methods. At the core of this approach is the development of a new class of discrete stimuli-responsive materials that report on their environment via shape change. At the five year mark, this research will have made three major contributions to the field of targeted drug delivery: 1) Established a general method for making "smart" biomaterials with very selective recognition profiles facilitated via the use of nucleic acids and/or peptides as structural and functional tools in soft material assembly and disassembly. 2) Utilized DNA as a cell tagging and targeting strategy for translating chemical information from a cell recognition element, into an encoded signal readable by a synthetic device, making this a potentially generalizable approach to tagging cells for detection and drug delivery. 3) Utilized shape-shifting materials in the detection of disease associated proteases in an effort to develop rapid diagnostic tools for disease. Furthermore, harnessing the specific binding properties of biological polymers in the assembly of synthetic nanoscale materials will quickly advance the area of targeted therapeutics by providing an opportunity to synthesize nanoscale objects in a predictable fashion. It is our intention that this program will kick start a long term investigation into the versatility and utility of these materials in treating and diagnosing human disease while contributing in the short term to our knowledge of these materials, in terms of synthesis and utility in selectively killing and detecting cancer cells in vitro. Breakthroughs in nanoscale synthesis of functional drug delivery vehicles will have a broad, long-term impact on human health especially related to chemotherapeutics where specificity is desperately needed.[8,14]

To approach the goals described herein, it is necessary to achieve three targets as described by the three specific aims of this proposal. Herein, the rationale for each specific aim is outlined and sets of experiments are proposed for achieving them.

Specific Aim #1: To synthesize and characterize nanoscale (20 nm to 1000 nm) polymeric nanoparticles with biomolecule shells and demonstrate predictable size and shape changes initiated by sequence specific interactions. Current nanoscale drug delivery systems rely on non-informational methods for triggering drug release.[4,5] Methods are needed for programming the formation of these systems, and for triggering drug release using a robust, informational strategy. We propose such an approach and aim to develop a general encoding strategy for functional, soft biomedical materials. This approach can be divided into two: A) DNA-based systems. B) Peptide-based systems. In part C) of this section we propose an approach to elucidating the mechanism of the shape change observed in our preliminary studies.

A feature common to both the proposed DNA and peptide-based systems is the use of ring-opening metathesis polymerization (ROMP)[12,35] to synthesize the backbone of the polymers for assembly into polymeric nanoparticles. This polymerization method will be used in initial systems because of its high functional group tolerance, low polydispersity and ability to provide well-defined block copolymers. Indeed, our preliminary data demonstrate the kind of control this polymerization method offers. Indeed, a key aspect of this specific aim is to produce particles in the size regime of 20 nm to 300 nm for their relevance and suitability to eventual chemotherapeutic applications.[36] While the proposed research is limited to in vitro cell studies, we aim to target materials that are medicinally relevant in size from the outset. Similarly, our goal is to synthesize polymers within the therapeutically relevant molecular weight range of less than 45 kD allowing renal clearance[37] as the product of micelle breakdown is the basic polymer backbone.[13] This is because these polynorbornene backbones are non-biodegradable, and their in vivo activities remain unknown. Therefore, the molecular weight limit of 45 kD, for the portion of the polymer that is non-biodegradable (i.e. excluding DNA, released drugs, fluorophores etc.), will be adhered to as a design principle. We will exploit the utility of ROMP to generate functionalized polynorbornene backbones in this proposed research because it provides a method for producing complex, multifunctional architectures not currently possible by other methods.[13] Studies in our laboratories currently underway in parallel with this proposed research are aimed at developing highly controlled methods for producing biodegradable, functionalized polymers to provide an alternate method for synthesizing these kinds of devices.

The rationale for the release of drugs upon phase change is that the hydrophobic core may become accessible to solvent during phase transitions, or may be more or less stable after transitions. If this proves sluggish we may adopt non-covalently incorporated drugs within the core of particles. These two approaches are discussed below. The release of dye molecules from a quenched state within the core follows similar lines and in turn, these may also be non-covalently incorporated (FIG. 17).

The rationale for the activation of MRI-contrast agents upon phase change is related to the change in local water concentrations expected during and after phase changes. MRI (Magnetic Resonance Imaging) imposes a magnetic field while exciting nuclear spins with radio frequency pulses. The images obtained are a result of the NMR signal from the protons of water molecules. The signal intensity is a function of water concentration and $T_1$ (spin-lattice) and $T_2$ (spin-spin) relaxation times. Decreases in $T_1$ make signals from protons brighter and paramagnetic metal ions achieve this by interacting with water molecules. Therefore, signal intensity increases with decreasing $T_1$ at the contrast agent location. In addition, previous studies have shown that macromolecular versions of MRI-contrast agents show high relaxivity because of the slow rotational motion of the macromolecule to which they are attached. Some studies have successfully built MRI-contrast agents into the shell of micelles to take advantage of this effect while still exposing the metal center to water. In these cases the water exchange rates are identical to monomeric versions of the metal chelates and thus, these assemblies increase relaxivity significantly. Our approach will be to begin with spherical particles with MRI-contrast agents in the core. Upon phase change the access to water will change and should be concomitant with a change in relaxivity. The slow rotational motion of the macromolecular assembly will be maintained, the high concentration of contrast agent is maintained, but we propose the water exchange rate will change concomitant with stimuli responsive phase shift. Moreover, we expect signal intensity to increase upon going from a well-defined core-shell sphere to the cylinder architectures. This conclusion is supported by observations showing uptake of dye molecules from solution during the expansion/aggregation of these materials (FIG. 17).

Studies towards achieving this specific aim focus on three areas: A) DNA-Based Shape-Shifting Particles. B) Peptide-Based Shape-Shifting Particles. C) Probing the Mechanism of the Observed Morphology Changes A) DNA-Based Shape-Shifting Particles. Rationale: This strategy is predicated on the idea that because a synthetic nucleic acid sequence is made up of a specific and user-defined base code, materials responding to and made of nucleic acids will be susceptible to base pairing rules and hence are encoded with the "language" of DNA.[17,38-40] The origin of this code lies in recognition elements allowing nucleic acids to recognize complements, and/or partial sequence complements. In addition, they are recognized by naturally occurring enzymes, or evolved DNAzymes in a sequence selective or structurally selective fashion. We can therefore, predictably cut and ligate DNA at set locations along the base sequence. Simply, we aim to utilize biochemical tools designed for manipulating DNA, to mold nanoscale architectures. Furthermore, 3-dimensional junctions and shapes are easily formed in a predictable fashion from DNA because of sequence selectivity, making this molecule an incredibly versatile construction tool in nanoscale synthesis.[38] Moreover, by making nanoparticles out of soft materials we can generate structures with architectural features synthetically inaccessible to solid metal, or semiconducting particles.[33,35] Certainly, a source of inspiration for this arrangement is multisubunit nanoscale virus particles that provide a powerful conceptual precedent for the effectiveness of the strategy proposed here—programmed subunit assembly and encapsulation of functional molecules.

Studies demonstrate the proof-of-concept of our DNA-directed approach to soft materials synthesis. The approach is to form micelle particles where the polar head group is a DNA oligomer, and the hydrophobic tail is a synthetic polymer with covalently linked drugs and fluorophores, made using ROMP. This polymerization method allows high drug loading capacity to be achieved because we do not rely on post-polymerization modification of the polymer with a functional (drug/signaling) molecule, and because the functional molecule is not necessarily loaded into the particle in a non-covalent fashion although this is also an option as will be discussed. DNA is readily synthesized in standard or modified form via automated solid phase synthesis (or purchased) and may be conjugated to the block copolymer, post-polymerization on solid support to facilitate ease of purification. DNA-polymer conjugates will be synthesized in organic solvent (THF, DMF) and particles formed via transition to buffered aqueous media via dialysis. The design rationale for this approach to micelles is governed by the principle of core aggregation and exclusion of water achieving a thermodynamically stable structure by dissolving the polar head groups in the aqueous phase. The competing forces of block aggregation, solvent exclusion and covalent linkages between blocks of different polarity are common to all micelle forming processes and block copolymer self-assembly. In this case the polar head group is a polyanion containing a defined sequence of DNA bases, but these structures are otherwise similar in principle to all amphiphilic micellar structures. A feature not accessible to the standard micelle however, is the ability to manipulate hydrophobic to hydrophilic block ratios in a sequence selective manner. Our preliminary studies indicate that this is possible and results in dramatic nanoscale shape-shifting via manipulation of aggregation properties following initial micelle formation.

Experimental Design and Methods: Studies demonstrate the necessary control over polymer and particle synthesis utilizing DNA as an assembly and programming tool. To extend this to functional systems and achieve the specific aim, we have set three goals: I) To replicate our preliminary data with a set of functional monomers within the hydrophobic block; II) to conduct a systematic exploration of parameter space to map out phase changes available to these materials; and III) to extend the DNA-based manipulation of these materials to sequence and structure selective enzymatic reactions as stimuli for phase change. These studies will go hand in hand as reporter molecules can signal phase changes if the approach is successful, giving us handles in addition to TEM and DLS with which to optimize the system.

Goal I). Signaling molecule containing monomers of two classes will be synthesized: 1) MRI contrast agents. 2) Fluorophores. Drug containing monomers of two types will be synthesized: 1) Cytotoxic drugs. 2) Enzyme inhibitors. Exemplary monomers show various linkers connecting the polymerizable group with the functional moieties. The biodegradable linkages (carbamates and esters) have been shown here as examples of the kinds of easily accessible groups we will use to facilitate the release of these monomers upon particle shape change and exposure of these molecules to solution conditions (enzymes etc.). More robust linkages (amides) have been shown for monomers 14 and 15 because MRI-contrast agent ligands are intended to remain attached to the particle. Etoposide (monomer 11) is a member of the podophyllotoxin family of antimitotics and though effective, has significant side effects making it an excellent candidate for targeted drug delivery.[41] Based on the exceptional functional group tolerance of ROMP[42] it is anticipated that these monomers will be amenable to polymerization.[13] Other drugs such as doxorubicin[43] (carbamate linkage to a norbornene group) and methotrexate[44] have functional groups in their structures enabling modification with norbornene, and will serve as alternate candidates for monomer synthesis. Initial studies will focus on polymerizing the etoposide monomer as a block copolymer with NHS-based conjugation monomers. The synthesis of copolymers $11_{30}$-b-$7_{10}$ will provide a starting point to generating particles with comparable hydrophobic to hydrophilic block lengths to those that have thus far successfully generated nanoparticles in our hands. Polymerization efficiency and optimization will be monitored for each monomer by $^1$H NMR by observing the disappearance of resonances associated with monomer alkene protons and the appearance of peaks associated with polymer backbone alkenes. In addition, polymerizations will be monitored by SEC-MALS, allowing determination of molecular weights of each block via termination of an aliquot of the first block just prior to second monomer addition. Weight fraction analysis using UV-Vis and refractive index (RI) detectors as dual concentration detectors in SEC-MALS, will be performed on the final block copolymers to further characterize the final polymers. This method allows us to compare molecular weight and concentration of the whole copolymer to the molecular weight and concentration of each block via Eqn (I) below relating refractive index terms and extinction coefficients:

$$(X_{BlockA})(dn/dc_{BlockA})+(1-X_{BlockA})(dn/dc_{BlockB})= (X_{BlockA})(\epsilon_{BlockA})(1-X_{BlockA})(\epsilon_{BlockB}) \quad (I)$$

wherein dn/dc=specific refractive index increment for given polymer block determined experimentally for each homopolymer; $\epsilon$=extinction coefficient of given polymer determined experimentally at specific wavelengths, L/g·cm; and X=weight fraction of one of the blocks.

The above weight fraction analysis coupled with molecular weight determination using standard SEC-MALS measurements is a critical and powerful method for the development of these systems, making it facile to develop the polymer chemistry required to achieve our downstream aims. Moreover, post-polymerization conjugation of 5'-amino DNA to the polymer will also be monitored using this copolymer weight fraction analysis method and reconciled with the known content of conjugation monomer in the initial copolymer. It is important to note these DNA brush copolymers are not immediately soluble in water or organic solvents such as THF or chloroform. Therefore, DMF will be used for SEC-MALS experiments because it performs as a solvent capable of dissolving the DNA block and the drug-containing block simultaneously while preventing nanoparticle formation.

A part of the studies tests the hypothesis that phase changes will result in changes in the relaxation times of MRI-contrast agents bound within the particle core. Therefore, initial experiments will be performed with polymers of 14 or 15 copolymerized with hydrophobic monomers, and capped with a DNA-brush shell to give structures as shown in our preliminary studies. Upon introduction of the appropriate DNAzyme, any change in $T_1$ of the material will be measured by NMR spectroscopy and compared to initial measurements in the absence of stimuli. Magnetic resonance images can be obtained by standard methods to compare stimulated vs non-stimulated particles. Unlike the other monomers discussed so far, incorporation of the contrast agents within the nanoparticles requires a post-polymerization modification approach. The $Gd^{3+}$ ligands shown (monomers 14 and 15) will be deprotected under acidic conditions post-polymerization as it is expected the free carboxylic acids will negatively affect the polymerization process. Again, the weight fraction analysis via SEC-MALS will play a role in characterizing these deprotected ligands as will $^1H$ NMR. By dialyzing the resulting polymers in the presence of $Gd^{3+}$ salts we expect these excellent ligands will take up the metal to form well-defined stable chelates. In order to drive these ligands into the hydrophobic core of the particles, these monomers will be copolymerized with hydrophobic monomers. If these copolymerizations do not provide enough hydrophobicity to drive formation of phase separated materials a number of excellent chelating ligands are known that are significantly more hydrophobic and could be perfect for incorporation, in particular the hydroxypyridonate (HOPO) ligand system developed by Raymond and coworkers. If successful, these agents will have several significant advantages over other MRI-contrast agent systems: 1) They are macromolecular, increasing signal intensity via slow rotational motion. 2) These proof-of-principle materials have promise as passive targeting agents via the EPR effect because they are nanoscale objects. 3) The MRI-agent is in high local concentration and therefore may result in high signal intensity when collectively switched on, or "turned up". 4) The phase change may be linked to biologically relevant signals (see next section on peptide-based systems) and may be useful in detection concomitant with drug release and in feedback loops capable of reporting drug efficacy.

Goal II). Concurrent with the functional monomer studies described above, we propose to conduct a systematic study on the relationship between various parameters in these self-assembled materials and their constituents. Key questions include: What is the stability of these materials (Zeta potential measurements and DLS)? What is the critical micelle concentration for a given block copolymer structure (fluorescence and DLS)? How does particle size and shape correlate to initial block copolymer size and constitution (DLS, TEM, AFM).

ROMP allows us to explore this parameter space in a facile manner. In addition, we can synthesize (solid support) and purify (HPLC) very well defined oligonucleotides with cut sites at any given portion of the base sequence. Variables of interest include the molecular weight of the overall polymers, length of the hydrophobic block ($\gamma$) length of DNA strands used in the hydrophilic brush ($\alpha$) and length of the conjugation block ($\beta$). Formation of these particles under a range of conditions such as concentration, buffer conditions (ionic strength, buffer type), and temperature will be analyzed using DLS as a screening tool for particle formation, confirming structures by TEM. Materials that form well-defined structures will be further treated with appropriate DNAzymes to determine the phase shifting capability of the material. In this manner, we expect to be able to quickly map out the parameters required to obtain particular shapes, and shape changes. If successful, the signaling molecule studies described in Objective I) will make system optimization a straightforward process.

Goal III). Preliminary data show that low concentrations of stimuli in the form of catalysts can be very effective in manipulating these materials. This effect is of great importance to the success of our overall proposed strategy. Moving beyond the DNAzyme susceptible systems, the DNA sequence built into the shell may contain sequences cleavable by specific endonucleases (nicking enzymes or standard double strand cleavage enzymes[22]) or exonucleases (Exo III).[25] Utilizing these enzymes will allow us to explore the versatility of this approach and extend these systems to enzyme-responsive materials and RNA-free strands for greater robustness. For example, an antibody tagged with a specific endonuclease can be used to initiate drug release and switch-on of signaling molecules. This approach is similar to antibody-directed prodrug therapy (ADEPT) except the prodrug is a nanoscale drug carrier that can target via the EPR effect and signal the recognition event if successful. We seek to test this principle in the proposed studies.

Initial studies using enzymes will focus on synthesizing fluorescently labeled shells and studying enzyme kinetics to assess the viability of this approach. Any concomitant phase changes will be characterized by TEM, AFM and DLS.

B) Peptide-Based Shape-Shifting Particles. Rationale: The design rationale for the peptide-based systems is predicated on the concept that enzymes have preferred substrates and that some enzymes are indicative of particular disease states.[45-49] By incorporating these substrates into the hydrophilic portion of a polymeric micelle, it should be possible to manipulate the ratio between hydrophilic and hydrophobic groups causing a change in overall shape of the material.[50,51]

The initial studies will focus on whether these particles can detect low concentrations of cancer associated matrix metalloproteinases (MMP-2 and MMP-9) and prostate serum antigen (PSA). Indeed, the ability to characterize the catalytic state of enzymes associated with particular diseases is very interesting in its own right and if successful these materials may offer a versatile tool for studying patterns of enzyme activity. In the long term materials such as this can be expected to impact the field of catalomics and perhaps aid in the discovery of novel disease markers and enzyme inhibitors. Towards this goal the proposed studies include studying the effectiveness of protease inhibitors in preventing micelle transformation. The goal being a particle with a shell made of protease substrate and a core laden with protease inhibitors and signaling molecules. These particles set up a feedback loop allowing one to rapidly analyze activity and efficacy of the inhibitor. This exciting possibility is discussed below.

Experimental Design and Methods: Armed with a set of monomers as discussed (Section A, DNA-Based Shape-Shifting Materials), we will study the propensity of peptide based systems to undergo shape changes similar to those observed in our preliminary studies in the context of the DNA-directed approach. Initial studies will utilize dye labeled shells to analyze enzyme kinetics (see section 4 for similar studies utilizing the DNA-based system). Shape, size and aggregation changes may be observed by TEM, AFM and DLS at a range of relevant protease concentrations. In addition, reporter molecules in the core will then be used to indicate if these changes translate into signaling events. The peptides chosen for incorporation into the shell are known substrate sequences for disease-associated proteases: matrix metalloproteinase (MMP-2 and MMP-9) and prostate serum antigen (PSA). These sequences have been synthesized in our lab in addition to fluorogenic peptide substrates of the same sequence that will enable us to examine differences between enzyme activity on the particles and on standard short peptide sequences.

C) Probing the Mechanism of the Observed Morphology Changes. Rationale: The observed shape change may be due to aggregation processes in addition to morphology changes in the absence of aggregation. Elucidating the mechanism will allow system optimization.

Figure 18:
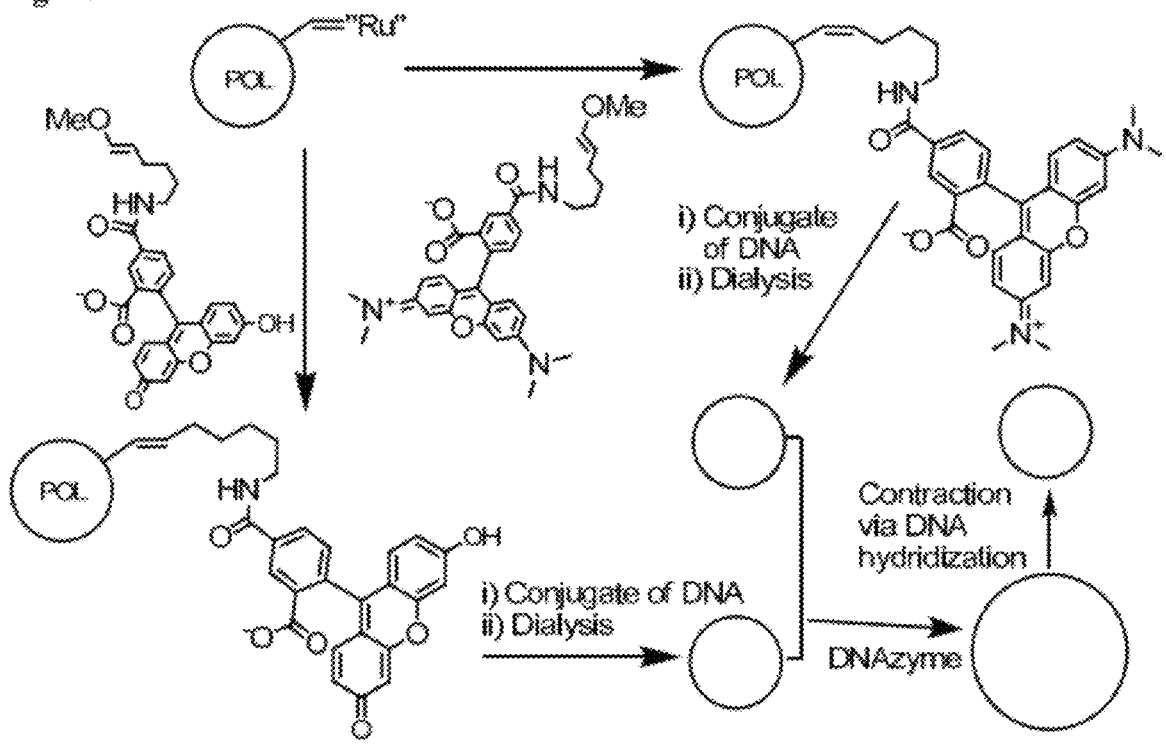
FIG. 18 depicts scheme for fluorescent micelles designed to observe the aggregation of the particles. Novel chain termination agents for ROMP are used to install fluorophores (fluorescein and rhodamine) at the end of each copolymer chain (POL). Mixing the two particles and adding the DNAzyme causes the mixing of the two types of particles, observable by mixing of the fluorophores.
Figures 19A, 19B, 19C, 19D, 19E, 19F:
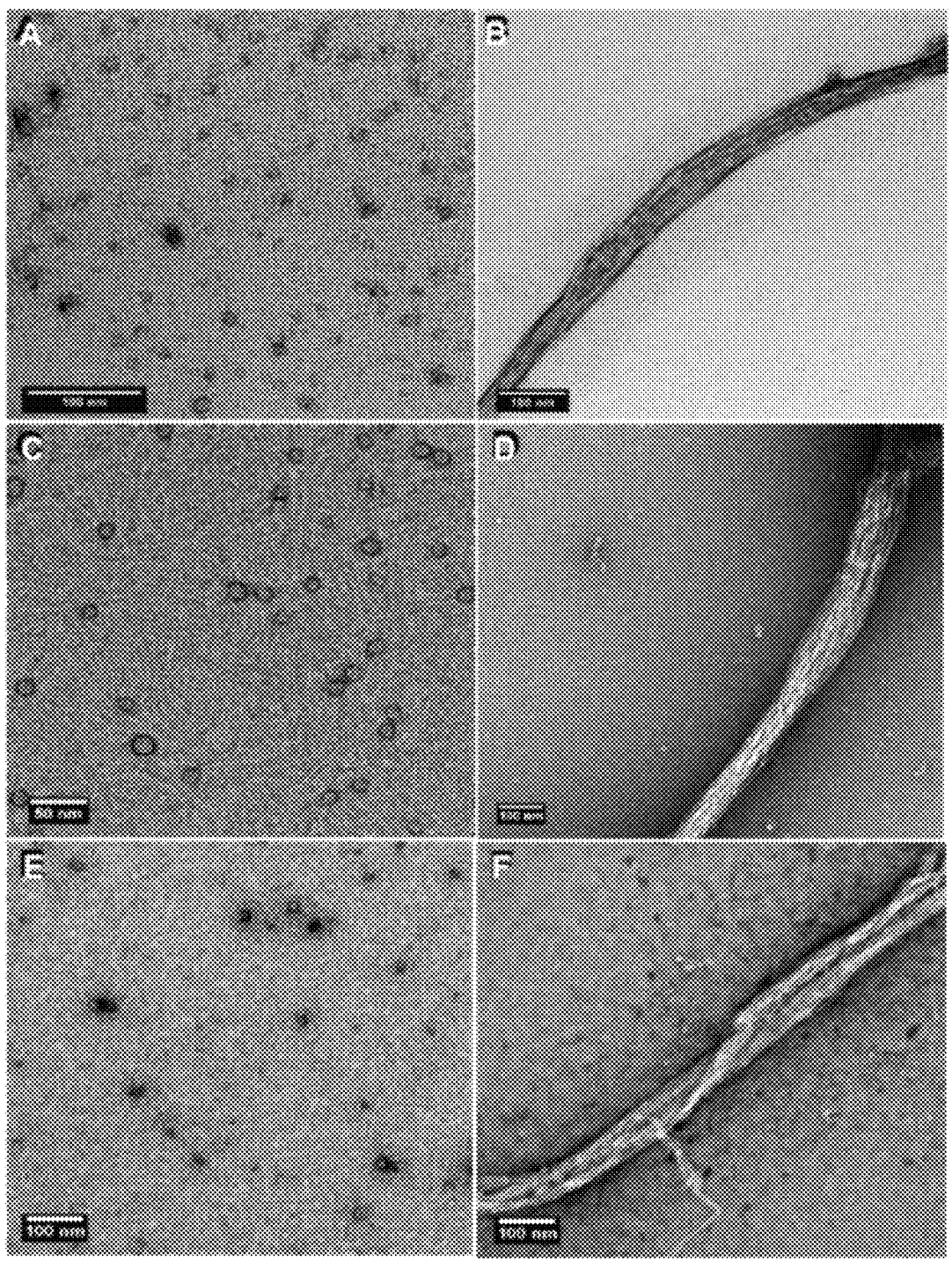
FIGS. 19A-19F depict characterization of spheres and fibers by TEM. Rhodamine-end-capping particles and fibers (FIGS. 19A-19B); dT-Fluorescein particles and fibers (FIGS. 19C-19D); dT-Tamra particles and fibers (FIGS. 19E-19F) are shown. Conditions: Particle DNA (1 μM), DNAzyme (5 nM). Buffer: Tris (20 mM, pH 7.4), MgCl$_2$ (50 mM), room temp.

Experimental Design and Methods: Our preliminary data suggest we have a great deal of control over the size of these particles, likely as a result of lengthening and shortening of the DNA brush. What remains to achieve this specific aim is the challenge of elucidating the mechanism of these transformations, and the structure of the larger aggregates. As mentioned in the last section, TEM and light scattering may enable us to garner some information regarding structure. These aggregates are large enough to be observed using fluorescence microscopy and flow cytometry once they grow to micron sizes. We propose to use two novel chain termination agents for ROMP[52] to install fluorophores on the copolymer strands (FIG. 18). By introducing these groups (one per polymer (POL)) we will be able to observe mixing of the fluorophores if interparticle aggregation is responsible for this phenomenon. Therefore, we expect scrambling of the fluorophores through successive expansion and contraction cycles. We propose to examine the co-localization of the fluorescent dyes using experiments performed on the large aggregates using confocal fluorescence microscopy and flow cytometry. These experiments will enable us to determine something about the mode of action of these systems, and will help elucidate the structures of the aggregates. Moreover, we aim to establish the programmability of these structures by examining multiple particles in solution made from multiple DNA sequences simultaneously. In this arrangement particles will respond to patterns of DNAzymes rather than single inputs. This kind of logic-based experiment will demonstrate that encoding particles in this manner is a robust method of programming size and shape change at the nanoscale. These experiments will confirm our preliminary data that suggest this is the case. In addition, the ability of particles to respond to more than one input signal may be interesting as a method of gating these systems. That is, more than one input would be needed to trigger drug release, making it possible to have targeting dependent on multiple disease markers.[53] This kind of logical encoding of drug delivery is greatly hampered by the lack of good methods for interfacing chemical signaling in synthetic devices. In addition, we will also be able to tag multiple antibodies and targeting groups for cancer cells, to examine these possibilities on cell surfaces as will be discussed in Specific Aim #3.

Specific Aim #2: To Demonstrate the controlled release and/or activation of reporter and/or drug molecules from the core of the particles concomitant with the programmed shape change. Rational: Our control over particle size in terms of expansion and contraction of the aggregates, presents two methods for the release of functional monomers into solution. METHOD 1: Noncovalently encapsulated drugs within large aggregates and/or spherical structures will be released upon particle contraction or expansion respectively. This approach is predicated on the idea that it may be possible to take up molecules in solution upon expansion of the small particles to larger aggregates as well as expel their contents upon contraction. Indeed our preliminary data suggest this kind of uptake and release strategy is feasible. In addition, the ability to reversibly cycle these materials through phases makes this plausible. METHOD 2: Covalently bound fluorophores or drugs will be released via the action of esterases and/or upon exposure to physiological pH. The rationale behind this method is that the rearrangement process may expose the core of the particles to solution allowing cleavage and expulsion of the functional portion of the monomers from the particle. The advantage this approach has over Method 1 is that higher drug/fluorophore loadings are possible by virtue of the particles being made from polymers containing covalently linked drugs/fluorophores. Furthermore, the ratios of these monomers to each other and to the polar head group are highly controlled by the living polymerization method employed (ROMP). However, a potential disadvantage of this approach may come from inhibition of enzyme activity because of the very fact the drug is linked to the polymer backbone. Several experiments have been designed to probe the plausibility of these respective methods for DNA-programmed drug/fluorophore release.

Experimental Design and Methods: These studies will be divided into three parts. A) Release of non-covalently linked fluorophores in response to specific stimuli. These studies will be performed for both the DNA-based system as described above and for the peptide-based system. B) Release of covalently linked fluorophores in response to specific stimuli. These studies will be performed for both the DNA-based system as described above and for the peptide-based system. C) Testing of this design concept towards theranostic devices.

A) Release of Non-covalently linked Fluorophores. Studies similar to those shown in FIG. 17 will enable us to measure the kinetics and thermodynamics of this process of uptake and release and determine the relative loading efficiency. In addition, we can use these systems for experiments to determine the critical micelle concentration by the standard method of observing differences in the concentration of free vs encapsulated dye for a range of particle concentrations. Indeed, the MRI-contrast agents should allow a similar, parallel analysis. Knowing this will be critical to understanding the stability of these materials and the minimum concentration for our cell studies. Together, these experiments will provide a means for optimizing the system and for understanding the mechanism of drug uptake and release. These experiments will be repeated under a variety of dye and particle concentrations and exposure times to elucidate the efficiency of this approach to uptake and release. We propose to synthesize particles (via dialysis) in the presence of dye molecules to determine if drugs and/or fluorophores can be incorporated successfully into the small particles, and released upon expansion or destruction of the particles. Destruction may proceed via the introduction of sequence, or structure selective nucleases rather than DNAzymes. The initial tests will be performed using exonuclease III (Exo III). This enzyme utilizes 3'-termini of blunt ends or 5'-overhang regions. Therefore, the particles will not react with Exo III until a complementary DNA strand is added that binds the shell and creates a substrate for the enzyme on the surface. One possibility is that the nuclease will not be very efficient because the substrate is sterically crowded on the particle, but this may be offset by the high effective concentration at the shell. This approach will facilitate particle destruction by completely removing the shell. These processes will be examined by fluorescence experiments in 96-well plate format, and will not require the molecular weight cut off spin tube approach described in the preliminary data section, because we are observing fluorescence increase upon dye release from a preformed and dialyzed particle.

B) Release of Covalently Linked Fluorophores. The successful covalent linkage of drug molecules to the particle core will play a key part in achieving Specific Aim #3. Towards this goal we have successfully formed 20 nm particles from copolymers of $5_{36}$-b-DNA$_3$ (5=coumarin dye modified norbornene monomer). The dye molecules in this structure are connected to the polymer via a cleavable ester linkage. The length and structure of these linkages may need to be optimized to enable enzyme access to the cleavage site, a process involving the synthesis of a set of easily accessible dye-based norbornene monomers. By mixing the particles with esterases and then adding DNAzyme in a 96-well plate format, we aim to test the ability of these systems to release dye during the shape change process when the polymer core may be exposed to buffer. The concentration of the micelles may play a key roll in optimizing this scheme because if we are close to the critical micelle concentration their instability may be exploited. Furthermore, it may be possible to achieve a step-wise release in a programmed dosing strategy. That is, release is initiated and halted sequentially by adding a counteracting nucleic acid sequence to solution. This may have eventual application in turning drugs on or off during treatment depending on patient response. This idea will be tested in vitro via XTT assays[54] run on cells treated with micelles and DNAzyme tagged antibodies. Peptide-based particles will be examined in a similar way for their ability to respond to proteases excreted by cells known to overexpress MMPs.[47,55,56] Therefore, the DNA-based systems act as translated response systems and the peptide-based systems act as direct response systems.

C) Testing of this Design Concept Towards Theranostic Devices. The copolymer strategy will allow us to assess these materials as potentially powerful and unique theranostic devices.[57] Initial studies will look at whether this copolymer and others containing contrast agents and protease inhibitors can report on the effectiveness of protease inhibition. Simply, a protease that initiates a reaction at the shell of the particle will be inhibited if the drug is successfully released. This approach will constitute a feedback approach to observing and detecting enzyme activity and analyzing enzyme inhibition. In particular it will be interesting to examine these systems over a range of enzyme concentrations with both fluorogenic cores (monomer 13) and the proposed MRI-agents as reporter molecules. Of course, one could envision linking inhibition with signaling in two separate steps using standard probe substrates and adding inhibitors. The distinct advantage here, moving forward, is that one could potentially study expression patterns of enzyme markers via colocalization of drugs and signaling molecules at specific diseased tissue allowing a real-time evaluation of the efficacy of a drug and the specificity of a targeting event. This is of course the power of a single theranostic device and we propose to explore the potential of these unique materials to provide this advantage. Furthermore, we seek to utilize these systems in the rapid detection of proteases at low concentrations in solutions doped with esterases capable of cleaving and activating fluorescent groups during particle morphology shifts. In addition, the contrast agents may report the presence of proteases via changes in relaxation times as noted above.

Specific Aim #3: To demonstrate that nanoparticles with programmable, shiftable morphologies can target, detect and kill cancer cells in vitro. Rationale: With methods in hand for releasing drugs and/or fluorophores and for activating MRI-contrast agents in a DNA-sequence selective or peptide selective fashion, we aim to adapt these systems for responding to cell-specific signals in cell culture. Initially, this will be achieved via a tagging strategy whereby particles will be activated for drug release at the cell surface. In an exemplary case, this occurs where DNAzyme acts on a small particle, causing aggregation shift, expansion and exposure of the biodegradable core to solution at the targeting site. Equally, this could be set up such that the antibody is tagged with a DNA sequence designed to hybridize to the vesicle structure causing a similar phase shift and expulsion of drug. These two-step approaches provide a means for translating an antibody specific cell receptor interaction into a sequence selective interaction with our delivery vehicle. In addition, if a particle can respond to proteases and signal that response as proposed, then they will respond to cells known to overexpress those proteases.

Experimental Design and Methods: The initial demonstration will utilize DNAzyme-tagged antibodies)(Herceptin[10]) specific to overexpressed receptors (Her2/neu) on cancer cell lines (SKBR-3, SKOV-3). To test for the differential targeting ability of these systems the same experiments will be run on MCF-7 cells that express lower amounts of Her2/neu and should not be targeted.[58] Antibody-DNA conjugates will be synthesized by labeling the antibodies with a maleimide group at lysine residues followed by addition of a thiol modified DNA sequence. These conjugates will be purified by ion exchange chromatography (FPLC) and characterized for molecular weight by static light scattering (SEC-MALS) in buffered water. The conjugates will tag cells with DNAzymes complementary and specific to the sequence encoded on the micelle surface. By lowering the temperature in vitro we can hinder internalization of the antibodies, rinse the cells with buffer, and add particles in a second step. In the presence of tagged cancer cells, the particles will undergo the programmed phase change, and emit drug molecules as described in previous sections for dye release. Standard cell assays (XTT—viability assay[30]), immunofluorescence assays, and flow cytometry will be used to show the selectivity and effectiveness of cytotoxic drug laden nucleic acid programmed micelles designed to target and kill cancer cells. This can be achieved by fluorescently labeling the particles to observe their co-localization at the cell surface with anti-human antibodies fluorescently tagged. In addition, copolymers of drug and fluorophore (monomers 5 and 11) can be made such that fluorescence increase will act as a tracer for drug release allowing simultaneous imaging and drug delivery capability. MRI-contrast agents will serve the same purpose.

When successful, the phase shifting nature of these materials may offer an unprecedented opportunity to correlate internalization of the particles themselves with their size and shape providing general design ideas for future nanoscale delivery systems, because we have a way of changing these properties in situ.[59,60] That is, while the goal here is to release drugs and activate signaling molecules at the cell surface, allowing drugs to diffuse at high concentrations into cells, it may also be possible that these carriers will themselves be internalized. It should be noted that having fluorophores and drugs on the same polymer delivery device is not only greatly beneficial in system characterization in vitro, this arrangement may eventually allow monitoring of drug release in vivo. For example, one could envision MRI contrast agents targeting along with drug molecules to confirm successful targeting during treatment. If this could be correlated with expression patterns at the cell surface or interior,[61] these programmed delivery vehicles could be adapted for true theranostic applications. Indeed, this kind of particle is an ideal candidate for these applications and the development of these materials over the course of the proposed research should enable us to assess the viability of such an approach.

REFERENCES FOR EXAMPLE 5

(1) Torchilin, V. P., *European Journal of Pharmaceutical Sciences* 2000, 11:S81-S91.
(2) Arap, W.; Pasqualini, R.; Ruoslllahti, E., *Science* (Washington, D.C.) 1998, 279:377-380.
(3) Stojanovic, M. N.; De Prada, P.; Landry, D. W., *Chem Bio Chem* 2001, 2:411-415.
(4) Sawant, R. M.; Hurley, J. P.; Salmaso, S.; Kale, A.; Tolcheva, E.; Levchenko, T. S.; Torchilin, V. P., *Bioconjugate Chem.* 2006, 17:943-949.
(5) Gil, E. S.; Hudson; S. M., *Prog. Polym. Sci.* 2004, 29:1173-1222.
(6) Carl, P. L.; Chakravarty, P. K.; Katzenellenbogen, J. A.; Weber, M. J., *Proc. Natl. Acad. Sci.* 1980, 77:2224-2228.
(7) Vasir, J. K.; Reddy, M. K.; Labhasetwar, V. D. "Nanosystems in drug targeting: opportunities and challenges"; *Current Nanoscience* 2005, 1:47-64.
(8) Arumugam, P.; Xu, H.; Srivastava, S.; Rotello, V. M. "'Bricks and mortar' nanoparticle self-assembly using polymers"; *Polym. Int.* 2007, 56:461-466.
(9) Sawyers, C. L. "The cancer biomarker problem"; *Nature* 2008, 452:548-552.
(10) Adams, G. P.; Weiner, L. M. "Monoclonal antibody therapy of cancer"; *Nat. Biotechnol.* 2005, 23:1147-1157.
(11) Breaker, R. R.; Joyce, G. F. "A DNA enzyme with Mg2+-dependent RNA phosphoesterase activity"; *Chemistry & Biology* 1995, 2:655-660.
(12) Sanford, M. S.; Love, J. A.; Grubbs, R. H. "Mechanism and activity of ruthenium olefin metathesis catalysts"; *J. Am. Chem. Soc.* 2001, 123:6543-6554.
(13) Slugovc, C. "The ring opening metathesis polymerisation toolbox"; *Macromol. Rapid Commun.* 2004, 25:1283-1297.
(14) Smith, D.; Pentzer, E. B.; Nguyen, S. T. "Bioactive and Therapeutic ROMP Polymers"; *Polymer Reviews* (Philadelphia, Pa., United States) 2007, 47:419-459.
(15) Carrillo, A.; Kane, R. S. "Block copolymer nanoparticles of controlled sizes via ring-opening metathesis polymerization"; *Journal of Polymer Science, Part A: Polymer Chemistry* 2004, 42:3352-3359.
(16) Bertin, P. A.; Watson, K. J.; Nguyen, S. T. "Indomethacin-containing nanoparticles derived from amphiphilic polynorbornene: a model ROMP-based drug encapsulation system"; *Macromolecules* 2004, 37:8364-8372.
(17) Li, Z.; Zhang, Y.; Fullhart, P.; Mirkin, C. A. "Reversible and Chemically Programmable Micelle Assembly with DNA Block-Copolymer Amphiphiles"; *Nano Lett.* 2004, 4:1055-1058.
(18) Cheng, C.; Qi, K.; Khoshdel, E.; Wooley, K. L. "Tandem Synthesis of Core-Shell Brush Copolymers and Their Transformation to Peripherally Cross-Linked and Hollowed Nanostructures"; *J. Am. Chem. Soc.* 2006, 128:6808-6809.
(19) Carrillo, A.; Yanjarappa, M. J.; Gujraty, K. V.; Kane, R. S. "Biofunctionalized block copolymer nanoparticles based on ring-opening metathesis polymerization"; *J. Pol. Sci.*, Part A: 2005, 44:928-939.
(20) Higgins, L. S.; Besnier, C.; Kong, H. "The nicking endonuclease N.BstNBI is closely related to type IIs restriction endonucleases MlyI and PleI"; *Nucleic Acids Research* 2001, 29:2492-2501.
(21) Okano, K.; Kambara, H. "DNA probe assay based on exonuclease III digestion of probes hybridized on target DNA"; *Analytical Biochemistry* 1995, 228:101-108.
(22) Xu, Y.; Lunnen, K. D.; Kong, H. "Engineering a nicking endonuclease N.AlwI by domain swapping"; *Proceedings of the National Academy of Sciences of the United States of America* 2001, 98:12990-12995.
(23) Heid, C. A.; Stevens, J.; Livak, K. J.; Williams, P. M. "Real time quantitative PCR"; *Genome Res.* 1996, 6:986-994.
(24) Saiki, R. K.; Scharf, S.; Faloona, F.; Mullis, K. B.; Horn, G. T.; Erlich, H. A.; Arnheim, N. "Enzymic amplification of beta-globin genomic sequences and restriction site analysis for diagnosis of sickle cell anemia"; *Science* 1985, 230:1350-1354.
(25) Smith, A. J. H. "The use of exonuclease III for preparing single stranded DNA for use as a template in the chain terminator sequencing method"; *Nucleic Acids Research* 1979, 6:831-848.
(26) Santoro, S. W.; Joyce, G. F. "A general purpose RNA-cleaving DNA enzyme"; *Proc. Natl. Acad. Sci. U.S.A.* 1997, 94:4262-4266.
(27) Saghatelian, A.; Guckian, K. M.; Thayer, D. A.; Ghadiri, M. R. "DNA Detection and Signal Amplification via an Engineered Allosteric Enzyme"; *Journal of the American Chemical Society* 2003, 125:344-345.
(28) Villaverde, A. "Allosteric enzymes as biosensors for molecular diagnosis"; *FEBS Letters* 2003, 554:169-172.
(29) Simon, P.; Dueymes, C.; Fontecave, M.; Decout, J.-L. "DNA detection through signal amplification by using NADH: Flavin oxidoreductase and oligonucleotide-flavin conjugates as cofactors"; *Angewandte Chemie International Edition* 2005, 44:2764-2767.
(30) Graf, N.; Goritz, M.; Kramer, R. "A Metal-Ion-Releasing Probe for DNA Detection by Catalytic Signal Amplification"; *Angewandte Chemie, International Edition* 2006, 45:4013-4015.
(31) Gianneschi, N. C.; Ghadiri, M. R. "Design of molecular logic devices based on a programmable DNA-regulated semisynthetic enzyme"; *Angew. Chem. Int. Ed.* 2007, 46:3955-3958, S3955/3951-S3955/3955.

(32) Tan, W.; Fang, X.; Li, J.; Liu, X. "Molecular beacons: a novel DNA probe for nucleic acid and protein studies"; *Chemistry—A European Journal* 2000, 6:1107-1111.

(33) Rosi, N. L.; Mirkin, C. A. "Nanostructures in Biodiagnostics"; *Chem. Rev.* 2005, 105:1547-1562.

(34) Schweitzer, B.; Kingsmore, S. "Combining nucleic acid amplification and detection"; *Curr. Opin. Biotechnol.* 2001, 12:21-27:

(35) Smith, D.; Pentzer, E. B.; Nguyen, S. T. "Bioactive and Therapeutic ROMP Polymers"; *Polym. Rev.* (Philadelphia, Pa., U.S.) 2007, 47:419-459.

(36) Bertin, P. A.; Smith, D.; Nguyen, S. T. "High-density doxorubicin-conjugated polymeric nanoparticles via ring-opening metathesis polymerization"; *Chem. Commun.* 2005, 3793-3795.

(37) Nori, A.; Kopecek, J. "Intracellular targeting of polymer-bound drugs for cancer chemotherapy"; *Advanced Drug Delivery Reviews* 2005, 57:609-636.

(38) Aldaye Faisal, A.; Palmer Alison, L.; Sleiman Hanadi, F. "Assembling materials with DNA as the guide"; *Science* 2008, 321:1795-1799.

(39) Alemdaroglu, F. E.; Herrmann, A. "DNA meets synthetic polymers-highly versatile hybrid materials"; *Organic & Biomolecular Chemistry* 2007, 5:1311-1320.

(40) Storhoff, J. J.; Mirkin, C. A. "Programmed Materials Synthesis with DNA"; *Chem. Rev* 1999, 99:1849-1862.

(41) You, Y. "Podophyllotoxin derivatives: current synthetic approaches for new anticancer agents"; *Current Pharmaceutical Design* 2005, 11:1695-1717.

(42) Fraser, C.; Grubbs, R. H. "Synthesis of Glycopolymers of Controlled Molecular Weight by Ring-Opening Metathesis Polymerization Using Well-Defined Functional Group Tolerant Ruthenium Carbene Catalysts"; *Macromolecules* 1995, 28:7248-7255.

(43) Hortobagyi, G. N. "Anthracyclines in the treatment of cancer. An overview"; *Drugs* 1997, 54:1-7.

(44) Kuefner, U.; Lohrmann, U.; Montejano, Y. D.; Vitols, K. S.; Huennekens, F. M. "Carboxypeptidase-mediated release of methotrexate from methotrexate alpha-peptides"; *Biochemistry* 1989, 28:2288-2297.

(45) Jiang, T.; Olson, E. S.; Nguyen, Q. T.; Roy, M.; Jennings, P. A.; Tsien, R. Y. "Tumor imaging by means of proteolytic activation of cell-penetrating peptides"; *Proc. Natl. Acad. Sci.* 2004, 101:17867-17872.

(46) Laromaine, A.; Koh, L.; Murugesan, M.; Ulijn, R. V.; Stevens, M. M. "Protease-Triggered Dispersion of Nanoparticle Assemblies"; *J. Am. Chem. Soc.* 2007, 129:4156-4157.

(47) Lee, G. Y.; Song, J.-h.; Kim, S. Y.; Park, K.; Byun, Y. "Peptide-doxorubicin conjugates specifically degraded by matrix metalloproteinases expressed from tumor"; *Drug Dev. Res.* 2006, 67:438-447.

(48) Lombard, C.; Saulnier, J.; Wallach, J. "Assays of matrix metalloproteinases (MMPs) activities: a review"; *Biochimie* 2005, 87:265-272.

(49) Mart, R. J.; Osborne, R. D.; Stevens, M. M.; Ulijn, R. V. "Peptide-based stimuli-responsive biomaterials"; *Soft Matter* 2006, 2:822-835.

(50) Matsen, M. W.; Bates, F. S. "Origins of Complex Self-Assembly in Block Copolymers"; *Macromolecules* 1996, 29:7641-7644.

(51) Rijcken, C. J. F.; Soga, O.; Hennink, W. E.; van Nostrum, C. F. "Triggered destabilization of polymeric micelles and vesicles by changing polymers polarity: An attractive tool for drug delivery"; *J. Controlled Release* 2007, 120:131-148.

(52) Owen, R. M.; Gestwicki, J. E.; Young, T.; Kiessling, L. L. "Synthesis and applications of end-labeled neoglycopolymers"; *Org. Lett.* 2002, 4:2293-2296.

(53) Sudimack, J.; Lee, R. J. "Targeted drug delivery via the folate receptor"; *Advanced Drug Delivery Reviews* 2000, 41:147-162.

(54) Roehm, N. W.; Rodgers, G. H.; Hatfield, S. M.; Glasebrook, A. L. "An improved colorimetric assay for cell proliferation and viability utilizing the tetrazolium salt XTT"; *J Immunol Methods* 1991, 142:257-265.

(55) Kline, T.; Torgov, M. Y.; Mendelsohn, B. A.; Cerveny, C. G.; Senter, P. D. "Novel Antitumor Prodrugs Designed for Activation by Matrix Metalloproteinases-2 and -9"; *Molecular Pharmaceutics* 2004, 1"9-22.

(56) Liu, S.; Netzel-Arnett, S.; Birkedal-Hansen, H.; Leppla, S. H. "Tumor cell-selective cytotoxicity of matrix metalloproteinase-activated anthrax toxin"; *Cancer Research* 2000, 60:6061-6067.

(57) Kamiya, M.; Kobayashi, H.; Hama, Y.; Koyama, Y.; Bernardo, M.; Nagano, T.; Choyke, P. L.; Urano, Y. "An Enzymatically Activated Fluorescence Probe for Targeted Tumor Imaging"; *J. Am. Chem. Soc.* 2007, 129:3918-3929.

(58) Kraus, M. H.; Popescu, N. C.; Amsbaugh, S.C.; King, C. R. "Overexpression of the EGF receptor-related proto-oncogene erbB-2 in human mammary tumor cell lines by different molecular mechanisms"; *EMBO J.* 1987, 6:605-610.

(59) Champion, J. A.; Mitragotri, S. "Role of target geometry in phagocytosis"; *Proc. Natl. Acad. Sci. U.S.A.* 2006, 103: 4930-4934.

(60) Geng, Y.; Dalhaimer, P.; Cai, S.; Tsai, R.; Tewari, M.; Minko, T.; Discher, D. E. "Shape effects of filaments versus spherical particles in flow and drug delivery"; *Nat. Nanotechnol.* 2007, 2:249-255.

(61) Louie, A. Y.; Huber, M. M.; Ahrens, E. T.; Rothbacher, U.; Moats, R.; Jacobs, R. E.; Fraser, S. E.; Meade, T. J. "In vivo visualization of gene expression using magnetic resonance imaging"; *Nat. Biotechnol.* 2000, 18:321-325.

Example 6

Figures 20A, 20B, 20C, 20D, 20E:
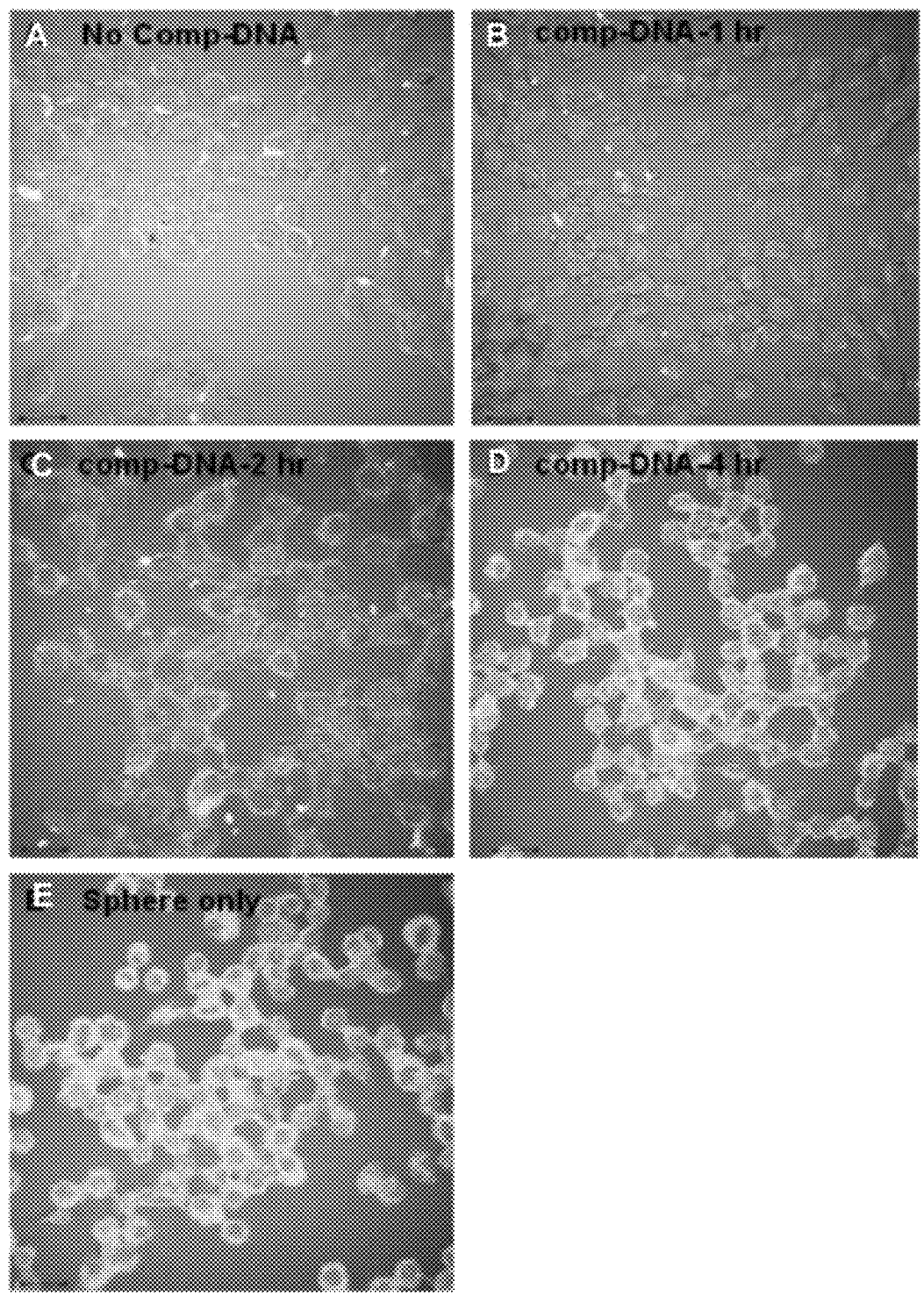
FIGS. 20A-20E depict In vitro study of fiber vs. sphere. $2\times10^5$ J772 macrophage cells were seeding in the glass chamber overnight and replaced with 150 uL of new DMEM medium before the experiment. 0.1 nmole of Rho-end-fibers (FIGS. 20A-20D) and spheres (FIG. 20E) were added in the chamber for 1 hr and followed by adding 0.1 nmole of complementary DNA for another 1 hr (FIG. 20B), 2 hrs (FIG. 20C), and 4 hrs (FIG. 20D). Cells were then fixed with paraformaldehyde for over 30 min. After fixation, cells were washed twice with PBS and added with one drop of mounting solution (60% glycerol in PBS) followed sealed with nail polish. Legends in figures.

Nanoparticle Morphology Switching for Controlling and Programming Pharmacokinetics It is known that particle morphology has an effect on circulation times,[1] and on cell-uptake rates,[2] however our systems are uniquely suited to studying how switching the morphology of a material can be used to alter and tune these rates, as well as contributing to our basic understanding of this nanoscale phenomenon.[3] In fact, the use of switchable morphology of a nanoscale material has not been used to regulate pharmacokinetics or targeting of a material before. Indeed, the chemical similarity between the surfactant in each phase offers the ability to potentially narrow down basic rules concerning the relationship between shape and particle-cell interactions.

FIGS. 19A-19F show TEM images of spheres and fibers labeled red (rhodamine) and green (fluorescein). These structures are formed from polymers as described for the DNA-based copolymers. FIGS. 20A-20E show differential uptake rates into human macrophage cells in vitro (J772 cells). In cell culture, dye labeled spherical and cylindrical (fiber) DNA-programmed micelles are taken up at different rates, and upon addition of a complementary DNA strand to a solution of fibers incubating with the cells, uptake rates are changed. FIG. 20A shows that fibers are taken up very slowly with little fluorescence visible after 5 hrs. FIGS. 20B-20D show how fluorescence increases with time as fibers are incubated with a short (20 mer) complementary DNA sequence. FIG. 20E shows that spherical micellar nanoparticles are taken up by the macrophages.

Figure 21:
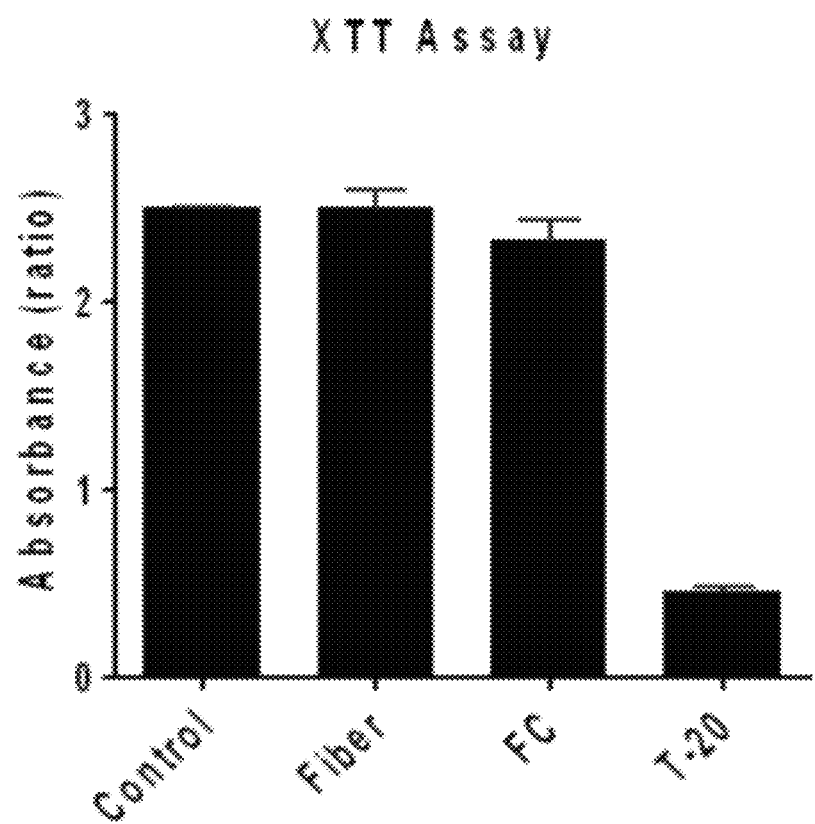
FIG. 21 depicts $5\times10^4$ J774 macrophage cells in 100 uL DMEM medium which were seeding in 96 well clear bottom plate overnight. Each group has 4 repeats. 0.1 nmole of dT-Flr fibers were added into the Fiber and FC groups for 0.1 hr and 0.1 nmole of complementary DNA was then added into FC group for another 1 hr. 0.2% Tween-20 (T-20) was added into T-20 group. Control is adding nothing except medium. After 1 hr of complementary DNA adding, 50 uL of pre-warmed (37° C.) XTT reagents (Roche) were added into 96 well plates and the UV absorption was measured at 485 nm after 4.5 hrs.
Figure 22A:
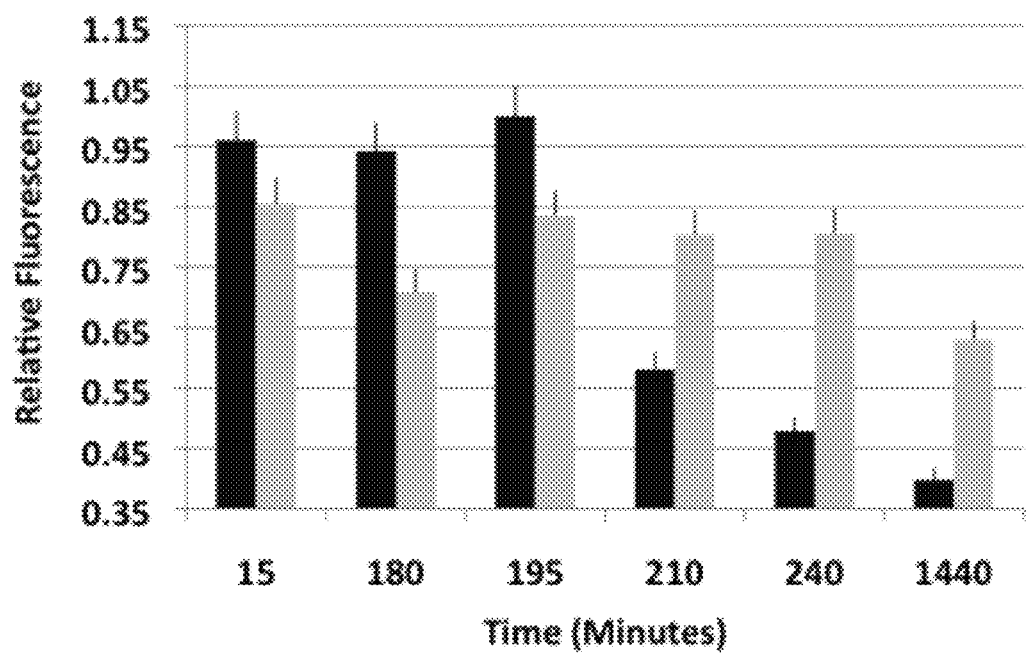
FIGS. 22A-22B depict pharmacokinetics assay.
Figure 22B:
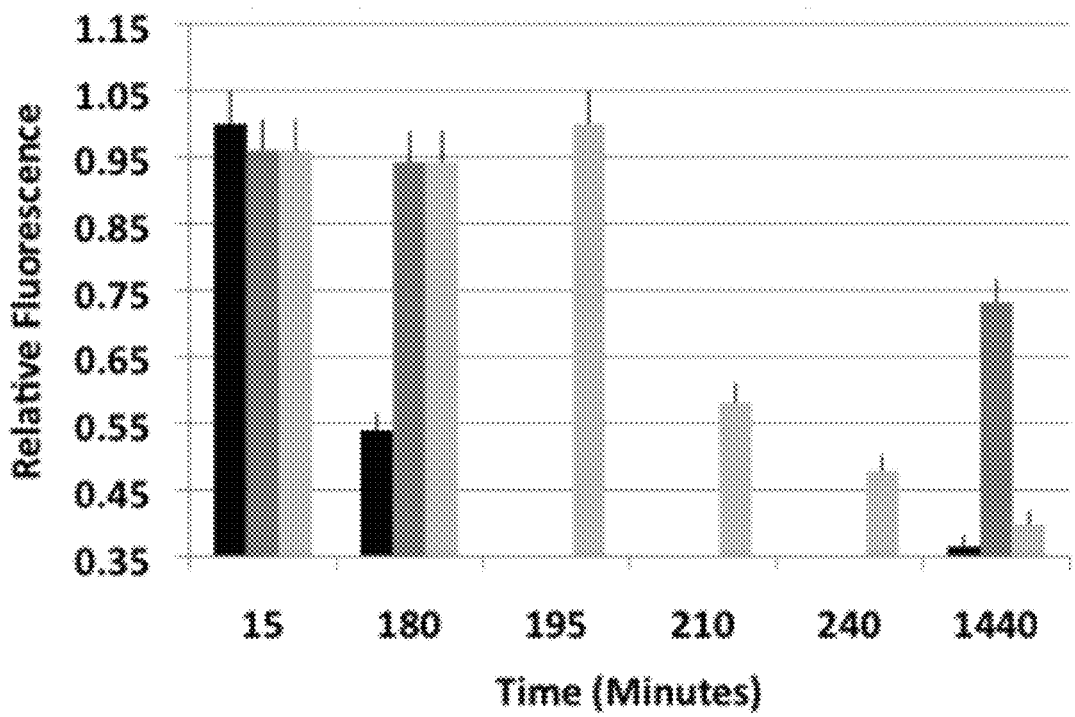
Figure 23A:
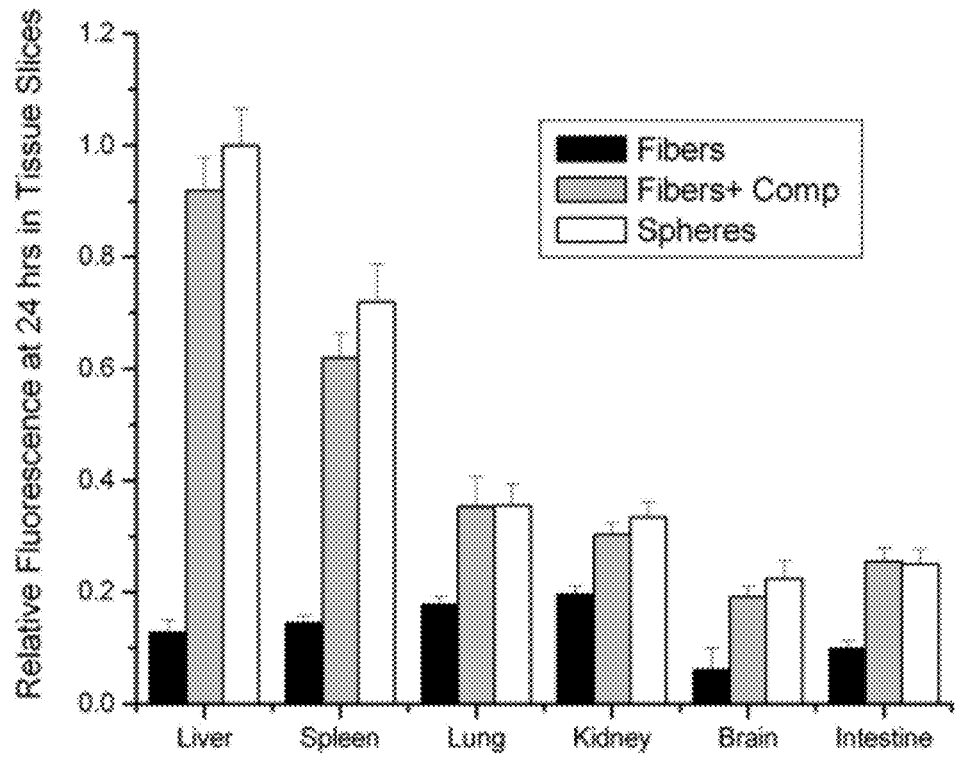
FIGS. 23A-23B depict fluorescent intensity of histological tissue samples. Mice from pharmacokinetic studies (FIGS. 22A-22B) were sacrificed at 24 hrs (FIG. 23A), and at 72 hrs (FIG. 23B). Organs were sliced and prepared as glass slides for imaging. The intensity of images were measured by using FV10-ASW 2.0 Viewer software and shown here as average relative fluorescence intensity across three slides per organ.
Figure 23B:
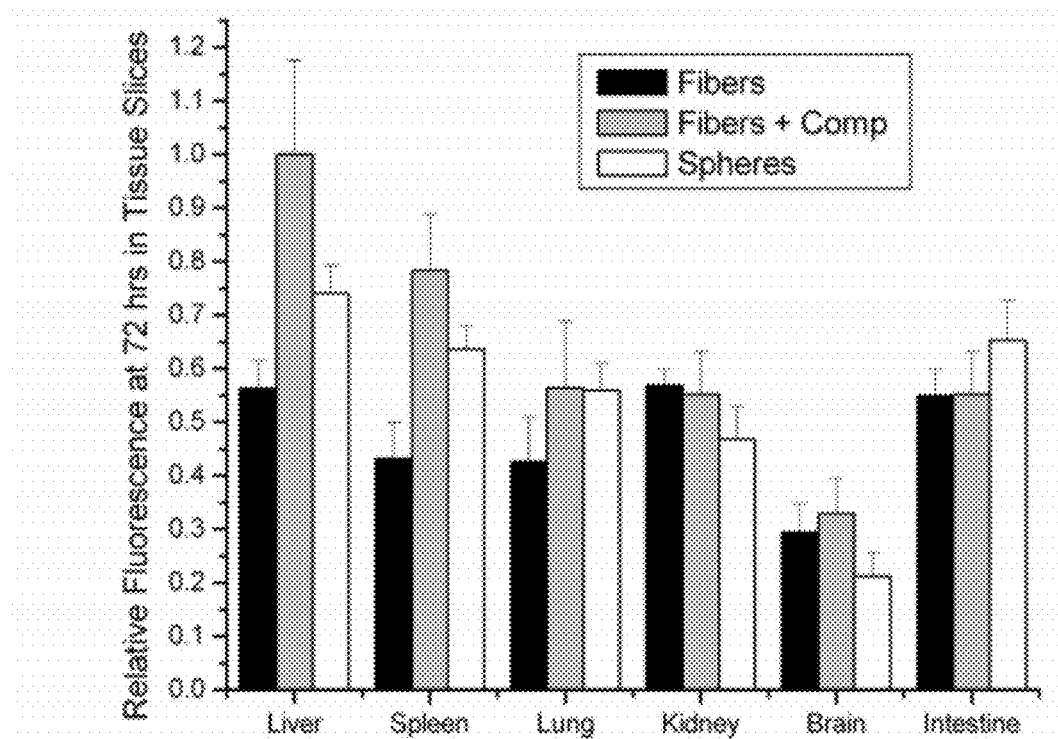

Cell viability assays (XTT[4]) confirm that the materials are not toxic in this form to the cells (FIG. 21). FIGS. 22A-22B shows the circulation times in the blood stream of fibers vs spheres and fibers plus complementary DNA (F+C). In this experiment mice were injected with fibers or spheres of two types, in their tail vein. The types were red labeled (rhodamine) and green labeled (fluorescein). The red and green particles were injected simultaneously, each encoded to respond to a different DNA sequence. The sequence complementary to the green fibers was injected into 4 of the mice after 3 hrs. Fluorescence was measured in both green and red channels in blood serum samples collected from the mice during the time course of the experiment as shown in FIGS. 22A-22B. FIG. 22A shows how green fluorescence drops away upon addition of the complementary DNA at 3 hrs, and red fluorescence holds steady. This proves sequence selectivity of the morphology change, in blood circulation. FIG. 22B depicts comparison of all green fluorescence data for Spheres, Fibers and Fibers+Complementary DNA. NOTE: data was collected in 4 mice per time point per particle type (12 mice total), with no data taken for sphere and fiber injected mice between 3 hrs and 24 hrs. This data was collected for the fiber+complement mice in order to monitor the change in that critical time following the injection. One can see that after 24 hrs, fluorescence is still observed for the fibers, but spheres have cleared with fluorescence dropping to background levels. FIGS. 23A-23B shows fluorescence in tissue slices at 24 hrs, and at 72 hrs for each morphology. One can clearly see accumulation of fluorescence in organs (especially liver and spleen—expected for nanoparticles) for spherical particles at 24 hrs. However, fibers continue to circulate (as shown in FIGS. 22A-22B), and do not appreciably accumulate until 72 hrs.

REFERENCES FOR EXAMPLE 6

1 Geng, Y., Dalhaimer, P., Cai, S., Tsai, R., Tewari, M., Minko, T., & Discher, D. E. Shape effects of filaments versus spherical particles in flow and drug delivery. *Nat. Nanotechnol.* 2:249-255 (2007).
2 Champion, J. A. & Mitragotri, S. Role of target geometry in phagocytosis. *Proc. Natl. Acad. Sci. U.S.A.* 103:4930-4934 (2006).
3 Mailander, V. & Landfester, K. Interaction of nanoparticles with cells. *Biomacromolecules* 10:2379-2400 (2009).
4 Roehm, N. W., Rodgers, G. H., Hatfield, S. M., & Glasebrook, A. L. An improved colorimetric assay for cell proliferation and viability utilizing the tetrazolium salt XTT. *J Immunol Methods* 142:257-265 (1991).

Example 7

MRI Contrast Agents

Rationale. The rationale for the use of MRI-contrast agents to monitor and characterize phase change is two fold: 1) TEM may be used to image the particles without staining. This will aid in elucidating structure before, during and after phase transition. 2) We expect a change in local water concentrations before, during and after phase changes. The signal intensity is a function of water concentration and $T_1$ (spin-lattice) and $T_2$ (spin-spin) relaxation times. Decreases in $T_1$ make signals from protons brighter. Therefore, signal intensity increases with decreasing $T_1$ at the contrast agent location. In addition, previous studies have shown that macromolecular versions of MRI-contrast agents show high relaxivity because of the slow rotational motion of the macromolecule to which they are attached. Some studies have successfully built MRI-contrast agents into the shell of micelles to take advantage of this effect while still exposing the metal center to water. In these cases the water exchange rates are identical to monomeric versions of the metal chelates and thus, these assemblies increase relaxivity significantly. Our approach begins with spherical particles with MRI-contrast agents in the core. Upon phase change the access to water will change and should be concomitant with a change in relaxivity. The slow rotational motion of the macromolecular assembly will be maintained and/or significantly slowed, the high concentration of contrast agent is maintained, but we propose the water exchange rate will change concomitant with stimuli responsive phase shift. Therefore, we expect signal intensity to increase upon going from a well-defined core-shell sphere to the cylinder architectures. This conclusion is supported by observations showing uptake of dye molecules from solution during the expansion/aggregation of these materials.

Alternatively, MRI contrast agents may be placed in the shell of spherical particles. Upon stimuli induced particle morphology change to large fiber architectures, the relaxivity increases concomitant with a slowing in the tumbling rate of the material to which the chelate is attached. The following discussion describes the synthesis of monomers containing chelates for contrast agents, in particular Gd. These monomers have been polymerized successfully in our laboratories.

The imaging of organs in the human body is an important diagnostic procedure commonly used today which include X-Ray, ultrasound, and magnetic resonance imaging (MRI).[1] Recent developments in nanotechnology has allowed for the therapeutic drug delivery and optimization using MRI contrast agents chelated to nanoparticle drug delivery vehicles.[2] It has been shown recently that chelating MRI contrast agents to a macromolecular structure such as nanoparticles can further increase the T1 relaxation times in T1 weighted images as opposed to the chelation of a single monomer.[1-5] Adding the use of stimuli responsive nanoparticles can further assist in visualizing the release of drugs only in response to specific stimuli such as enzymes and pH. One of the options of monitoring the change in morphology would be the addition of an MRI contrast agent appended either to the core or the shell. The T1 relaxation time should change in response to enzymes due to a morphological shift in the nanoparticle and therefore a different interaction with surrounding water molecules.

Previous work with MRI contrast agents has shown an "on switch" by blocking the ninth coordination site of gadolinium-DOTA ligand by galactopyranose and in the presence of β-galatosidase removes the galactopyranose and allowing for a visualization via MRI.[6,7] Most MRI agents using gadolinium leaves the ninth coordination site open to allow for interaction with water protons. This method of having an "on switch" can be applied to nanoparticleschelated to the core, as shown in Scheme 7-1 following. Depending on whether the gadolinium is chelated to the core or to the shell will determine the extent of the change in relaxivity by blocking the access to water sterically. Our laboratories have shown so far that addition of an enzyme to a peptide shell can convert our particles into vesicular structure and addition of DNAzyme to a DNA shell particle can convert our particles into rods. In addition to visualizing this change by transfer electron microscopy (TEM), the use of an MRI contrast agent could provide further indication of a change in morphology not only in vitro but also in vivo. As shown in Scheme 7-1, phase transitions are probed by installing functional monomers into the polymers. Dye-linked boronate esters cross-link with α-hydroxyacids upon sphere fusion during phase transitions resulting in dye release by displacement. MRI-agents are installed for monitoring morphology changes. MRI-chelate may be driven to the shell or the core by copolymerizing with appropriate monomers. Access of water to Gd(III) is determined by morphology. It is observed that relaxation rates are also influenced by size of aggregates.

clododecane-1,4,7,10-tetraacetic acid (DOTA) has not been accomplished. The system proposed here will create an amphiphilic system where the hydrophilic shell will contain a combination of either DNA, dendrimers and contrast agent or peptide, dendrimer, contrast agent. The hydrophobic core will be composed of styrene or naphthalene like blocks with and without a co-block of an MRI contrast agent depending on the desired system outlined in Scheme 7-1.

ROMP polymerization of MRI contrast agents. A simultaneous effort has been focused on the synthesis of DTPA and DOTA MRI contrast agent monomers. Scheme 4 outlines the synthesis of the t-butyl protected DTPA[14] monomer. Starting

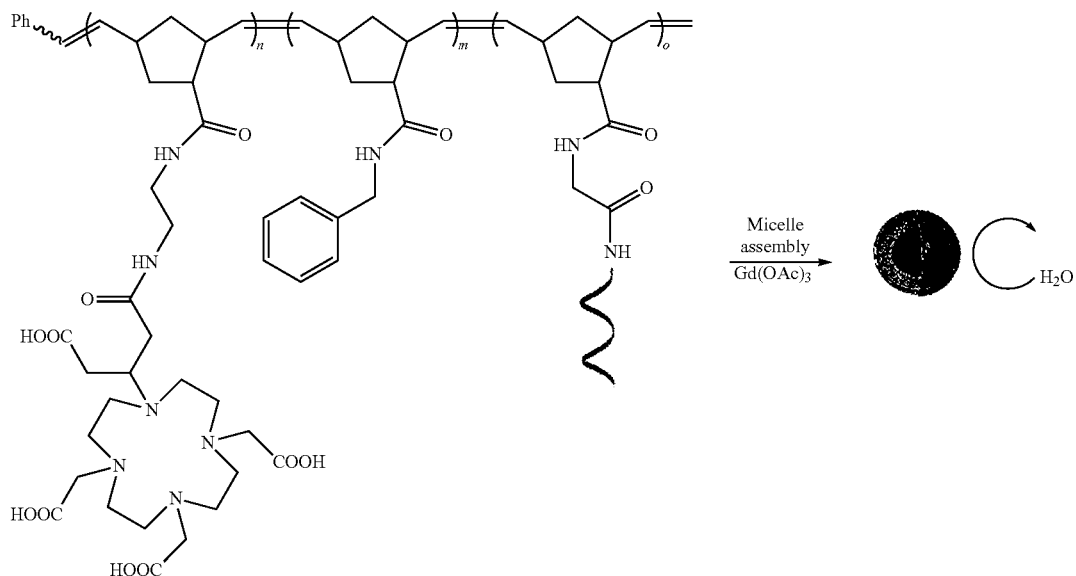

Scheme 7-1.

A facile synthesis of MRI contrast agents that incorporates multiple gadolinium chelates have included ring opening metathesis polymerization (ROMP),[8] encapsulation in a poly(lactide-co-glyclolide) (PLGA) or polylactide-poly(ethylene glycol) (PLGA-PLA),[7] use of a metal chelated core as a seed for post modification polymerization of a hydrophilic shell,[1] synthetically producing surfactants with an MRI contrast agent as the hydrophilic shell,[4] forming multimeric contrast agent,[9] and lastly using polymerized liposomes.[10] In contrast to previous work, MRI contrast agents have not been used as a tool to monitor change in morphology. Additionally, the polymerization using ROMP and micellization of diethylenetriaminepentaacetic acid (DTPA) and 1,4,7,10-tetraazacywith (S)-nitro-p-phenylalanine 13 addition of ethylenediamine at room temperature yields compound 14 in a 99% yield. From here, $BH_3$.THF reduces the amide and subsequent treatment of 6M HCl results in amine 15 with an overall yield of 80%. The free amines of 15 are reacted with t-butyl bromoacetate to give nitrophenyl t-butyl protected DTPA followed by reduction with Pd/C to give compound 17. Lastly, the t-butyl protected DTPA is conjugated to an NHS monomer 9 in the presence of EDCI. Once the impure DTPA monomer is purified, it can be polymerized and deprotected with TFA. The monomer can either be copolymerized with a hydrophobic monomer to give a core particle or a hydrophilic monomer to give a MRI contrast agent appended to the shell.

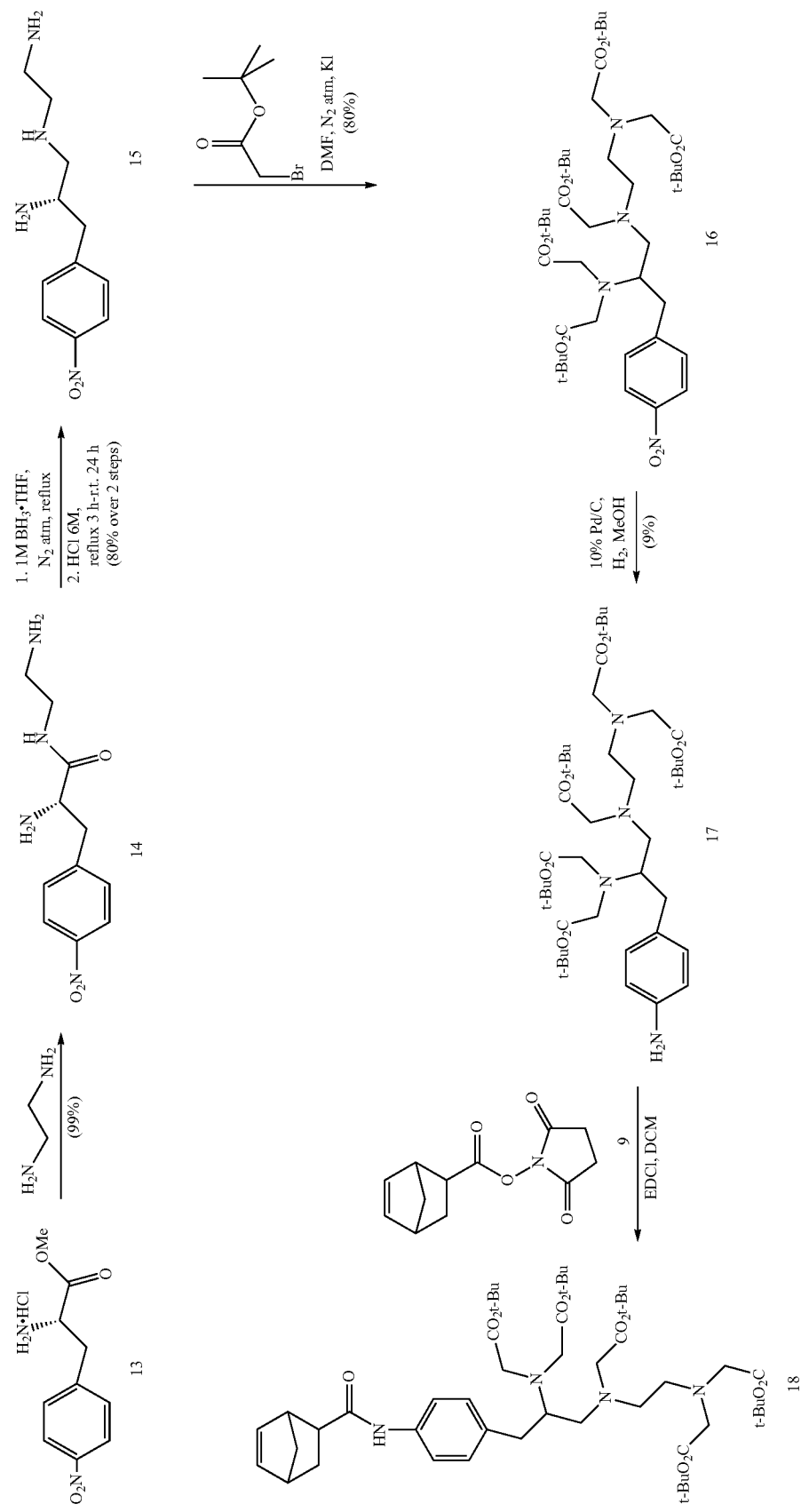

The second target monomer contains a DOTA MRI contrast agent. Scheme 5 outlines the originally synthetic approach to making this monomer, where addition of a mono-Boc protected ethylenediamine is added to NHS monomer 9 to produce compound 19 in a 70 yield. From here, the protecting group is removed with TFA to give the free amine monomer 20 that can react with bromo-methyl benzoic acid to give 21. The synthesis of 21 using both DCC and HBTU resulted in an undesired product. The NMR showed a mixture of aromatic peaks that did not correspond to the compound 21. After analysis of gadolinium coordination chemistry, it was also discovered that the target monomer 22 would not have been sufficient to chelate to eight of the nine available coordination sites in gadolinium. A new approach to making a DOTA monomer will be taken as outlined in scheme 6.

Scheme 5. Initial ynthesis of the DOTA monomer.

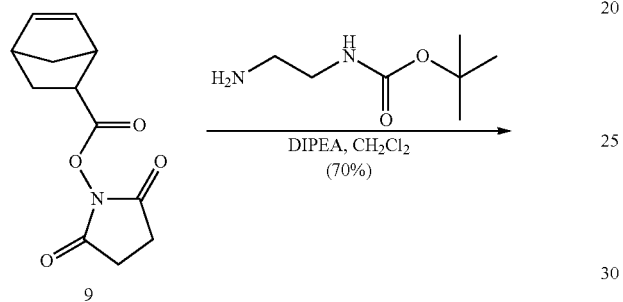

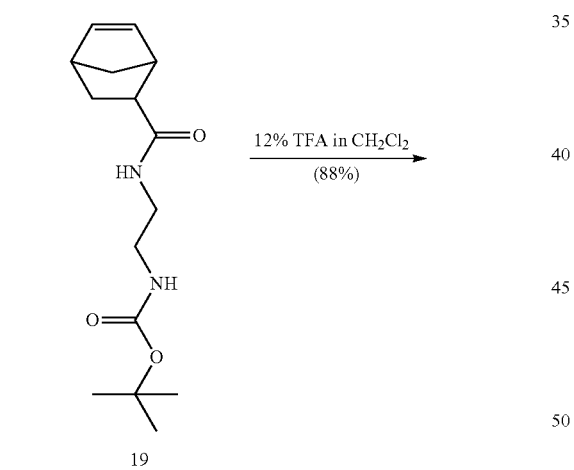

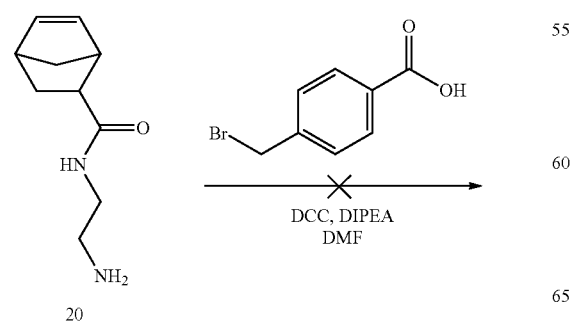

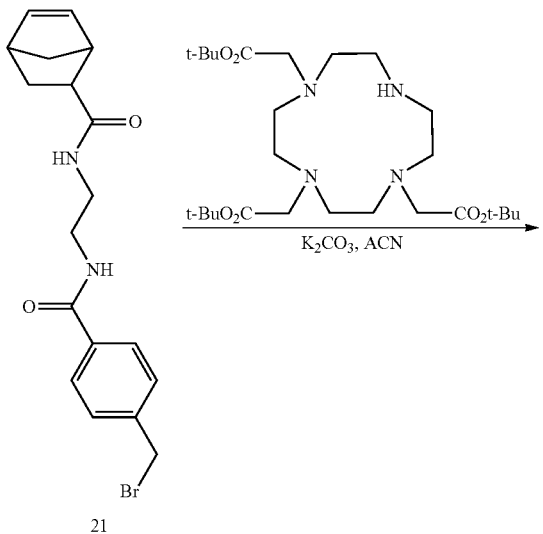

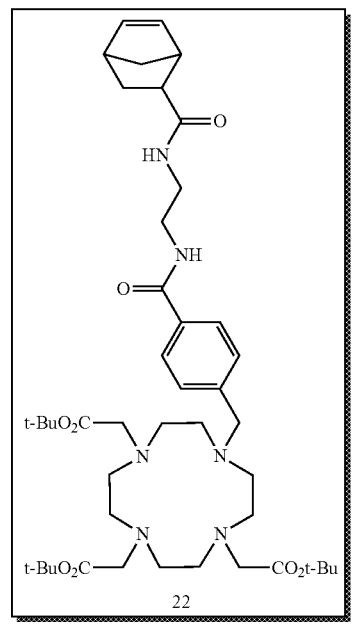

A new synthetic scheme for the DOTA monomer is shown in Scheme 6. Starting with the amine monomer 20, addition of 2,5-dioxopyrrolidin-1-yl 2-bromoacetate will give the bromo-monomer 24. Addition of tris-t-butyl-DOTA will yield the new target DOTA monomer 25. From here a polymerization with both a hydrophobic or hydrophilic monomer and subsequent dialysis will give either an MRI particle with the contrast agent in the core or shell, respectively.

Scheme 6. new synthetic scheme for DOTA monomer 25.

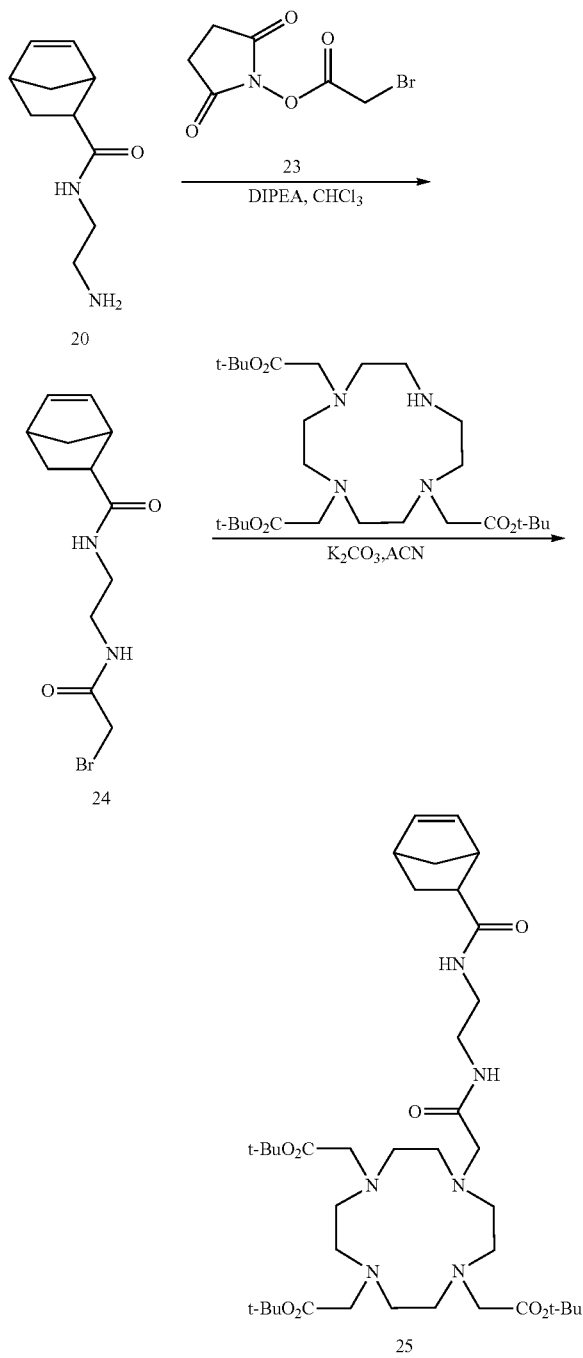

A theranostic tool using MRI contrast agents to observe the change in morphology of our materials after contact specific stimuli like DNAzymes, protease or pH will allow for in vitro and in vivo monitoring.

Amphiphilic MRI-Contrast Agent ROMP Polymers. Ring-opening metathesis polymerization (ROMP) has been used to polymerize amphiphilic block copolymers containing the DOTA and DTPA monomers. These amphiphiles, when dialyzed into buffered water, assemble into particles that are observable by TEM without staining with uranyl acetate. This is evidence for the successful incorporation of Gd into the micelle structure. Dynamic light scattering confirms the formation of nano-micro-scale aggregates. This process can be repeated to put the chelate agent in the core, or the shell.

Experimental

Materials. Di-t-butyl-4-[2-O-butoxycarbonyl)ethyl]-4-aminoheptanedicarboxylate purchased from Frontier Scientific. Nitromethanetrispropionic acid, Raney Nickel, DIPEA, TFA, (S)-methyl 2-amino-3-(4-nitrophenyl)propanoate hydrochloride, and $BH_3$.THF purchased from Sigma-Aldrich. HBTU purchased from Novabiochem. Ethanol purchased from Gold Shield. Dichloromethane, sodium bicarbonate, ethylenediamine, potassium carbonate and THF purchased from Fischer Scientific. DMF and methanol purchased from Alfa Aesar. Chloroform purchased from VWR. Palladium on carbon and t-butylbromoacetate purchased from Acros Organics. 4-(bromomethyl)benzoic acid purchased from TCI America. Hydrochloric acid purchased from EMD. All nucleotide bases and modifiers purchased from Glen Research. Trichloracetic acid in dichloromethane deblocking mix purchased from Azco Biotech, Inc. All dry solvents received from the solvent room at the University of California, San Diego.

Characterization: Instrumentation. NMR spectra were recorded on a 400 MHz Varian Mercury Plus. $^1$HNMR characterization with samples dissolved in DMF-d7 or $CDCl_3$ used for deuterium shimming and locking. ESI was performed on a Finnigan LCQDECA equipped with a HP 1100 LC station. Static Light Scattering, RI, and UV-Vis Data performed on a Wyatt Dawn Helios, Hitachi L-2490, Hitachi L-2420 equipped with a Hitachi L-2130 pump. Dynamic Light Scattering performed on a Malvern ZetasizerNano with Multi Purpose Titrator.

Purification. HPLC performed on Hitachi Elite LaChrom equipped with a UV-Vis detector L-2420, pump L-2130, and phenomenex column clarity 5u oligo-RP deionized water and reduced the volume in a speed vacuum.

Synthesis of DTPA (14-17).Please see procedure outlined by Meares.[14] The DTPA chelate is a FDA approved agent. By connecting it to the seven membered norbornene ringg, it is amenable to direct incorporation in the polymer backbones as described for the other copolymers described herein.

Synthesis of DOTA monomer. DOTA is another Gd chelate. Please see procedures outlined by Li et al. (Li et al., J. Am. Chem. Soc. 128:15072-15073, 2006). Again, the goal of this synthetic scheme is its incorporation into the polymer backbone by ring opening the strained seven membered norbornene ring attached to the DOTA moiety.

Synthesis of t-butyl protected DTPA monomer, 18. Dissolved 17 (37 mg, 0.047 mmol) in 2.3 mL of dry $CH_2Cl_2$ and transferred to a 10 mL schlink flask. Added DIPEA (8 μL, 0.047 mmol) and the NHS monomer 9 (11 mg, 0.047 mmol) and stirred at room temperature under $N_2$ for 21 hours. TLC showed only starting material at this time point. Added 1 mLdry $CH_2Cl_2$ and one more equivalent of DIPEA. Continued to stir at room temperature for another 48 hours under $N_2$. Concentrate solution down resulting in a gold oil. Purification is over silica eluting with 1:1 hexanes:ethyl acetate and 1% TEA.

Synthesis of Boc-protected amine monomer (19) and deprotected amine monomer (20). Procedures are known in the art, (e.g., as outlined by Pfeffer).[16]

REFERENCES FOR EXAMPLE 7

(1) Reynolds, C. H.; Annan, N.; Beshah, K.; Huber, J. H.; Shaber, S. H.; Lenkinski, R. E.; Wortman, J. A. *J. Am. Chem. Soc.* 2000, 122:8940-8945.

(2) Zhang, G.; Zhang, R.; Wen, X.; Li, L.; Li, C. *Biomacromolecules,* 2007, 9:36-42.
(3) Joao P. Andre, H. R. M., Eva Toth, Andre A. Merbach *JBIC* 1999, 4:341-347.
(4) Joao P. Andre, E. T., Holger Fischer, Anna Seelig, Helmut R. Macke, and Andre E. Merbach Chem. *Eur. J.* 1999, 5:2977-2983.
(5) Amber L. Doiron, K. C., Adeel Ali, ands Lisa Brannon-Peppas *PNAS* 2008, 105:17232-17237.
(6) Angelique Y. Louie, M. M. H., Eric T. Ahrens, Ute Rothbacher, Rex Moats, Russell E. Jacobs, Scott E. Fraser, and Thomas J. Meade *Nat. Biotechnol.* 2000, 18:321-325.
(7) Rex, A. M.; Scott, E. F.; Thomas, J. M. *Angew. Chem. In. Ed.* 1997, 36:726-728.
(8) Allen, M. J.; Raines, R. T.; Kiessling, L. L. *J. Am. Chem. Soc.* 2006, 128:6534-6535.
(9) Song, Y.; Kohlmeir, E. K.; Meade, T. J. *J. Am. Chem. Soc.* 2008, 130, 6662-6663.
(10) Ghaghada, K.; Hawley, C.; Kawaji, Annapragada, A.; Mukundan Jr, S. *Academic Radiology* 2008, 15:1259-1263.
(11) Schenning, A. P. H. J.; Elissen-Roman, C.; Weener, J.-W.; Baars, M. W. P. L.; van derGaast, S. J.; Meijer, E. W. *J. Am. Chem. Soc.* 1998, 120:8199-8208.
(12) Ornelas, C.; Ruiz, J.; Belin, C.; Astruc, D. *J. Am. Chem. Soc.* 2008, 131:590-601.
(13) Brettreich, M.; Hirsch, A. *Synlett Letters* 1998, 1396-1398.
(14) Corson, D. T.; Meares, C. F. *Bioconjugate Chem.* 2000, 11:292-299.
(15) Pontrello, J. K.; Allen, M. J.; Underbakke, E. S.; Kiessling, L. L. *J. Am. Chem. Soc.* 2005, 127:14536-14537.
(16) Adam, J. L.; Gail, A. D.; Frederick, M. P. *Eur. J. Org. Chem.* 2008, 2008:1559-1567.

Example 7

DNA-Nanoparticle Micelles as Supramolecular Fluorogenic Substrates Enabling Catalytic Signal Amplification and Detection by DNAzyme Probes To enzymatically amplify a signal one requires a triggering mechanism that connects the detection event to the catalytic signal transduction process. This is the cornerstone of biologically regulated catalytic systems for signal transduction in living systems. Several effective enzymatic systems have been reported that use various types of DNA sequence and structure selective processes for detecting DNA via catalytic turnover for signal amplification.[1-19] These have included several efforts to harness catalytic single-stranded DNA (ssDNA) sequences as phosphodiesterases with ribonuclease activity (DNAzymes[20-23]) in a variety of assay formats usually aimed at activating fluorogenic nucleic acid substrates via strand cleavage reactions (FIG. 24).[24-32] DNAzymes offer a unique opportunity for detection and signal amplification because unlike proteinaceous enzymatic endonucleases, DNAzymes are not restricted to a given sequence but rather are synthesized in the laboratory to desired specifications making them selective for any given sequence. In this respect, DNAzymes are unique and potentially powerful tools in biodiagnostics because they have tailorable sequence selectivity and are potentially catalytic. Herein, their utility as selective, triggerable catalysts for signal amplification by true turnover is demonstrated in the context of a DNA detection protocol enabled by supramolecular fluorogenic substrates.[33] Given the numerous modes of selective recognition open to ssDNA (e.g. hybridization,[34-36] aptamer-based recognition,[18,37] enzymatic substrates,[38] thermal responsiveness[39]) it is expected that harnessing DNAzymes in catalytic detection protocols will have broad utility.

Figure 24:
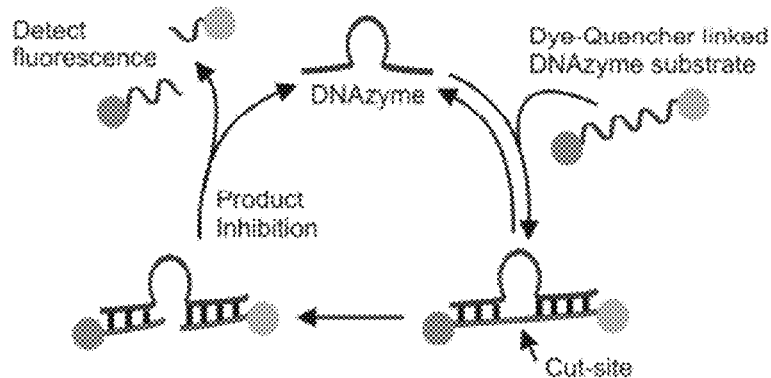
FIG. 24 depicts the design of supramolecular substrates capable of multiple turnovers compared to single-stranded DNA (ssDNA) substrates. Active DNAzymes recognize fluorogenic substrates and catalyze strand cleavage at RNA bases. a) ssDNA substrates are typically modified with fluorophore and quencher pairs for activation via sequence selective cleavage. b) The DNA-nanoparticle micelles formed via the assembly of DNA-brush copolymer surfactants. Dye-labelled DNA strands within the particles are recognized and cleaved by a DNAzyme enabling detection of fluorescence.
Figure 24:
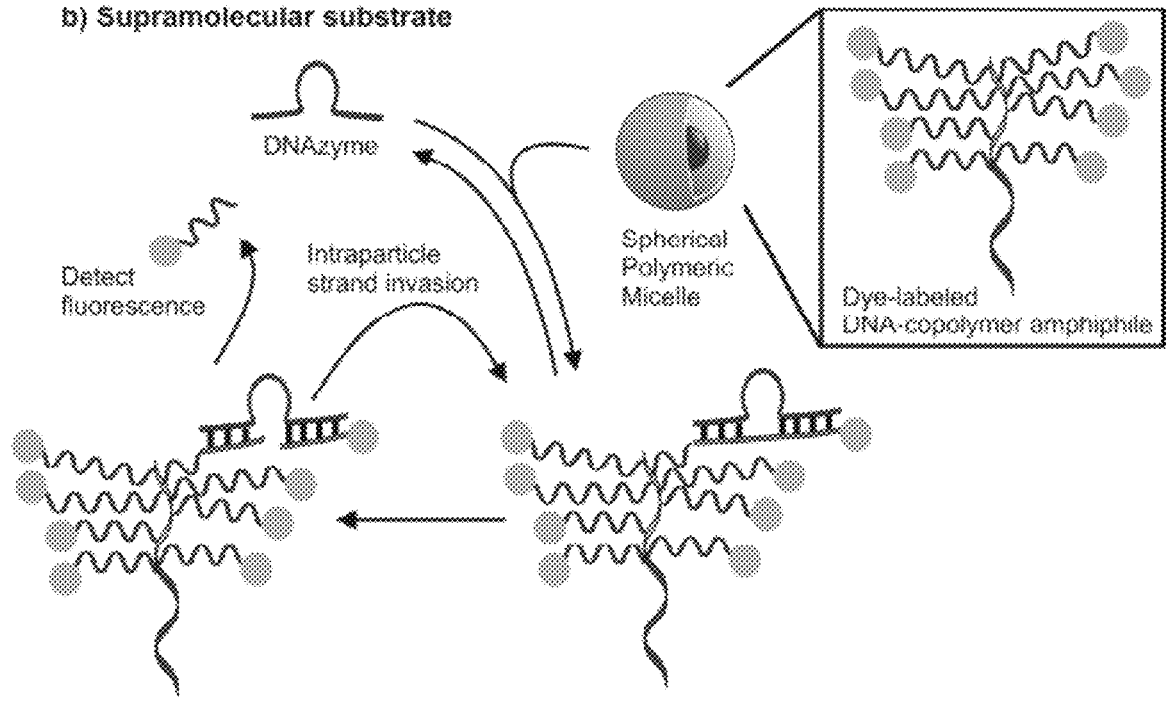

Currently, a major limitation of DNAzymes in signal amplification and detection via catalysis, is that they are product inhibited and are therefore typically limited to a single turnover or less. This limitation is caused by, substrate and product having the same DNA sequence and one must balance turnover of cleaved substrate with binding energy as with any system designed with substrate selectivity and turnover in mind. We reasoned that if one could generate a cooperatively assembled supramolecular fluorogenic substrate then DNAzyme catalytic activity would be enhanced by virtue of increasing effective DNA substrate concentration upon DNAzyme recognition of the probe.[17, 40-43] A DNA-brush copolymer capable of assembling into an aggregate structure was found to be capable of achieving this goal (FIG. 24). The key benefit to this assembly over material simply decorated with DNA is that in this system the substrate is within the internal structure increasing the density of the probe. We reasoned that a micellar aggregate consisting of a material formed from the DNA substrate itself, would allow sequence selective turnover not accessible to single-stranded DNA fluorogenic substrates such as molecular beacons.[34,36]

Figure 25:
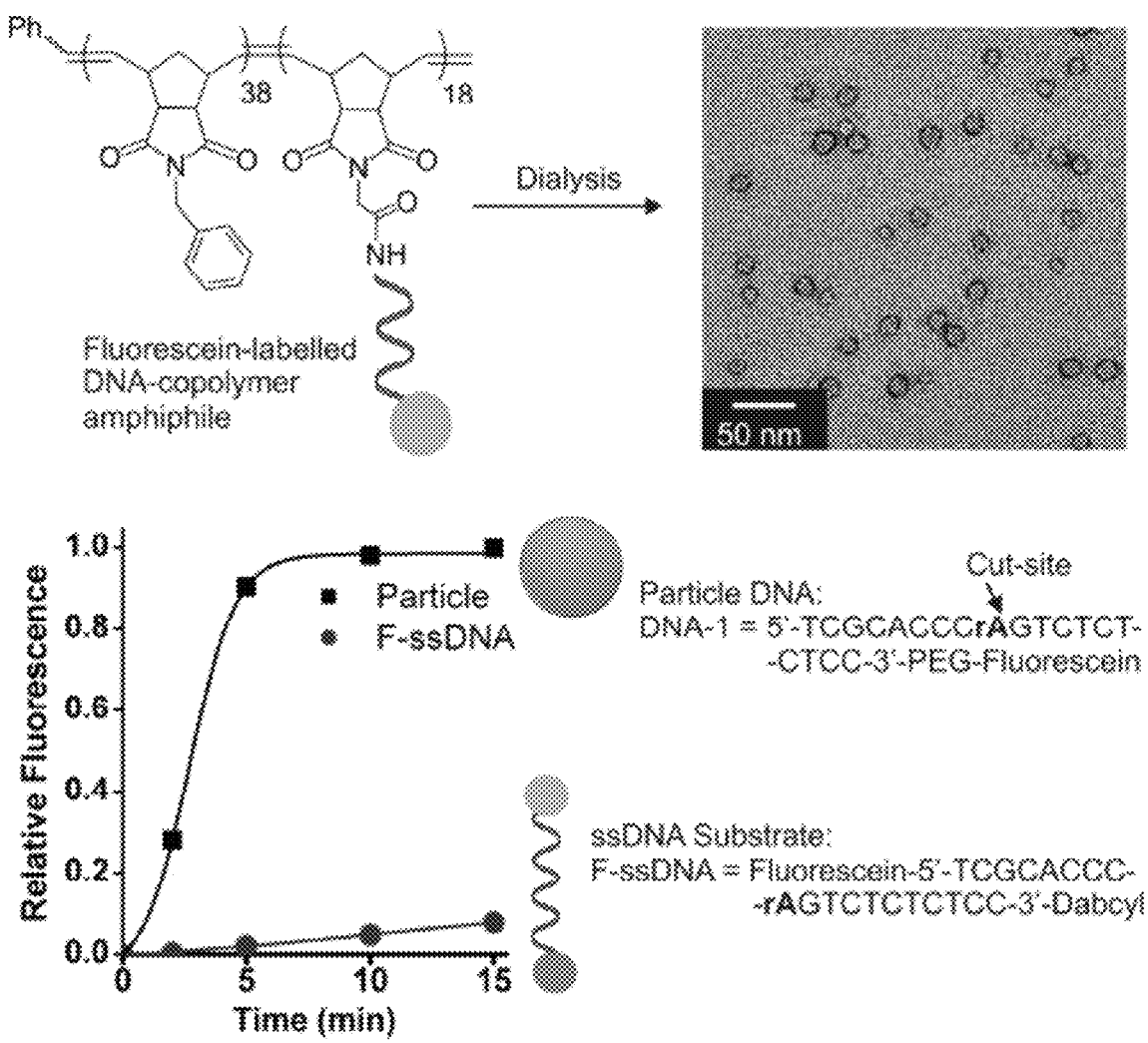
FIG. 25 depicts the structure of supramolecular substrate micelles and turnover of supramolecular fluorogenic substrate particle vs. single-stranded fluorescent substrate (F-ssDNA). TEM data indicates 20 nm particles assembled from the DNA-brush copolymer. PEG=polyethylene glycol incorporated via phosphoramidite chemistry, see ESI for structural details. Conditions: Particle DNA (1 μM), F-ssDNA (1 μM), DNAzyme (5 nM). Buffer: Tris (20 mM, pH 7.4), MgCl$_2$ (50 mM), room temp. DNAzyme utilized in these studies has sequence; DNAzyme-1: 5'-GGAGAGAGATCCGAGCCG-GAAGGGTGCGA-3' (SEQ ID NO:29). Sequences in FIG. 25: DNA-1 (5'-TCGCACCCrAGTCTCTCTCC-3'-PEG-Fluorescein) (SEQ ID NO:32); F-ssDNA Substrate (Fluorescein-5'-TCGCACCCrAGTCTCTCTCC-3'-Dabcyl) (SEQ ID NO:20).

The DNAzyme catalyst consists of a conserved DNA sequence forming a catalytic domain with 5'- and 3'-ends as recognition sequences.[22] Therefore, a DNA substrate with a single RNA base (rA) as the site of cleavage was chosen for incorporation in the DNA-brush copolymer architecture used to form micellar aggregates (FIG. 25). The DNA substrate was designed to incorporate two sequences complementary to the recognition portions of the DNAzyme on either side of the RNA-base cut-site as well as incorporating a fluorescein moiety on the 3'-termini of the strand to allow for detection and analysis of the cleavage reaction by fluorescence spectroscopy. The polymers utilized in these systems were formed with low polydispersity and well-defined block structure amenable to post-polymerization modification with the 5'-amino modified oligonucleotide (see ESI). The resulting DNA-brush copolymer was dialyzed in buffered water (Tris, 20 mM, pH 7.4) to obtain spherical DNA nanoparticles approximately 20 nm in diameter as shown by transmission electron microscopy (TEM, FIG. 25), dynamic light scattering (DLS) and atomic force microscopy (AFM).[33] Initially, particles were mixed with DNAzymes in 10,000 g/mol molecular weight cut off (MWCO) centrifuge tubes. Cleavage of the DNA shell at the RNA base (rA) cut-site releases a fluorescent 10 base ssDNA product into solution from the particle surface resulting in a shell containing a truncated 9-base long sequence. By centrifuging at 14,000×g for 30 seconds at given time points, the ssDNA product was separated from particles as it passed through the MWCO filter for analysis by fluorescence. The identity of the product was confirmed by MALDI mass spectrometry (see ESI). The DNAzyme catalytic efficiency in the supramolecular fluorogenic substrate particle is greatly enhanced compared to the single-stranded fluorescent DNA substrate (F-ssDNA) (FIG. 25). The multiple turnovers observed for the DNAzyme on the particle compared with the F-ssDNA is presumably due to the high effective concentration of substrate in the particle shell enabling enhanced, efficient shell strand truncation. Importantly, the ordinarily product inhibited DNAzyme is capable of multiple turnovers and complete shell degradation occurs within 15 minutes following addition to a solution of the particles (complete turnover was confirmed via calibration curve, see ESI). This is in comparison to the low turnover observed for F-ssDNA substrate over the same time scale.

Figure 26:
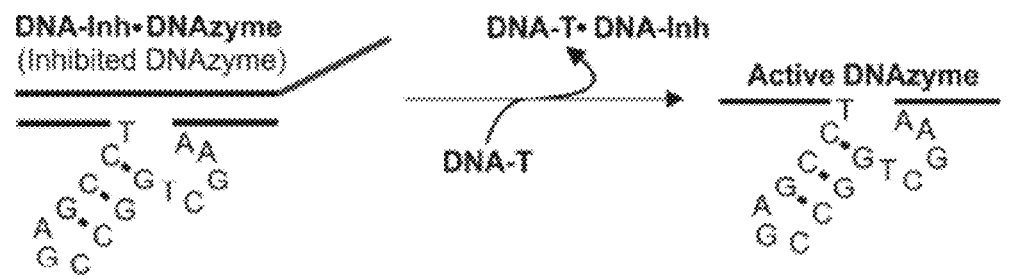
FIG. 26 depicts the selective and sensitive DNAzyme catalyzed DNA-shell truncation. Inhibited DNAzyme-1 (Duplex: DNAzyme-1•DNA-Inh) is treated with target strand (DNA-T) over a range of concentrations causing displacement of DNAzyme-1 and formation of a new duplex, DNA-T•DNA-Inh. Activated DNAzyme-1 binds to and cleaves the particle shell releasing fluorescein-labeled ssDNA.
Figure 26:
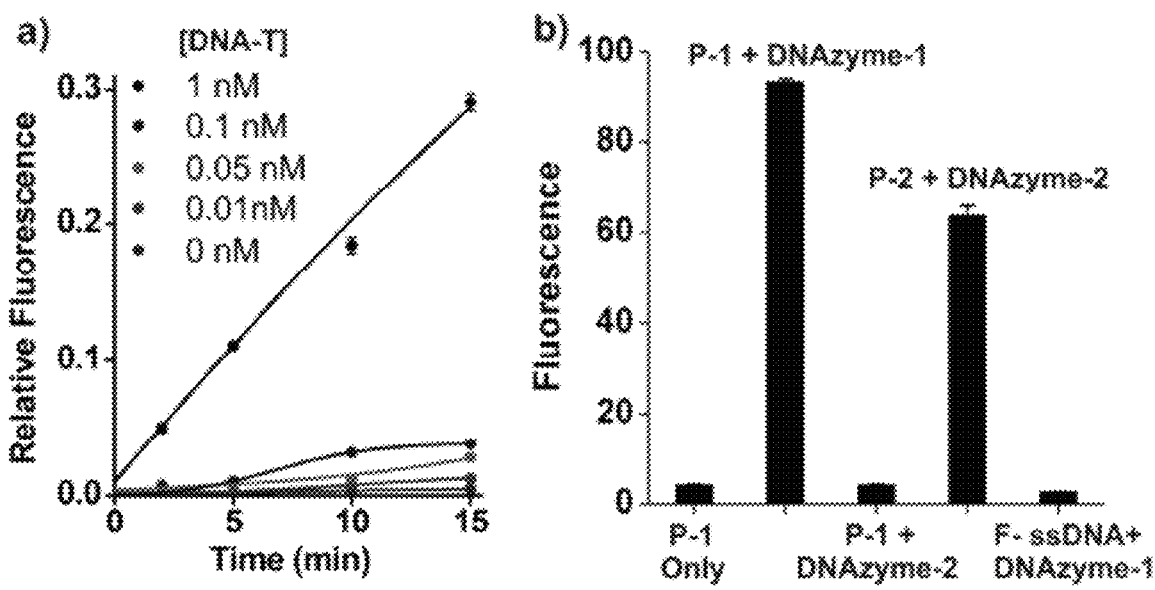

To demonstrate the utility of this substrate design in signal amplification via DNAzyme-mediated sensing,[26,28] we designed an assay (FIG. 26) composed of a DNAzyme (DNAzyme-1), its inhibitor (DNA-Inh), a target sequence (DNA-T; sequence from HIV-1 gag/pol gene) and a supramolecular substrate particle, labeled P-1 in FIG. 26, encoded with single-stranded substrate (sequence=DNA-1). First, DNAzyme-1 was mixed for 30 min with DNA-Inh, designed to hybridize via the recognition sequences in the DNAzyme and block the active site. This inhibited DNAzyme complex was then mixed with varying concentrations DNA-T and incubated for 30 min. Once added, DNA-T rapidly invades into the inhibited DNAzyme duplex (DNAzyme-1•DNA-Inh), releasing active DNAzyme-1 and forming the new, longer duplex DNA-T•DNA-Inh. Substrate particle's (P-1) were added to the solution of activated DNAzyme-1 causing particle shell recognition and cleavage. Product strands were again separated by filtration from particles and analyzed by fluorescence. The observed pM sensitivities (FIG. 26a) for the detection and signal amplification of ssDNA confirm the turnover of substrate on the particle by DNAzyme-1.

In addition, this process is sequence selective, as evidenced by the selective inhibition and triggering of DNAzyme-1 and the observation that the non-complementary DNAzyme-2 has no effect on P-1 (FIG. 26b). In turn, DNAzyme-2 catalyzes shell degradation when mixed with particles containing the complementary sequence, DNA-2 (P-2). The above studies illustrate two key features of this system: 1) Particles are sensitive to low concentrations of catalytically active DNAzyme. 2) The particles are susceptible to degradation in a sequence selective and concentration dependent fashion.

In conclusion, the present study has introduced a novel approach to substrate design enabling a DNAzyme to be utilized in a truly catalysis-based amplification and detection assay. This affords a route toward DNAzyme detection assays of various types where the myriad ways of recognizing ssDNA sequences may be used as triggers.[44]

REFERENCES FOR EXAMPLE 7

1 B. Schweitzer and S. Kingsmore, *Curr. Opin. Biotech.*, 2001, 12:21-27.
2 B. W. Kirk, M. Feinsod, R. Favis, R. M. Kliman and F. Barany, *Nucleic Acids Res.*, 2002, 30:3295-3311.
3 L. Zhu and E. V. Anslyn, *Angew. Chem. Int. Ed.*, 2006, 45:1190-1196.
4 A. J. H. Smith, *Nucleic Acids Res.*, 1979, 6:831-848.
5 L. H. Guo and R. Wu, *Nucleic Acids Res.*, 1982, 10:2065-2084.
6 R. K. Saiki, S. Scharf, F. Faloona, K. B. Mullis, G. T. Horn, H. A. Erlich and N. Arnheim, *Science* 1985, 230:1350-1354.
7 P. Duck, G. Alvarado-Urbina, B. Burdick and B. Collier, *Bio Techniques*, 1990, 9:142-143, 145-146, 148.
8 K. Okano and H. Kambara, *Anal. Biochem.*, 1995, 228:101-108.
9 F. Bekkaoui, I. Poisson, W. Crosby, L. Cloney and P. Duck, *BioTechniques*, 1996, 20:240-244, 246-248.
10 C. A. Mein, B. J. Barratt, M. G. Dunn, T. Siegmund, A. N. Smith, L. Esposito, S, Nutland, H. E. Stevens, A. J. Wilson, M. S. Phillips, N. Jarvis, S. Law, M. De Arruda and J. A. Todd, *Genome Res.*, 2000, 10:330-343.
11 T. M. Hsu, S. M. Law, S. Duan, B. P. Neri and P.-Y. Kwok, *Clin. Chem.* 2001, 47:1373-1377.
12 Z. Wang and J. Moult, *Hum. Mutat.*, 2001, 17:263-270.
13 M. Levy and A. D. Ellington, *Proc. Natl. Acad. Sci. USA.*, 2003, 100:6416-6421.
14 A. Saghatelian, K. M. Guckian, D. A. Thayer and M. R. Ghadiri, *J. Am. Chem. Soc.*, 2003, 125:344-345.
15 B. Ren, J.-M. Zhou and M. Komiyama, *Nucleic Acids Res.*, 2004, 32:e42/41-e42/49.
16 K. Nakatani, *Chem Bio Chem*, 2004, 5:1623-1633.
17 J. M. Gibbs, S.-J. Park, D. R. Anderson, K. J. Watson, C. A. Mirkin and S. T. Nguyen, *J. Am. Chem. Soc.*, 2005, 127:1170-1178.
18 V. Pavlov, B. Shlyahovsky and I. Willner, *J Am Chem Soc*, 2005, 127:6522-6523.
19 P. Simon, C. Dueymes, M. Fontecave and J.-L. Decout, *Angew. Chem. Int. Ed.*, 2005, 44:2764-2767.
20 R. R. Breaker and G. F. Joyce, *Chem. Biol.*, 1994, 1:223-229.
21 S. W. Santoro and G. F. Joyce, *Proc. Natl. Acad. Sci. USA.*, 1997, 94:4262-4266.
22 J. Li, W. Zheng, A. H. Kwon and Y. Lu, *Nucleic Acids Res.*, 2000, 28:481-488.
23 M. N. Stojanovic and D. Stefanovic, *Nat. Biotechnol.*, 2003, 21:1069-1074.
24 M. N. Stojanovic, P. de Prada and D. W. Landry, *Nucleic Acids Res.*, 2000, 28:2915-2918.
25 A. V. Todd, C. J. Fuery, H. L. Impey, T. L. Applegate and M. A. Haughton, *Clin. Chem.*, 2000, 46:625-630.
26 M. N. Stojanovic, P. de Prada and D. W. Landry, *Chem Bio Chem*, 2001, 2:411-415.
27 S. Schubert and J. Kurreck, *Curr. Drug Targets*, 2004, 5:667-681.
28 Y. Tian and C. Mao, *Talanta*, 2005, 67:532-537.
29 Y. Tian, Y. He and C. Mao, *Chem Bio Chem*, 2006, 7:1862-1864.
30 J. Liu and Y. Lu, *Angew. Chem. Int. Ed.*, 2007, 46:7587-7590.
31 D. P. Wernette, C. Mead, P. W. Bohn and Y. Lu, *Langmuir*, 2007, 23:9513-9521.
32 A. K. Brown, J. Liu, Y. He and Y. Lu, *Chem Bio Chem*, 2009, 10:486-492.
33 M. P. Chien, A. M. Rush, M. P. Thompson and N. C. Gianneschi, *Angew. Chem. Int. Ed.*, 2010.
34 S. Tyagi and F. R. Kramer, *Nat. Biotechnol.*, 1996, 14:303-308.
35 M. Singh-Zocchi, S. Dixit, V. Ivanov and G. Zocchi, *Proc. Natl. Acad. Sci. USA.*, 2003, 100:7605-7610.
36 K. Wang, Z. Tang, Chaoyong J. Yang, Y. Kim, X. Fang, W. Li, Y. Wu, Colin D. Medley, Z. Cao, J. Li, P. Colon, H. Lin and W. Tan, *Angew. Chem. Int. Ed.*, 2009, 48:856-870.
37 J.-L. He, Z.-S. Wu, H. Zhou, H.-Q. Wang, J.-H. Jiang, G.-L. Shen and R.-Q. Yu, *Anal. Chem.*, 2010, 82:1358-1364.
38 V. S. Trubetskoy, J. E. Hagstrom and V. G. Budker, *Anal. Biochem.*, 2002, 300:22-26.
39 H. S. Bisht, D. S. Manickam, Y. You and D. Oupicky, *Biomacromolecules*, 2006, 7:1169-1178.
40 M. L. Collins, B. Irvine, D. Tyner, E. Fine, C. Zayati, C.-a. Chang, T. Horn, D. Ahle, J. Detmer, L.-P. Shen, J. Kolberg, S. Bushnell, M. S. Urdea and D. D. Ho, *Nucleic Acids Res.*, 1997, 25:2979-2984.
41 M. S. Shchepinov, I. A. Udalova, A. J. Bridgman and E. M. Southern, *Nucleic Acids Res.*, 1997, 25:4447-4454.
42 M. S. Shchepinov, K. U. Mir, J. K. Elder, M. D. Frank-Kamenetskii and E. M. Southern, *Nucleic Acids Res.*, 1999, 27:3035-3041.
43 A. K. R. Lytton-Jean and C. A. Mirkin, *J. Am. Chem. Soc.*, 2005, 127:12754-12755.
44 S. K. Silverman, *Chem. Commun.* 2008, 15:211-213.

What is claimed is:

1. A method of altering a morphology of a micelle from a rod to a sphere, said method comprising, subjecting said micelle to a stimulus wherein said micelle comprises a plurality of aggregated amphiphilic molecules each having a single-strand nucleic acid hydrophilic portion comprising at least one nucleic acid moiety covalently linked to a polymer within said amphiphilic molecules, and a hydrophobic portion, and wherein said stimulus is a single-strand nucleic acid hydrophilic portion binder capable of hybridizing to one of said single-strand nucleic acid hydrophilic portions thereby altering the morphology of said micelle from a rod to a sphere.

2. The method of claim 1, wherein said single-strand nucleic acid hydrophilic portion is a plurality of nucleic acid moieties.

3. The method of claim 1, wherein said single-strand nucleic acid binder is a single strand DNA.

4. The method of claim 1, wherein said single-strand nucleic acid binder is DNA, RNA, PNA or DNA/RNA hybrid.

5. The method of claim 1, wherein said morphology of said micelle is altered from a rod to a sphere when more than 25% of the nucleic acid moieties of the single-strand nucleic acid hydrophilic portion is hybridized by the single-strand nucleic acid binder.

6. The method of claim 1, wherein said morphology of said micelle is altered from a rod to a sphere when more than 50% of the nucleic acid moieties of the single-strand nucleic acid hydrophilic portion is hybridized by the single-strand nucleic acid binder.

7. The method of claim 1, wherein said morphology of said micelle is altered from a rod to a sphere when more than 75% of the nucleic acid moieties of the single-strand nucleic acid hydrophilic portion is hybridized by the single-strand nucleic acid binder.

8. The method of claim 1, wherein said micelle further comprises a drug or a fluorogenic tag.

9. The method of claim 8, wherein said drug or said fluorogenic tag is covalently attached to said amphiphilic molecules.

10. The method of claim 9, wherein said drug or said fluorogenic tag is non-covalently bound to said amphiphilic molecules.

11. The method of claim 10, wherein said drug or said fluorogenic tag is released or uptaken upon contacting said micelle with a stimulus.

12. The method of claim 1, wherein said micelle further comprises a contrast agent.

13. The method of claim 12, wherein said contrast agent is an X-ray reagent, a radiography reagent, a magnetic resonance imaging agent, a quantum dot, a contrast agent nanoparticle, or an ultrasound agent.

14. The method of claim 13, wherein relaxivity of said contrast agent is altered upon contacting said amphiphilic molecules with a stimulus.

15. The method of claim 13, wherein said contrast agent is covalently attached to said amphiphilic molecules.

16. The method of claim 13, wherein said contrast agent is non-covalently bound to said amphiphilic molecules.

17. The method of claim 13, wherein said contrast agent is released or uptaken upon contacting said micelle with a stimulus.

* * * * *